United States Patent
Krebs et al.

(10) Patent No.: US 11,884,718 B2
(45) Date of Patent: Jan. 30, 2024

(54) POTENT ZIKA VIRUS-SPECIFIC AND CROSS-NEUTRALIZING MONOCLONAL ANTIBODIES TO ZIKA AND DENGUE VIRUSES FOLLOWING ZIKV INFECTION OR VACCINATION

(71) Applicants: The Henry M. Jackson Foundation for the Advancement of Military Medicine, Inc., Bethesda, MD (US); The Beth Israel Deaconess Medical Center, Inc., Boston, MA (US); The Government of the United States as Represented by the Secretary of the Army, Silver Spring, MD (US)

(72) Inventors: Shelly Krebs, Bethesda, MD (US); Gina Donofrio, Rockville, MD (US); Vincent Dussupt, Silver Spring, MD (US); Kayvon Modjarrad, Bethesda, MD (US); Dan Barouch, Boston, MA (US); Richard G. Jarman, III, Silver Spring, MD (US); Nelson L. Michael, Silver Spring, MD (US); Gordon Joyce, Silver Spring, MD (US); Rajeshwer Singh Sankhala, Silver Spring, MD (US); Kathryn Elaine Stephenson, Boston, MA (US)

(73) Assignees: The Henry M. Jackson Foundation for the Advancement of Military Medicine, Inc., Bethesda, MD (US); The Beth Israeli Deaconess Medical Center, Inc., Boston, MA (US); The Government Of The United States As Represented By The Secretary Of The Army, Fort Detrick, MD (US)

( * ) Notice: Subject to any disclaimer, the term of this patent is extended or adjusted under 35 U.S.C. 154(b) by 627 days.

(21) Appl. No.: 17/049,800

(22) PCT Filed: Apr. 24, 2019

(86) PCT No.: PCT/US2019/028952
§ 371 (c)(1),
(2) Date: Oct. 22, 2020

(87) PCT Pub. No.: WO2019/209974
PCT Pub. Date: Oct. 31, 2019

(65) Prior Publication Data
US 2021/0238262 A1   Aug. 5, 2021

Related U.S. Application Data

(60) Provisional application No. 62/697,347, filed on Jul. 12, 2018, provisional application No. 62/662,211, filed on Apr. 24, 2018.

(51) Int. Cl.
| | |
|---|---|
| C07K 16/10 | (2006.01) |
| A61P 31/14 | (2006.01) |
| A61K 39/12 | (2006.01) |
| C12N 7/00 | (2006.01) |
| G01N 33/563 | (2006.01) |
| G01N 33/569 | (2006.01) |
| A61K 39/00 | (2006.01) |

(52) U.S. Cl.
CPC .......... *C07K 16/1081* (2013.01); *A61K 39/12* (2013.01); *A61P 31/14* (2018.01); *C12N 7/00* (2013.01); *G01N 33/563* (2013.01); *G01N 33/56983* (2013.01); *A61K 2039/505* (2013.01); *A61K 2039/5252* (2013.01); *C07K 2317/21* (2013.01); *C07K 2317/24* (2013.01); *C07K 2317/31* (2013.01); *C07K 2317/55* (2013.01); *C07K 2317/565* (2013.01); *C07K 2317/622* (2013.01); *C07K 2317/76* (2013.01); *C07K 2317/92* (2013.01); *C12N 2770/24134* (2013.01)

(58) Field of Classification Search
CPC combination set(s) only.
See application file for complete search history.

(56) References Cited

U.S. PATENT DOCUMENTS

| | | | |
|---|---|---|---|
| 2009/0258011 A1 | 10/2009 | Diamond et al. | |
| 2017/0174752 A1* | 6/2017 | Mazor | G01N 33/5308 |
| 2018/0021426 A1 | 1/2018 | Thomas et al. | |
| 2018/0105583 A1 | 4/2018 | Sasisekharan et al. | |

FOREIGN PATENT DOCUMENTS

| | | |
|---|---|---|
| WO | 2016/145149 A1 | 9/2016 |
| WO | 2017/139065 A1 | 8/2017 |
| WO | 2017181098 A2 | 10/2017 |
| WO | 2017/210215 A1 | 12/2017 |
| WO | 2018011283 A1 | 1/2018 |
| WO | 2018017497 A1 | 1/2018 |
| WO | 2018053478 A1 | 3/2018 |
| WO | 2018071822 A2 | 4/2018 |
| WO | 2018/152496 A1 | 8/2018 |

OTHER PUBLICATIONS

International Search Report issued in corresponding International Patent Application No. PCT/US2019/028952 dated Oct. 16, 2019.
Written Opinion issued in corresponding International Patent Application No. PCT/US2019/028952 dated Oct. 16, 2019.

\* cited by examiner

*Primary Examiner* — Adam Weidner
*Assistant Examiner* — Laura Ann Essex
(74) *Attorney, Agent, or Firm* — McNeill Baur, PLLC

(57) ABSTRACT

The invention described herein provides antibodies to Zika virus. The novel polypeptides are useful alone or as portions of larger molecules, such as antibodies or antibody fragments, that can be used to treat or prevent infection of Zika virus.

17 Claims, 77 Drawing Sheets
Specification includes a Sequence Listing.

| mAb ID | Heavy chain | | | | Light chain | | | | Type | sE binding (nm) | ZIKV neutralization |
|---|---|---|---|---|---|---|---|---|---|---|---|
| | V gene | % SHM | CDR3 length | CDR3 sequence | V gene | % SHM | CDR3 length | CDR3 sequence | | | |
| mAbZ100-C | VH3.63 | 4.1 | 14 | AKDITAPGRNGLDS | VL11.42 | 1.6 | 9 | QVYDNSARV | IgG | 1.65 | Yes |
| mAbZ201-B | VH3.15 | 4.4 | 14 | ARVLYSGSYYYFDY | VL11.42 | 0.6 | 10 | QVYDSSANIV | IgG | 0.94 | Yes |
| mAbZ203-A | VH4.40 | 5.7 | 21 | ARPAYYEDDYGYYYTPIFDY | VL1.27 | 0.0 | 11 | AAWDNSLSSVL | IgG | 0.28 | Yes |
| mAbZ204-D | VH3.15 | 0.3 | 20 | ARERYCSGGVCYAGTNYFDY | VL11.42 | 0.0 | 10 | QVYDSSANWV | IgG | 3.55 | Yes |
| mAbZ105 | VH3.31 | 8.8 | 10 | ARHEGGALDS | VL11.42 | 4.2 | 10 | QVYAGTARV | IgG | 0.30 | No |
| mAbZ106 | VH4.26 | 0.7 | 20 | AREGGPYSGGYYPRYWYSDL | VL5.28 | 1.0 | 9 | MWHNNAWV | IgG | 0.26 | No |
| mAbZ207-B | VH4.34 | 0.0 | 17 | ARHDRVGSYPYYYGLDS | VL11.42 | 0.6 | 10 | QVYDSSANDV | IgG | 1.97 | Yes |
| mAbZ113 | VH7.21 | 17.7 | 11 | AKYDDRNGLDS | VL11.42 | 19.9 | 9 | QVYDGSANI | IgM | 0.61 | No |
| mAbZ115 | VH5.7 | 17.9 | 12 | AKGDDRLAHFDY | VL5.28 | 21.2 | 9 | QVYDSSAGL | IgM | 0.15 | No |
| mAbZ118 | VH3.52 | 0.3 | 13 | ATKRLYEQRLSDY | VL5.28 | 7.7 | 9 | ANHSSAWV | IgG | 0.65 | No |
| mAbZ119-D | VH5.7 | 0.7 | 12 | AKEGAARSLDV | VL3.4 | 0.7 | 11 | YSTDSSQYHGL | IgG | 3.48 | Yes |
| mAbZ120 | VH3.58 | 4.8 | 15 | AKYPSGSYYYDWFDV | VL5.28 | 7.7 | 9 | ANHSSAWV | IgG | 0.50 | No |
| mAbZ121-A | VH4.34 | 0.0 | 13 | ARGNYYSGSYYLF | VL3.15 | 0.0 | 11 | QVWDSSSDHWV | IgM | 0.34 | Yes |
| mAbZ122-A | VH5.7 | 3.1 | 14 | AKVDSSGWTNYFDY | VL2.44 | 1.0 | 10 | CSYRSGSTYI | IgG | 0.70 | Yes |
| mAbZ124-D | VH4.34 | 4.7 | 16 | ARLGHPRGIAAGGVDY | VL11.42 | 5.4 | 10 | QVYDRAANL | IgG | 3.20 | Yes |
| mAbZ125 | VH4.34 | 3.7 | 20 | ARGQVYEDDYGYYYTGYFDY | VL2.13 | 9.8 | 10 | SSYEASDTFI | IgG | 0.87 | No |
| mAbZ129 | VH5.7 | 5.1 | 11 | AKGVGGNRFDV | VL11.42 | 1.0 | 9 | QVYDSSFYI | IgM | 0.24 | No |
| mAbZ130 | VH3.58 | 4.5 | 11 | ADIAAAGKAGY | VL3.58 | 0.3 | 9 | QVYDGSAGL | IgM | 0.25 | No |
| mAbZ132 | VH7.21 | 8.2 | 18 | ARHWEYCTGSGCYASFDY | VL2.51 | 0.0 | 10 | CSYTTSSTFL | IgM | 0.95 | No |
| mAbZ133-C | VH3.30 | 1.0 | 17 | AMHYCTGSGCYGAGLDS | VL2.44 | 1.4 | 9 | CSYRSGSTL | IgM | 2.47 | Yes |
| mAbZ134-B | VH3.15 | 0.3 | 30 | ARGPEYCSSTYCSSAYCTGSGCYVDYGLDS | VL3.46 | 2.8 | 11 | QVWDSSSDHVL | IgM | 1.88 | Yes |
| mAbZ136 | VH3.52 | 1.0 | 15 | ARRRGPNNFWSGWDH | VL11.42 | 0.0 | 9 | QVYDSSAVL | IgM | 0.30 | No |
| mAbZ140 | VH3.58 | 4.5 | 13 | ASLYYSGSYYSDY | VL11.42 | 0.3 | 9 | QVYDGSAWV | IgM | 0.11 | No |

Fig. 1C

| mAb ID | ZIKV sE Binding (nm) | ZIKV MN50 (ng/ml) | ZIKV FlowNT50 (ng/ml) | DENV1-4, JEV, WNV, YFV (ng/ml) |
|---|---|---|---|---|
| rhMZ103-A | 0.28 | 5,398 | 2,152 | >100,000 |
| rhMZ121-A | 0.34 | 106,982 | 4,626 | >100,000 |
| rhMZ123-A | 0.70 | 390.4 | 6,010 | >100,000 |
| rhMZ101-B | 0.94 | 9,912 | 8,208 | >100,000 |
| rhMZ107-B | 1.97 | 1,251 | 1,443 | >100,000 |
| rhMZ134-B | 1.88 | 3.6 | 22.3 | >100,000 |
| rhMZ100-C | 1.65 | 1,009 | 2,674 | >100,000 |
| rhMZ133-C | 2.47 | 39.0 | 1,214 | >100,000 |
| rhMZ104-D | 3.55 | 33,892 | 2,945 | >100,000 |
| rhMZ119-D | 3.46 | 388.5 | 30.8 | >100,000 |
| rhMZ124-D | 3.20 | 840.1 | 2,462 | >100,000 |
| 2A10G6 | 3.24 | NT | NT | all* |
| EDE1-C8 | 2.94 | 58.1 | 25.9 | DENV1,2,3,4 |
| Z004 | 4.03 | 1.4 | 7.1 | DENV-1** |

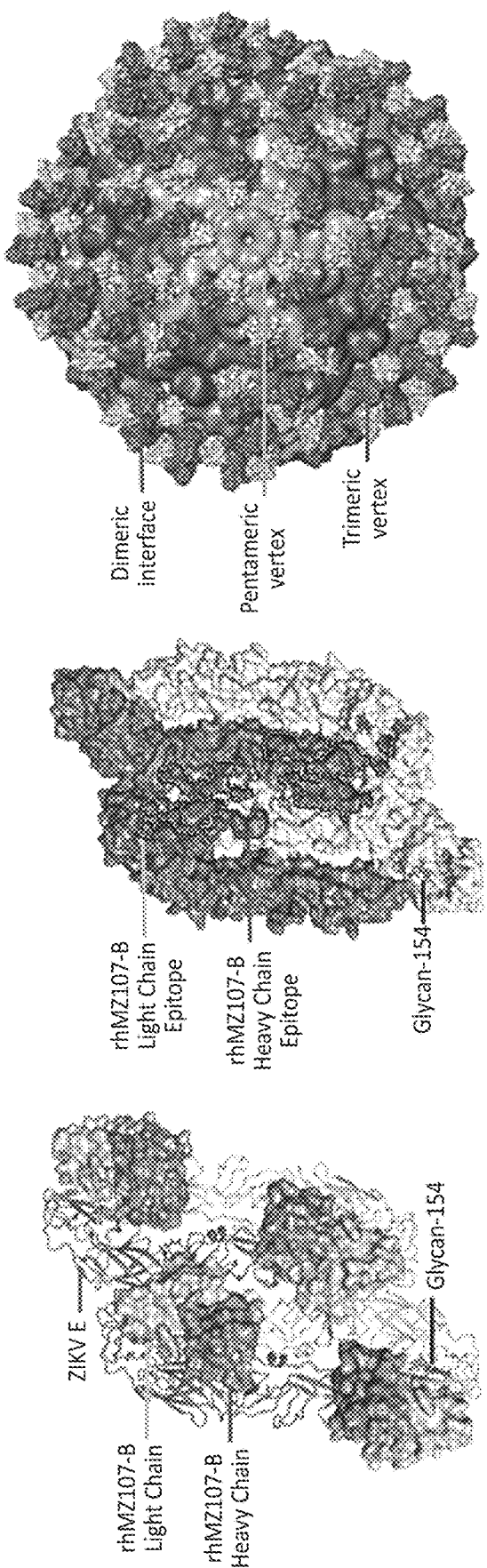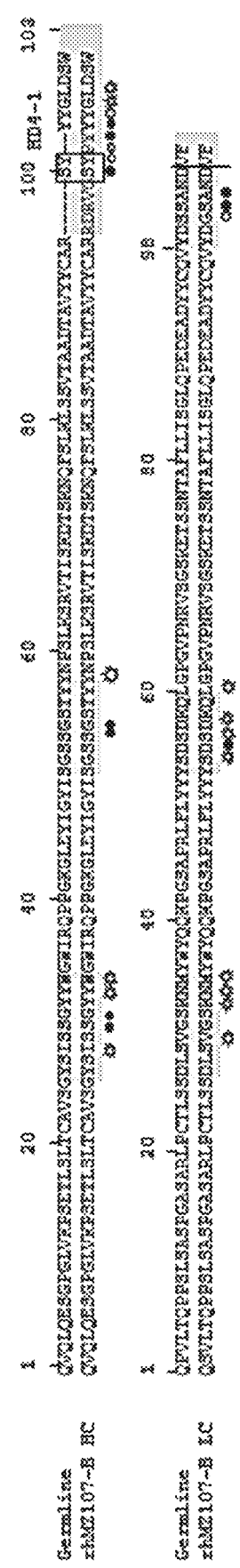
Fig. 3A  Fig. 3B  Fig. 3C  Fig. 3D

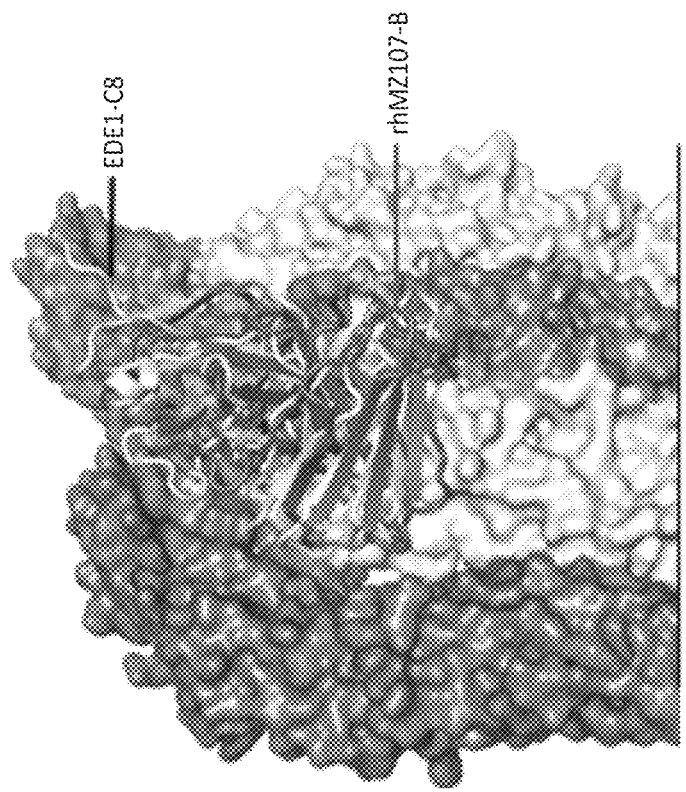
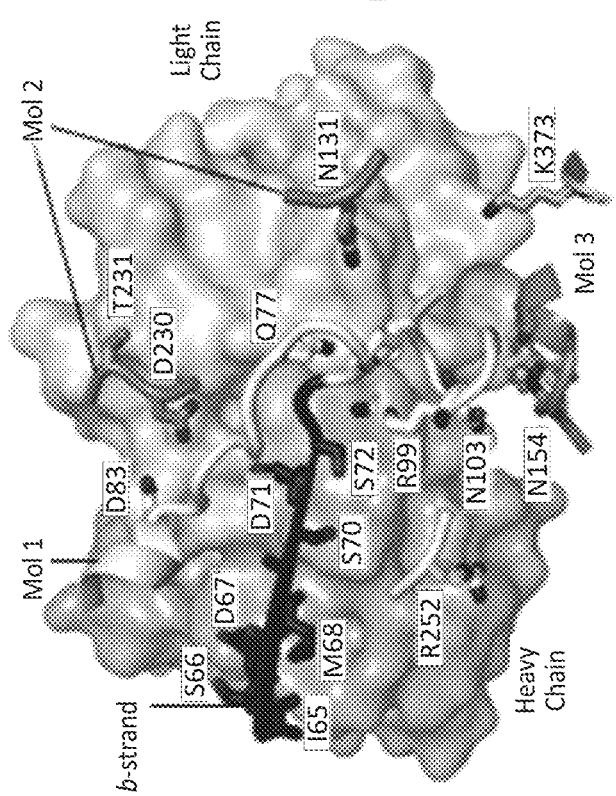
Fig. 3F
Fig. 3G

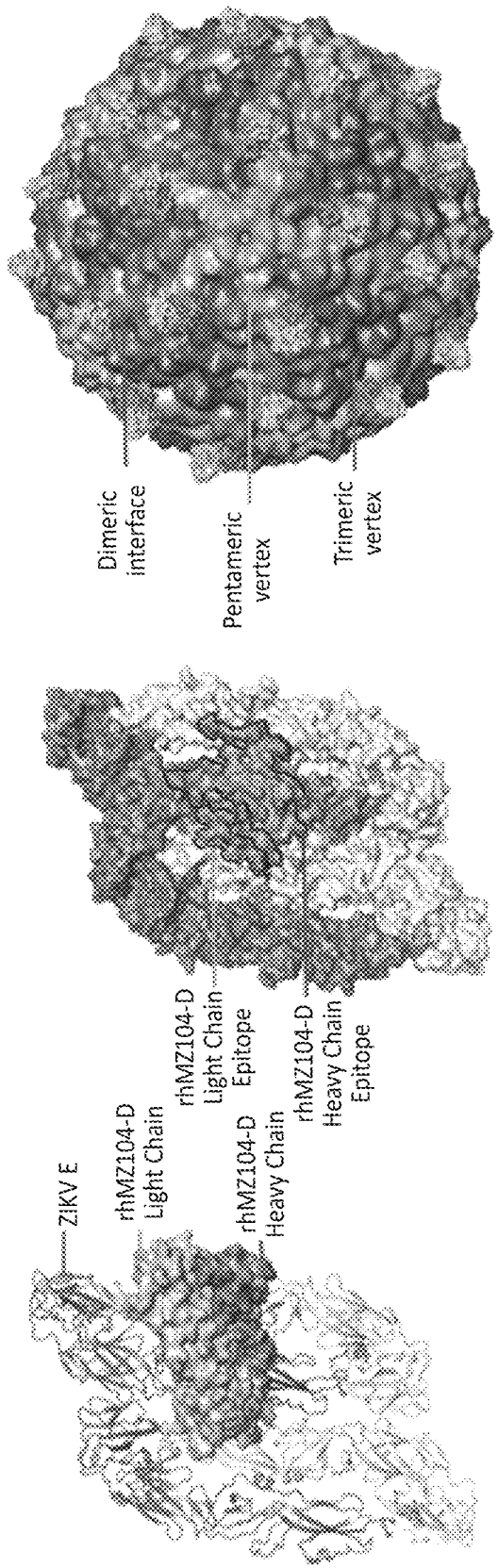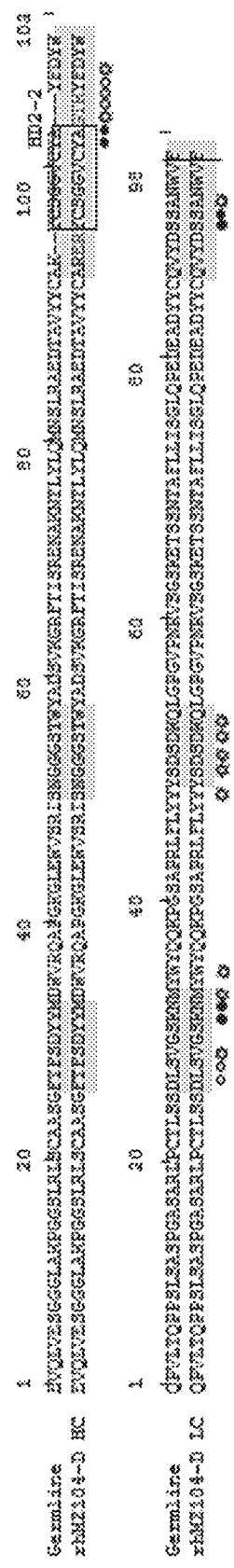
Fig. 7A
Fig. 7B
Fig. 7C
Fig. 7D

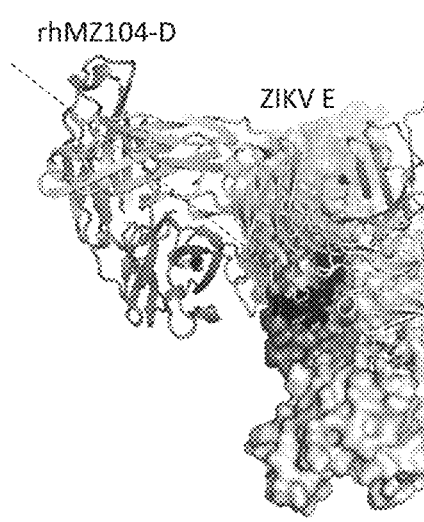
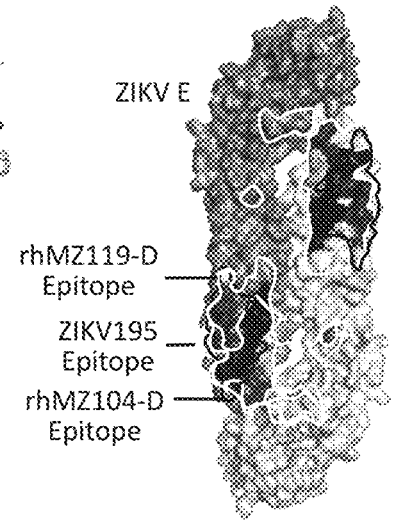
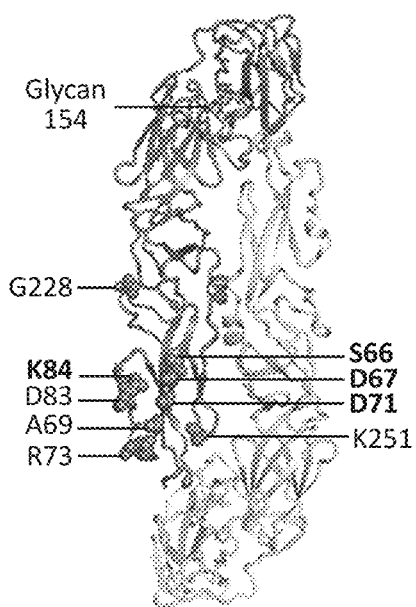
Epitope Shotgun Mutagenesis
| | rhMZ104 | rhMZ119 | rhMZ124 |
|---|---|---|---|
| S66A | ✓ | ✓ | ✓ |
| D67A | ✓ | ✓ | ✓ |
| A69S | | ✓ | |
| D71A | ✓ | ✓ | ✓ |
| R73A | ✓ | | ✓ |
| D83A | ✓ | | ✓ |
| MZ4 | ✓ | ✓ | ✓ |
| G228A | ✓ | ✓ | |
| K251A | | ✓ | |

| mAb ID | ZIKV E binding (BLI) | ZIKV E binding (ELISA) | Whole ZIKV binding (ELISA) | ZIKV Neutralization (MN50) | DENV-2 E binding (BLI) | Whole DENV-2 binding (ELISA) | Flavivirus Neutralization (MN50) |
|---|---|---|---|---|---|---|---|
| rhMZ100-C | ++ | + | +++ | ++ | - | - | - |
| rhMZ101-B | + | - | + | + | - | + | - |
| rhMZ103-A | + | - | ++ | + | - | - | - |
| rhMZ104-D | +++ | +++ | +++ | +++ | - | - | - |
| rhMZ105 | + | + | + | - | - | - | - |
| rhMZ106 | + | - | - | - | - | - | - |
| rhMZ107-B | ++ | - | +++ | ++ | - | - | - |
| rhMZ113 | + | - | + | - | - | - | - |
| rhMZ115 | + | - | + | + | - | - | - |
| rhMZ118 | + | - | ++ | - | + | +++ | - |
| rhMZ119-D | +++ | + | +++ | + | + | ++ | - |
| rhMZ120 | + | - | ++ | - | - | - | - |
| rhMZ121-A | + | - | +++ | ++ | - | - | - |
| rhMZ123-A | + | + | +++ | + | - | - | - |
| rhMZ124-D | +++ | - | +++ | ++ | - | - | - |
| rhMZ125 | + | - | + | - | - | - | - |
| rhMZ129 | + | + | + | - | - | - | - |
| rhMZ130 | + | + | + | - | - | - | - |
| rhMZ132 | + | - | + | - | - | - | - |
| rhMZ133-C | ++ | - | +++ | +++ | - | - | - |
| rhMZ134-B | ++ | - | +++ | +++ | - | - | - |
| rhMZ136 | + | - | + | - | - | - | - |
| rhMZ140 | + | + | + | - | - | - | - |
| 2A10G6 | ++++ | ++++ | +++ | NT | NT | +++ | NT |
| EDE1-C8 | +++ | + | +++ | +++ | ++++ | +++ | All* DENV-1/-2/-3/-4 |
| Z004 | ++++ | NT | +++ | ++++ | - | NT | DENV-1** |

Fig. 14A

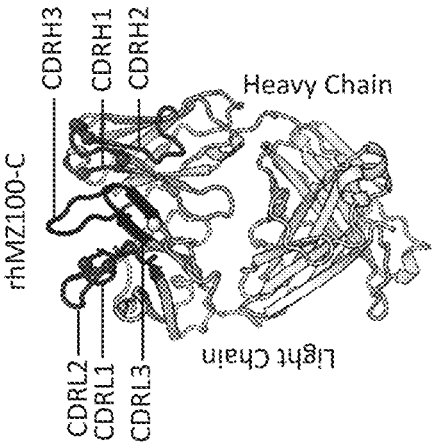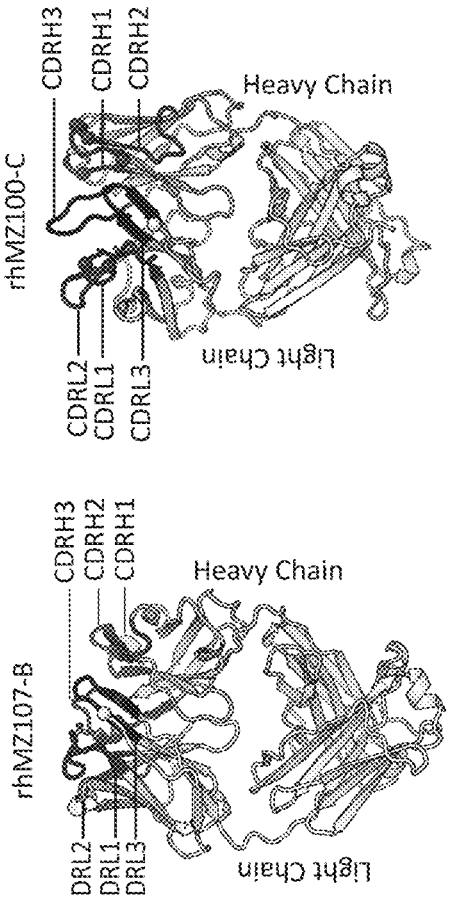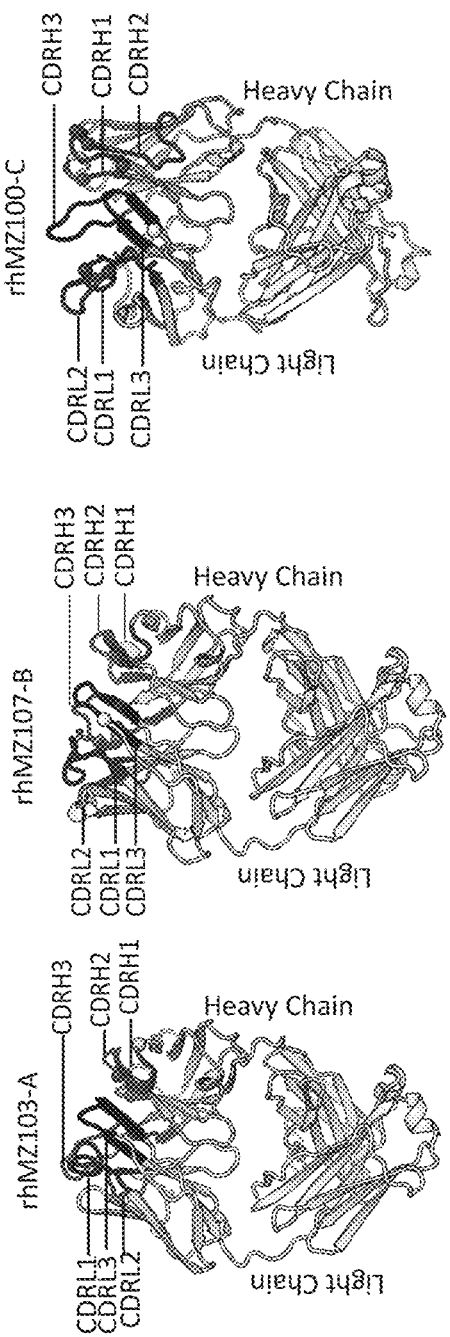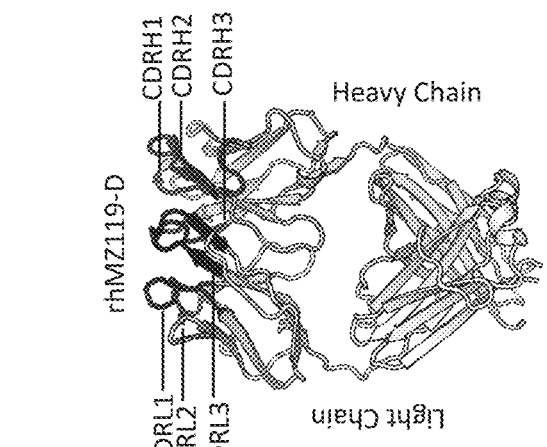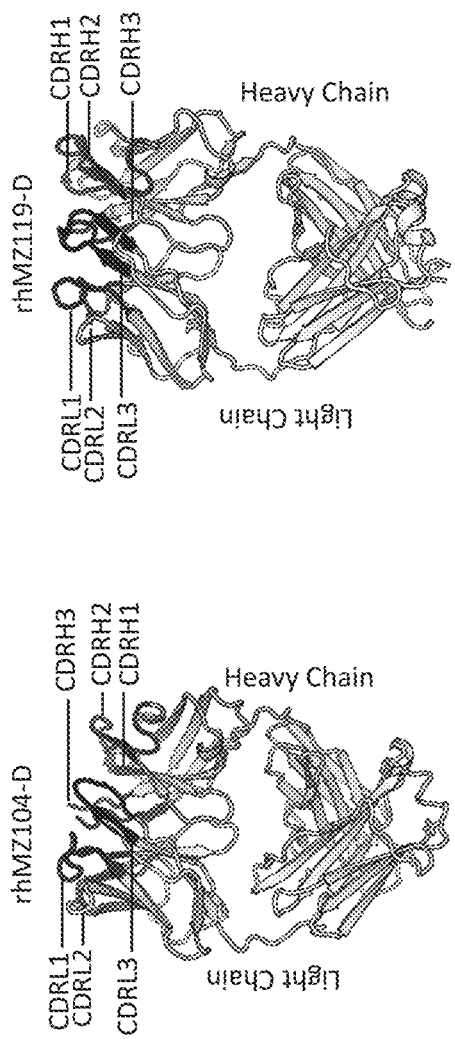

rhMZ107-B ZIKV E complex

Light Chain
Heavy Chain
ZIKV E

*Fig. 18A* rhMZ100-C ZIKV E complex

Light Chain
Heavy Chain
ZIKV E

*Fig. 18B* rhMZ104-D ZIKV E complex

Light Chain
Heavy Chain
ZIKV E

*Fig. 18C*

ZIKV neutralization

*Fig. 19A*

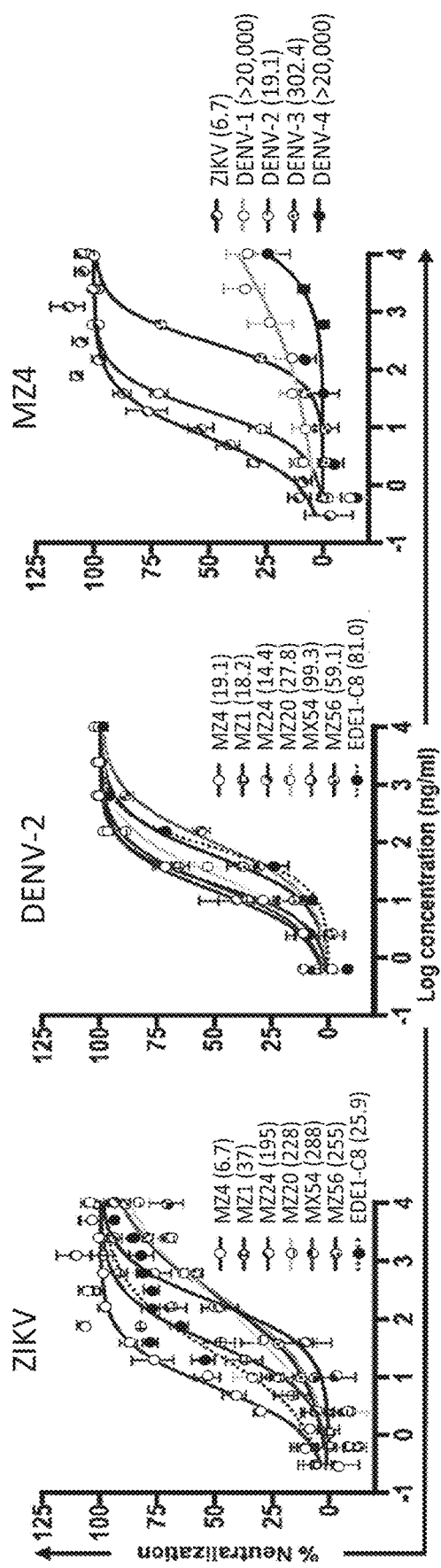

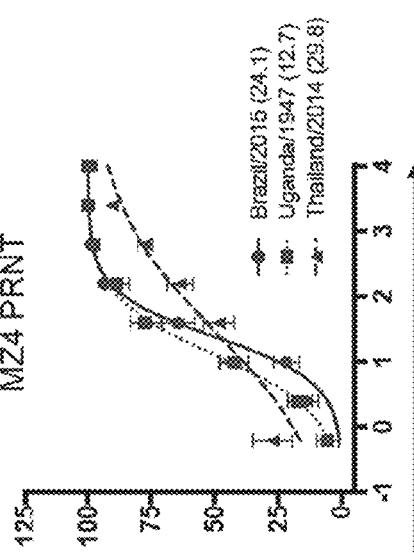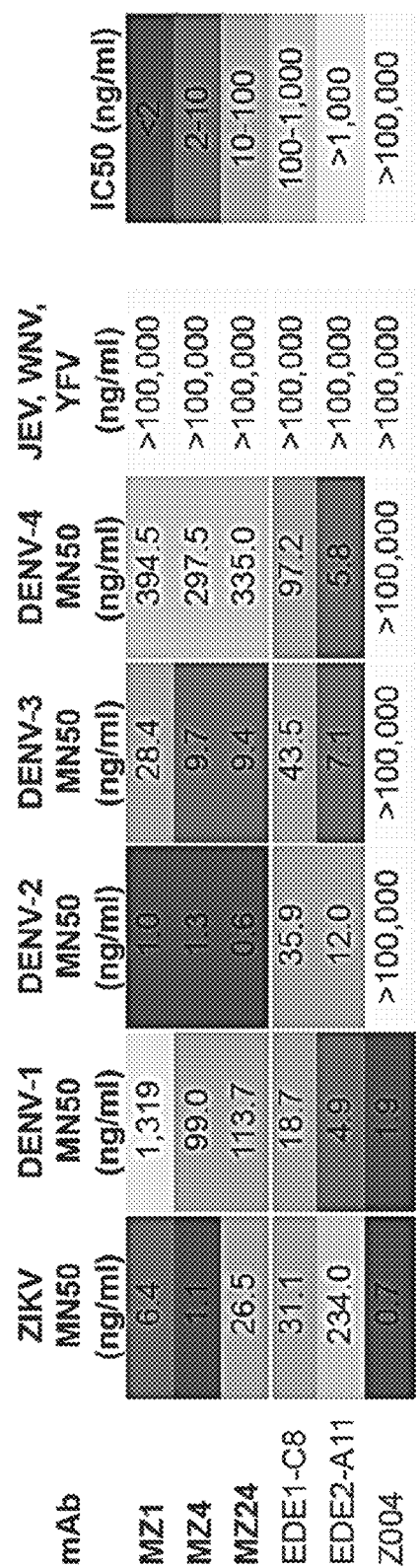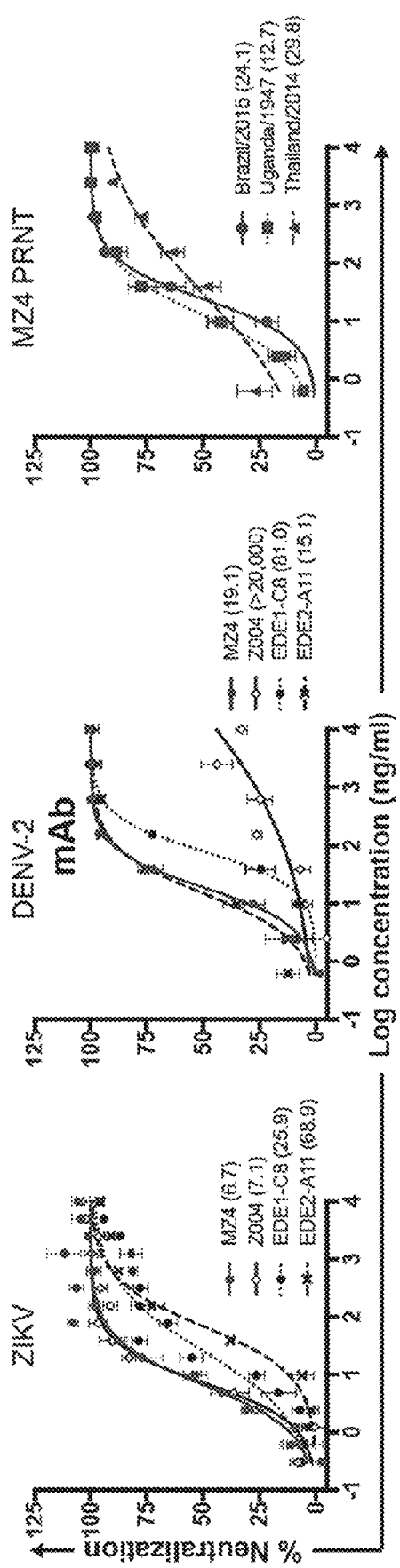
Fig. 20B
Fig. 20C
Fig. 20D
Fig. 20E

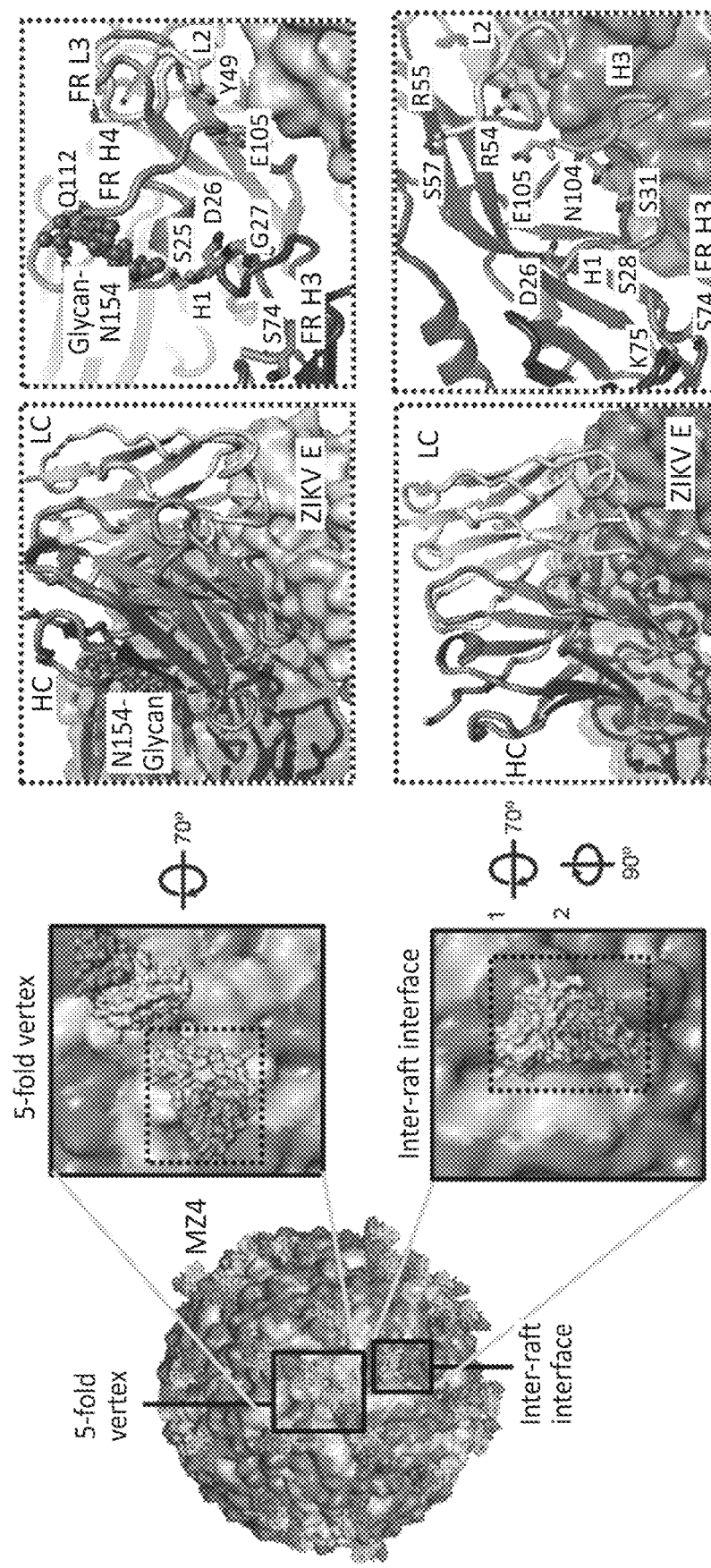
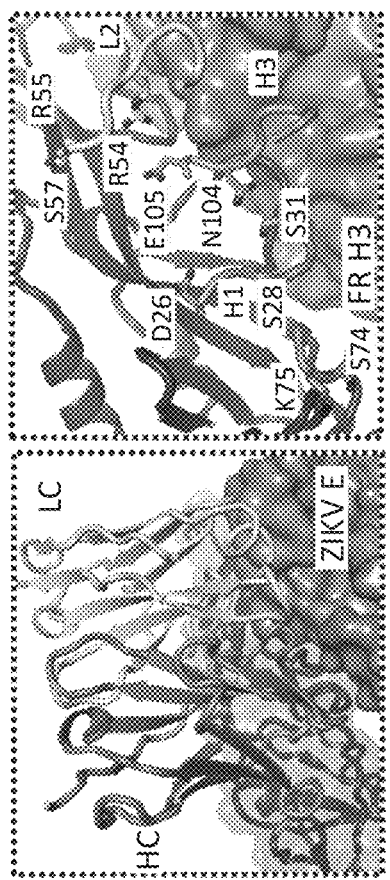
Fig. 22C
Fig. 22D
Fig. 22E

```
         177 182 184 297 299      306 335  338 366 368
          |   |   |   |   |        |   |    |   |   |
ZIKV      E   G   G   K   RLKGVSYS TDGP     TES
DENV1     E   D   G   K   ILKGMSYV TDAP     TDK
DENV2     E   G   G   K   QLKGMSYS DGSP     TEK
DENV3     E   E   G   K   ELKGMSYA EDAP     TKK
DENV4     E   D   G   K   RLKGMSYT AGAP     ENT
          *       *   *   .****:**.  .  :*  ...
```

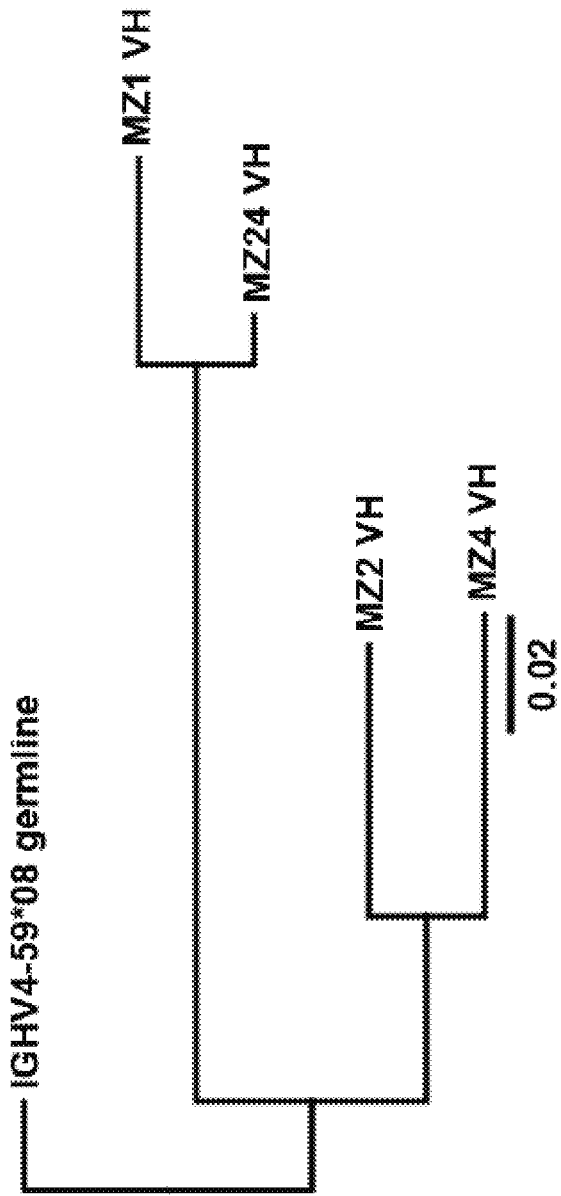

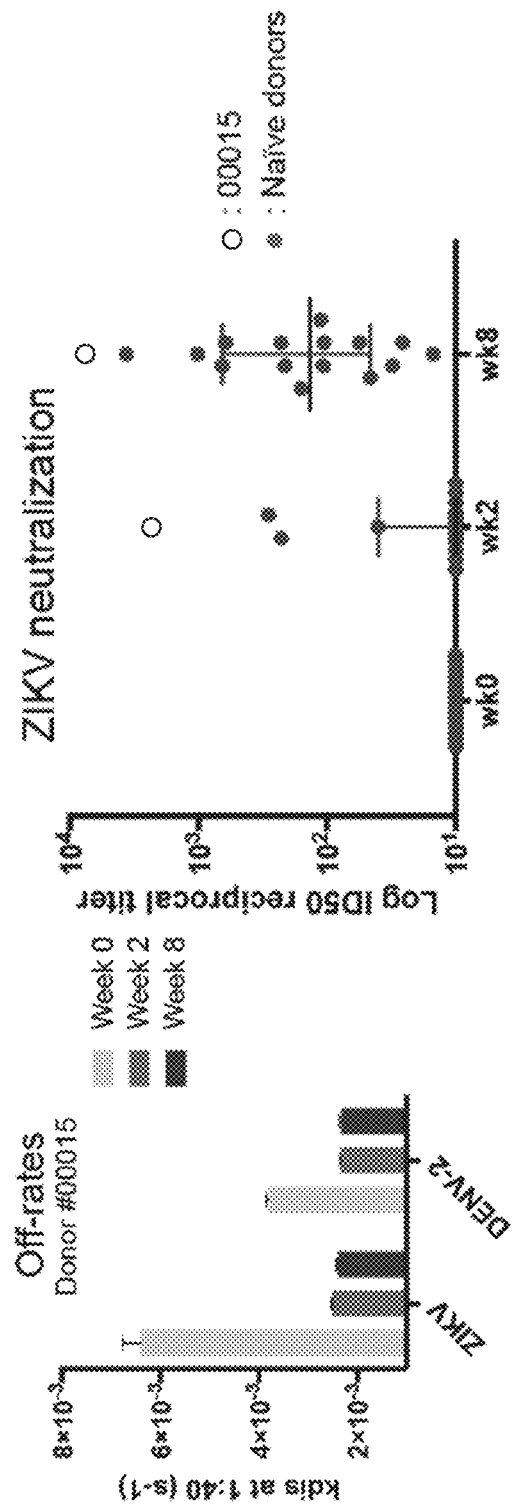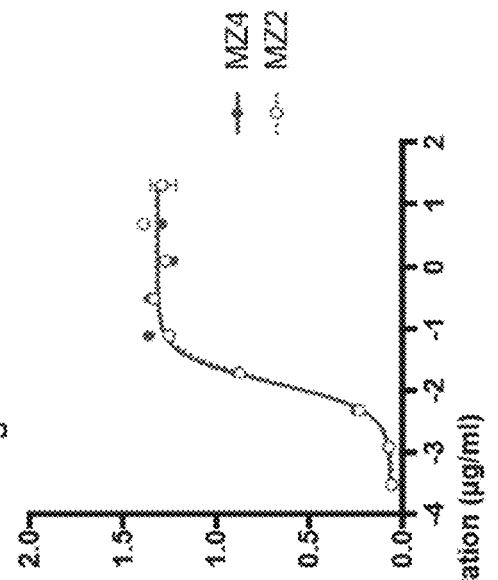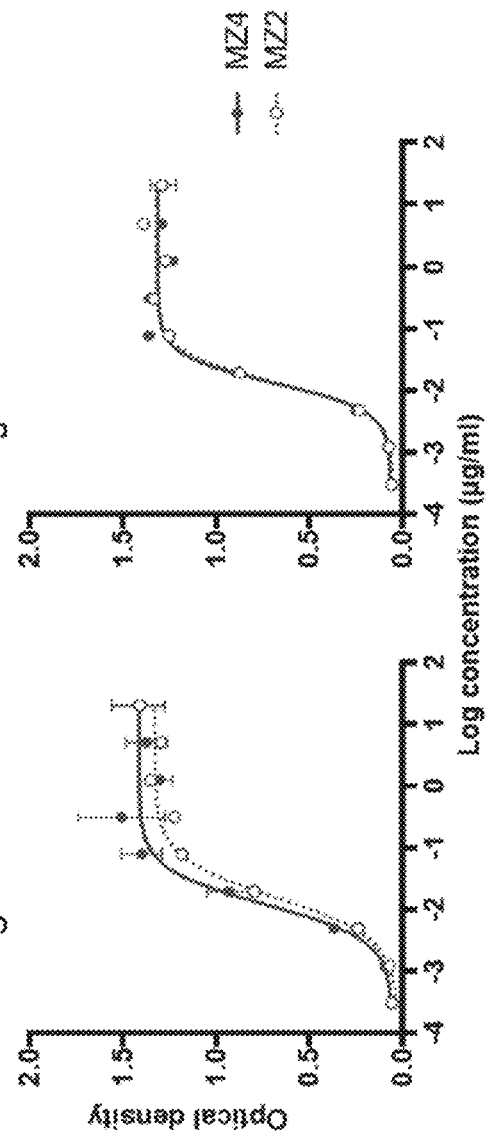
Fig. 27A
Fig. 27B
Fig. 27C

|  | All wt template | All Stop4 template |
|---|---|---|
|  | Tmpl: ───→<br>Library: (multiple strands with arrows) Displayed Protein? + + + + + + + | Tmpl: ●─●─●─→<br>Library: (strands with dots and arrows) Displayed Protein? · + · · + · |
|  | Proteins will be displayed whether or not they are library members, but majority will contain wild-type sequences | Only library members will be displayed (wild-type is part of the mix) |
| Pros: | Most of the variants will be full length → less size-based amplification bias | No overrepresentation of WT in the selections |
| Cons: | WT will be overrepresented in the selection steps, could be harder to fish out variants | Truncated variants (still containing Stop 4 somewhere) may have a growth advantage |

*Fig. 28B*

Type-B
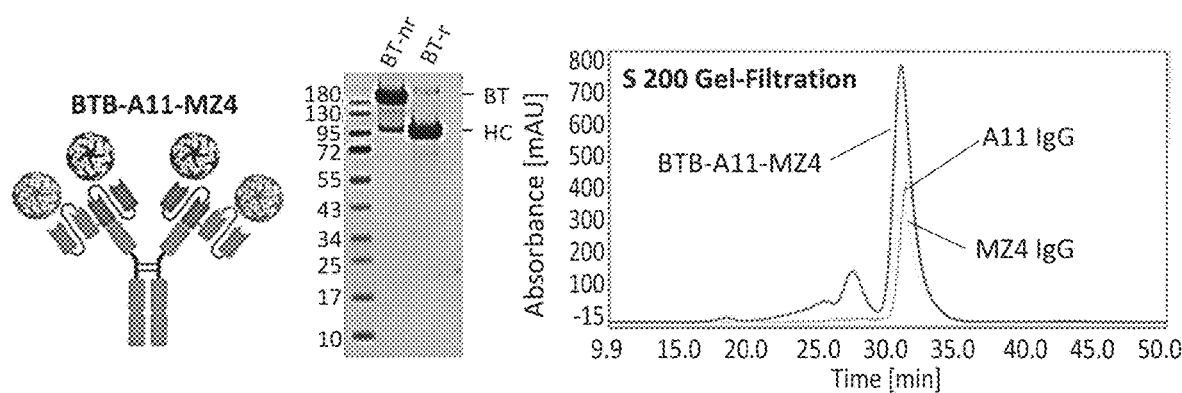
Fig. 35A
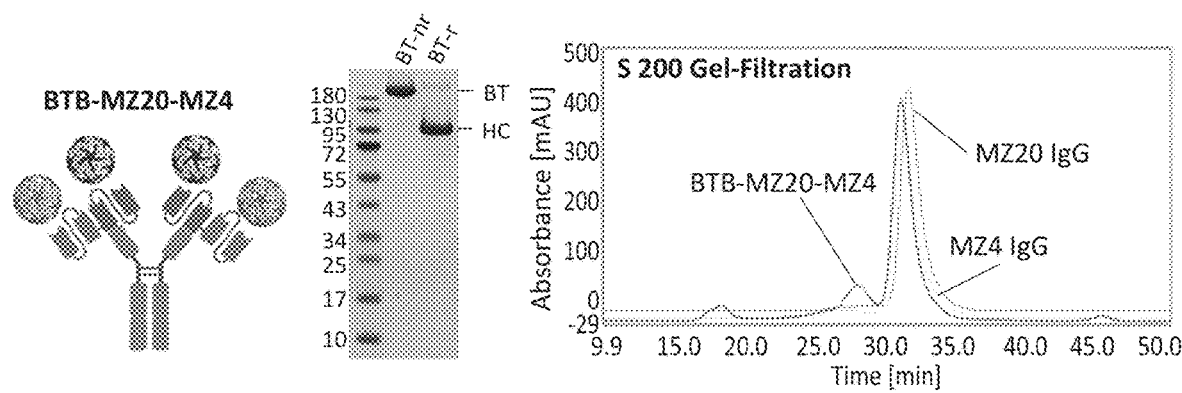
Fig. 35B
Fig. 35C

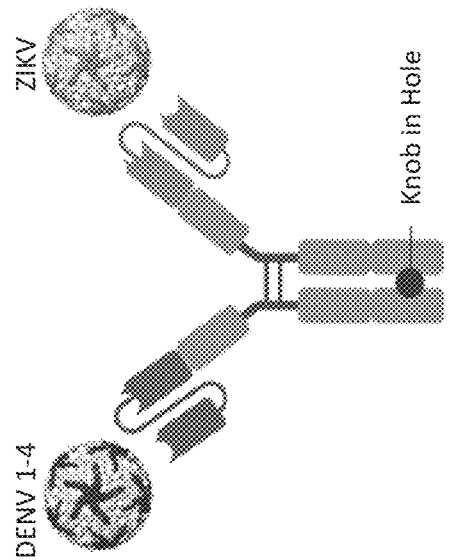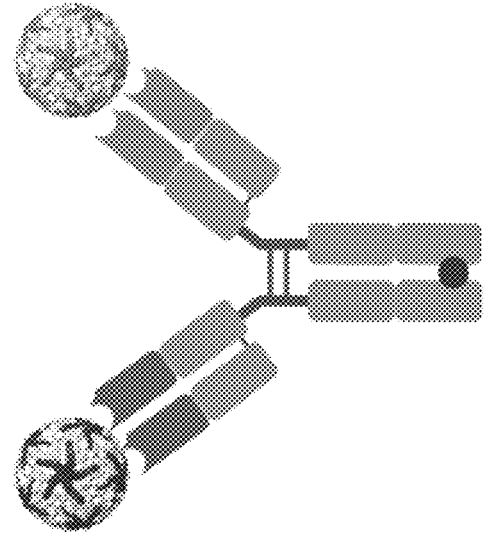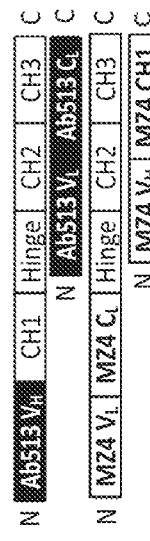
*Fig. 37A*
*Fig. 37B*

SEQUENCE LISTING

<160> NUMBER OF SEQ ID NOS: 236

<210> SEQ ID NO 1

```
<211> LENGTH: 363
<212> TYPE: DNA
<213> ORGANISM: Artificial Sequence
<220> FEATURE:
<223> OTHER INFORMATION: rhMZ100 heavy chain variable domain nucleotide
      sequence

<400> SEQUENCE: 1
gaggtgcagc tggtggagtc tggaggaggc ttggtccagc cggggggtc cctgagactc      60 tcctgtgcag cctctggatt caccttcagt agtgatggca tgagttgggt ccgccaggct    120
ccagggaagg gctggagtg gtctcttac attagtagtg gtggtgctac acatactac      180 gcagactccg tgaagggccg attcaccatc tccagagaca actctaagaa cacgctctcc   240
ctgcaaatga acagcctgag aggtgaggac acggccgtgt actactgtgc aaagacata    300 acggcacctg gaaggaatgg tttggattcc tggggccaag ggtcgtcgt caccgtctcc   360 tca                                                                 363

<210> SEQ ID NO 2
<211> LENGTH: 346
<212> TYPE: DNA
<213> ORGANISM: Artificial Sequence
<220> FEATURE:
<223> OTHER INFORMATION: rhMZ100 light chain variable domain nucleotide
      sequence

<400> SEQUENCE: 2
cagtctgtgc tgactcagcc accctccctg tctgcatccc cggagcatc ggccagactc      60 ccctgcaccc tgagcagtga cctcaatgtt ggtactaaaa acatgtactg gtaccagcag    120
aagccaggga gcgctcccag gttattcctg tactactact ccgactcaga caagcagctg    180
ggacctgggg tccccaatcg agtctctggc tccaaggaga cctcaagtaa cacagcgttt    240
ttgctcatct ctgggctcca gcctgaggac gaggccgatt attactgtca ggtatatgac    300
aatagtgcta gggtattcgg cggagggacc cggctgaccg tcctag                  346

<210> SEQ ID NO 3
<211> LENGTH: 121
<212> TYPE: PRT
<213> ORGANISM: Artificial Sequence
<220> FEATURE:
<223> OTHER INFORMATION: rhMZ100 heavy chain variable domain amino acid
      sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Gly Met Ser Trp Val Arg Gln Ala Pro Gly Lys Gly Leu Glu Trp Val
        35                  40                  45

Ser Tyr Ile Ser Ser Gly Gly Ala Thr Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Gly Glu Asp Thr Ala Val Tyr Tyr Cys
                85                  90                  95

Ala Lys Asp Ile Thr Ala Pro Gly Arg Asn Gly Leu Asp Ser Trp Gly
            100                 105                 110

Gln Gly Val Val Val Thr Val Ser Ser
```

<210> SEQ ID NO 4
<211> LENGTH: 116
<212> TYPE: PRT
<213> ORGANISM: Artificial Sequence
<220> FEATURE:
<223> OTHER INFORMATION: rhMZ100 light chain variable domain amino acid
      sequence

<400> SEQUENCE: 4

```
Gln Ser Val Leu Thr Gln Pro Pro Ser Leu Ser Ala Ser Pro Gly Ala
1               5                   10                  15

Ser Ala Arg Leu Pro Cys Thr Leu Ser Ser Asp Leu Asn Val Gly Thr
            20                  25                  30

Lys Asn Met Tyr Trp Tyr Gln Gln Lys Pro Gly Ser Ala Pro Arg Leu
        35                  40                  45

Phe Leu Tyr Tyr Tyr Ser Asp Ser Asp Lys Gln Leu Gly Pro Gly Val
    50                  55                  60

Pro Asn Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Asp Asn Ser Ala Arg Val Phe Gly Gly Gly Thr Arg Leu
                100                 105                 110

Thr Val Leu Gly
        115
```

<210> SEQ ID NO 5
<211> LENGTH: 8
<212> TYPE: PRT
<213> ORGANISM: Artificial Sequence
<220> FEATURE:
<223> OTHER INFORMATION: rhMZ100 heavy chain CDR1 sequence

<400> SEQUENCE: 5

```
Gly Phe Thr Phe Ser Ser Asp Gly
1               5
```

<210> SEQ ID NO 6
<211> LENGTH: 8
<212> TYPE: PRT
<213> ORGANISM: Artificial Sequence
<220> FEATURE:
<223> OTHER INFORMATION: rhMZ100 heavy chain CDR2 sequence

<400> SEQUENCE: 6

```
Ile Ser Ser Gly Gly Ala Thr Thr
1               5
```

<210> SEQ ID NO 7
<211> LENGTH: 16
<212> TYPE: PRT
<213> ORGANISM: Artificial Sequence
<220> FEATURE:
<223> OTHER INFORMATION: rhMZ100 heavy chain CDR3 sequence

<400> SEQUENCE: 7

```
Cys Ala Lys Asp Ile Thr Ala Pro Gly Arg Asn Gly Leu Asp Ser Trp
1               5                   10                  15
```

<210> SEQ ID NO 8
<211> LENGTH: 9

```
<212> TYPE: PRT
<213> ORGANISM: Artificial Sequence
<220> FEATURE:
<223> OTHER INFORMATION: rhMZ100 light chain CDR1 sequence

<400> SEQUENCE: 8

Ser Asp Leu Asn Val Gly Thr Lys Asn
1               5

<210> SEQ ID NO 9
<211> LENGTH: 7
<212> TYPE: PRT
<213> ORGANISM: Artificial Sequence
<220> FEATURE:
<223> OTHER INFORMATION: rhMZ100 light chain CDR2 sequence

<400> SEQUENCE: 9

Tyr Tyr Ser Asp Ser Asp Lys
1               5

<210> SEQ ID NO 10
<211> LENGTH: 11
<212> TYPE: PRT
<213> ORGANISM: Artificial Sequence
<220> FEATURE:
<223> OTHER INFORMATION: rhMZ100 light chain CDR3 sequence

<400> SEQUENCE: 10

Cys Gln Val Tyr Asp Asn Ser Ala Arg Val Phe
1               5                   10

<210> SEQ ID NO 11
<211> LENGTH: 363
<212> TYPE: DNA
<213> ORGANISM: Artificial Sequence
<220> FEATURE:
<223> OTHER INFORMATION: rhMZ101 heavy chain variable domain nucleotide
      sequence

<400> SEQUENCE: 11
gaggtgcagc tggtggagtc tgggggcggc ttggcaaagc ctgggggtc cctgagactc      60 tcctgtgcag cctctggatt cagcttcagt gactactaca tgtactgggt ccgccaggct    120
ccagggaagg gctgagtg gtctcaggt attagttata ctggtggtag cacatactat       180
gcagactccg tgaagggcag attcaccatc tccagagaga cgccaagaa cacactgtat     240 cttcaaatgg acagcctgag agctgaggac acggctgtct attactgtgc gagagttcta    300
tatagtggta gttattacta ctttgactac tggggccagg gagtcctggt caccgtctcc    360
tca                                                                  363

<210> SEQ ID NO 12
<211> LENGTH: 349
<212> TYPE: DNA
<213> ORGANISM: Artificial Sequence
<220> FEATURE:
<223> OTHER INFORMATION: rhMZ101 light chain variable domain nucleotide
      sequence

<400> SEQUENCE: 12
cagtctgtgc tgactcagcc accctccctg tctgcatccc cgggagcatc ggccagactc     60
ccctgcaccc tgagcagtga cctcagtgtt ggtagtaaaa acatgtactg gtaccagcag    120
aagccaggga gcgctcccag gttattcctg tactactact ccgactcaga caagcagctg    180
ggacctgggg tccccaatcg agtctctggc tccaaggaga cctcaagtaa cacagcgttt    240
```

```
ttggtcatct ctgggctcca gcctgaggac gaggccgatt attactgtca ggtgtatgac    300
agtagtgcta atattgtgtt cggaagtggc accaagttga ccgtcctcg                349
```

<210> SEQ ID NO 13
<211> LENGTH: 121
<212> TYPE: PRT
<213> ORGANISM: Artificial Sequence
<220> FEATURE:
<223> OTHER INFORMATION: rhMZ101 heavy chain variable domain amino acid
      sequence

<400> SEQUENCE: 13

Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Ser Phe Ser Asp Tyr
            20                  25                  30

Tyr Met Tyr Trp Val Arg Gln Ala Pro Gly Lys Gly Leu Glu Trp Val
        35                  40                  45

Ser Gly Ile Ser Tyr Thr Gly Gly Ser Thr Tyr Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Val Leu Tyr Ser Gly Ser Tyr Tyr Tyr Phe Asp Tyr Trp Gly
            100                 105                 110

Gln Gly Val Leu Val Thr Val Ser Ser
        115                 120

<210> SEQ ID NO 14
<211> LENGTH: 117
<212> TYPE: PRT
<213> ORGANISM: Artificial Sequence
<220> FEATURE:
<223> OTHER INFORMATION: rhMZ101 light chain variable domain amino acid
      sequence

<400> SEQUENCE: 14

Gln Ser Val Leu Thr Gln Pro Pro Ser Leu Ser Ala Ser Pro Gly Ala
1               5                   10                  15

Ser Ala Arg Leu Pro Cys Thr Leu Ser Ser Asp Leu Ser Val Gly Ser
            20                  25                  30

Lys Asn Met Tyr Trp Tyr Gln Gln Lys Pro Gly Ser Ala Pro Arg Leu
        35                  40                  45

Phe Leu Tyr Tyr Tyr Ser Asp Ser Asp Lys Gln Leu Gly Pro Gly Val
    50                  55                  60

Pro Asn Arg Val Ser Gly Ser Lys Glu Thr Ser Ser Asn Thr Ala Phe
65                  70                  75                  80

Leu Val Ile Ser Gly Leu Gln Pro Glu Asp Glu Ala Asp Tyr Tyr Cys
                85                  90                  95

Gln Val Tyr Asp Ser Ser Ala Asn Ile Val Phe Gly Ser Gly Thr Lys
            100                 105                 110

Leu Thr Val Leu Gly
        115

<210> SEQ ID NO 15
<211> LENGTH: 8
<212> TYPE: PRT

```
<213> ORGANISM: Artificial Sequence
<220> FEATURE:
<223> OTHER INFORMATION: rhMZ101 heavy chain CDR1 sequence

<400> SEQUENCE: 15

Gly Phe Ser Phe Ser Asp Tyr Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: rhMZ101 heavy chain CDR2 sequence

<400> SEQUENCE: 16

Ile Ser Tyr Thr Gly Gly Ser Thr
1               5

<210> SEQ ID NO 17
<211> LENGTH: 16
<212> TYPE: PRT
<213> ORGANISM: Artificial Sequence
<220> FEATURE:
<223> OTHER INFORMATION: rhMZ101 heavy chain CDR3 sequence

<400> SEQUENCE: 17

Cys Ala Arg Val Leu Tyr Ser Gly Ser Tyr Tyr Tyr Phe Asp Tyr Trp
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: rhMZ101 light chain CDR1 sequence

<400> SEQUENCE: 18

Ser Asp Leu Ser Val Gly Ser Lys Asn
1               5

<210> SEQ ID NO 19
<211> LENGTH: 7
<212> TYPE: PRT
<213> ORGANISM: Artificial Sequence
<220> FEATURE:
<223> OTHER INFORMATION: rhMZ101 light chain CDR2 sequence

<400> SEQUENCE: 19

Tyr Tyr Ser Asp Ser Asp Lys
1               5

<210> SEQ ID NO 20
<211> LENGTH: 12
<212> TYPE: PRT
<213> ORGANISM: Artificial Sequence
<220> FEATURE:
<223> OTHER INFORMATION: rhMZ101 light chain CDR3 sequence

<400> SEQUENCE: 20

Cys Gln Val Tyr Asp Ser Ser Ala Asn Ile Val Phe
1               5                   10

<210> SEQ ID NO 21
<211> LENGTH: 387
<212> TYPE: DNA
<213> ORGANISM: Artificial Sequence
```

<220> FEATURE:
<223> OTHER INFORMATION: rhMZ103 heavy chain variable domain nucleotide
sequence

<400> SEQUENCE: 21

| | | | | | |
|---|---|---|---|---|---|
| caggtgcagc | tgcaggagtc | gggcccagga | ctggtgaagc | cttcagagac | cctgtccctc | 60 |
| acctgcgctg | tttctggagg | ctctatcagc | ggtggttatg | actggagctg | gatccgccag | 120 |
| cccccaggga | aggggctgga | gtggattggg | tatatctatg | gtagtagtgg | gagcaccaac | 180 |
| tacaacccgt | ccctcaagaa | tcgagtcacc | atttcaaaag | acacgtccaa | gaaccagttc | 240 |
| tccctgaagc | tgagctctgt | gaccgccgcg | gacacggccg | tgtattactg | tgcgagaccc | 300 |
| gcgtattacg | aggatgatta | cggttactat | acaccacccc | ccatctttga | ctactggggc | 360 |
| cagggagtcc | tggtcaccgt | ctcctca | | | | 387 |

<210> SEQ ID NO 22
<211> LENGTH: 333
<212> TYPE: DNA
<213> ORGANISM: Artificial Sequence
<220> FEATURE:
<223> OTHER INFORMATION: rhMZ103 light chain variable domain nucleotide
sequence

<400> SEQUENCE: 22

| | | | | | |
|---|---|---|---|---|---|
| cagtctgtgc | tgactcagcc | accctcagcg | tctggggctc | ccgggcagag | tgtcaccatc | 60 |
| tcttgctctg | gaagcagctc | caacattgga | agtaattatg | tatactggta | ccagcagctc | 120 |
| ccaggaacgg | cccccaaact | cctcatctat | tatagtaatc | agcgaccctc | aggggtccct | 180 |
| gaccgattct | ctggctctaa | gtctggcacc | tcagcctccc | tggccatcac | tggtctccga | 240 |
| tctgaggatg | aggctgatta | ttactgtgca | gcatgggata | cagcctgag | cagtgtgtta | 300 |
| ttcggaggag | ggacccggct | gaccgtccta | ggt | | | 333 |

<210> SEQ ID NO 23
<211> LENGTH: 129
<212> TYPE: PRT
<213> ORGANISM: Artificial Sequence
<220> FEATURE:
<223> OTHER INFORMATION: rhMZ103 heavy chain variable domain amino acid
sequence

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Asp Trp Ser Trp Ile Arg Gln Pro Pro Gly Lys Gly Leu Glu Trp
        35                  40                  45

Ile Gly Tyr Ile Tyr Gly Ser Ser Gly Ser Thr Asn Tyr Asn Pro Ser
    50                  55                  60

Leu Lys Asn Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Pro Ala Tyr Tyr Glu Asp Asp Tyr Gly Tyr Tyr Tyr Thr
            100                 105                 110

Thr Pro Ile Phe Asp Tyr Trp Gly Gln Gly Val Leu Val Thr Val Ser
        115                 120                 125

Ser

<210> SEQ ID NO 24
<211> LENGTH: 111
<212> TYPE: PRT
<213> ORGANISM: Artificial Sequence
<220> FEATURE:
<223> OTHER INFORMATION: rhMZ103 light chain variable domain amino acid
      sequence

<400> SEQUENCE: 24

Gln Ser Val Leu Thr Gln Pro Pro Ser Ala Ser Gly Ala Pro Gly Gln
1               5                   10                  15

Ser Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Tyr Ser Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Arg
65                  70                  75                  80

Ser Glu Asp Glu Ala Asp Tyr Tyr Cys Ala Ala Trp Asp Asn Ser Leu
                85                  90                  95

Ser Ser Val Leu Phe Gly Gly Gly Thr Arg Leu Thr Val Leu Gly
            100                 105                 110

<210> SEQ ID NO 25
<211> LENGTH: 8
<212> TYPE: PRT
<213> ORGANISM: Artificial Sequence
<220> FEATURE:
<223> OTHER INFORMATION: rhMZ103 heavy chain CDR1 sequence

<400> SEQUENCE: 25

Gly Ser Ile Ser Gly Gly Tyr Asp
1               5

<210> SEQ ID NO 26
<211> LENGTH: 8
<212> TYPE: PRT
<213> ORGANISM: Artificial Sequence
<220> FEATURE:
<223> OTHER INFORMATION: rhMZ103 heavy chain CDR2 sequence

<400> SEQUENCE: 26

Ile Tyr Gly Ser Ser Gly Ser Thr
1               5

<210> SEQ ID NO 27
<211> LENGTH: 23
<212> TYPE: PRT
<213> ORGANISM: Artificial Sequence
<220> FEATURE:
<223> OTHER INFORMATION: rhMZ103 heavy chain CDR3 sequence

<400> SEQUENCE: 27

Cys Ala Arg Pro Ala Tyr Tyr Glu Asp Asp Tyr Gly Tyr Tyr Tyr Thr
1               5                   10                  15

Thr Pro Ile Phe Asp Tyr Trp
            20

<210> SEQ ID NO 28
<211> LENGTH: 8
<212> TYPE: PRT

<210> SEQ ID NO 28
<211> LENGTH: 7
<212> TYPE: PRT
<213> ORGANISM: Artificial Sequence
<220> FEATURE:
<223> OTHER INFORMATION: rhMZ103 light chain CDR1 sequence

<400> SEQUENCE: 28

Ser Ser Asn Ile Gly Ser Asn Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: rhMZ103 light chain CDR2 sequence

<400> SEQUENCE: 29

Tyr Ser Asn
1

<210> SEQ ID NO 30
<211> LENGTH: 13
<212> TYPE: PRT
<213> ORGANISM: Artificial Sequence
<220> FEATURE:
<223> OTHER INFORMATION: rhMZ103 light chain CDR3 sequence

<400> SEQUENCE: 30

Cys Ala Ala Trp Asp Asn Ser Leu Ser Ser Val Leu Phe
1               5                   10

<210> SEQ ID NO 31
<211> LENGTH: 381
<212> TYPE: DNA
<213> ORGANISM: Artificial Sequence
<220> FEATURE:
<223> OTHER INFORMATION: rhMZ104 heavy chain variable domain nucleotide
      sequence

<400> SEQUENCE: 31
gaggtgcagc tggtggagtc tgggggcggc ttggcaaagc ctggggggtc cctgagactc      60
tcctgcgcag cctccggatt caccttcagt gactactaca tggactgggt ccgccaggct     120
ccagggaagg ggctggagtg ggtctcacgt attagtaatg gtggtggtag cacatggtac     180
gcagactccg tgaagggcag attcaccatc tccagagaa acgccaagaa cacactgtat     240
cttcaaatga acagcctgag agctgaggac acggctgtct attactgtgc gagagagaga     300
tattgtagtg gtggtgtctg ctacgccggg acaaaatact ttgactactg gggccaggga     360
gtcctggtca ccgtctcctc a                                               381

<210> SEQ ID NO 32
<211> LENGTH: 351
<212> TYPE: DNA
<213> ORGANISM: Artificial Sequence
<220> FEATURE:
<223> OTHER INFORMATION: rhMZ104 light chain variable domain nucleotide
      sequence

<400> SEQUENCE: 32
cagcctgtgc tgactcagcc accctccctg tctgcatccc cgggagcatc ggccagactc      60
ccctgcaccc tgagcagtga cctcagtgtt ggtagtaaaa acatgtactg gtaccagcag     120
aagccaggga gcgctcccag gttattcctg tactactact ccgactcaga caagcagctg     180
ggacctgggg tccccaatcg agtctctggc tccaaggaga cctcaagtaa cacagcgttt     240

```
ttgctcatct ctgggctcca gcctgaggac gaggccgatt attactgtca ggtgtatgac      300
agtagtgcta ttgggtatt cggcggaggg acccggctga ccgtcctagg t                351
```

<210> SEQ ID NO 33
<211> LENGTH: 127
<212> TYPE: PRT
<213> ORGANISM: Artificial Sequence
<220> FEATURE:
<223> OTHER INFORMATION: rhMZ104 heavy chain variable domain amino acid
      sequence

<400> SEQUENCE: 33

Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Glu Trp Val
        35                  40                  45

Ser Arg Ile Ser Asn Gly Gly Ser Thr Trp Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Cys Ser Gly Gly Val Cys Tyr Ala Gly Thr Lys
            100                 105                 110

Tyr Phe Asp Tyr Trp Gly Gln Gly Val Leu Val Thr Val Ser Ser
        115                 120                 125

<210> SEQ ID NO 34
<211> LENGTH: 117
<212> TYPE: PRT
<213> ORGANISM: Artificial Sequence
<220> FEATURE:
<223> OTHER INFORMATION: rhMZ104 light chain variable domain amino acid
      sequence

<400> SEQUENCE: 34

Gln Pro Val Leu Thr Gln Pro Pro Ser Leu Ser Ala Ser Pro Gly Ala
1               5                   10                  15

Ser Ala Arg Leu Pro Cys Thr Leu Ser Ser Asp Leu Ser Val Gly Ser
            20                  25                  30

Lys Asn Met Tyr Trp Tyr Gln Gln Lys Pro Gly Ser Ala Pro Arg Leu
        35                  40                  45

Phe Leu Tyr Tyr Tyr Ser Asp Ser Asp Lys Gln Leu Gly Pro Gly Val
    50                  55                  60

Pro Asn Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Asp Ser Ser Ala Asn Trp Val Phe Gly Gly Gly Thr Arg
            100                 105                 110

Leu Thr Val Leu Gly
        115

<210> SEQ ID NO 35
<211> LENGTH: 8
<212> TYPE: PRT
<213> ORGANISM: Artificial Sequence

```
<220> FEATURE:
<223> OTHER INFORMATION: rhMZ104 heavy chain CDR1 sequence

<400> SEQUENCE: 35

Gly Phe Thr Phe Ser Asp Tyr Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: rhMZ104 heavy chain CDR2 sequence

<400> SEQUENCE: 36

Ile Ser Asn Gly Gly Gly Ser Thr
1               5

<210> SEQ ID NO 37
<211> LENGTH: 22
<212> TYPE: PRT
<213> ORGANISM: Artificial Sequence
<220> FEATURE:
<223> OTHER INFORMATION: rhMZ104 heavy chain CDR3 sequence

<400> SEQUENCE: 37

Cys Ala Arg Glu Arg Tyr Cys Ser Gly Gly Val Cys Tyr Ala Gly Thr
1               5                   10                  15

Lys Tyr Phe Asp Tyr Trp
            20

<210> SEQ ID NO 38
<211> LENGTH: 9
<212> TYPE: PRT
<213> ORGANISM: Artificial Sequence
<220> FEATURE:
<223> OTHER INFORMATION: rhMZ104 light chain CDR1 sequence

<400> SEQUENCE: 38

Ser Asp Leu Ser Val Gly Ser Lys Asn
1               5

<210> SEQ ID NO 39
<211> LENGTH: 7
<212> TYPE: PRT
<213> ORGANISM: Artificial Sequence
<220> FEATURE:
<223> OTHER INFORMATION: rhMZ104 light chain CDR2 sequence

<400> SEQUENCE: 39

Tyr Tyr Ser Asp Ser Asp Lys
1               5

<210> SEQ ID NO 40
<211> LENGTH: 12
<212> TYPE: PRT
<213> ORGANISM: Artificial Sequence
<220> FEATURE:
<223> OTHER INFORMATION: rhMZ104 light chain CDR3 sequence

<400> SEQUENCE: 40

Cys Gln Val Tyr Asp Ser Ser Ala Asn Trp Val Phe
1               5                   10

<210> SEQ ID NO 41
<211> LENGTH: 375
```

<212> TYPE: DNA
<213> ORGANISM: Artificial Sequence
<220> FEATURE:
<223> OTHER INFORMATION: rhMZ107 heavy chain variable domain nucleotide
      sequence

<400> SEQUENCE: 41

```
caggtgcagc tgcaggagtc gggcccagga ctggtgaagc cttcggagac cctgtccctc    60
acctgcgctg tctctggtta ctccatcagc agtggttact actggggctg gatccgtcag   120
cccccaggga agggactgga gtatattggg tatatcagtg gtagtagtgg gagcacctac   180
tacaacccct ccctcaagag tcgagtcacc atttcaaaag acacgtccaa gaaccagttc   240
tccctgaagc tgagctctgt gaccgccgcg gacacggccg tgtattactg tgcgagacga   300
gatcgtgtgg gcagctaccc ttattactac ggtttggatt cctggggcca agggtcctg    360 gtcaccgtct cctca                                                    375
```

<210> SEQ ID NO 42
<211> LENGTH: 351
<212> TYPE: DNA
<213> ORGANISM: Artificial Sequence
<220> FEATURE:
<223> OTHER INFORMATION: rhMZ107 light chain variable domain nucleotide
      sequence

<400> SEQUENCE: 42

```
cagtctgtgc tgactcagcc accctccctg tctgcatccc cgggagcatc ggccagactc    60
ccctgcaccc tgagcagtga cctcagtgtt ggtagtaaaa acatgtactg gtaccagcag   120
aagccaggga gcgctcccag gttattcctg tactactact ccgactcaga caagcagctg   180
ggacctgggg tccccaatcg agtctctggc tccaaggaga cctcaagtaa cacagcgttt   240
ttgctcatct ctgggctcca gcctgaggac gaggccgatt attactgtca ggtgtatgac   300
ggtagtgcta atgatgtgtt cggaagtggc accaagttga ccgtcctcgg t            351
```

<210> SEQ ID NO 43
<211> LENGTH: 125
<212> TYPE: PRT
<213> ORGANISM: Artificial Sequence
<220> FEATURE:
<223> OTHER INFORMATION: rhMZ107 heavy chain variable domain amino acid
      sequence

<400> SEQUENCE: 43

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Tyr
        35                  40                  45

Ile Gly Tyr Ile Ser Gly Ser Ser Gly Ser Thr Tyr Tyr Asn Pro Ser
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Asp Arg Val Gly Ser Tyr Pro Tyr Tyr Gly Leu
            100                 105                 110

Asp Ser Trp Gly Gln Gly Val Leu Val Thr Val Ser Ser
        115                 120                 125
```

```
<210> SEQ ID NO 44
<211> LENGTH: 117
<212> TYPE: PRT
<213> ORGANISM: Artificial Sequence
<220> FEATURE:
<223> OTHER INFORMATION: rhMZ107 light chain variable domain amino acid
      sequence

<400> SEQUENCE: 44

Gln Ser Val Leu Thr Gln Pro Pro Ser Leu Ser Ala Ser Pro Gly Ala
1               5                   10                  15

Ser Ala Arg Leu Pro Cys Thr Leu Ser Ser Asp Leu Ser Val Gly Ser
            20                  25                  30

Lys Asn Met Tyr Trp Tyr Gln Gln Lys Pro Gly Ser Ala Pro Arg Leu
        35                  40                  45

Phe Leu Tyr Tyr Tyr Ser Asp Ser Asp Lys Gln Leu Gly Pro Gly Val
    50                  55                  60

Pro Asn Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Asp Gly Ser Ala Asn Asp Val Phe Gly Ser Gly Thr Lys
            100                 105                 110

Leu Thr Val Leu Gly
        115

<210> SEQ ID NO 45
<211> LENGTH: 8
<212> TYPE: PRT
<213> ORGANISM: Artificial Sequence
<220> FEATURE:
<223> OTHER INFORMATION: rhMZ107 heavy chain CDR1 sequence

<400> SEQUENCE: 45

Tyr Ser Ile Ser Ser Gly Tyr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: rhMZ107 heavy chain CDR2 sequence

<400> SEQUENCE: 46

Ile Ser Gly Ser Ser Gly Ser Thr
1               5

<210> SEQ ID NO 47
<211> LENGTH: 19
<212> TYPE: PRT
<213> ORGANISM: Artificial Sequence
<220> FEATURE:
<223> OTHER INFORMATION: rhMZ107 heavy chain CDR3 sequence

<400> SEQUENCE: 47

Cys Ala Arg Arg Asp Arg Val Gly Ser Tyr Pro Tyr Tyr Tyr Gly Leu
1               5                   10                  15

Asp Ser Trp

<210> SEQ ID NO 48
```

```
<211> LENGTH: 9
<212> TYPE: PRT
<213> ORGANISM: Artificial Sequence
<220> FEATURE:
<223> OTHER INFORMATION: rhMZ107 light chain CDR1 sequence

<400> SEQUENCE: 48

Ser Asp Leu Ser Val Gly Ser Lys Asn
1               5

<210> SEQ ID NO 49
<211> LENGTH: 7
<212> TYPE: PRT
<213> ORGANISM: Artificial Sequence
<220> FEATURE:
<223> OTHER INFORMATION: rhMZ107 light chain CDR2 sequence

<400> SEQUENCE: 49

Tyr Tyr Ser Asp Ser Asp Lys
1               5

<210> SEQ ID NO 50
<211> LENGTH: 12
<212> TYPE: PRT
<213> ORGANISM: Artificial Sequence
<220> FEATURE:
<223> OTHER INFORMATION: rhMZ107 light chain CDR3 sequence

<400> SEQUENCE: 50

Cys Gln Val Tyr Asp Gly Ser Ala Asn Asp Val Phe
1               5                   10

<210> SEQ ID NO 51
<211> LENGTH: 357
<212> TYPE: DNA
<213> ORGANISM: Artificial Sequence
<220> FEATURE:
<223> OTHER INFORMATION: rhMZ119 heavy chain variable domain nucleotide
      sequence

<400> SEQUENCE: 51
gaggtgcagc tggtgcagtc tggagcagag gtgaaaaggc ccggggagtc tctgaagatc    60
tcctgtaaga cttctggata cagctttacc agctactgga tcagctgggt gcgccagatg   120
cccggaaaag gcctggagtg gatgggggcg attgatccta gtgattctga taccagatac   180
agcccgtcct ccaaggcca ggtcaccatc tcagccgaca gtccatcag caccgcctac    240 ctgcagtgga gcagcctgaa ggcctcggac tccgccacgt attactgtgc gaaagagggg   300
atagcggcac ggtcattgga tgtctggggc cggggagttc tggtcaccgt ctcctca      357

<210> SEQ ID NO 52
<211> LENGTH: 330
<212> TYPE: DNA
<213> ORGANISM: Artificial Sequence
<220> FEATURE:
<223> OTHER INFORMATION: rhMZ119 light chain variable domain nucleotide
      sequence

<400> SEQUENCE: 52
tcctatgagc tgacacagcc accctcggtg tcagtgtccc caggacagac ggccaggatc    60
acctgctctg gagatgcatt gccaaaaaaa tatgcttatt ggttccagca gaagccaggc   120
cagtcccctg tgctgatcat ctatgaggac agcaaacggc cctctgggat ccctgagaga   180
ttctctggct ccagctcagg gacagtggcc accttgacta tcagtggggc ccaggtggag   240
```
gatgaagctg actactactg ttactcaaca gatagcagtg gttaccatgg cttattcgga    300
ggagggaccc ggctgaccgt cctaggtcag                                     330

<210> SEQ ID NO 53
<211> LENGTH: 119
<212> TYPE: PRT
<213> ORGANISM: Artificial Sequence
<220> FEATURE:
<223> OTHER INFORMATION: rhMZ119 heavy chain variable domain amino acid
      sequence

<400> SEQUENCE: 53

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Ser Ala Thr Tyr Tyr Cys
                85                  90                  95

Ala Lys Glu Gly Ile Ala Ala Arg Ser Leu Asp Val Trp Gly Arg Gly
            100                 105                 110

Val Leu Val Thr Val Ser Ser
        115

<210> SEQ ID NO 54
<211> LENGTH: 110
<212> TYPE: PRT
<213> ORGANISM: Artificial Sequence
<220> FEATURE:
<223> OTHER INFORMATION: rhMZ119 light chain variable domain amino acid
      sequence

<400> SEQUENCE: 54

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Phe Gln Gln Lys Pro Gly Gln Ser Pro Val Leu Ile Ile Tyr
        35                  40                  45

Glu Asp Ser Lys Arg Pro Ser Gly Ile Pro Glu Arg Phe Ser Gly Ser
    50                  55                  60

Ser Ser Gly Thr Val Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Tyr His
                85                  90                  95

Gly Leu Phe Gly Gly Gly Thr Arg Leu Thr Val Leu Gly Gln
            100                 105                 110

<210> SEQ ID NO 55
<211> LENGTH: 8
<212> TYPE: PRT
<213> ORGANISM: Artificial Sequence
<220> FEATURE:
<223> OTHER INFORMATION: rhMZ119 heavy chain CDR1 sequence

```
<400> SEQUENCE: 55

Gly Tyr Ser Phe Thr Ser Tyr Trp
1               5

<210> SEQ ID NO 56
<211> LENGTH: 8
<212> TYPE: PRT
<213> ORGANISM: Artificial Sequence
<220> FEATURE:
<223> OTHER INFORMATION: rhMZ119 heavy chain CDR2 sequence

<400> SEQUENCE: 56

Ile Asp Pro Ser Asp Ser Asp Thr
1               5

<210> SEQ ID NO 57
<211> LENGTH: 14
<212> TYPE: PRT
<213> ORGANISM: Artificial Sequence
<220> FEATURE:
<223> OTHER INFORMATION: rhMZ119 heavy chain CDR3 sequence

<400> SEQUENCE: 57

Cys Ala Lys Glu Gly Ile Ala Ala Arg Ser Leu Asp Val Trp
1               5                   10

<210> SEQ ID NO 58
<211> LENGTH: 6
<212> TYPE: PRT
<213> ORGANISM: Artificial Sequence
<220> FEATURE:
<223> OTHER INFORMATION: rhMZ119 light chain CDR1 sequence

<400> SEQUENCE: 58

Ala Leu Pro Lys Lys Tyr
1               5

<210> SEQ ID NO 59
<211> LENGTH: 3
<212> TYPE: PRT
<213> ORGANISM: Artificial Sequence
<220> FEATURE:
<223> OTHER INFORMATION: rhMZ119 light chain CDR2 sequence

<400> SEQUENCE: 59

Glu Asp Ser
1

<210> SEQ ID NO 60
<211> LENGTH: 13
<212> TYPE: PRT
<213> ORGANISM: Artificial Sequence
<220> FEATURE:
<223> OTHER INFORMATION: rhMZ119 light chain CDR3 sequence

<400> SEQUENCE: 60

Cys Tyr Ser Thr Asp Ser Ser Gly Tyr His Gly Leu Phe
1               5                   10

<210> SEQ ID NO 61
<211> LENGTH: 363
<212> TYPE: DNA
<213> ORGANISM: Artificial Sequence
<220> FEATURE:
<223> OTHER INFORMATION: rhMZ121 heavy chain variable domain nucleotide
      sequence
```

-continued

<400> SEQUENCE: 61

```
caggtgcagc tgcaggagtc gggcccagga ctggtgaagc cttcggagac cctgtccctc    60
acctgcgctg tctctggtta ctccatcagc agtggttact actggggctg gatccgtcag   120
cccccaggga agggactgga gtatattggg tatatcagtg gtagtagtgg gagcacctac   180
tacaacccct ccctcaagag tcgagtcacc atttcaaaag acacgtccaa gaaccagttc   240
tccctgaagc tgagctctgt gaccgccgcg gacacggccg tgtattactg tgcgagaggg   300
aattactata gtggtagtta ttacttgttc tggggccagg gagtcctggt caccgtctcc   360
tca                                                                 363
```

<210> SEQ ID NO 62
<211> LENGTH: 339
<212> TYPE: DNA
<213> ORGANISM: Artificial Sequence
<220> FEATURE:
<223> OTHER INFORMATION: rhMZ121 light chain variable domain nucleotide
      sequence

<400> SEQUENCE: 62

```
tcctatgagc tgactcagcc accctcggtg tcagtgtccc caggacagac ggccaggatc    60
acctgtgggg gagacaacct tggaagtaaa tatgtgcact ggtaccagca gaagccagcg   120
caggccctg tgctggtcat ctattatgat agtgaccggc cctcaggat ccctgagcga   180
ttctctggct ccaaatcagg gaacaccgcc accctgacca tcagcggggt cgaggccggg   240
gatgaggctg actattactg tcaggtgtgg gacagtagta gtgatcattg ggtattcggc   300
ggagggaccc ggctgaccgt cctaggtcag gtctcctca                          339
```

<210> SEQ ID NO 63
<211> LENGTH: 121
<212> TYPE: PRT
<213> ORGANISM: Artificial Sequence
<220> FEATURE:
<223> OTHER INFORMATION: rhMZ121 heavy chain variable domain amino acid
      sequence

<400> SEQUENCE: 63

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Tyr
        35                  40                  45

Ile Gly Tyr Ile Ser Gly Ser Ser Gly Ser Thr Tyr Tyr Asn Pro Ser
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Tyr Tyr Ser Gly Ser Tyr Tyr Leu Phe Trp Gly
            100                 105                 110

Gln Gly Val Leu Val Thr Val Ser Ser
        115                 120
```

<210> SEQ ID NO 64
<211> LENGTH: 110
<212> TYPE: PRT
<213> ORGANISM: Artificial Sequence

```
<220> FEATURE:
<223> OTHER INFORMATION: rhMZ121 light chain variable domain amino acid
      sequence

<400> SEQUENCE: 64

Ser Tyr Glu Leu Thr Gln Pro Pro Ser Val Ser Val Ser Pro Gly Gln
1               5                   10                  15

Thr Ala Arg Ile Thr Cys Gly Gly Asp Asn Leu Gly Ser Lys Tyr Val
            20                  25                  30

His Trp Tyr Gln Gln Lys Pro Ala Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Lys Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Arg Leu Thr Val Leu Gly Gln
            100                 105                 110

<210> SEQ ID NO 65
<211> LENGTH: 8
<212> TYPE: PRT
<213> ORGANISM: Artificial Sequence
<220> FEATURE:
<223> OTHER INFORMATION: rhMZ121 heavy chain CDR1 sequence

<400> SEQUENCE: 65

Tyr Ser Ile Ser Ser Gly Tyr Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: rhMZ121 heavy chain CDR2 sequence

<400> SEQUENCE: 66

Ile Ser Gly Ser Ser Gly Ser Thr
1               5

<210> SEQ ID NO 67
<211> LENGTH: 15
<212> TYPE: PRT
<213> ORGANISM: Artificial Sequence
<220> FEATURE:
<223> OTHER INFORMATION: rhMZ121 heavy chain CDR3 sequence

<400> SEQUENCE: 67

Cys Ala Arg Gly Asn Tyr Tyr Gly Ser Tyr Tyr Leu Phe Trp
1               5                   10                  15

<210> SEQ ID NO 68
<211> LENGTH: 6
<212> TYPE: PRT
<213> ORGANISM: Artificial Sequence
<220> FEATURE:
<223> OTHER INFORMATION: rhMZ121 light chain CDR1 sequence

<400> SEQUENCE: 68

Asn Leu Gly Ser Lys Tyr
1               5
```

<210> SEQ ID NO 69
<211> LENGTH: 3
<212> TYPE: PRT
<213> ORGANISM: Artificial Sequence
<220> FEATURE:
<223> OTHER INFORMATION: rhMZ121 light chain CDR2 sequence

<400> SEQUENCE: 69

Tyr Asp Ser
1

<210> SEQ ID NO 70
<211> LENGTH: 13
<212> TYPE: PRT
<213> ORGANISM: Artificial Sequence
<220> FEATURE:
<223> OTHER INFORMATION: rhMZ121 light chain CDR3 sequence

<400> SEQUENCE: 70

Cys Gln Val Trp Asp Ser Ser Ser Asp His Trp Val Phe
1               5                   10

<210> SEQ ID NO 71
<211> LENGTH: 357
<212> TYPE: DNA
<213> ORGANISM: Artificial Sequence
<220> FEATURE:
<223> OTHER INFORMATION: rhMZ123 heavy chain variable domain nucleotide
      sequence

<400> SEQUENCE: 71
cagctggtgc agtctggagc agaggtgaaa aggcccgggg aatctctgag gatctcctgt       60
aagacttctg gatacagctt taccagctac tggatcagct gggtgcgcca gatgcccggg      120
aaaggcctgg agtggatggg gatgatctat cctggtgatt ctgataccag atacagcccg      180
tccttccaag gccaggtcac catctcagcc gacaagtcca tcagcaccgc ctacctgcag      240
tggagcagcc tgaaggcctc ggacaccgcc acgtattact gtgcgaaagt ggatagcagc      300
ggctggacca actactttga ctactggggc cagggagtcc tggtcaccgt ctcctca        357

<210> SEQ ID NO 72
<211> LENGTH: 336
<212> TYPE: DNA
<213> ORGANISM: Artificial Sequence
<220> FEATURE:
<223> OTHER INFORMATION: rhMZ123 light chain variable domain nucleotide
      sequence

<400> SEQUENCE: 72
cagtctgccc tgactcagcc tccctcagtg tccaagtctc ttggacagtc ggtcaccatc       60
tcctgcactg gaaccagcag tgacattggt ggttataatg gcgtctcctg gtaccagcag      120
cactcaggga cagcccccag actcctgatt tatgatgtca gtaagcggcc ctcaggggtc      180
tctgatcgct tctctggctc caagtctggc aacacggcct ccctgaccat ctctgggctc      240
caggctgagg acgaggctga ttattactgc tgctcatata ggagtggaag cacttacatc      300
ttcggtgctg ggacccggct caccgtccta ggtcag                                336

<210> SEQ ID NO 73
<211> LENGTH: 119
<212> TYPE: PRT
<213> ORGANISM: Artificial Sequence
<220> FEATURE:
<223> OTHER INFORMATION: rhMZ123 heavy chain variable domain amino acid sequence

<400> SEQUENCE: 73

Gln Leu Val Gln Ser Gly Ala Glu Val Lys Arg Pro Gly Glu Ser Leu
1               5                   10                  15

Arg Ile Ser Cys Lys Thr Ser Gly Tyr Ser Phe Thr Tyr Trp Ile
            20                  25                  30

Ser Trp Val Arg Gln Met Pro Gly Lys Gly Leu Glu Trp Met Gly Met
        35                  40                  45

Ile Tyr Pro Gly Asp Ser Asp Thr Arg Tyr Ser Pro Ser Phe Gln Gly
    50                  55                  60

Gln Val Thr Ile Ser Ala Asp Lys Ser Ile Thr Ala Tyr Leu Gln
65                  70                  75                  80

Trp Ser Ser Leu Lys Ala Ser Asp Thr Ala Thr Tyr Tyr Cys Ala Lys
                85                  90                  95

Val Asp Ser Ser Gly Trp Thr Asn Tyr Phe Asp Tyr Trp Gly Gln Gly
            100                 105                 110

Val Leu Val Thr Val Ser Ser
        115

<210> SEQ ID NO 74
<211> LENGTH: 112
<212> TYPE: PRT
<213> ORGANISM: Artificial Sequence
<220> FEATURE:
<223> OTHER INFORMATION: rhMZ123 light chain variable domain amino acid
      sequence

<400> SEQUENCE: 74

Gln Ser Ala Leu Thr Gln Pro Pro Ser Val Ser Lys Ser Leu Gly Gln
1               5                   10                  15

Ser Val Thr Ile Ser Cys Thr Gly Thr Ser Ser Asp Ile Gly Gly Tyr
            20                  25                  30

Asn Gly Val Ser Trp Tyr Gln Gln His Ser Gly Thr Ala Pro Arg Leu
        35                  40                  45

Leu Ile Tyr Asp Val Ser Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Arg Ser Gly
                85                  90                  95

Ser Thr Tyr Ile Phe Gly Ala Gly Thr Arg Leu Thr Val Leu Gly Gln
            100                 105                 110

<210> SEQ ID NO 75
<211> LENGTH: 8
<212> TYPE: PRT
<213> ORGANISM: Artificial Sequence
<220> FEATURE:
<223> OTHER INFORMATION: rhMZ123 heavy chain CDR1 sequence

<400> SEQUENCE: 75

Gly Tyr Ser Phe Thr Ser Tyr Trp
1               5

<210> SEQ ID NO 76
<211> LENGTH: 8
<212> TYPE: PRT
<213> ORGANISM: Artificial Sequence
<220> FEATURE:

<223> OTHER INFORMATION: rhMZ123 heavy chain CDR2 sequence

<400> SEQUENCE: 76

Ile Tyr Pro Gly Asp Ser Asp Thr
1               5

<210> SEQ ID NO 77
<211> LENGTH: 16
<212> TYPE: PRT
<213> ORGANISM: Artificial Sequence
<220> FEATURE:
<223> OTHER INFORMATION: rhMZ123 heavy chain CDR3 sequence

<400> SEQUENCE: 77

Cys Ala Lys Val Asp Ser Ser Gly Trp Thr Asn Tyr Phe Asp Tyr Trp
1               5                   10                  15

<210> SEQ ID NO 78
<211> LENGTH: 9
<212> TYPE: PRT
<213> ORGANISM: Artificial Sequence
<220> FEATURE:
<223> OTHER INFORMATION: rhMZ123 light chain CDR1 sequence

<400> SEQUENCE: 78

Ser Ser Asp Ile Gly Gly Tyr Asn Gly
1               5

<210> SEQ ID NO 79
<211> LENGTH: 3
<212> TYPE: PRT
<213> ORGANISM: Artificial Sequence
<220> FEATURE:
<223> OTHER INFORMATION: rhMZ123 light chain CDR2 sequence

<400> SEQUENCE: 79

Asp Val Ser
1

<210> SEQ ID NO 80
<211> LENGTH: 12
<212> TYPE: PRT
<213> ORGANISM: Artificial Sequence
<220> FEATURE:
<223> OTHER INFORMATION: rhMZ123 light chain CDR3 sequence

<400> SEQUENCE: 80

Cys Cys Ser Tyr Arg Ser Gly Ser Thr Tyr Ile Phe
1               5                   10

<210> SEQ ID NO 81
<211> LENGTH: 372
<212> TYPE: DNA
<213> ORGANISM: Artificial Sequence
<220> FEATURE:
<223> OTHER INFORMATION: rhMZ124 heavy chain variable domain nucleotide
      sequence

<400> SEQUENCE: 81
caggtgcagc tgcaggagtc gggcccagga ctggtgaagc cttcggagac cctgtccctc    60
acctgcgctg tctctggtga ctccatcagc agtggttact actggggctg gatccgtcag   120
tccccaggga ggggactgga gtcttttggg tttattagtg gcagtggtgg gaccacctac   180
tacaacccct ccctcaagac tcgagtcacc atttcaaaag acacgtccaa gaaccagttc   240
tccctgaaac tgagttctgt gaccgccgcg gacacggccg tatattactg tgcgagactc   300

```
ggacacccccc ggggtatagc ggcaggtgga gttgactact ggggccaggg agtcctggtc    360
accgtctcct ca                                                        372
```

<210> SEQ ID NO 82
<211> LENGTH: 351
<212> TYPE: DNA
<213> ORGANISM: Artificial Sequence
<220> FEATURE:
<223> OTHER INFORMATION: rhMZ124 light chain variable domain nucleotide
      sequence

<400> SEQUENCE: 82

```
cagtctgccc tgactcagcc accctccctg tctgcatccc cgggagcatc ggccagactc     60
ccctgcaccc tgagcagtga cttcagtgtt ggtaataaaa acatgtactg gtaccagcag    120
aagccaggga gcgctcccgg tttattccta tacttctact ccgactcaga caatcagctg    180
ggacctgggg tccccaatcg agtctctggc tccaaggagg cctcaagcaa cacagcgttt    240
ttgctcatct ctggcctcca gcctgaggac gaggccgatt attactgtca ggtatatgac    300
agagctgcta atatcctatt cggaggaggg acccggctga ccgtcctagg t             351
```

<210> SEQ ID NO 83
<211> LENGTH: 124
<212> TYPE: PRT
<213> ORGANISM: Artificial Sequence
<220> FEATURE:
<223> OTHER INFORMATION: rhMZ124 heavy chain variable domain amino acid
      sequence

<400> SEQUENCE: 83

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Asp Ser Ile Ser Ser Gly
            20                  25                  30

Tyr Tyr Trp Gly Trp Ile Arg Gln Ser Pro Gly Arg Gly Leu Glu Ser
        35                  40                  45

Phe Gly Phe Ile Ser Gly Ser Gly Gly Thr Thr Tyr Tyr Asn Pro Ser
    50                  55                  60

Leu Lys Thr Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly His Pro Arg Gly Ile Ala Ala Gly Gly Val Asp
            100                 105                 110

Tyr Trp Gly Gln Gly Val Leu Val Thr Val Ser Ser
        115                 120
```

<210> SEQ ID NO 84
<211> LENGTH: 117
<212> TYPE: PRT
<213> ORGANISM: Artificial Sequence
<220> FEATURE:
<223> OTHER INFORMATION: rhMZ124 light chain variable domain amino acid
      sequence

<400> SEQUENCE: 84

```
Gln Ser Ala Leu Thr Gln Pro Pro Ser Leu Ser Ala Ser Pro Gly Ala
1               5                   10                  15

Ser Ala Arg Leu Pro Cys Thr Leu Ser Ser Asp Phe Ser Val Gly Asn
            20                  25                  30
```

```
Lys Asn Met Tyr Trp Tyr Gln Gln Lys Pro Gly Ser Ala Pro Gly Leu
            35                  40                  45

Phe Leu Tyr Phe Tyr Ser Asp Ser Asp Asn Gln Leu Gly Pro Gly Val
 50                  55                  60

Pro Asn Arg Val Ser Gly Ser Lys Glu Ala Ser Ser Asn Thr Ala Phe
 65                  70                  75                  80

Leu Leu Ile Ser Gly Leu Gln Pro Glu Asp Glu Ala Asp Tyr Tyr Cys
                 85                  90                  95

Gln Val Tyr Asp Arg Ala Ala Asn Ile Leu Phe Gly Gly Gly Thr Arg
            100                 105                 110

Leu Thr Val Leu Gly
        115

<210> SEQ ID NO 85
<211> LENGTH: 8
<212> TYPE: PRT
<213> ORGANISM: Artificial Sequence
<220> FEATURE:
<223> OTHER INFORMATION: rhMZ124 heavy chain CDR1 sequence

<400> SEQUENCE: 85

Asp Ser Ile Ser Ser Gly Tyr Tyr
1               5

<210> SEQ ID NO 86
<211> LENGTH: 8
<212> TYPE: PRT
<213> ORGANISM: Artificial Sequence
<220> FEATURE:
<223> OTHER INFORMATION: rhMZ124 heavy chain CDR2 sequence

<400> SEQUENCE: 86

Ile Ser Gly Ser Gly Gly Thr Thr
1               5

<210> SEQ ID NO 87
<211> LENGTH: 18
<212> TYPE: PRT
<213> ORGANISM: Artificial Sequence
<220> FEATURE:
<223> OTHER INFORMATION: rhMZ124 heavy chain CDR3 sequence

<400> SEQUENCE: 87

Cys Ala Arg Leu Gly His Pro Arg Gly Ile Ala Ala Gly Gly Val Asp
1               5                   10                  15

Tyr Trp

<210> SEQ ID NO 88
<211> LENGTH: 9
<212> TYPE: PRT
<213> ORGANISM: Artificial Sequence
<220> FEATURE:
<223> OTHER INFORMATION: rhMZ124 light chain CDR1 sequence

<400> SEQUENCE: 88

Ser Asp Phe Ser Val Gly Asn Lys Asn
1               5

<210> SEQ ID NO 89
<211> LENGTH: 7
<212> TYPE: PRT
<213> ORGANISM: Artificial Sequence
<220> FEATURE:
```

<223> OTHER INFORMATION: rhMZ124 light chain CDR2 sequence

<400> SEQUENCE: 89

Phe Tyr Ser Asp Ser Asp Asn
1               5

<210> SEQ ID NO 90
<211> LENGTH: 12
<212> TYPE: PRT
<213> ORGANISM: Artificial Sequence
<220> FEATURE:
<223> OTHER INFORMATION: rhMZ124 light chain CDR3 sequence

<400> SEQUENCE: 90

Cys Gln Val Tyr Asp Arg Ala Ala Asn Ile Leu Phe
1               5                   10

<210> SEQ ID NO 91
<211> LENGTH: 378
<212> TYPE: DNA
<213> ORGANISM: Artificial Sequence
<220> FEATURE:
<223> OTHER INFORMATION: rhMZ133 heavy chain variable domain nucleotide
      sequence

<400> SEQUENCE: 91
gaggtgcagc tggtggagtc tgggggaggc ttggtccagc ctggcgggtc cctgagactc        60
tcctgtgcag cctctggatt caccttcagt gactactaca tgagctgggt ccgccaggct       120
ccagggaagg ggccggagtg ggtaggtttc attagaaaca agctaacgg tgggacagca        180 gaatacgccg cgtctgtgaa aggcagattc accgtctcaa gagatgattc aaaaagcatt       240
gccagtctgc aaatgaacag cctgaaaacc gaggacacgg ccgtgtatta ctgtgctaaa       300
cattactgta ctggtagtgg ttgctacggg gcgggtttgg attcctgggg ccaagggtc        360 gtcgtcaccg tctcctca                                                    378

<210> SEQ ID NO 92
<211> LENGTH: 333
<212> TYPE: DNA
<213> ORGANISM: Artificial Sequence
<220> FEATURE:
<223> OTHER INFORMATION: rhMZ133 light chain variable domain nucleotide
      sequence

<400> SEQUENCE: 92
cagtctgtcc tgactcagcc tccctcagtg tccaagtctc ttggacagtc ggtcaccatc        60
tcctgcactg gaaccagcag tgacattggt ggttctaatg acgtctcctg gtaccaacag       120
cacccaggca gcccccag actcctgatt tataatgtca gtaagcggcc ctcaggggtc         180
tctgatcgct tctctggctc caagtctggc aacacggcct ccctgaccat ctctgggctc       240
caggctgagg acgaggctga ttattactgc tgctcatata ggagtggaag cactttattc       300
ggcggaggga cccggctgac cgtcctaggt cag                                   333

<210> SEQ ID NO 93
<211> LENGTH: 126
<212> TYPE: PRT
<213> ORGANISM: Artificial Sequence
<220> FEATURE:
<223> OTHER INFORMATION: rhMZ133 heavy chain variable domain amino acid
      sequence

<400> SEQUENCE: 93

```
Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Pro Glu Trp Val
        35                  40                  45

Gly Phe Ile Arg Asn Lys Ala Asn Gly Gly Thr Ala Glu Tyr Ala Ala
    50                  55                  60

Ser Val Lys Gly Arg Phe Thr Val Ser Arg Asp Asp Ser Lys Ser Ile
65                  70                  75                  80

Ala Ser Leu Gln Met Asn Ser Leu Lys Thr Glu Asp Thr Ala Val Tyr
            85                  90                  95

Tyr Cys Ala Lys His Tyr Cys Thr Gly Ser Gly Cys Tyr Gly Ala Gly
        100                 105                 110

Leu Asp Ser Trp Gly Gln Gly Val Val Thr Val Ser Ser
            115                 120                 125
```

<210> SEQ ID NO 94
<211> LENGTH: 111
<212> TYPE: PRT
<213> ORGANISM: Artificial Sequence
<220> FEATURE:
<223> OTHER INFORMATION: rhMZ133 light chain variable domain amino acid
      sequence

<400> SEQUENCE: 94

```
Gln Ser Val Leu Thr Gln Pro Pro Ser Val Ser Lys Ser Leu Gly Gln
1               5                   10                  15

Ser Val Thr Ile Ser Cys Thr Gly Thr Ser Ser Asp Ile Gly Gly Ser
            20                  25                  30

Asn Asp Val Ser Trp Tyr Gln Gln His Pro Gly Thr Ala Pro Arg Leu
        35                  40                  45

Leu Ile Tyr Asn Val Ser Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Arg Ser Gly
            85                  90                  95

Ser Thr Leu Phe Gly Gly Gly Thr Arg Leu Thr Val Leu Gly Gln
        100                 105                 110
```

<210> SEQ ID NO 95
<211> LENGTH: 8
<212> TYPE: PRT
<213> ORGANISM: Artificial Sequence
<220> FEATURE:
<223> OTHER INFORMATION: rhMZ133 heavy chain CDR1 sequence

<400> SEQUENCE: 95

```
Gly Phe Thr Phe Ser Asp Tyr Tyr
1               5
```

<210> SEQ ID NO 96
<211> LENGTH: 10
<212> TYPE: PRT
<213> ORGANISM: Artificial Sequence
<220> FEATURE:
<223> OTHER INFORMATION: rhMZ133 heavy chain CDR2 sequence

<400> SEQUENCE: 96

Ile Arg Asn Lys Ala Asn Gly Gly Thr Ala
1               5                   10

<210> SEQ ID NO 97
<211> LENGTH: 19
<212> TYPE: PRT
<213> ORGANISM: Artificial Sequence
<220> FEATURE:
<223> OTHER INFORMATION: rhMZ133 heavy chain CDR3 sequence

<400> SEQUENCE: 97

Cys Ala Lys His Tyr Cys Thr Gly Ser Gly Cys Tyr Gly Ala Gly Leu
1               5                   10                  15

Asp Ser Trp

<210> SEQ ID NO 98
<211> LENGTH: 9
<212> TYPE: PRT
<213> ORGANISM: Artificial Sequence
<220> FEATURE:
<223> OTHER INFORMATION: rhMZ133 light chain CDR1 sequence

<400> SEQUENCE: 98

Ser Ser Asp Ile Gly Gly Ser Asn Asp
1               5

<210> SEQ ID NO 99
<211> LENGTH: 3
<212> TYPE: PRT
<213> ORGANISM: Artificial Sequence
<220> FEATURE:
<223> OTHER INFORMATION: rhMZ133 light chain CDR2 sequence

<400> SEQUENCE: 99

Asn Val Ser
1

<210> SEQ ID NO 100
<211> LENGTH: 11
<212> TYPE: PRT
<213> ORGANISM: Artificial Sequence
<220> FEATURE:
<223> OTHER INFORMATION: rhMZ133 light chain CDR3 sequence

<400> SEQUENCE: 100

Cys Cys Ser Tyr Arg Ser Gly Ser Thr Leu Phe
1               5                   10

<210> SEQ ID NO 101
<211> LENGTH: 411
<212> TYPE: DNA
<213> ORGANISM: Artificial Sequence
<220> FEATURE:
<223> OTHER INFORMATION: rhMZ134 heavy chain variable domain nucleotide
      sequence

<400> SEQUENCE: 101
gaggtgcagc tggtggagtc tgggggcggc ttggcaaagc ctggggggtc cctgagactc      60
tcctgcgcag cctccggatt caccttcagt gactactaca tggactgggt ccgccaggct     120
ccagggaagg ggctggagtg gtctcacgt attagtaatg gtggtggtag cacatggtac     180
gcagactccg tgaagggcag attcaccatc tccagagaga cgccaagaa cacactgtat     240 cttcaaatga acagcctgag agctgaggac acggctgtct attactgtgc gagagggcct     300
gaatattgta gtagtactta ctgctcctcg gcatactgta ctggtagtgg ttgctacgtt     360

```
gactacggtt tggattcctg gggccaaggg gtcgtcgtca ccgtctcctc a         411
```

<210> SEQ ID NO 102
<211> LENGTH: 325
<212> TYPE: DNA
<213> ORGANISM: Artificial Sequence
<220> FEATURE:
<223> OTHER INFORMATION: rhMZ134 light chain variable domain nucleotide
      sequence

<400> SEQUENCE: 102

```
tcctatgagc tgactcagcc accctcggtg tcggtgtccc caggacagat ggccaggatc    60
acctgtgggg gagacaacat tggaagtaaa aatgtgcagt ggtaccagca gaagccagcg   120 caggccctg tgctggtcat ctatgctgat agcgaacggc cctcagggat ccctgagcga   180
ttctctggct ccaactcagg gaacacggcc accctgacca tcagcggggt cgaggccggg   240
gatgaggctg actattactg tcaggtgtgg gatagtagta gtgatcatgt gttattcgga   300
ggagggaccc ggctgaccgt cctag                                         325
```

<210> SEQ ID NO 103
<211> LENGTH: 137
<212> TYPE: PRT
<213> ORGANISM: Artificial Sequence
<220> FEATURE:
<223> OTHER INFORMATION: rhMZ134 heavy chain variable domain amino acid
      sequence

<400> SEQUENCE: 103

```
Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Glu Trp Val
        35                  40                  45

Ser Arg Ile Ser Asn Gly Gly Gly Ser Thr Trp Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Glu Tyr Cys Ser Ser Thr Tyr Cys Ser Ser Ala Tyr
            100                 105                 110

Cys Thr Gly Ser Gly Cys Tyr Val Asp Tyr Gly Leu Asp Ser Trp Gly
        115                 120                 125

Gln Gly Val Val Val Thr Val Ser Ser
    130                 135
```

<210> SEQ ID NO 104
<211> LENGTH: 109
<212> TYPE: PRT
<213> ORGANISM: Artificial Sequence
<220> FEATURE:
<223> OTHER INFORMATION: rhMZ134 light chain variable domain amino acid
      sequence

<400> SEQUENCE: 104

```
Ser Tyr Glu Leu Thr Gln Pro Pro Ser Val Ser Val Ser Pro Gly Gln
1               5                   10                  15

Met Ala Arg Ile Thr Cys Gly Gly Asp Asn Ile Gly Ser Lys Asn Val
```

```
                20                  25                  30

Gln Trp Tyr Gln Gln Lys Pro Ala Gln Ala Pro Val Leu Val Ile Tyr
            35                  40                  45

Ala Asp Ser Glu Arg Pro Ser Gly Ile Pro Glu Arg Phe Ser Gly Ser
        50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Ser Asp His
                85                  90                  95

Val Leu Phe Gly Gly Gly Thr Arg Leu Thr Val Leu Gly
            100                 105

<210> SEQ ID NO 105
<211> LENGTH: 8
<212> TYPE: PRT
<213> ORGANISM: Artificial Sequence
<220> FEATURE:
<223> OTHER INFORMATION: rhMZ134 heavy chain CDR1 sequence

<400> SEQUENCE: 105

Gly Phe Thr Phe Ser Asp Tyr Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: rhMZ134 heavy chain CDR2 sequence

<400> SEQUENCE: 106

Ile Ser Asn Gly Gly Gly Ser Thr
1               5

<210> SEQ ID NO 107
<211> LENGTH: 32
<212> TYPE: PRT
<213> ORGANISM: Artificial Sequence
<220> FEATURE:
<223> OTHER INFORMATION: rhMZ134 heavy chain CDR3 sequence

<400> SEQUENCE: 107

Cys Ala Arg Gly Pro Glu Tyr Cys Ser Ser Thr Tyr Cys Ser Ser Ala
1               5                   10                  15

Tyr Cys Thr Gly Ser Gly Cys Tyr Val Asp Tyr Gly Leu Asp Ser Trp
            20                  25                  30

<210> SEQ ID NO 108
<211> LENGTH: 6
<212> TYPE: PRT
<213> ORGANISM: Artificial Sequence
<220> FEATURE:
<223> OTHER INFORMATION: rhMZ134 light chain CDR1 sequence

<400> SEQUENCE: 108

Asn Ile Gly Ser Lys Asn
1               5

<210> SEQ ID NO 109
<211> LENGTH: 3
<212> TYPE: PRT
<213> ORGANISM: Artificial Sequence
<220> FEATURE:
<223> OTHER INFORMATION: rhMZ134 light chain CDR2 sequence
```

<400> SEQUENCE: 109

Ala Asp Ser
1

<210> SEQ ID NO 110
<211> LENGTH: 11
<212> TYPE: PRT
<213> ORGANISM: Artificial Sequence
<220> FEATURE:
<223> OTHER INFORMATION: rhMZ134 light chain CDR3 sequence

<400> SEQUENCE: 110

Gln Val Trp Asp Ser Ser Ser Asp His Val Leu
1               5                   10

<210> SEQ ID NO 111
<211> LENGTH: 360
<212> TYPE: DNA
<213> ORGANISM: Artificial Sequence
<220> FEATURE:
<223> OTHER INFORMATION: MZ4 heavy chain variable domain nucleotide
      sequence

<400> SEQUENCE: 111

```
caggtgcatc tgcaggagtc gggcccagga ctggtgaggc cttcggagac cctgtccctc      60
acctgcactg tctctgatgg atccatcagc agttattatt ggagctggat ccggcagccc    120
ccagggaagg gactggagtg gattgggtct atctattaca ctgggagtac caactacaac    180
ccctccctca gagtcgagt caccatgtca gtagacacgt ccaagaacca gttctccctg    240
aggctgaatt ctgtgaccgc cgcagacacg gccatgtatt actgtgcggg acttgaccgg    300
tatagctgga cgaaggagg tgaccactgg ggccagggaa tcctggtcag cgtctcctca    360
```

<210> SEQ ID NO 112
<211> LENGTH: 336
<212> TYPE: DNA
<213> ORGANISM: Artificial Sequence
<220> FEATURE:
<223> OTHER INFORMATION: MZ4 light chain variable domain nucleotide
      sequence

<400> SEQUENCE: 112

```
cagcctgtgc tgactcagcc gcccctcagcg tctgggaccc ccgggcagag ggtctccatc     60
tcttgttctg gcagcagatc caacctcgga aagaatactg tgaactggta ccagcaactc    120
ccaggaacgg ccccccaaact cctcatctat aatcatagtc ggcggccctc aggggtccct    180
gaacgattct ctggctccaa gtctggcacc tcagcctccc tggccatcag tgggctccag    240
tctgaggatg aggctgatta tttctgtgca gcatgggatg acagtctgaa tggcctttat    300
gtcttcggaa ctgggaccaa ggtcaccgtc ctacgt                               336
```

<210> SEQ ID NO 113
<211> LENGTH: 120
<212> TYPE: PRT
<213> ORGANISM: Artificial Sequence
<220> FEATURE:
<223> OTHER INFORMATION: MZ4 heavy chain variable domain amino acid
      sequence

<400> SEQUENCE: 113

Gln Val His Leu Gln Glu Ser Gly Pro Gly Leu Val Arg Pro Ser Glu
1               5                   10                  15

Thr Leu Ser Leu Thr Cys Thr Val Ser Asp Gly Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Thr Gly Ser Thr Asn Tyr Asn Pro Ser Leu Lys
50                  55                  60

Ser Arg Val Thr Met Ser Val Asp Thr Ser Lys Asn Gln Phe Ser Leu
65                  70                  75                  80

Arg Leu Asn Ser Val Thr Ala Ala Asp Thr Ala Met Tyr Tyr Cys Ala
                85                  90                  95

Gly Leu Asp Arg Tyr Ser Trp Asn Glu Gly Gly Asp His Trp Gly Gln
            100                 105                 110

Gly Ile Leu Val Ser Val Ser Ser
        115                 120

<210> SEQ ID NO 114
<211> LENGTH: 112
<212> TYPE: PRT
<213> ORGANISM: Artificial Sequence
<220> FEATURE:
<223> OTHER INFORMATION: MZ4 light chain variable domain amino acid
      sequence

<400> SEQUENCE: 114

Gln Pro Val Leu Thr Gln Pro Pro Ser Ala Ser Gly Thr Pro Gly Gln
1               5                   10                  15

Arg Val Ser Ile Ser Cys Ser Gly Ser Arg Ser Asn Leu Gly Lys Asn
            20                  25                  30

Thr Val Asn Trp Tyr Gln Gln Leu Pro Gly Thr Ala Pro Lys Leu Leu
        35                  40                  45

Ile Tyr Asn His Ser Arg Arg Pro Ser Gly Val Pro Glu Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Leu Tyr Val Phe Gly Thr Gly Thr Lys Val Thr Val Leu Arg
            100                 105                 110

<210> SEQ ID NO 115
<211> LENGTH: 8
<212> TYPE: PRT
<213> ORGANISM: Artificial Sequence
<220> FEATURE:
<223> OTHER INFORMATION: MZ4 heavy chain CDR1 sequence

<400> SEQUENCE: 115

Asp Gly Ser Ile Ser Ser Tyr Tyr
1               5

<210> SEQ ID NO 116
<211> LENGTH: 7
<212> TYPE: PRT
<213> ORGANISM: Artificial Sequence
<220> FEATURE:
<223> OTHER INFORMATION: MZ4 heavy chain CDR2 sequence

<400> SEQUENCE: 116

Ile Tyr Tyr Thr Gly Ser Thr
1               5

```
<210> SEQ ID NO 117
<211> LENGTH: 16
<212> TYPE: PRT
<213> ORGANISM: Artificial Sequence
<220> FEATURE:
<223> OTHER INFORMATION: MZ4 heavy chain CDR3 sequence

<400> SEQUENCE: 117

Cys Ala Gly Leu Asp Arg Tyr Ser Trp Asn Glu Gly Gly Asp His Trp
1               5                   10                  15

<210> SEQ ID NO 118
<211> LENGTH: 8
<212> TYPE: PRT
<213> ORGANISM: Artificial Sequence
<220> FEATURE:
<223> OTHER INFORMATION: MZ4 light chain CDR1 sequence

<400> SEQUENCE: 118

Arg Ser Asn Leu Gly Lys Asn Thr
1               5

<210> SEQ ID NO 119
<211> LENGTH: 3
<212> TYPE: PRT
<213> ORGANISM: Artificial Sequence
<220> FEATURE:
<223> OTHER INFORMATION: MZ4 light chain CDR2 sequence

<400> SEQUENCE: 119

Asn His Ser
1

<210> SEQ ID NO 120
<211> LENGTH: 14
<212> TYPE: PRT
<213> ORGANISM: Artificial Sequence
<220> FEATURE:
<223> OTHER INFORMATION: MZ4 light chain CDR3 sequence

<400> SEQUENCE: 120

Cys Ala Ala Trp Asp Asp Ser Leu Asn Gly Leu Tyr Val Phe
1               5                   10

<210> SEQ ID NO 121
<211> LENGTH: 360
<212> TYPE: DNA
<213> ORGANISM: Artificial Sequence
<220> FEATURE:
<223> OTHER INFORMATION: MZ1 heavy chain variable domain nucleotide
      sequence

<400> SEQUENCE: 121
caggtgcagc tgcaggagtc gggcccagga ctggtgaagt cttcggagac cctgtccctc      60
agttgcactg tctctggtgc ctccatcagt aatttctatt ggagttgggt ccggcagccc     120
ccagggaagg gactggaatg gatgggatcc atatattaca ctggaactat cacctacaac     180
ccctccctca agagtcgact caccatgtca gtggacacgt ccaagaacca gttctccctg     240
aagttgaact ctgtgaccgc cgcagacacg gccgtctatt tctgtgcggg acttgaccgg     300
tttaactgga acgacgaagg tgactgctgg ggccagggca ccctggtcac cgtcttctca     360

<210> SEQ ID NO 122
<211> LENGTH: 336
<212> TYPE: PRT
```

```
<213> ORGANISM: Artificial Sequence
<220> FEATURE:
<223> OTHER INFORMATION: MZ1 light chain variable domain nucleotide
      sequence

<400> SEQUENCE: 122

Cys Ala Gly Thr Cys Thr Gly Thr Gly Cys Thr Gly Ala Cys Thr Cys
1               5                   10                  15

Ala Gly Cys Cys Ala Cys Cys Cys Thr Cys Ala Gly Cys Gly Thr Cys
            20                  25                  30

Thr Gly Gly Gly Ala Cys Cys Cys Cys Cys Gly Gly Gly Cys Ala Gly
        35                  40                  45

Ala Gly Gly Gly Thr Cys Ala Cys Cys Ala Thr Cys Thr Cys Thr Thr
    50                  55                  60

Gly Thr Thr Cys Thr Gly Gly Ala Ala Gly Cys Ala Gly Gly Thr Cys
65                  70                  75                  80

Cys Ala Ala Cys Cys Thr Cys Gly Gly Ala Ala Gly Gly Ala Ala Thr
                85                  90                  95

Ala Cys Thr Gly Thr Ala Ala Ala Cys Thr Gly Gly Thr Ala Thr Cys
            100                 105                 110

Ala Gly Cys Ala Gly Cys Thr Cys Cys Cys Ala Gly Gly Ala Gly Thr
        115                 120                 125

Gly Gly Cys Cys Cys Cys Cys Ala Ala Ala Cys Thr Cys Cys Thr Cys
    130                 135                 140

Ala Thr Cys Thr Ala Thr Ala Gly Thr Ala Ala Thr Ala Ala Thr Cys
145                 150                 155                 160

Gly Gly Cys Gly Gly Cys Cys Cys Thr Cys Ala Gly Gly Ala Gly Thr
                165                 170                 175

Cys Cys Cys Thr Gly Ala Thr Cys Gly Ala Thr Thr Thr Thr Cys Thr
            180                 185                 190

Gly Gly Cys Thr Cys Cys Ala Ala Gly Thr Cys Thr Gly Ala Cys Ala
        195                 200                 205

Cys Cys Thr Cys Ala Gly Cys Cys Thr Cys Cys Cys Thr Gly Gly Cys
    210                 215                 220

Cys Ala Thr Cys Ala Gly Cys Gly Gly Gly Cys Thr Cys Cys Ala Gly
225                 230                 235                 240

Thr Cys Thr Gly Ala Gly Gly Ala Thr Gly Ala Gly Gly Cys Thr Gly
                245                 250                 255

Ala Thr Thr Ala Thr Thr Thr Cys Thr Gly Thr Gly Cys Ala Gly Cys
            260                 265                 270

Ala Thr Gly Gly Gly Ala Thr Gly Ala Cys Ala Gly Cys Cys Thr Gly
        275                 280                 285

Ala Ala Thr Gly Gly Cys Cys Thr Thr Thr Ala Thr Gly Thr Cys Thr
    290                 295                 300

Thr Cys Gly Gly Ala Ala Cys Thr Gly Gly Gly Ala Cys Cys Ala Ala
305                 310                 315                 320

Gly Gly Thr Cys Ala Cys Cys Gly Thr Cys Cys Thr Ala Gly Gly Thr
                325                 330                 335

<210> SEQ ID NO 123
<211> LENGTH: 120
<212> TYPE: PRT
<213> ORGANISM: Artificial Sequence
<220> FEATURE:
<223> OTHER INFORMATION: MZ1 heavy chain variable domain amino acid
      sequence
```

<400> SEQUENCE: 123

Gln Val Gln Leu Gln Glu Ser Gly Pro Gly Leu Val Lys Ser Glu
1               5                   10                  15

Thr Leu Ser Leu Ser Cys Thr Val Ser Gly Ala Ser Ile Ser Asn Phe
            20                  25                  30

Tyr Trp Ser Trp Val Arg Gln Pro Pro Gly Lys Gly Leu Glu Trp Met
        35                  40                  45

Gly Ser Ile Tyr Tyr Thr Gly Thr Ile Thr Tyr Asn Pro Ser Leu Lys
50                  55                  60

Ser Arg Leu Thr Met Ser Val Asp Thr Ser Lys Asn Gln Phe Ser Leu
65                  70                  75                  80

Lys Leu Asn Ser Val Thr Ala Ala Asp Thr Ala Val Tyr Ser Cys Ala
                85                  90                  95

Gly Leu Asp Arg Phe Asn Trp Asn Asp Glu Gly Asp Cys Trp Gly Gln
            100                 105                 110

Gly Thr Leu Val Thr Val Phe Ser
        115                 120

<210> SEQ ID NO 124
<211> LENGTH: 112
<212> TYPE: PRT
<213> ORGANISM: Artificial Sequence
<220> FEATURE:
<223> OTHER INFORMATION: MZ1 light chain variable domain amino acid
      sequence

<400> SEQUENCE: 124

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Leu Gly Arg Asn
            20                  25                  30

Thr Val Asn Trp Tyr Gln Gln Leu Pro Gly Val Ala Pro Lys Leu Leu
        35                  40                  45

Ile Tyr Ser Asn Asn Arg Arg Pro Ser Gly Val Pro Asp Arg Phe Ser
50                  55                  60

Gly Ser Lys Ser Asp Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Leu Tyr Val Phe Gly Thr Gly Thr Lys Val Thr Val Leu Gly
            100                 105                 110

<210> SEQ ID NO 125
<211> LENGTH: 8
<212> TYPE: PRT
<213> ORGANISM: Artificial Sequence
<220> FEATURE:
<223> OTHER INFORMATION: MZ1 heavy chain CDR1 sequence

<400> SEQUENCE: 125

Gly Ala Ser Ile Ser Asn Phe Tyr
1               5

<210> SEQ ID NO 126
<211> LENGTH: 7
<212> TYPE: PRT
<213> ORGANISM: Artificial Sequence
<220> FEATURE:
<223> OTHER INFORMATION: MZ1 heavy chain CDR2 sequence

<400> SEQUENCE: 126

Ile Tyr Tyr Thr Gly Thr Ile
1               5

<210> SEQ ID NO 127
<211> LENGTH: 16
<212> TYPE: PRT
<213> ORGANISM: Artificial Sequence
<220> FEATURE:
<223> OTHER INFORMATION: MZ1 heavy chain CDR3 sequence

<400> SEQUENCE: 127

Cys Ala Gly Leu Asp Arg Phe Asn Trp Asn Asp Glu Gly Asp Cys Trp
1               5                   10                  15

<210> SEQ ID NO 128
<211> LENGTH: 8
<212> TYPE: PRT
<213> ORGANISM: Artificial Sequence
<220> FEATURE:
<223> OTHER INFORMATION: MZ1 light chain CDR1 sequence

<400> SEQUENCE: 128

Arg Ser Asn Leu Gly Arg Asn Thr
1               5

<210> SEQ ID NO 129
<211> LENGTH: 3
<212> TYPE: PRT
<213> ORGANISM: Artificial Sequence
<220> FEATURE:
<223> OTHER INFORMATION: MZ1 light chain CDR2 sequence

<400> SEQUENCE: 129

Ser Asn Asn
1

<210> SEQ ID NO 130
<211> LENGTH: 14
<212> TYPE: PRT
<213> ORGANISM: Artificial Sequence
<220> FEATURE:
<223> OTHER INFORMATION: MZ1 light chain CDR3 sequence

<400> SEQUENCE: 130

Cys Ala Ala Trp Asp Asp Ser Leu Asn Gly Leu Tyr Val Phe
1               5                   10

<210> SEQ ID NO 131
<211> LENGTH: 360
<212> TYPE: DNA
<213> ORGANISM: Artificial Sequence
<220> FEATURE:
<223> OTHER INFORMATION: MZ24 heavy chain variable domain nucleotide
      sequence

<400> SEQUENCE: 131
caggtgcagc tgcaggagtc gggcccagga ctggtaaagt cttcggagac cctgtccctc      60
agctgcactg tctctggtgc ctccatcagt agtyattatt ggagctgggt ccgacagtcc     120
ccagggaagg gactggagtg gatgggatct atatattaca ctggaaccac acctacaac     180 ccctccctca agagtcgact caccatatca gtggacacgt ccaagaacca gttctccctg     240
aagctgaact ctgtgaccgc cgcagacacg gccgtatatt cctgtgcggg acttgaccgg     300
tttaactgga acgacgaagg tgactgctgg ggccagggca ccctggtcac cgtcttctca     360

<210> SEQ ID NO 132
<211> LENGTH: 336
<212> TYPE: DNA
<213> ORGANISM: Artificial Sequence
<220> FEATURE:
<223> OTHER INFORMATION: MZ24 light chain variable domain nucleotide
      sequence

<400> SEQUENCE: 132

```
cagtctgtgc tgactcagcc accctcagcg tctgggaccc ccgggcagag ggtcaccatc    60
tcttgttctg gaagcaggtc caacctcgga aggaatactg taaactggta ccagcagctc   120
ccaggagtgg cccccaaact cctcatctat agtaatagtc ggcggccctc aggagtccct   180
gaccgatttt ctggctccaa gtctgacacc tcagcctccc tggccatcag tgggctccag   240
tctgaggatg aggctgatta ttactgtgca gcatgggatg acagcctgaa tggcctttat   300
gtctttggaa ctgggaccag tgtcaccgtc ctaggt                              336
```

<210> SEQ ID NO 133
<211> LENGTH: 120
<212> TYPE: PRT
<213> ORGANISM: Artificial Sequence
<220> FEATURE:
<223> OTHER INFORMATION: MZ24 heavy chain variable domain amino acid
      sequence

<400> SEQUENCE: 133

Gln Val Gln Leu Gln Glu Ser Gly Pro Gly Leu Val Lys Ser Glu
1               5                   10                  15

Thr Leu Ser Leu Ser Cys Thr Val Ser Gly Ala Ser Ile Ser Ser Tyr
            20                  25                  30

Tyr Trp Ser Trp Val Arg Gln Ser Pro Gly Lys Gly Leu Glu Trp Met
        35                  40                  45

Gly Ser Ile Tyr Tyr Thr Gly Thr Thr Tyr Asn Pro Ser Leu Lys
    50                  55                  60

Ser Arg Leu Thr Ile Ser Val Asp Thr Ser Lys Asn Gln Phe Ser Leu
65                  70                  75                  80

Lys Leu Asn Ser Val Thr Ala Ala Asp Thr Ala Val Tyr Ser Cys Ala
                85                  90                  95

Gly Leu Asp Arg Phe Asn Trp Asn Asp Glu Gly Asp Cys Trp Gly Gln
            100                 105                 110

Gly Thr Leu Val Thr Val Phe Ser
        115                 120

<210> SEQ ID NO 134
<211> LENGTH: 112
<212> TYPE: PRT
<213> ORGANISM: Artificial Sequence
<220> FEATURE:
<223> OTHER INFORMATION: MZ24 light chain variable domain amino acid
      sequence

<400> SEQUENCE: 134

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Leu Gly Arg Asn
            20                  25                  30

Thr Val Asn Trp Tyr Gln Gln Leu Pro Gly Val Ala Pro Lys Leu Leu
        35                  40                  45

```
Ile Tyr Ser Asn Ser Arg Arg Pro Ser Gly Val Pro Asp Arg Phe Ser
         50                  55                  60
Gly Ser Lys Ser Asp Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Leu Tyr Val Phe Gly Thr Gly Thr Ser Val Thr Val Leu Gly
                100                 105                 110

<210> SEQ ID NO 135
<211> LENGTH: 8
<212> TYPE: PRT
<213> ORGANISM: Artificial Sequence
<220> FEATURE:
<223> OTHER INFORMATION: MZ24 heavy chain CDR1 sequence

<400> SEQUENCE: 135

Gly Ala Ser Ile Ser Ser Tyr Tyr
1               5

<210> SEQ ID NO 136
<211> LENGTH: 7
<212> TYPE: PRT
<213> ORGANISM: Artificial Sequence
<220> FEATURE:
<223> OTHER INFORMATION: MZ24 heavy chain CDR2 sequence

<400> SEQUENCE: 136

Ile Tyr Tyr Thr Gly Thr Thr
1               5

<210> SEQ ID NO 137
<211> LENGTH: 16
<212> TYPE: PRT
<213> ORGANISM: Artificial Sequence
<220> FEATURE:
<223> OTHER INFORMATION: MZ24 heavy chain CDR3 sequence

<400> SEQUENCE: 137

Cys Ala Gly Leu Asp Arg Phe Asn Trp Asn Asp Glu Gly Asp Cys Trp
1               5                   10                  15

<210> SEQ ID NO 138
<211> LENGTH: 8
<212> TYPE: PRT
<213> ORGANISM: Artificial Sequence
<220> FEATURE:
<223> OTHER INFORMATION: MZ24 light chain CDR1 sequence

<400> SEQUENCE: 138

Arg Ser Asn Leu Gly Arg Asn Thr
1               5

<210> SEQ ID NO 139
<211> LENGTH: 3
<212> TYPE: PRT
<213> ORGANISM: Artificial Sequence
<220> FEATURE:
<223> OTHER INFORMATION: MZ24 light chain CDR2 sequence

<400> SEQUENCE: 139

Ser Asn Ser
1

<210> SEQ ID NO 140
```

-continued

```
<211> LENGTH: 14
<212> TYPE: PRT
<213> ORGANISM: Artificial Sequence
<220> FEATURE:
<223> OTHER INFORMATION: MZ24 light chain CDR3 sequence

<400> SEQUENCE: 140

Cys Ala Ala Trp Asp Asp Ser Leu Asn Gly Leu Tyr Val Phe
1               5                   10

<210> SEQ ID NO 141
<211> LENGTH: 351
<212> TYPE: DNA
<213> ORGANISM: Artificial Sequence
<220> FEATURE:
<223> OTHER INFORMATION: MZ20 heavy chain variable domain nucleotide
      sequence

<400> SEQUENCE: 141
gaagtgcagg tggtggagtc tgggggaggc ttggtcaagc ctggagggtc cctgagactc      60
tcctgtgcag cctctggatt caccttcagt cacttctaca tgacctggat ccgccaggct     120
ccagggaagg gcctggagtc tatttcatac attggaggta ctggatctcc cacctactac     180
gctgactctg tggtgggccg tttcaccatc tccaggggaca cgccaagaa ctcagtgtat     240 ctggaaatga acagcctgag agccgaagac acggccatat attattgtgt gagggctggt     300
ggggcgagga ttgagaactg gggccaggga accctggtca tcgtctcgtc a             351

<210> SEQ ID NO 142
<211> LENGTH: 324
<212> TYPE: DNA
<213> ORGANISM: Artificial Sequence
<220> FEATURE:
<223> OTHER INFORMATION: MZ20 light chain variable domain nucleotide
      sequence

<400> SEQUENCE: 142
gacattgtga tgacccagtc tccatcctcc ctgtctgcat ctgtggggga cagagtcacc      60
atcacttgcc aggcgagtca cgacattaac atctatttaa attggtatca acagagacca     120
gggaaagccc ctaaactcct gatctacgat gcatccagat tagagacagg ggtcccatca     180
aggttcagtg gactggatc tgggacagat ttcactttca ccatcagcaa cctgcagcct     240
gaagattttg caacatattt ctgtcaacat tattatactc tcccgcggac gttcggccaa     300
gggaccaagg ttgacatcaa acga                                            324

<210> SEQ ID NO 143
<211> LENGTH: 117
<212> TYPE: PRT
<213> ORGANISM: Artificial Sequence
<220> FEATURE:
<223> OTHER INFORMATION: MZ20 heavy chain variable domain amino acid
      sequence

<400> SEQUENCE: 143

Glu Val Gln Val Val Glu Ser Gly Gly Gly Leu Val Lys Pro Gly Gly
1               5                   10                  15

Ser Leu Arg Leu Ser Cys Ala Ala Ser Gly Phe Thr Phe Ser His Phe
            20                  25                  30

Tyr Met Thr Trp Ile Arg Gln Ala Pro Gly Lys Gly Leu Glu Ser Ile
        35                  40                  45

Ser Tyr Ile Gly Gly Thr Gly Ser Pro Thr Tyr Tyr Ala Asp Ser Val
    50                  55                  60
```

```
Val Gly Arg Phe Thr Ile Ser Arg Asp Asn Ala Lys Asn Ser Val Tyr
 65                  70                  75                  80

Leu Glu Met Asn Ser Leu Arg Ala Glu Asp Thr Ala Ile Tyr Tyr Cys
                 85                  90                  95

Val Arg Ala Gly Gly Ala Arg Ile Glu Asn Trp Gly Gln Gly Thr Leu
            100                 105                 110

Val Ile Val Ser Ser
            115

<210> SEQ ID NO 144
<211> LENGTH: 108
<212> TYPE: PRT
<213> ORGANISM: Artificial Sequence
<220> FEATURE:
<223> OTHER INFORMATION: MZ20 light chain variable domain amino acid
      sequence

<400> SEQUENCE: 144

Asp Ile Val Met Thr Gln Ser Pro Ser Ser Leu Ser Ala Ser Val Gly
 1               5                  10                  15

Asp Arg Val Thr Ile Thr Cys Gln Ala Ser His Asp Ile Asn Ile Tyr
             20                  25                  30

Leu Asn Trp Tyr Gln Gln Arg Pro Gly Lys Ala Pro Lys Leu Leu Ile
         35                  40                  45

Tyr Asp Ala Ser Arg Leu Glu Thr Gly Val Pro Ser Arg Phe Ser Gly
 50                  55                  60

Thr Gly Ser Gly Thr Asp Phe Thr Phe Thr Ile Ser Asn Leu Gln Pro
 65                  70                  75                  80

Glu Asp Phe Ala Thr Tyr Phe Cys Gln His Tyr Tyr Thr Leu Pro Arg
                 85                  90                  95

Thr Phe Gly Gln Gly Thr Lys Val Asp Ile Lys Arg
            100                 105

<210> SEQ ID NO 145
<211> LENGTH: 8
<212> TYPE: PRT
<213> ORGANISM: Artificial Sequence
<220> FEATURE:
<223> OTHER INFORMATION: MZ20 heavy chain CDR1 sequence

<400> SEQUENCE: 145

Gly Phe Thr Phe Ser His Phe Tyr
 1               5

<210> SEQ ID NO 146
<211> LENGTH: 8
<212> TYPE: PRT
<213> ORGANISM: Artificial Sequence
<220> FEATURE:
<223> OTHER INFORMATION: MZ20 heavy chain CDR2 sequence

<400> SEQUENCE: 146

Ile Gly Gly Thr Gly Ser Pro Thr
 1               5

<210> SEQ ID NO 147
<211> LENGTH: 12
<212> TYPE: PRT
<213> ORGANISM: Artificial Sequence
<220> FEATURE:
<223> OTHER INFORMATION: MZ20 heavy chain CDR3 sequence
```

<400> SEQUENCE: 147

Cys Val Arg Ala Gly Gly Ala Arg Ile Glu Asn Trp
1               5                   10

<210> SEQ ID NO 148
<211> LENGTH: 6
<212> TYPE: PRT
<213> ORGANISM: Artificial Sequence
<220> FEATURE:
<223> OTHER INFORMATION: MZ20 light chain CDR1 sequence

<400> SEQUENCE: 148

His Asp Ile Asn Ile Tyr
1               5

<210> SEQ ID NO 149
<211> LENGTH: 3
<212> TYPE: PRT
<213> ORGANISM: Artificial Sequence
<220> FEATURE:
<223> OTHER INFORMATION: MZ20 light chain CDR2 sequence

<400> SEQUENCE: 149

Asp Ala Ser
1

<210> SEQ ID NO 150
<211> LENGTH: 11
<212> TYPE: PRT
<213> ORGANISM: Artificial Sequence
<220> FEATURE:
<223> OTHER INFORMATION: MZ20 light chain CDR3 sequence

<400> SEQUENCE: 150

Cys Gln His Tyr Tyr Thr Leu Pro Arg Thr Phe
1               5                   10

<210> SEQ ID NO 151
<211> LENGTH: 351
<212> TYPE: DNA
<213> ORGANISM: Artificial Sequence
<220> FEATURE:
<223> OTHER INFORMATION: MZ54 heavy chain variable domain nucleotide
      sequence

<400> SEQUENCE: 151
gaagtgcagc tggtggagtc tgggggaggc ttggtcaagc ctgggggtc cctgagactc      60 tcctgttcag cctctggatt caactttcgt gacttctaca tggctgggt ccgccaggct     120 ccaggaaagg gtctacagtg ggtttcacac attggtgata gtggtggtgc catatattac    180
acagactctg tgagggccg attctccatc tccaggaca acgccaagaa ctcccttttat    240 ctccaaatga acagcctgag agtcgaggac acggctatct attactgtgt gtgtgcgggg    300
gggggccgga ctgactactg gggccaggga accctagtca ccgtctcctc a            351

<210> SEQ ID NO 152
<211> LENGTH: 324
<212> TYPE: DNA
<213> ORGANISM: Artificial Sequence
<220> FEATURE:
<223> OTHER INFORMATION: MZ54 light chain variable domain nucleotide
      sequence

<400> SEQUENCE: 152
gacattgtga tgacccagtc tccatcctcc ctgtctgcat ctgtaggaga cagagtcacc      60

```
atcacttgcc aggcgactca ggacattaac atatatttaa attggtatca acagaagcca    120
gggcaggccc cgaaactcct catctacgat gcatccaggt tggagacagg ggtcccatca    180
aggttcagtg gacgtggatc tgggacagat tttaccttca ccatcagcag cctgcagcct    240
gaagatttcg gaacatatta ttgtcaacac tattatactg tccctcgaac gttcggccaa    300
gggaccaagg tggaaagcag acga                                          324
```

```
<210> SEQ ID NO 153
<211> LENGTH: 117
<212> TYPE: PRT
<213> ORGANISM: Artificial Sequence
<220> FEATURE:
<223> OTHER INFORMATION: MZ54 heavy chain variable domain amino acid
      sequence

<400> SEQUENCE: 153
```

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asn Phe Arg Asp Phe
            20                  25                  30

Tyr Met Gly Trp Val Arg Gln Ala Pro Gly Lys Gly Leu Gln Trp Val
        35                  40                  45

Ser His Ile Gly Asp Ser Gly Gly Ala Ile Tyr Tyr Thr Asp Ser Val
    50                  55                  60

Glu Gly Arg Phe Ser Ile Ser Arg Asp Asn Ala Lys Asn Ser Leu Tyr
65                  70                  75                  80

Leu Gln Met Asn Ser Leu Arg Val Glu Asp Thr Ala Ile Tyr Tyr Cys
                85                  90                  95

Val Cys Ala Gly Gly Gly Arg Thr Asp Tyr Trp Gly Gln Gly Thr Leu
            100                 105                 110

Val Thr Val Ser Ser
        115

```
<210> SEQ ID NO 154
<211> LENGTH: 108
<212> TYPE: PRT
<213> ORGANISM: Artificial Sequence
<220> FEATURE:
<223> OTHER INFORMATION: MZ54 light chain variable domain amino acid
      sequence

<400> SEQUENCE: 154
```

Asp Ile Val Met Thr Gln Ser Pro Ser Ser Leu Ser Ala Ser Val Gly
1               5                   10                  15

Asp Arg Val Thr Ile Thr Cys Gln Ala Thr Gln Asp Ile Asn Ile Tyr
            20                  25                  30

Leu Asn Trp Tyr Gln Gln Lys Pro Gly Gln Ala Pro Lys Leu Leu Ile
        35                  40                  45

Tyr Asp Ala Ser Arg Leu Glu Thr Gly Val Pro Ser Arg Phe Ser Gly
    50                  55                  60

Arg Gly Ser Gly Thr Asp Phe Thr Phe Thr Ile Ser Ser Leu Gln Pro
65                  70                  75                  80

Glu Asp Phe Gly Thr Tyr Tyr Cys Gln His Tyr Tyr Thr Val Pro Arg
                85                  90                  95

Thr Phe Gly Gln Gly Thr Lys Val Glu Ser Arg Arg
            100                 105

```
<210> SEQ ID NO 155
<211> LENGTH: 8
<212> TYPE: PRT
<213> ORGANISM: Artificial Sequence
<220> FEATURE:
<223> OTHER INFORMATION: MZ54 heavy chain CDR1 sequence

<400> SEQUENCE: 155

Gly Phe Asn Phe Arg Asp Phe Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: MZ54 heavy chain CDR2 sequence

<400> SEQUENCE: 156

Ile Gly Asp Ser Gly Gly Ala Ile
1               5

<210> SEQ ID NO 157
<211> LENGTH: 12
<212> TYPE: PRT
<213> ORGANISM: Artificial Sequence
<220> FEATURE:
<223> OTHER INFORMATION: MZ54 heavy chain CDR3 sequence

<400> SEQUENCE: 157

Cys Val Cys Ala Gly Gly Gly Arg Thr Asp Tyr Trp
1               5                   10

<210> SEQ ID NO 158
<211> LENGTH: 6
<212> TYPE: PRT
<213> ORGANISM: Artificial Sequence
<220> FEATURE:
<223> OTHER INFORMATION: MZ54 light chain CDR1 sequence

<400> SEQUENCE: 158

Gln Asp Ile Asn Ile Tyr
1               5

<210> SEQ ID NO 159
<211> LENGTH: 3
<212> TYPE: PRT
<213> ORGANISM: Artificial Sequence
<220> FEATURE:
<223> OTHER INFORMATION: MZ54 light chain CDR2 sequence

<400> SEQUENCE: 159

Asp Ala Ser
1

<210> SEQ ID NO 160
<211> LENGTH: 11
<212> TYPE: PRT
<213> ORGANISM: Artificial Sequence
<220> FEATURE:
<223> OTHER INFORMATION: MZ54 light chain CDR3 sequence

<400> SEQUENCE: 160

Cys Gln His Tyr Tyr Thr Val Pro Arg Thr Phe
1               5                   10

<210> SEQ ID NO 161
```

<211> LENGTH: 372
<212> TYPE: DNA
<213> ORGANISM: Artificial Sequence
<220> FEATURE:
<223> OTHER INFORMATION: MZ56 heavy chain variable domain nucleotide sequence

<400> SEQUENCE: 161

```
gaagtgcagc tggtggagtc tgggggagac ttggtccagc ctggggggtc cctgagactc    60
tcctgtgcag cctctggatt caccttcagt aactatgcta tgcactgggt ccgccaggcg   120
ccagggaagg gactggagtc tgtttcagct attggtagta atgggatag tatattttat    180
gcaagctctg tgaagggcag attcaccatc tccagagaca attccaagaa cacgctgtat   240
cttcaaatgg gcagcctgag agctgacgac atggctgtgt atttctgtgc gagaggctgg   300
tattactatg atagtcgtgc ttattggtac ttcgatctct ggggccgtgg caccctggtc   360
actgtctcct ca                                                       372
```

<210> SEQ ID NO 162
<211> LENGTH: 330
<212> TYPE: DNA
<213> ORGANISM: Artificial Sequence
<220> FEATURE:
<223> OTHER INFORMATION: MZ56 light chain variable domain nucleotide sequence

<400> SEQUENCE: 162

```
cagyctgtgc tgactcagcc tgcctccgtg tctgggtctc ctggacagtc gatcaccatc    60
tcctgcactg gaaccaccag tgacgttgat gattataatc atgtctcctg gtaccaacaa   120
tatccaggca agcccccag agtcatgctt tatgatgtca ctaagcggcc ctcaggggtc    180
cctgatcgct tctctggctc caagtctggc aacacggcct ccctgaccat ctccggggctc  240
caatctgagg atgaggctga ttattactgc tgctcatttg cagacagtca cgcgatattc    300
ggtggaggga ccaaggtgac cgtcctaggt                                   330
```

<210> SEQ ID NO 163
<211> LENGTH: 124
<212> TYPE: PRT
<213> ORGANISM: Artificial Sequence
<220> FEATURE:
<223> OTHER INFORMATION: MZ56 heavy chain variable domain amino acid sequence

<400> SEQUENCE: 163

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Ser Val
        35                  40                  45

Ser Ala Ile Gly Ser Asn Gly Asp Ser Ile Phe Tyr Ala Ser Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Asp Asp Met Ala Val Tyr Phe Cys
                85                  90                  95

Ala Arg Gly Trp Tyr Tyr Tyr Asp Ser Arg Ala Tyr Trp Tyr Phe Asp
            100                 105                 110

Leu Trp Gly Arg Gly Thr Leu Val Thr Val Ser Ser

<210> SEQ ID NO 164
<211> LENGTH: 110
<212> TYPE: PRT
<213> ORGANISM: Artificial Sequence
<220> FEATURE:
<223> OTHER INFORMATION: MZ56 light chain variable domain amino acid
      sequence

<400> SEQUENCE: 164

Gln Pro Val Leu Thr Gln Pro Ala Ser Val Ser Gly Ser Pro Gly Gln
1               5                   10                  15

Ser Ile Thr Ile Ser Cys Thr Gly Thr Thr Ser Asp Val Asp Asp Tyr
            20                  25                  30

Asn His Val Ser Trp Tyr Gln Gln Tyr Pro Gly Lys Ala Pro Arg Val
        35                  40                  45

Met Leu Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Cys Ser Phe Ala Asp Ser
                85                  90                  95

His Ala Ile Phe Gly Gly Gly Thr Lys Val Thr Val Leu Gly
            100                 105                 110

<210> SEQ ID NO 165
<211> LENGTH: 8
<212> TYPE: PRT
<213> ORGANISM: Artificial Sequence
<220> FEATURE:
<223> OTHER INFORMATION: MZ56 heavy chain CDR1 sequence

<400> SEQUENCE: 165

Gly Phe Thr Phe Ser Asn Tyr Ala
1               5

<210> SEQ ID NO 166
<211> LENGTH: 8
<212> TYPE: PRT
<213> ORGANISM: Artificial Sequence
<220> FEATURE:
<223> OTHER INFORMATION: MZ56 heavy chain CDR2 sequence

<400> SEQUENCE: 166

Ile Gly Ser Asn Gly Asp Ser Ile
1               5

<210> SEQ ID NO 167
<211> LENGTH: 19
<212> TYPE: PRT
<213> ORGANISM: Artificial Sequence
<220> FEATURE:
<223> OTHER INFORMATION: MZ56 heavy chain CDR3 sequence

<400> SEQUENCE: 167

Cys Ala Arg Gly Trp Tyr Tyr Tyr Asp Ser Arg Ala Tyr Trp Tyr Phe
1               5                   10                  15

Asp Leu Trp

<210> SEQ ID NO 168
<211> LENGTH: 9
<212> TYPE: PRT

<213> ORGANISM: Artificial Sequence
<220> FEATURE:
<223> OTHER INFORMATION: MZ58 light chain CDR1 sequence

<400> SEQUENCE: 168

Thr Ser Asp Val Asp Asp Tyr Asn His
1               5

<210> SEQ ID NO 169
<211> LENGTH: 3
<212> TYPE: PRT
<213> ORGANISM: Artificial Sequence
<220> FEATURE:
<223> OTHER INFORMATION: MZ56 light chain CDR2 sequence

<400> SEQUENCE: 169

Asp Val Thr
1

<210> SEQ ID NO 170
<211> LENGTH: 11
<212> TYPE: PRT
<213> ORGANISM: Artificial Sequence
<220> FEATURE:
<223> OTHER INFORMATION: MZ56 light chain CDR3 sequence

<400> SEQUENCE: 170

Cys Cys Ser Phe Ala Asp Ser His Ala Ile Phe
1               5                   10

<210> SEQ ID NO 171
<211> LENGTH: 360
<212> TYPE: DNA
<213> ORGANISM: Artificial Sequence
<220> FEATURE:
<223> OTHER INFORMATION: MZ22 heavy chain variable domain nucleotide
      sequence

<400> SEQUENCE: 171

```
cagctgcatc tgcaggagtc gggcccagga ctggtgaagc cttcggagac cctgtccctc    60
acctgcactg tctctggtgg ctccttcagc agttactact ggagctggat ccggcagccc   120
ccagggaagg gactggagtg gattgggtct atctattaca ctgggagtac caactacaac   180
ccctccctca gagtcgagt caccatatca gttgacgcgt ccaagaacca gttctccctg   240
aggctgaact ctgtgaccgc cgcagacacg gccatatatt actgtgcggg acttgaccgt   300
tatgcctgga cgacggaggt gaccactgg ggccagggaa ccctggtcag cgtcccctca    360
```

<210> SEQ ID NO 172
<211> LENGTH: 327
<212> TYPE: DNA
<213> ORGANISM: Artificial Sequence
<220> FEATURE:
<223> OTHER INFORMATION: MZ22 light chain variable domain nucleotide
      sequence

<400> SEQUENCE: 172

```
cagtctgtgc tgactcagcc accctcagcg tctgggaccc ccgggcagag ggtctccatt    60
tcttgttctg gaagcagctc caacctcgga aggaatactg tgcactggta ccagcaactc   120
ccaggaacgg cccccaaact cctcatctat aataatagtc ggcggccctc agggggtccct   180 gaacgattct ctggctccaa gtctggcacc tcagcctccc tggccatcag tgggctccag   240
tctgaggatg aggctgatta tttctgtgca tcatgggatg acagcctgaa cggccttat   300
```

```
gtcttcggaa ctggaccaag gtcacct                                              327
```

```
<210> SEQ ID NO 173
<211> LENGTH: 120
<212> TYPE: PRT
<213> ORGANISM: Artificial Sequence
<220> FEATURE:
<223> OTHER INFORMATION: MZ22 heavy chain variable domain amino acid
      sequence

<400> SEQUENCE: 173
```

Gln Leu His Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Thr Gly Ser Thr Asn Tyr Asn Pro Ser Leu Lys
    50                  55                  60

Ser Arg Val Thr Ile Ser Val Asp Ala Ser Lys Asn Gln Phe Ser Leu
65                  70                  75                  80

Arg Leu Asn Ser Val Thr Ala Ala Asp Thr Ala Ile Tyr Tyr Cys Ala
                85                  90                  95

Gly Leu Asp Arg Tyr Ala Trp Asn Asp Gly Gly Asp His Trp Gly Gln
            100                 105                 110

Gly Thr Leu Val Ser Val Pro Ser
        115                 120

```
<210> SEQ ID NO 174
<211> LENGTH: 109
<212> TYPE: PRT
<213> ORGANISM: Artificial Sequence
<220> FEATURE:
<223> OTHER INFORMATION: MZ22 light chain variable domain amino acid
      sequence

<400> SEQUENCE: 174
```

Gln Ser Val Leu Thr Gln Pro Pro Ser Ala Ser Gly Thr Pro Gly Gln
1               5                   10                  15

Arg Val Ser Ile Ser Cys Ser Gly Ser Ser Asn Leu Gly Arg Asn
            20                  25                  30

Thr Leu His Trp Tyr Gln Gln Leu Pro Gly Thr Ala Pro Lys Leu Leu
        35                  40                  45

Ile Tyr Asn Asn Ser Arg Arg Pro Ser Gly Val Pro Glu Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ser Trp Asp Asp Ser Leu
                85                  90                  95

Asn Gly Leu Tyr Val Phe Gly Thr Gly Pro Arg Ser Pro
            100                 105

```
<210> SEQ ID NO 175
<211> LENGTH: 8
<212> TYPE: PRT
<213> ORGANISM: Artificial Sequence
<220> FEATURE:
<223> OTHER INFORMATION: MZ22 heavy chain CDR1 sequence

<400> SEQUENCE: 175
```

-continued

Gly Gly Ser Phe Ser Ser Tyr Tyr
1               5

<210> SEQ ID NO 176
<211> LENGTH: 7
<212> TYPE: PRT
<213> ORGANISM: Artificial Sequence
<220> FEATURE:
<223> OTHER INFORMATION: MZ22 heavy chain CDR2 sequence

<400> SEQUENCE: 176

Ile Tyr Tyr Thr Gly Ser Thr
1               5

<210> SEQ ID NO 177
<211> LENGTH: 16
<212> TYPE: PRT
<213> ORGANISM: Artificial Sequence
<220> FEATURE:
<223> OTHER INFORMATION: MZ22 heavy chain CDR3 sequence

<400> SEQUENCE: 177

Cys Ala Gly Leu Asp Arg Tyr Ala Trp Asn Asp Gly Gly Asp His Trp
1               5                   10                  15

<210> SEQ ID NO 178
<211> LENGTH: 8
<212> TYPE: PRT
<213> ORGANISM: Artificial Sequence
<220> FEATURE:
<223> OTHER INFORMATION: MZ22 light chain CDR1 sequence

<400> SEQUENCE: 178

Ser Ser Asn Leu Gly Arg Asn Thr
1               5

<210> SEQ ID NO 179
<211> LENGTH: 3
<212> TYPE: PRT
<213> ORGANISM: Artificial Sequence
<220> FEATURE:
<223> OTHER INFORMATION: MZ22 light chain CDR2 sequence

<400> SEQUENCE: 179

Asn Asn Ser
1

<210> SEQ ID NO 180
<211> LENGTH: 14
<212> TYPE: PRT
<213> ORGANISM: Artificial Sequence
<220> FEATURE:
<223> OTHER INFORMATION: MZ22 light chain CDR3 sequence

<400> SEQUENCE: 180

Cys Ala Ser Trp Asp Asp Ser Leu Asn Gly Leu Tyr Val Phe
1               5                   10

<210> SEQ ID NO 181
<211> LENGTH: 375
<212> TYPE: DNA
<213> ORGANISM: Artificial Sequence
<220> FEATURE:
<223> OTHER INFORMATION: MZ18 heavy chain variable domain nucleotide
      sequence

<400> SEQUENCE: 181

```
caggtgcagt tggtgcagtc tggggctgag gtgaagaagc ctggggcctc agtgaaggtc    60
tcctgcaagg cttctggatc cactttcatc ggctattata tacactgggt gcgacaggcc   120
cctggacaag ggcttgagtg gatgggatgg atcaactcta atagtggtgg cacaaagttt   180
gcacagaagt tcagggcag gtcaccatg accagggaca cgtccatcag tacagtctac   240
gcagagctga gcagactgag atctgacgac acggccgtgt attactgtgc gagcaacaaa   300
tggttcagtg gcgatgatgc ttactactcc tacatggacg tctggggcaa agggaccacg   360
gtcatcgtct cctca                                                    375
```

```
<210> SEQ ID NO 182
<211> LENGTH: 297
<212> TYPE: DNA
<213> ORGANISM: Artificial Sequence
<220> FEATURE:
<223> OTHER INFORMATION: MZ18 light chain variable domain nucleotide
      sequence

<400> SEQUENCE: 182
```

```
tctgtgtcct tgggacagac agtcaggatc acatgccagg gagacatcct cagaagctat    60
tatgcaagtt ggtatcagca gaagccagga caggcccctg tacttgtcct ctatggtaaa   120
aactaccggc cctcagggat cccagaccga ttctctggct ccagctcagg aaacacagct   180
tctttgacca tcactggggc tcaggcgaa gatgaggctg actattactg taactcccga   240
gacaacagtg gtaatcaagt gattttcggc ggagggacca agctgaccgt cctaggt     297
```

```
<210> SEQ ID NO 183
<211> LENGTH: 125
<212> TYPE: PRT
<213> ORGANISM: Artificial Sequence
<220> FEATURE:
<223> OTHER INFORMATION: MZ18 heavy chain variable domain amino acid
      sequence

<400> SEQUENCE: 183
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ile Gly Tyr
            20                  25                  30

Tyr Ile His Trp Val Arg Gln Ala Pro Gly Gln Gly Leu Glu Trp Met
        35                  40                  45

Gly Trp Ile Asn Ser Asn Ser Gly Gly Thr Lys Phe Ala Gln Lys Phe
    50                  55                  60

Gln Gly Arg Val Thr Met Thr Arg Asp Thr Ser Ile Ser Thr Val Tyr
65                  70                  75                  80

Ala Glu Leu Ser Arg Leu Arg Ser Asp Asp Thr Ala Val Tyr Tyr Cys
                85                  90                  95

Ala Ser Asn Lys Trp Phe Ser Gly Asp Asp Ala Tyr Tyr Ser Tyr Met
            100                 105                 110

Asp Val Trp Gly Lys Gly Thr Thr Val Ile Val Ser Ser
        115                 120                 125
```

```
<210> SEQ ID NO 184
<211> LENGTH: 99
<212> TYPE: PRT
<213> ORGANISM: Artificial Sequence
<220> FEATURE:
<223> OTHER INFORMATION: MZ18 light chain variable domain amino acid
      sequence
```

-continued

```
<400> SEQUENCE: 184

Ser Val Ser Leu Gly Gln Thr Val Arg Ile Thr Cys Gln Gly Asp Ile
1               5                   10                  15

Leu Arg Ser Tyr Tyr Ala Ser Trp Tyr Gln Gln Lys Pro Gly Gln Ala
            20                  25                  30

Pro Val Leu Val Leu Tyr Gly Lys Asn Tyr Arg Pro Ser Gly Ile Pro
        35                  40                  45

Asp Arg Phe Ser Gly Ser Ser Ser Gly Asn Thr Ala Ser Leu Thr Ile
    50                  55                  60

Thr Gly Ala Gln Ala Glu Asp Glu Ala Asp Tyr Tyr Cys Asn Ser Arg
65                  70                  75                  80

Asp Asn Ser Gly Asn Gln Val Ile Phe Gly Gly Thr Lys Leu Thr
                85                  90                  95

Val Leu Gly

<210> SEQ ID NO 185
<211> LENGTH: 8
<212> TYPE: PRT
<213> ORGANISM: Artificial Sequence
<220> FEATURE:
<223> OTHER INFORMATION: MZ18 heavy chain CDR1 sequence

<400> SEQUENCE: 185

Gly Ser Thr Phe Ile Gly Tyr Tyr
1               5

<210> SEQ ID NO 186
<211> LENGTH: 8
<212> TYPE: PRT
<213> ORGANISM: Artificial Sequence
<220> FEATURE:
<223> OTHER INFORMATION: MZ18 heavy chain CDR2 sequence

<400> SEQUENCE: 186

Ile Asn Ser Asn Ser Gly Gly Thr
1               5

<210> SEQ ID NO 187
<211> LENGTH: 20
<212> TYPE: PRT
<213> ORGANISM: Artificial Sequence
<220> FEATURE:
<223> OTHER INFORMATION: MZ18 heavy chain CDR3 sequence

<400> SEQUENCE: 187

Cys Ala Ser Asn Lys Trp Phe Ser Gly Asp Asp Ala Tyr Tyr Ser Tyr
1               5                   10                  15

Met Asp Val Trp
            20

<210> SEQ ID NO 188
<211> LENGTH: 6
<212> TYPE: PRT
<213> ORGANISM: Artificial Sequence
<220> FEATURE:
<223> OTHER INFORMATION: MZ18 light chain CDR1 sequence

<400> SEQUENCE: 188

Ile Leu Arg Ser Tyr Tyr
1               5

<210> SEQ ID NO 189
```

```
<211> LENGTH: 3
<212> TYPE: PRT
<213> ORGANISM: Artificial Sequence
<220> FEATURE:
<223> OTHER INFORMATION: MZ18 light chain CDR2 sequence

<400> SEQUENCE: 189

Gly Lys Asn
1

<210> SEQ ID NO 190
<211> LENGTH: 13
<212> TYPE: PRT
<213> ORGANISM: Artificial Sequence
<220> FEATURE:
<223> OTHER INFORMATION: MZ18 light chain CDR3 sequence

<400> SEQUENCE: 190

Cys Asn Ser Arg Asp Asn Ser Gly Asn Gln Val Ile Phe
1               5                   10

<210> SEQ ID NO 191
<211> LENGTH: 336
<212> TYPE: DNA
<213> ORGANISM: Artificial Sequence
<220> FEATURE:
<223> OTHER INFORMATION: MZ19 heavy chain variable domain nucleotide
      sequence

<400> SEQUENCE: 191
caggtgcagc tacagcagtg gggcgcagga ctgttgaagc cttcggagac cctgtccctc      60
acctgcgctg tctatgatgg gtccttcagt ggttactact ggagctggat ccgccagccc     120
ccagggaagg gctggagtg gattggggaa atcaatcata gtggaagcac caactacaac     180
ccgtccctca agagtcgagt caccatatca gtagacacgt ccaagaacca gttctccctg     240
aaactgagtt ctgtgaccgc cgcggacacg gctgtgtatt actgtgcgag gggggtccag     300
cactggggcc agggcaccct ggtcatcgtc tcttca                               336

<210> SEQ ID NO 192
<211> LENGTH: 333
<212> TYPE: DNA
<213> ORGANISM: Artificial Sequence
<220> FEATURE:
<223> OTHER INFORMATION: MZ19 light chain variable domain nucleotide
      sequence

<400> SEQUENCE: 192
cagtctgtgc tgactcagcc accctcggtg tccaagggct tgagacagac cgccacactc      60
acctgcactg ggaacagcga caatgttgac agccaaggag cagcttggct gcagcagcac     120
cagggccacc ctcccaaact cctatcgtac aggaataaca accggccctc tgggatctca     180
gagagattct ctgcatccag gtcagggaat acagcctccc tgaccattac tggactccag     240
cctgaggacg aggctgacta ttactgctca gcatgggacg cagcctcag tgcgtgggtg      300 ttcggcgggg ggaccaagct gaccgtccta ggt                                  333

<210> SEQ ID NO 193
<211> LENGTH: 112
<212> TYPE: PRT
<213> ORGANISM: Artificial Sequence
<220> FEATURE:
<223> OTHER INFORMATION: MZ19 heavy chain variable domain amino acid
      sequence
```

<400> SEQUENCE: 193

Gln Val Gln Leu Gln Gln Trp Gly Ala Gly Leu Leu Lys Pro Ser Glu
1               5                   10                  15

Thr Leu Ser Leu Thr Cys Ala Val Tyr Asp Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Gln His Trp Gly Gln Gly Thr Leu Val Ile Val Ser Ser
            100                 105                 110

<210> SEQ ID NO 194
<211> LENGTH: 111
<212> TYPE: PRT
<213> ORGANISM: Artificial Sequence
<220> FEATURE:
<223> OTHER INFORMATION: MZ19 light chain variable domain amino acid
      sequence

<400> SEQUENCE: 194

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asp Asn Val Asp Ser Gln
            20                  25                  30

Gly Ala Ala Trp Leu Gln Gln His Gln Gly His Pro Pro Lys Leu Leu
        35                  40                  45

Ser Tyr Arg Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Gly Ser Leu
                85                  90                  95

Ser Ala Trp Val Phe Gly Gly Gly Thr Lys Leu Thr Val Leu Gly
            100                 105                 110

<210> SEQ ID NO 195
<211> LENGTH: 8
<212> TYPE: PRT
<213> ORGANISM: Artificial Sequence
<220> FEATURE:
<223> OTHER INFORMATION: MZ19 heavy chain CDR1 sequence

<400> SEQUENCE: 195

Asp Gly Ser Phe Ser Gly Tyr Tyr
1               5

<210> SEQ ID NO 196
<211> LENGTH: 7
<212> TYPE: PRT
<213> ORGANISM: Artificial Sequence
<220> FEATURE:
<223> OTHER INFORMATION: MZ19 heavy chain CDR2 sequence

<400> SEQUENCE: 196

Ile Asn His Ser Gly Ser Thr

```
<210> SEQ ID NO 197
<211> LENGTH: 8
<212> TYPE: PRT
<213> ORGANISM: Artificial Sequence
<220> FEATURE:
<223> OTHER INFORMATION: MZ19 heavy chain CDR3 sequence

<400> SEQUENCE: 197

Cys Ala Arg Gly Val Gln His Trp
1               5

<210> SEQ ID NO 198
<211> LENGTH: 8
<212> TYPE: PRT
<213> ORGANISM: Artificial Sequence
<220> FEATURE:
<223> OTHER INFORMATION: MZ19 light chain CDR1 sequence

<400> SEQUENCE: 198

Ser Asp Asn Val Asp Ser Gln Gly
1               5

<210> SEQ ID NO 199
<211> LENGTH: 3
<212> TYPE: PRT
<213> ORGANISM: Artificial Sequence
<220> FEATURE:
<223> OTHER INFORMATION: MZ19 light chain CDR2 sequence

<400> SEQUENCE: 199

Arg Asn Asn
1

<210> SEQ ID NO 200
<211> LENGTH: 13
<212> TYPE: PRT
<213> ORGANISM: Artificial Sequence
<220> FEATURE:
<223> OTHER INFORMATION: MZ19 light chain CDR2 sequence

<400> SEQUENCE: 200

Cys Ser Ala Trp Asp Gly Ser Leu Ser Ala Trp Val Phe
1               5                   10

<210> SEQ ID NO 201
<211> LENGTH: 348
<212> TYPE: DNA
<213> ORGANISM: Artificial Sequence
<220> FEATURE:
<223> OTHER INFORMATION: MZ23 heavy chain variable domain nucleotide
      sequence

<400> SEQUENCE: 201
gaagtgcagc tggtggagtc cgggggaggc tcagttcagc ctgggggtc cctgagactc        60 tcctgtgcag cctctggatt caccttcaat atctaccgga tgcactgggt ccgccaggct      120
ccagggaagg ggctcgtgtg ggtctcagat atttataatg atggcagtag cacaaactac      180
gcggacagcg tgaagggccg attcaccatc tccagagaca cgccaagaa cacgctgttt       240 ctgcaaatga acagtctgag agccgaggac acggctgtct actactgtgt cagatctagt      300
ggtgcctttg actactgggg ccaggggagcc ctggtcaccg tctcatca                  348

<210> SEQ ID NO 202
```

```
<211> LENGTH: 342
<212> TYPE: DNA
<213> ORGANISM: Artificial Sequence
<220> FEATURE:
<223> OTHER INFORMATION: MZ23 light chain variable domain nucleotide
      sequence

<400> SEQUENCE: 202
gaaattgtga tgacccagtc tccagactcc ctggctgtgt ctctgggcga gagggccacc      60
atcaactgca gtccagcca gagtatttta aacagctcca acaataagaa ctacttagct     120
tggtaccagc agaaaccagg acagcctcct acattgctcg tttactgggc ttctatccgg     180
ggatccgggg tccctgaccg attcagtggc agcgggtctg ggacagactt cactctcacc     240
atcagcagcc tgcagcctga agatgtggct gtgtattact gtcagcacca ttatagtttt     300
ccgatcacct tcggccaagg gacacgactg gagattaaac ga                        342

<210> SEQ ID NO 203
<211> LENGTH: 116
<212> TYPE: PRT
<213> ORGANISM: Artificial Sequence
<220> FEATURE:
<223> OTHER INFORMATION: MZ23 heavy chain variable domain amino acid
      sequence

<400> SEQUENCE: 203

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Asn Ile Tyr
            20                  25                  30

Arg Met His Trp Val Arg Gln Ala Pro Gly Lys Gly Leu Val Trp Val
        35                  40                  45

Ser Asp Ile Tyr Asn Asp Gly Ser Thr Asn Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Ala Glu Asp Thr Ala Val Tyr Tyr Cys
                85                  90                  95

Val Arg Ser Ser Gly Ala Phe Asp Tyr Trp Gly Gln Gly Ala Leu Val
            100                 105                 110

Thr Val Ser Ser
        115

<210> SEQ ID NO 204
<211> LENGTH: 114
<212> TYPE: PRT
<213> ORGANISM: Artificial Sequence
<220> FEATURE:
<223> OTHER INFORMATION: MZ23 light chain variable domain amino acid
      sequence

<400> SEQUENCE: 204

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Asn Ser
            20                  25                  30

Ser Asn Asn Lys Asn Tyr Leu Ala Trp Tyr Gln Gln Lys Pro Gly Gln
        35                  40                  45

Pro Pro Thr Leu Leu Val Tyr Trp Ala Ser Ile Arg Gly Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Leu Gln Pro Glu Asp Val Ala Val Tyr Tyr Cys Gln His
                 85                  90                  95

His Tyr Ser Phe Pro Ile Thr Phe Gly Gln Gly Thr Arg Leu Glu Ile
            100                 105                 110

Lys Arg

<210> SEQ ID NO 205
<211> LENGTH: 8
<212> TYPE: PRT
<213> ORGANISM: Artificial Sequence
<220> FEATURE:
<223> OTHER INFORMATION: MZ23 heavy chain CDR1 sequence

<400> SEQUENCE: 205

Gly Phe Thr Phe Asn Ile Tyr Arg
 1               5

<210> SEQ ID NO 206
<211> LENGTH: 8
<212> TYPE: PRT
<213> ORGANISM: Artificial Sequence
<220> FEATURE:
<223> OTHER INFORMATION: MZ23 heavy chain CDR2 sequence

<400> SEQUENCE: 206

Ile Tyr Asn Asp Gly Ser Ser Thr
 1               5

<210> SEQ ID NO 207
<211> LENGTH: 11
<212> TYPE: PRT
<213> ORGANISM: Artificial Sequence
<220> FEATURE:
<223> OTHER INFORMATION: MZ23 heavy chain CDR3 sequence

<400> SEQUENCE: 207

Cys Val Arg Ser Ser Gly Ala Phe Asp Tyr Trp
 1               5                  10

<210> SEQ ID NO 208
<211> LENGTH: 12
<212> TYPE: PRT
<213> ORGANISM: Artificial Sequence
<220> FEATURE:
<223> OTHER INFORMATION: MZ23 light chain CDR1 sequence

<400> SEQUENCE: 208

Gln Ser Ile Leu Asn Ser Ser Asn Asn Lys Asn Tyr
 1               5                  10

<210> SEQ ID NO 209
<211> LENGTH: 3
<212> TYPE: PRT
<213> ORGANISM: Artificial Sequence
<220> FEATURE:
<223> OTHER INFORMATION: MZ23 light chain CDR2 sequence

<400> SEQUENCE: 209

Trp Ala Ser
 1

<210> SEQ ID NO 210
<211> LENGTH: 11
```

<212> TYPE: PRT
<213> ORGANISM: Artificial Sequence
<220> FEATURE:
<223> OTHER INFORMATION: MZ23 light chain CDR3 sequence

<400> SEQUENCE: 210

Cys Gln His His Tyr Ser Phe Pro Ile Thr Phe
1               5                   10

<210> SEQ ID NO 211
<211> LENGTH: 360
<212> TYPE: PRT
<213> ORGANISM: Artificial Sequence
<220> FEATURE:
<223> OTHER INFORMATION: MZ2 heavy chain variable domain nucleotide
      sequence

<400> SEQUENCE: 211

Cys Ala Gly Cys Thr Gly Cys Ala Thr Cys Thr Gly Cys Ala Gly Gly
1               5                   10                  15

Ala Gly Thr Cys Gly Gly Cys Cys Cys Ala Gly Gly Ala Cys Thr
            20                  25                  30

Gly Gly Thr Gly Ala Ala Gly Cys Cys Thr Thr Cys Gly Gly Ala Gly
        35                  40                  45

Ala Cys Cys Cys Thr Gly Thr Cys Cys Cys Thr Cys Ala Cys Cys Thr
    50                  55                  60

Gly Cys Ala Cys Thr Gly Thr Cys Thr Cys Thr Gly Gly Thr Gly Gly
65                  70                  75                  80

Cys Thr Cys Cys Thr Cys Ala Gly Cys Ala Gly Thr Thr Ala Cys
                85                  90                  95

Thr Ala Cys Thr Gly Gly Ala Gly Cys Thr Gly Gly Ala Thr Cys Cys
            100                 105                 110

Gly Gly Cys Ala Gly Cys Cys Cys Cys Ala Gly Gly Gly Ala Ala
        115                 120                 125

Gly Gly Gly Ala Cys Thr Gly Gly Ala Gly Thr Gly Gly Ala Thr Thr
    130                 135                 140

Gly Gly Gly Thr Cys Thr Ala Thr Cys Thr Ala Thr Thr Ala Cys Ala
145                 150                 155                 160

Cys Thr Gly Gly Gly Ala Gly Thr Ala Cys Cys Ala Ala Cys Thr Ala
                165                 170                 175

Cys Ala Ala Cys Cys Cys Cys Thr Cys Cys Cys Thr Cys Ala Ala Gly
            180                 185                 190

Ala Gly Thr Cys Gly Ala Gly Thr Cys Ala Cys Ala Thr Ala Thr
        195                 200                 205

Cys Ala Gly Thr Thr Gly Ala Cys Gly Cys Gly Thr Cys Cys Ala Ala
    210                 215                 220

Gly Ala Ala Cys Cys Ala Gly Thr Thr Cys Thr Cys Cys Cys Thr Gly
225                 230                 235                 240

Ala Gly Gly Cys Thr Gly Ala Ala Cys Thr Cys Thr Gly Thr Gly Ala
                245                 250                 255

Cys Cys Gly Cys Cys Gly Cys Ala Gly Ala Cys Ala Cys Gly Gly Cys
            260                 265                 270

Cys Ala Thr Ala Thr Ala Thr Thr Ala Cys Thr Gly Thr Gly Cys Gly
        275                 280                 285

Gly Gly Ala Cys Thr Thr Gly Ala Cys Gly Thr Thr Ala Thr Gly
    290                 295                 300

Cys Cys Thr Gly Gly Ala Ala Cys Gly Ala Cys Gly Gly Ala Gly Gly 305 310 315 320

Thr Gly Ala Cys Cys Ala Cys Thr Gly Gly Gly Gly Cys Cys Ala Gly
325 330 335

Gly Gly Ala Ala Cys Cys Cys Thr Gly Gly Thr Cys Ala Gly Cys Gly
340 345 350

Thr Cys Cys Cys Cys Thr Cys Ala
355 360

<210> SEQ ID NO 212
<211> LENGTH: 336
<212> TYPE: PRT
<213> ORGANISM: Artificial Sequence
<220> FEATURE:
<223> OTHER INFORMATION: MZ2 light chain variable domain nucleotide sequence

<400> SEQUENCE: 212

Cys Ala Gly Thr Cys Thr Gly Thr Gly Cys Thr Gly Ala Cys Thr Cys
1 5 10 15

Ala Gly Cys Cys Ala Cys Cys Cys Thr Cys Ala Gly Cys Gly Thr Cys
20 25 30

Thr Gly Gly Gly Ala Cys Cys Cys Cys Cys Gly Gly Gly Cys Ala Gly
35 40 45

Ala Gly Gly Gly Thr Cys Thr Cys Cys Ala Thr Thr Thr Cys Thr Thr
50 55 60

Gly Thr Thr Cys Thr Gly Gly Ala Ala Gly Cys Ala Gly Cys Thr Cys
65 70 75 80

Cys Ala Ala Cys Cys Thr Cys Gly Gly Ala Ala Gly Gly Ala Ala Thr
85 90 95

Ala Cys Thr Cys Thr Gly Cys Ala Cys Thr Gly Gly Thr Ala Cys Cys
100 105 110

Ala Gly Cys Ala Ala Cys Thr Cys Cys Cys Ala Gly Gly Ala Ala Cys
115 120 125

Gly Gly Cys Cys Cys Cys Cys Ala Ala Ala Cys Thr Cys Cys Thr Cys
130 135 140

Ala Thr Cys Thr Ala Thr Ala Ala Thr Ala Ala Thr Ala Gly Thr Cys
145 150 155 160

Gly Gly Cys Gly Gly Cys Cys Cys Thr Cys Ala Gly Gly Gly Gly Thr
165 170 175

Cys Cys Cys Thr Gly Ala Ala Cys Gly Ala Thr Thr Cys Thr Cys Thr
180 185 190

Gly Gly Cys Thr Cys Cys Ala Ala Gly Thr Cys Thr Gly Gly Cys Ala
195 200 205

Cys Cys Thr Cys Ala Gly Cys Cys Thr Cys Cys Cys Thr Gly Gly Cys
210 215 220

Cys Ala Thr Cys Ala Gly Thr Gly Gly Gly Cys Thr Cys Cys Ala Gly
225 230 235 240

Thr Cys Thr Gly Ala Gly Gly Ala Thr Gly Ala Gly Gly Cys Thr Gly
245 250 255

Ala Thr Thr Ala Thr Thr Thr Cys Thr Gly Thr Gly Cys Ala Thr Cys
260 265 270

Ala Thr Gly Gly Gly Ala Thr Gly Ala Cys Ala Gly Cys Cys Thr Gly
275 280 285

Ala Ala Cys Gly Gly Cys Cys Thr Thr Thr Ala Thr Gly Thr Cys Thr
290 295 300

```
Thr Cys Gly Gly Ala Ala Cys Thr Gly Gly Ala Cys Cys Ala Ala
305                 310                 315                 320

Gly Gly Thr Cys Ala Cys Cys Gly Thr Cys Cys Thr Ala Cys Gly Thr
            325                 330                 335
```

<210> SEQ ID NO 213
<211> LENGTH: 120
<212> TYPE: PRT
<213> ORGANISM: Artificial Sequence
<220> FEATURE:
<223> OTHER INFORMATION: MZ2 heavy chain variable domain amino acid
      sequence

<400> SEQUENCE: 213

```
Gln Leu His Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Thr Gly Ser Thr Asn Tyr Asn Pro Ser Leu Lys
    50                  55                  60

Ser Arg Val Thr Ile Ser Val Asp Ala Ser Lys Asn Gln Phe Ser Leu
65                  70                  75                  80

Arg Leu Asn Ser Val Thr Ala Ala Asp Thr Ala Ile Tyr Tyr Cys Ala
                85                  90                  95

Gly Leu Asp Arg Tyr Ala Trp Asn Asp Gly Gly Asp His Trp Gly Gln
            100                 105                 110

Gly Thr Leu Val Ser Val Pro Ser
        115                 120
```

<210> SEQ ID NO 214
<211> LENGTH: 112
<212> TYPE: PRT
<213> ORGANISM: Artificial Sequence
<220> FEATURE:
<223> OTHER INFORMATION: MZ2 light chain variable domain amino acid
      sequence

<400> SEQUENCE: 214

```
Gln Ser Val Leu Thr Gln Pro Pro Ser Ala Ser Gly Thr Pro Gly Gln
1               5                   10                  15

Arg Val Ser Ile Ser Cys Ser Gly Ser Ser Asn Leu Gly Arg Asn
            20                  25                  30

Thr Leu His Trp Tyr Gln Gln Leu Pro Gly Thr Ala Pro Lys Leu Leu
        35                  40                  45

Ile Tyr Asn Asn Ser Arg Arg Pro Ser Gly Val Pro Glu Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ser Trp Asp Asp Ser Leu
                85                  90                  95

Asn Gly Leu Tyr Val Phe Gly Thr Gly Thr Lys Val Thr Val Leu Arg
            100                 105                 110
```

<210> SEQ ID NO 215
<211> LENGTH: 8
<212> TYPE: PRT
<213> ORGANISM: Artificial Sequence
<220> FEATURE:

```
<223> OTHER INFORMATION: MZ2 heavy chain CDR1 sequence

<400> SEQUENCE: 215

Gly Gly Ser Phe Ser Ser Tyr Tyr
1               5

<210> SEQ ID NO 216
<211> LENGTH: 7
<212> TYPE: PRT
<213> ORGANISM: Artificial Sequence
<220> FEATURE:
<223> OTHER INFORMATION: MZ2 heavy chain CDR2 sequence

<400> SEQUENCE: 216

Ile Tyr Tyr Thr Gly Ser Thr
1               5

<210> SEQ ID NO 217
<211> LENGTH: 16
<212> TYPE: PRT
<213> ORGANISM: Artificial Sequence
<220> FEATURE:
<223> OTHER INFORMATION: MZ2 heavy chain CDR3 sequence

<400> SEQUENCE: 217

Cys Ala Gly Leu Asp Arg Tyr Ala Trp Asn Asp Gly Gly Asp His Trp
1               5                   10                  15

<210> SEQ ID NO 218
<211> LENGTH: 8
<212> TYPE: PRT
<213> ORGANISM: Artificial Sequence
<220> FEATURE:
<223> OTHER INFORMATION: MZ2 light chain CDR1 sequence

<400> SEQUENCE: 218

Ser Ser Asn Leu Gly Arg Asn Thr
1               5

<210> SEQ ID NO 219
<211> LENGTH: 3
<212> TYPE: PRT
<213> ORGANISM: Artificial Sequence
<220> FEATURE:
<223> OTHER INFORMATION: MZ2 light chain CDR2 sequence

<400> SEQUENCE: 219

Asn Asn Ser
1

<210> SEQ ID NO 220
<211> LENGTH: 14
<212> TYPE: PRT
<213> ORGANISM: Artificial Sequence
<220> FEATURE:
<223> OTHER INFORMATION: MZ2 light chain CDR3 sequence

<400> SEQUENCE: 220

Cys Ala Ser Trp Asp Asp Ser Leu Asn Gly Leu Tyr Val Phe
1               5                   10

<210> SEQ ID NO 221
<211> LENGTH: 133
<212> TYPE: PRT
<213> ORGANISM: Artificial Sequence
<220> FEATURE:
<223> OTHER INFORMATION: EDE2-A11 heavy chain variable domain amino acid
```

-continued sequence

<400> SEQUENCE: 221

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
            20                  25                  30

Trp Met His Trp Val Arg Gln Ala Pro Gly Lys Gly Leu Val Trp Val
        35                  40                  45

Ser Arg Ile Asn Ser Asp Gly Ser Thr Arg Asn Tyr Ala Asp Phe Val
    50                  55                  60

Lys Gly Arg Phe Thr Ile Ser Arg Asp Asn Ala Glu Asn Thr Leu Tyr
65                  70                  75                  80

Leu Glu Met Asn Ser Leu Thr Ala Asp Asp Thr Ala Val Tyr Tyr Cys
                85                  90                  95

Val Arg Asp Gly Val Arg Phe Tyr Tyr Asp Ser Thr Gly Tyr Tyr Pro
            100                 105                 110

Asp Ser Phe Phe Lys Tyr Gly Met Asp Val Trp Gly Gln Gly Thr Thr
        115                 120                 125

Val Thr Val Ser Ser
    130

<210> SEQ ID NO 222
<211> LENGTH: 105
<212> TYPE: PRT
<213> ORGANISM: Artificial Sequence
<220> FEATURE:
<223> OTHER INFORMATION: EDE2-A11 light chain variable domain amino acid
      sequence

<400> SEQUENCE: 222

Gln Ser Val Leu Thr Gln Pro Val Ser Val Ser Gly Ser Pro Gly Gln
1               5                   10                  15

Ser Ile Thr Ile Ser Cys Thr Gly Thr Ser Ser Asn Ala Asp Thr Tyr
            20                  25                  30

Asn Leu Val Ser Trp Tyr Gln Gln Arg Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Ala Ser Lys Ser Ala Thr Ala Ala Ser Leu Thr Ile Ser Gly Leu
65                  70                  75                  80

Gln Pro Glu Asp Glu Ala Asp Tyr Tyr Cys Cys Ser Tyr Ala Thr Ser
                85                  90                  95

Arg Thr Leu Val Phe Gly Gly Gly Thr
            100                 105

<210> SEQ ID NO 223
<211> LENGTH: 5
<212> TYPE: PRT
<213> ORGANISM: Artificial Sequence
<220> FEATURE:
<223> OTHER INFORMATION: EDE2-A11 heavy chain CDR1 sequence

<400> SEQUENCE: 223

Asn His Trp Met His
1               5

<210> SEQ ID NO 224
<211> LENGTH: 17

<212> TYPE: PRT
<213> ORGANISM: Artificial Sequence
<220> FEATURE:
<223> OTHER INFORMATION: EDE2-A11 heavy chain CDR2 sequence

<400> SEQUENCE: 224

Arg Ile Asn Ser Asp Gly Ser Thr Arg Asn Tyr Ala Asp Phe Val Lys
1               5                   10                  15
Gly

<210> SEQ ID NO 225
<211> LENGTH: 24
<212> TYPE: PRT
<213> ORGANISM: Artificial Sequence
<220> FEATURE:
<223> OTHER INFORMATION: EDE2-A11 heavy chain CDR3 sequence

<400> SEQUENCE: 225

Asp Gly Val Arg Phe Tyr Tyr Asp Ser Thr Gly Tyr Tyr Pro Asp Ser
1               5                   10                  15
Phe Phe Lys Tyr Gly Met Asp Val
            20

<210> SEQ ID NO 226
<211> LENGTH: 14
<212> TYPE: PRT
<213> ORGANISM: Artificial Sequence
<220> FEATURE:
<223> OTHER INFORMATION: EDE2-A11 light chain CDR1 sequence

<400> SEQUENCE: 226

Thr Gly Thr Ser Ser Asn Ala Asp Thr Tyr Asn Leu Val Ser
1               5                   10

<210> SEQ ID NO 227
<211> LENGTH: 7
<212> TYPE: PRT
<213> ORGANISM: Artificial Sequence
<220> FEATURE:
<223> OTHER INFORMATION: EDE2-A11 light chain CDR2 sequence

<400> SEQUENCE: 227

Glu Gly Thr Lys Arg Pro Ser
1               5

<210> SEQ ID NO 228
<211> LENGTH: 10
<212> TYPE: PRT
<213> ORGANISM: Artificial Sequence
<220> FEATURE:
<223> OTHER INFORMATION: EDE2-A11 light chain CDR3 sequence

<400> SEQUENCE: 228

Cys Ser Tyr Ala Thr Ser Arg Thr Leu Val
1               5                   10

<210> SEQ ID NO 229
<211> LENGTH: 115
<212> TYPE: PRT
<213> ORGANISM: Artificial Sequence
<220> FEATURE:
<223> OTHER INFORMATION: Ab513 heavy chain amino acid sequence

<400> SEQUENCE: 229

Gln Val Gln Leu Val Gln Ser Gly Ala Glu Val Lys Lys Pro Gly Ala
1               5                   10                  15

```
Ser Val Lys Val Ser Cys Lys Ala Gly Phe Asn Ile Lys Asp Val Tyr
            20                  25                  30

Met Ser Trp Val Arg Gln Ala Pro Glu Gln Gly Leu Glu Trp Met Gly
        35                  40                  45

Arg Ile Asp Pro Glu Asn Gly Asp Thr Lys Tyr Asp Pro Lys Leu Gln
 50                  55                  60

Gly Arg Val Thr Met Thr Ala Asp Thr Ser Asn Thr Ala Tyr Met
 65                  70                  75                  80

Glu Leu Arg Ser Leu Arg Ser Asp Asp Thr Ala Val Tyr Tyr Cys Ala
                85                  90                  95

Arg Gly Trp Glu Gly Phe Ala Tyr Trp Gly Gln Gly Thr Leu Val Thr
            100                 105                 110

Val Ser Ser
        115

<210> SEQ ID NO 230
<211> LENGTH: 111
<212> TYPE: PRT
<213> ORGANISM: Artificial Sequence
<220> FEATURE:
<223> OTHER INFORMATION: Ab513 light chain amino acid sequence

<400> SEQUENCE: 230

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Asn Val Asp Lys Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Glu Leu Gln Trp Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Arg Ser Asn
                85                  90                  95

Glu Val Pro Trp Thr Phe Gly Gln Gly Thr Lys Leu Glu Ile Lys
            100                 105                 110

<210> SEQ ID NO 231
<211> LENGTH: 4
<212> TYPE: PRT
<213> ORGANISM: Artificial Sequence
<220> FEATURE:
<223> OTHER INFORMATION: Ab513 heavy chain CDR1 sequence

<400> SEQUENCE: 231

Val Tyr Met Ser
1

<210> SEQ ID NO 232
<211> LENGTH: 17
<212> TYPE: PRT
<213> ORGANISM: Artificial Sequence
<220> FEATURE:
<223> OTHER INFORMATION: Ab513 heavy chain CDR2 sequence

<400> SEQUENCE: 232

Arg Ile Asp Pro Glu Asn Gly Asp Thr Lys Tyr Asp Pro Lys Leu Gln
1               5                   10                  15
```

```
Gly

<210> SEQ ID NO 233
<211> LENGTH: 7
<212> TYPE: PRT
<213> ORGANISM: Artificial Sequence
<220> FEATURE:
<223> OTHER INFORMATION: Ab513 heavy chain CDR3 sequence

<400> SEQUENCE: 233

Gly Trp Glu Gly Phe Ala Tyr
1               5

<210> SEQ ID NO 234
<211> LENGTH: 15
<212> TYPE: PRT
<213> ORGANISM: Artificial Sequence
<220> FEATURE:
<223> OTHER INFORMATION: Ab513 light chain CDR1 sequence

<400> SEQUENCE: 234

Arg Ala Ser Glu Asn Val Asp Lys Tyr Gly Asn Ser Phe Met His
1               5                   10                  15

<210> SEQ ID NO 235
<211> LENGTH: 7
<212> TYPE: PRT
<213> ORGANISM: Artificial Sequence
<220> FEATURE:
<223> OTHER INFORMATION: Ab513 light chain CDR2 sequence

<400> SEQUENCE: 235

Arg Ala Ser Glu Leu Gln Trp
1               5

<210> SEQ ID NO 236
<211> LENGTH: 9
<212> TYPE: PRT
<213> ORGANISM: Artificial Sequence
<220> FEATURE:
<223> OTHER INFORMATION: Ab513 light chain CDR3 sequence

<400> SEQUENCE: 236

Gln Arg Ser Asn Glu Val Pro Trp Thr
1               5
```

POTENT ZIKA VIRUS-SPECIFIC AND CROSS-NEUTRALIZING MONOCLONAL ANTIBODIES TO ZIKA AND DENGUE VIRUSES FOLLOWING ZIKV INFECTION OR VACCINATION

STATEMENT REGARDING FEDERALLY SPONSORED RESEARCH OR DEVELOPMENT

Part of the work performed during development of this invention utilized U.S. Government funds from the Department of Defense (W81XWH-07-2-0067 and 0130602D16) and the National Institutes of Health (W81XWH-07-2-0067). The U.S. Government has certain rights in this invention.

REFERENCE TO SEQUENCE LISTING

A computer readable text file entitled "Sequence Listing_044508-5089WO," created on or about Apr. 22, 2019, with a file size of about 111 kb contains the sequence listing for this application and is hereby incorporated by reference in its entirety.

BACKGROUND OF THE INVENTION

Zika virus (ZIKV) has caused significant worldwide disease. In 2016, ZIKV infected more than 500,000 people in Central and South America, and more than 5,000 people in the United States. Although the majority of ZIKV infections are asymptomatic or cause only a mild illness, ZIKV has become a significant public health concern due to its link with congenital neurological complications such as microcephaly and Guillain-Barre syndrome.

ZIKV was first isolated in 1947 from a febrile sentinel rhesus monkey in Uganda and is a member of the Flaviviridae family, which also includes West Nile virus (WNV), Yellow Fever virus (YFV), Japanese Encephalitis virus (JEV) and four dengue virus (DENV) serotypes (Dick et al. 1947). The first human ZIKV infection was observed in 1952. ZIKV is usually transmitted by *Aedes aegypti* mosquitoes, but can also spread by blood transfusions, sexual contact, and perinatal transmission. ZIKV. While the majority of ZIKV infections worldwide occur in DENV-endemic areas, most (97%) U.S. cases occurred in travelers returning from affected areas.

Identifying neutralizing monoclonal antibodies (mAbs) and their epitopes is a critical step towards understanding protective antibody responses, and further enables the development of antibody-based therapies and vaccines. Most neutralizing antibodies bind to the envelope (E) glycoprotein, which mediates ZIKV attachment to cells, cell entry, and fusion of the viral envelope with endosomal membranes. The E glycoprotein consists of three domains (DI, DII, and DIII) that are connected by flexible hinges. The surface of a mature virion has exactly 90 E glycoprotein homodimers. Protomer-protomer interactions between homodimers facilitate the formation of a sophisticated icosahedral symmetry on the surface of the virus, with dimeric, trimeric, and pentameric vertices (Yu, 2017). Critical targets of ZIKV neutralizing antibodies are mainly conformational and quaternary epitopes that require higher-order structures on intact virions not fully available on individual E protomers (Wu, 2017).

Analysis of mAbs from ZIKV-infected humans and mice demonstrated that recognition of different domains is associated with differences in neutralizing activity in vitro and protective capacity in animal models. In general, mAbs against DIII were Zika-specific, highly neutralizing and protective. In addition, DI/II antibodies developed early in infection, whereas DIII antibodies developed later and were durably maintained (Yu, 2017).

The ZIKV E protein shares a considerable amount of sequence and structural similarity with DENV envelope (E) glycoprotein, resulting in immunological cross-reactivity. The majority of prior studies isolating monoclonal antibodies and defining their structural epitopes have focused on individuals with prior flavi-exposure (Collins, 2017). These individuals have B cells primed from pre-existing DENV immune responses. Flavivirus-exposure primes B cell responses and impacts the specificity of antibody responses to ZIKV in subsequent infection through original antigenic sin (Walker, 2017). Since DENV is also endemic in many areas with ZIKV infection, determining how previous DENV immunity affects subsequent ZIKV infection has been an important area of research.

Less is known about the antibodies targeting ZIKV E glycoprotein in flavi-naïve individuals. Analysis of the B cell antibody repertoire in a flavi-naïve human indicated that >60% of B cell responses were to unknown regions of the E glycoprotein (Walker, 2017). Therefore, further studies are needed to delineate antibody responses in flavivirus naïve ZIKV infection. Understanding immune responses to Zika infection without prior flavi-exposure is of vital importance for travelers not living in endemic areas.

For humans, the induction of high titer neutralizing antibodies is a major goal of vaccination. Rapid vaccine development led to a number of candidates and modalities capable of eliciting high titers of ZIKV-neutralizing antibodies (reviewed in Morabito, 2017). However, these prior studies did not explain how ZIKV vaccination affects humans with prior exposure to DENV.

Therefore, the development of neutralizing or inhibiting antibodies and antibody fragments against ZIKV and DENV could have important implications for prophylaxis and passive immunotherapy. In addition, the characterization of the epitopes of the antibodies and antibody fragments and the mechanisms of neutralization and inhibition of ZIKV and DENV infection could provide helpful information for development of candidate vaccines and drugs. Finally, such antibodies and antibody fragments could also be used for diagnosis and as research reagents.

SUMMARY OF THE INVENTION

Non-human primates (NHPs) infected with ZIKV developed high titers of neutralizing antibody responses (McCracken, 2017). This application describes the isolation of eleven neutralizing antibodies from a convalescent ZIKV infected rhesus macaque using a unique B cell sorting strategy with whole ZIKV virions. All NHP mAbs were Zika-specific, originated from different B cell lineages, had low somatic hypermutation (SHM), and defined 4 new classes of antibodies targeting cross-protomer antigenic epitopes on the viral envelope. High-resolution crystal structures revealed targeting of cross-protomer epitopes at the inter- and intra-E-dimer interfaces, including a newly described E Tetramer Epitope (ETE). The three other antibody classes recognized different conformational epitopes and potently neutralized Zika on par with some of the most potent Zika-neutralizing mAbs described to date. In addition, in vivo passive transfer studies of these mAbs in mice demonstrated full protection against ZIKV infection. These are the first NHP monoclonal antibodies described to date, but the epitopes targeted were prevalent in both macaque and human ZIKV infections with and without flavi-priming. Overall, these results demonstrate targeting of the viral envelope by several different classes of Zika-specific neutralizing antibodies with distinct modes of recognition that have therapeutic potential. The findings described herein indicate that potent ZIKV neutralizing antibodies can be generated during acute infection in absence of pre-existing flavivirus immunity, which has broad implications for vaccine design.

Additional studies showed that vaccination of a DENV-experienced human with ZIKV purified inactivated vaccine (ZPIV) elicited potent cross-ZIKV-DENV immune responses after a single immunization. Using a unique sorting strategy, potently neutralizing antibodies were isolated and characterized, including one termed MZ4, which targeted a novel site of vulnerability. MZ4 neutralized ZIKV and DENV-2 with half-maximum inhibitory concentrations (IC50) in the low ng/ml range. Biophysical mapping and structural studies demonstrated that MZ4 binds to a conserved epitope centered on the E domain I/III linker region. MZ4 protected mice from viraemia following ZIKV challenge with a median effective dose (ED50) of 0.1275 mgkg-1. In addition, only one ZPIV vaccination was required to achieve potent MZ4-like mAbs. These data demonstrate that ZPIV vaccination in DENV experienced individuals can elicit rapid potent neutralizing responses against ZIKV and boosts pre-existing immunity through recall of protective cross-neutralizing DENV immune responses, which have significant implications for flavivirus vaccine design and prophylactic therapeutics.

The present application is directed to novel peptides, antibodies and antibody fragments that bind ZIKV. The present application is also directed to methods of using the novel peptides, antibodies and antibody fragments, such as methods on inhibiting ZIKV infection, methods of treatment, methods of prevention, diagnostic methods, and pharmaceutical compositions.

The present application also relates to nucleic acids encoding the novel peptides, antibodies and antibody fragments of the present application, including vectors and host cells containing the nucleic acids.

The present application also relates to a method of isolating an antibody that binds to cross-protomer epitopes of a virus. In this method, peripheral blood mononuclear cells from an infected primate are contacted first with the virus and then with a fluorescently-labeled antibody that binds the virus. Polynucleotides encoding the heavy and light chains of an antibody that binds to cross-protomer epitopes of a virus are isolated from the fluorescent PBMC. The polynucleotides are then used to express the antibody in a host cell.

In certain embodiments, the application relates to an antibody or fragment thereof comprising the CDR sequences of any row of Table 1. In certain embodiments, the application relates to an antibody or fragment thereof that selectively binds Zika virus, wherein the heavy chain CDR1 sequence differs from SEQ ID NO: 5 by four or less substitutions, wherein the heavy chain CDR2 sequence differs from SEQ ID NO: 6 by two or less substitutions, wherein the heavy chain CDR3 sequence differs from SEQ ID NO: 7 by five or less substitutions, wherein the light chain CDR1 sequence differs from SEQ ID NO: 8 by one or less substitutions, wherein the light chain CDR2 sequence differs from SEQ ID NO: 9 by three or less substitutions, and wherein the light chain CDR3 sequence differs from SEQ ID NO: 10 by one or less substitutions.

In certain embodiments, the application relates to an antibody or antibody fragment comprising the CDR sequences of any row of Table 1 that inhibits Zika virus infection, Dengue virus infection, Dengue virus serotype 2 infection, Dengue virus serotype 3 infection, Zika virus transmission from a pregnant female to her unborn child, and/or sexual transmission of a flavivirus.

In certain embodiments, the application relates to an antibody or antibody fragment comprising the CDR sequences from any row of Table 1 with an ED50 for neutralizing Zika infection of less than less than 10 mg kg-1, less than 5 mg kg-1, less than 1 mg kg-1, less than 0.5 mg kg-1, less than 0.2 mg kg-1, less than 0.1 mg kg-1, less than 0.05 mg kg-1, less than 0.02 mg kg-1, or less than 0.01 mg kg-1.

In certain embodiments, the application relates to an antibody or antibody fragment comprising the CDR sequences from any row of Table 1 with an IC50 for neutralizing Zika infection of less than 10 µM, less than 5 µM, less than 2 µM, less than 1 µM, less than 500 nM, less than 200 nM, or less than 100 nM, and 100 ag/ml of said antibody or antibody fragment does not neutralize infection by a flavivirus selected from the group of Dengue virus, Japanese Encephalitis virus, West Nile virus, or Yellow Fever virus.

In certain embodiments, the application relates to an antibody or antibody fragment comprising the CDR sequences from any of rows 1-11 of Table 1 and having an equilibrium dissociation constant (KD) is in the range from $10^{-7}$ to $10^{-9}$ molar and/or a (KD) of less than $10^{-7}$ molar.

In certain embodiments, the application relates to an Fd fragment, an Fab fragment, a single chain variable fragment, and/or a human or humanized antibody or antibody fragment comprising the CDR sequences of any row of Table 1.

In certain embodiments, the application relates to a polynucleotide comprising a nucleotide sequence that encodes an antibody or antibody fragment comprising the CDR sequences from any row of Table 1; a host cell comprising a polynucleotide comprising a nucleotide sequence that encodes an antibody or antibody fragment comprising the CDR sequences from any row of Table 1; and/or a method of isolating an antibody from a host cell comprising a polynucleotide comprising a nucleotide sequence that encodes an antibody or antibody fragment comprising the CDR sequences from any row of Table 1.

In certain embodiments, the application relates to a pharmaceutical composition comprising a pharmaceutically acceptable carrier and an antibody or antibody fragment comprising the CDR sequences of any row of Table 1.

In certain embodiments, the application relates to a method for the prevention or treatment of flavivirus infection, a method for inhibiting or preventing transmission of a flavivirus infection from a pregnant female to her unborn child, a method for inhibiting or preventing sexual transmission of a flavivirus infection, and/or a method of reducing the likelihood of a subject developing a disease caused by flavivirus, wherein the method comprises administering a pharmaceutical composition comprising a pharmaceutically acceptable carrier and an antibody or antibody fragment comprising the CDR sequences of any of rows 1-11 of Table 1, and wherein the flavivirus may be Zika virus, Dengue virus, Dengue virus serotype 2, Dengue virus serotype 3, West Nile virus, and/or Japanese Encephalitis virus.

In other embodiments, the application relates to a method for the prevention or treatment of Zika virus infection, a method for inhibiting or preventing transmission of a Zika virus infection from a pregnant female to her unborn child, a method for inhibiting or preventing sexual transmission of a Zika virus infection, and/or a method of reducing the likelihood of a subject developing a disease caused by flavivirus, wherein the method comprises administering a pharmaceutical composition comprising a pharmaceutically acceptable carrier and an antibody or antibody fragment comprising the CDR sequences of any of rows 12-21 of Table 1, and wherein the method is specific for Zika virus and has no effect on Dengue virus, Dengue virus serotype 2, Dengue virus serotype 3, West Nile virus, and/or Japanese Encephalitis virus.

In certain embodiments, the application relates to a method of detecting the presence of a flavivirus in a biological sample, the method comprising contacting an antibody or antibody fragment comprising the CDR sequences of any of rows 1-11 of Table 1 with the biological sample and detecting the binding of the antibody or antibody fragment to a flavivirus, wherein the flavivirus is Zika virus, Dengue virus, Dengue virus serotype 2, Dengue virus serotype 2, West Nile virus and/or Japanese Encephalitis virus.

In other embodiments, the application relates to a method of detecting the presence of Zika virus in a biological sample, the method comprising contacting an antibody or antibody fragment comprising the CDR sequences of any of rows 12-21 of Table 1 with the biological sample and detecting the binding of the antibody or antibody fragment to a Zika virus, and wherein the method is specific to Zika virus and does not detect any other flavivirus including Dengue virus, Dengue virus serotype 2, Dengue virus serotype 2, West Nile virus and/or Japanese Encephalitis virus.

In certain embodiments, the application relates to a kit for detecting the presence of a flavivirus such as Zika virus, Dengue virus, Dengue virus serotype 2, Dengue virus serotype 2, West Nile virus and/or Japanese Encephalitis virus in a biological sample comprising an antibody or fragment thereof comprising the CDR sequences of any of rows 1-11 of Table 1.

In other embodiments, the application relates to a kit for detecting the presence of a Zika virus in a biological sample comprising an antibody or fragment thereof comprising the CDR sequences of any of rows 12-21 of Table 1, wherein the kit does not detect any other flavivirus including Dengue virus, Dengue virus serotype 2, Dengue virus serotype 2, West Nile virus and/or Japanese Encephalitis virus.

In certain embodiments, the application relates to a method of diagnosing infection by a flavivirus, the method comprising obtaining a biological sample for a subject at risk of flavivirus infection; contacting the biological sample with an antibody or antibody fragment comprising the CDR sequences of any of rows 1-11 of Table 1; and determining if the antibody or antibody fragment has bound to a flavivirus antigen; wherein binding of the antibody or antibody fragment to a flavivirus antigen indicates that the subject is infected with flavivirus; and wherein the flavivirus may be Zika virus, Dengue virus, Dengue virus serotype 2, Dengue virus serotype 3, West Nile virus, and/or Japanese Encephalitis virus.

In other embodiments, the application relates to a method of diagnosing infection by a Zika virus, the method comprising obtaining a biological sample for a subject at risk of flavivirus infection; contacting the biological sample with an antibody or antibody fragment comprising the CDR sequences of any of rows 12-21 of Table 1; and determining if the antibody or antibody fragment has bound to a Zika virus antigen; wherein binding of the antibody or antibody fragment to a Zika virus antigen indicates that the subject is infected with Zika virus.

In certain embodiments, the application relates to a method of detecting a latent infection by a flavivirus, the method comprising obtaining a biological sample for a subject at risk of flavivirus infection; stimulating the biological sample to induce viral outgrowth; contacting the biological sample with an antibody or antibody fragment comprising the CDR sequences of any of rows 1-11 of Table 1; and determining if the antibody or antibody fragment has bound to a flavivirus antigen; wherein binding of the antibody or antibody fragment to a flavivirus antigen indicates that the subject is infected with a flavivirus; and wherein the flavivirus may be Zika virus, Dengue virus, Dengue virus serotype 2, Dengue virus serotype 3, West Nile virus, and/or Japanese Encephalitis virus.

In other embodiments, the application relates to a method of detecting a latent infection by a Zika virus, the method comprising obtaining a biological sample for a subject at risk of flavivirus infection; stimulating the biological sample to induce viral outgrowth; contacting the biological sample with an antibody or antibody fragment comprising the CDR sequences of any of rows 12-21 of Table 1; and determining if the antibody or antibody fragment has bound to a Zika virus antigen; wherein binding of the antibody or antibody fragment to a Zika virus antigen indicates that the subject is infected with a Zika virus.

In certain embodiments, the application relates to a method of inducing immunity to a flavivirus in a subject at risk of flavivirus infection comprising injecting a single dose of Zika virus purified inactivated vaccine to the subject, wherein the subject was previously infected by a flavivirus, and wherein the flavivirus may be Zika virus, Dengue virus, Dengue virus serotype 2, Dengue virus serotype 3, West Nile virus, and/or Japanese Encephalitis virus.

In certain embodiments, the application relates to a method of measuring the efficacy of a flavivirus vaccine comprising contacting the vaccine with an antibody or antibody fragment comprising the CDR sequences of any of rows 1-11 of Table 1.

In other embodiments, the application relates to a method of measuring the efficacy of a Zika virus vaccine comprising contacting the vaccine with an antibody or antibody fragment comprising the CDR sequences of any of rows 12-21 of Table 1.

In certain embodiments, the application relates to an antibody or fragment thereof that binds to the DI-DIII linker domain of a Zika virus. The antibody or fragment thereof may have an MN50 in a 100 PFU Zika virus microneutralization assay of 100 ng, 50 ng, 20 ng, 10 ng, 5 ng, 2 ng, 1 ng, 0.5 ng, 0.2 ng or 0.1 ng. Binding to Zika Virus of the antibody or fragment thereof may be reduced by at least 70% when Zika virus E glycoprotein residue Tyrosine 305 is substituted with alanine.

In certain embodiments, the application relates to a method for isolating an antibody that binds to cross-protomer epitopes of a virus comprising, (a) immunizing a primate with an intact virus, (b) isolating peripheral blood mononuclear cells (PBMCs) from the primate, (c) contacting the PBMCs with intact virus to create PBMC-virus complexes, (d) contacting the PBMC-virus complexes with a fluorescently-labeled antibody that binds the virus, (e) isolating a fluorescent PBMC, (f) isolating polynucleotides encoding the heavy and light chains of an antibody from the fluorescent PBMC, (g) expressing the isolated polynucleotides in a host cell, and (h) isolating an antibody expressed by the host cell.

BRIEF DESCRIPTION OF THE DRAWINGS

The accompanying drawings, which are included to provide a further understanding of the disclosure, are incorporated in and constitute a part of this specification. The drawings illustrate embodiments of the disclosure and, together with the detailed description, serve to explain the principles of the disclosure. No attempt is made to show structural details of the disclosure in more detail than may be necessary for a fundamental understanding of the disclosure and various ways in which it may be practiced.

Figures 4A, 4B:
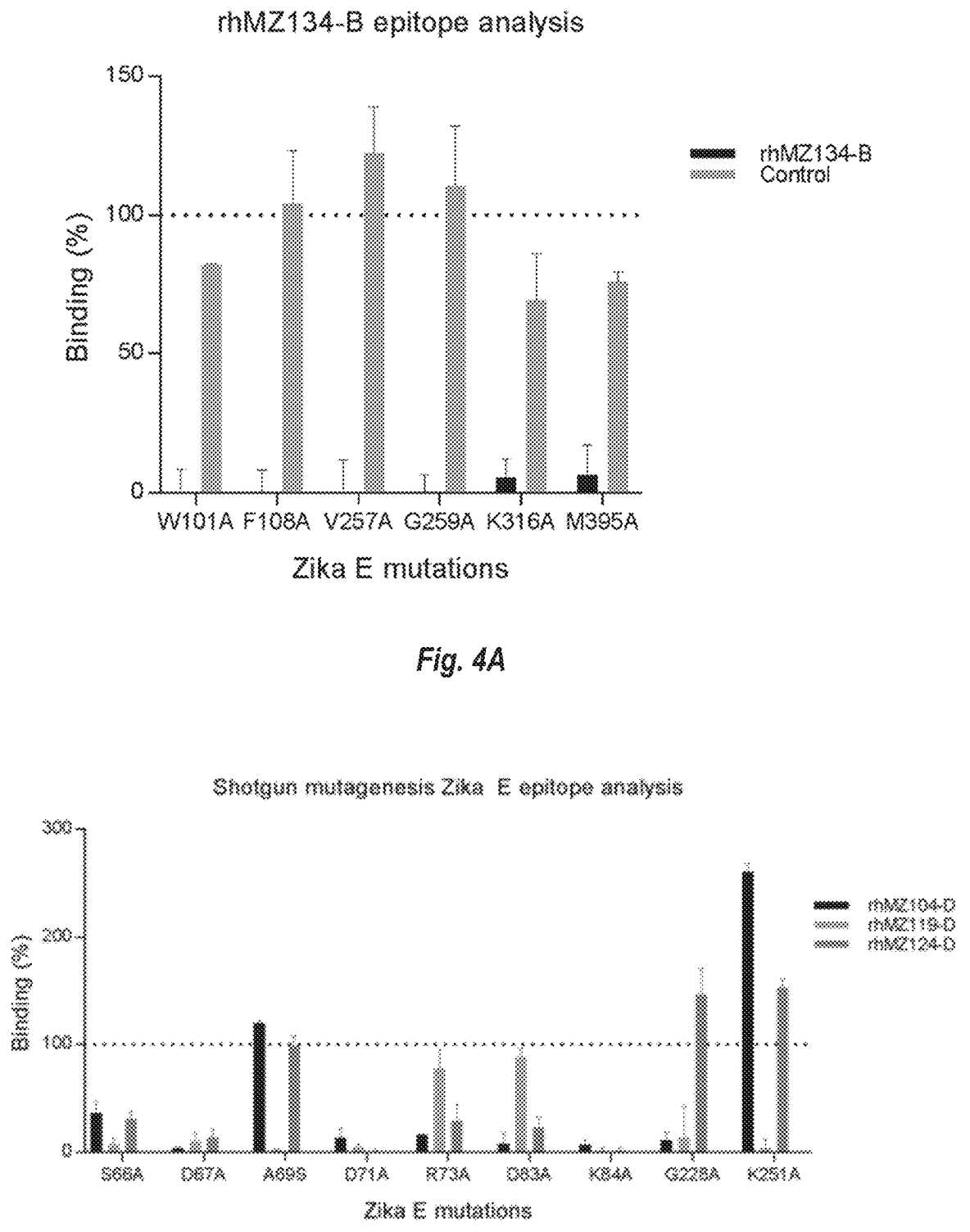

FIG. 4. rhMZ antibody epitope mapping. (A) Shotgun mutagenesis epitope mapping of ZIKV E to identify critical residues that effect rhMZ134-B antibody binding. (B) Shotgun mutagenesis epitope mapping data for group D antibodies. The average of two experiments is plotted with standard deviation indicated by error bars.

FIG. 18. Asymmetric unit components of rhMZ antibody ZIKV E complex structures. (A) The asymmetric unit of the rhMZ107-B ZIKV E complex contains four rhMZ107-B Fv molecules in complex with four ZIKV E protomers. (B) The asymmetric unit of the rhMZ100-C ZIKV E complex contains two rhMZ100-C Fab molecules and two ZIKV E dimers. (C) The asymmetric unit of the rhMZ104-D ZIKV E complex contains one rhMZ104-D Fab, one rhMZ104-D Fv, and a single ZIKV E dimer.

FIG. 26. A single ZPIV vaccination induces broad neutralization responses and elicits MZ2, a potent MZ4-like antibody. a, b, Plasma binding and neutralization activities of donor #00015 and flavivirus-naïve donors. a, Polyclonal binding and neutralizing responses to ZIKV and DENV-2 in donor #00015 (red). Binding responses to the indicated E protein (nM) were measured after 900 s association time by BLI. and flavivirus-naïve donors (blue, average of 5 donors) plasma measured by BLI. Data are mean values±SEM calculated from two independent experiments. Differences in neutralization titers between week 0 and 2 were statistically significant (Wilcoxon matched-pairs test). b, Neutralization activities (FowNT) observed in plasma against ZIKV and all 4 DENV serotypes. Shown are reciprocal dilution at which 50% of neutralization (ID50) is achieved. Flavivirus-naïve donor plasmas were only tested against ZIKV and DENV-2. Data are mean values±SEM calculated from two independent experiments performed in triplicate. Dotted line indicates lower limit of detection. c, Phylogenetic tree of MZ4 and the week 2 mAb, MZ2 VH sequences rooted on the germ line sequence. d, MZ2 shotgun mutagenesis epitope mapping. Residues critical for binding to ZIKV (black check mark) and DENV-2 (red check mark) prM/E are indicated. e, Binding and neutralization characteristics of MZ2. f, g, Neutralization activities (FowNT) of MZ2 and MZ4 against ZIKV (Brazil/2015) (f), DENV-2 (S16803) (g). Shown are neutralization curves obtained by 2-fold serial dilutions of the indicated antibodies and fitted using a 4-parameter logistic regression model. Data are mean±SEM calculated from at least two-independent experiments performed in triplicate. The concentrations (ng/ml) at which 50% neutralization is observed are indicated in parentheses next to antibody names.

FIG. 35. Design and biochemical characterization of bi-specific tetravalent flavivirus neutralizing antibodies. (A) Schematic of Bi-specific tetravalent type B antibodies. Two examples are shown (i) BTB-A11-MZ4 and (ii) BTB-MZ20-MZ4. (B) BTB-A11-MZ4 design schematic, SDS-PAGE profile (reduced and non-reduced), and gel filtration purification profile. (C) BTB-MZ20-MZ4 design schematic, SDS-PAGE profile following expression in 293 Expi cells, and gel filtration profile.

FIG. 37. Design and biochemical characterization of bi-specific bivalent flavivirus neutralizing antibodies. (A) Schematic of Bi-specific bivalent Heavy chain-only knob in hole multi-specific antibodies. Four examples are shown on the left of possible combinations. In a given BB antibody, two chains are combined with the cartoon (right side) indicating the dual specificity and knob in hole design. (B) Schematic of Bi-specific bivalent Cross-Mab knob in hole multi-specific antibodies. An example is shown on the left of combinations e.g. Ab513 with MZ4, with a cartoon (right side) indicating the dual specificity and knob in hole design.

DETAILED DESCRIPTION OF THE INVENTION

Figure 1A:
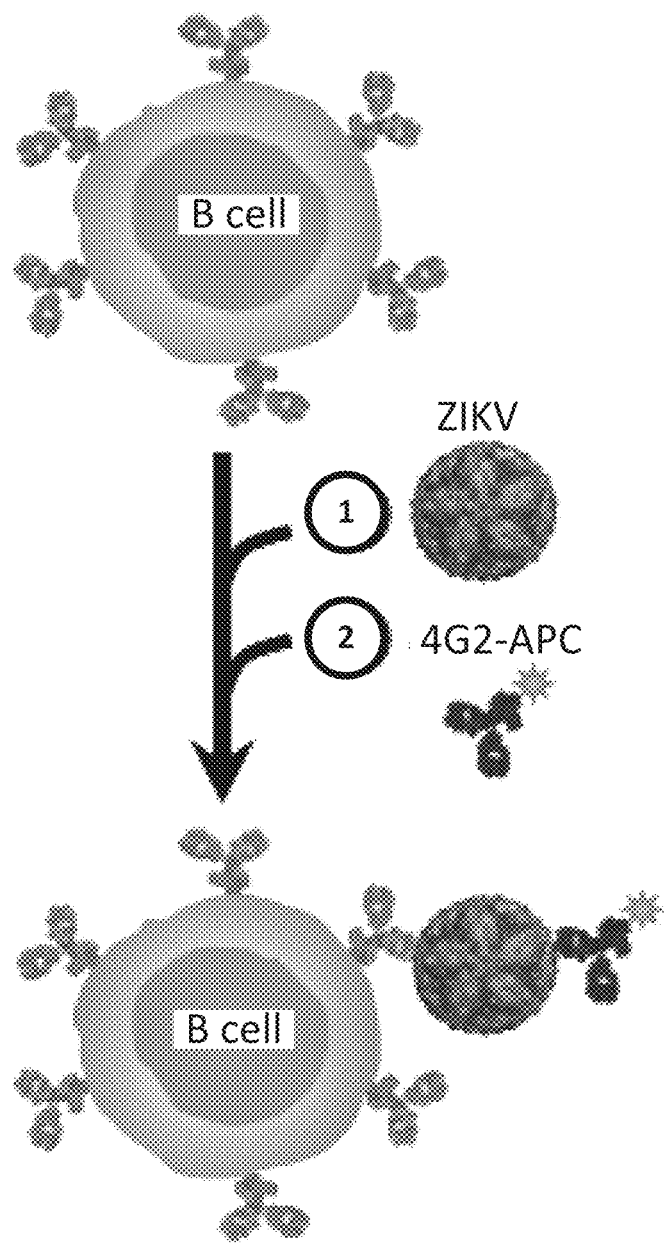
FIG. 1. Isolation of ZIKV reactive antibodies from a flavivirus naïve ZIKV-infected macaque using whole ZIKV. (A) Schematic of the sequential sorting strategy of ZIKV-specific B cells by (1) incubation of PBMCs with unlabeled whole ZIKV followed by (2) incubation with fusion-loop targeted 4G2-APC antibody-conjugate. (B) Isolation of ZIKV reactive activated B cells from peripheral blood of animal 10U032 at 14 days post-infection. Flow cytometry gates show the percentage of cells identified for each phenotypic population. $CD19^+CD38^+4G2^+$ ZIKV-specific B cells that were sorted and sequenced are shown in the last gate, with cells from which the neutralizing antibodies were isolated are labeled with the matching antibody number. (C) Gene usage and characteristics of isolated mAbs that bound to ZIKV sE using Biolayer Interference (BLI). V(D)J assignments were performed using IgBLAST. Antibodies positive in the ZIKV (PRVABC59) micro-neutralization screen are highlighted in gray.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

An aspect of the present application relates to novel peptides as set forth in Table 1. The terms "peptide," "polypeptide" and "protein" are used interchangeably herein. In particular, the present invention provides for peptides comprising amino acid sequences at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the specified amino acid sequences.

In other embodiments, the present application provides for peptides that consist essentially of, or consist of an amino acid sequence at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the specified amino acid sequences in Table 1. In other embodiments, the present invention provides polypeptides with CDR sequences that differ from the CDR sequences of table 1 by 0, 1, 2, 3, 4, 5, or 6 amino acids.

In certain select embodiments of the present application, the peptides of the present application comprise, consist essentially of, or consist of an amino acid sequence that includes but is not limited to the amino acid sequences referred to in Table 1.

methionine (M), asparagine (N), or glutamine (Q). In additional select embodiments of the present invention, residue X4 can be phenylalanine (F), histidine (H), tryptophan (W), or tyrosine (Y). In additional select embodiments of the present invention, residue X5 can be serine (S), cysteine (C), threonine (T), methionine (M), asparagine (N), or glutamine (Q). In additional select embodiments of the present invention, residue X6 can be serine (S), cysteine (C), threonine (T), methionine (M), asparagine (N), or glutamine (Q). In additional select embodiments of the present invention, residue X7 can be aspartic acid (D), glutamic acid (E), lysine (K), or arginine (R). In additional select embodiments of the

TABLE 1 sequence identifiers of selected embodiments of the present invention

| | | Variable domain polynucleotide sequence | | Variable domain amino acid sequence | | Heavy Chain CDR | | | Light Chain CDR | | |
|---|---|---|---|---|---|---|---|---|---|---|---|
| Row | Antibody | Heavy Chain | Light Chain | Heavy Chain | Light Chain | CDR1 | CDR2 | CDR3 | CDR1 | CDR2 | CDR3 |
| 1 | rhMZ100 | 1 | 2 | 3 | 4 | 5 | 6 | 7 | 8 | 9 | 10 |
| 2 | rhMZ101 | 11 | 12 | 13 | 14 | 15 | 16 | 17 | 18 | 19 | 20 |
| 3 | rhMZ103 | 21 | 22 | 23 | 24 | 25 | 26 | 27 | 28 | 29 | 30 |
| 4 | rhMZ104 | 31 | 32 | 33 | 34 | 35 | 36 | 37 | 38 | 39 | 40 |
| 5 | rhMZ107 | 41 | 42 | 43 | 44 | 45 | 46 | 47 | 48 | 49 | 50 |
| 6 | rhMZ119 | 51 | 52 | 53 | 54 | 55 | 56 | 57 | 58 | 59 | 60 |
| 7 | rhMZ121 | 61 | 62 | 63 | 64 | 65 | 66 | 67 | 68 | 69 | 70 |
| 8 | rhMZ123 | 71 | 72 | 73 | 74 | 75 | 76 | 77 | 78 | 79 | 80 |
| 9 | rhMZ124 | 81 | 82 | 83 | 84 | 85 | 86 | 87 | 88 | 89 | 90 |
| 10 | rhMZ133 | 91 | 92 | 93 | 94 | 95 | 96 | 97 | 98 | 99 | 100 |
| 11 | rhMZ134 | 101 | 102 | 103 | 104 | 105 | 106 | 107 | 108 | 109 | 110 |
| 12 | MZ4 | 111 | 112 | 113 | 114 | 115 | 116 | 117 | 118 | 119 | 120 |
| 13 | MZ1 | 121 | 122 | 123 | 124 | 125 | 126 | 127 | 128 | 129 | 130 |
| 14 | MZ24 | 131 | 132 | 133 | 134 | 135 | 136 | 137 | 138 | 139 | 140 |
| 15 | MZ20 | 141 | 142 | 143 | 144 | 145 | 146 | 147 | 148 | 149 | 150 |
| 16 | MZ54 | 151 | 152 | 153 | 154 | 155 | 156 | 157 | 158 | 159 | 160 |
| 17 | MZ56 | 161 | 162 | 163 | 164 | 165 | 166 | 167 | 168 | 169 | 170 |
| 18 | MZ22 | 171 | 172 | 173 | 174 | 175 | 176 | 177 | 178 | 179 | 180 |
| 19 | MZ18 | 181 | 182 | 183 | 184 | 185 | 186 | 187 | 188 | 189 | 190 |
| 20 | MZ19 | 191 | 192 | 193 | 194 | 195 | 196 | 197 | 198 | 199 | 200 |
| 21 | MZ23 | 201 | 202 | 203 | 204 | 205 | 206 | 207 | 208 | 209 | 210 |
| 22 | MZ2 | 211 | 212 | 213 | 214 | 215 | 216 | 217 | 218 | 219 | 220 |

As disclosed herein, the novel peptides of the present invention comprising amino acid sequences of SEQ ID NO: 5-10, 15-20, 25-30, 35-40, 45-50, 55-60, 65-70, 75-80, 85-90, 95-100, 105-110, 115-120, 125-130, 135-140, 145-150, 155-160, 165-170, 175-180, 185-190, 195-200 and 205-210 are each useful as complementarity determining region (CDR) of an antibody or antibody fragment that binds to ZIKV. In one embodiment, the novel peptides with amino acid sequences of any one of SEQ ID NO: 5-10, 15-20, 25-30, 35-40, 45-50, 55-60, 65-70, 75-80, 85-90, 95-100, 105-110, 115-120, 125-130, 135-140, 145-150, 155-160, 165-170, 175-180, 185-190, 195-200 and 205-210 of the present invention are, alone, considered to be an antibody fragment that could be useful in binding ZIKV.

For example, any of residues X1-8 of SEQ ID NO: 5 can be present or absent and can be any single amino acid. In select embodiments of the present invention, residue X1 can be glycine (G), alanine (A), proline (P), isoleucine (I), leucine (L) or valine (V). In additional select embodiments of the present invention, residue X2 can be phenylalanine (F), histidine (H), tryptophan (W), or tyrosine (Y). In additional select embodiments of the present invention, residue X3 can be threonine (T), cysteine (C), serine (S), present invention, residue X8 can be glycine (G), alanine (A), proline (P), isoleucine (I), leucine (L) or valine (V).

For example, any of residues X1-16 of SEQ ID NO: 117 can be present or absent and can be any single amino acid. In select embodiments of the present invention, residue X1 can be cysteine (C), serine (S), threonine (T), methionine (M), asparagine (N), or glutamine (Q). In additional select embodiments of the present invention, residue X2 can be alanine (A), glycine (G), proline (P), isoleucine (I), leucine (L) or valine (V). In additional select embodiments of the present invention, residue X3 can be glycine (G), alanine (A), proline (P), isoleucine (I), leucine (L) or valine (V). In additional select embodiments of the present invention, residue X4 can be leucine (L), glycine (G), alanine (A), proline (P), isoleucine (I) or valine (V). In additional select embodiments of the present invention, residue X5 can be aspartic acid (D), glutamic acid (E), lysine (K), or arginine (R). In additional select embodiments of the present invention, residue X6 can be arginine (R), aspartic acid (D), glutamic acid (E) or lysine (K). In additional select embodiments of the present invention, residue X7 can be aspartic acid phenylalanine (F), histidine (H), tryptophan (W), or tyrosine (Y). In additional select embodiments of the present invention, residue X8 can be asparagine (N), serine (S), cysteine (C), threonine (T), methionine (M), or glutamine (Q). In additional select embodiments of the present invention, residue X9 can be tryptophan (W), histidine (H), phenylalanine (F), or tyrosine (Y). In additional select embodiments of the present invention, residue X10 can be asparagine (N), serine (S), cysteine (C), threonine (T), methionine (M), or glutamine (Q). In additional select embodiments of the present invention, residue X11 can be aspartic acid (D), glutamic acid (E), lysine (K), or arginine (R). In additional select embodiments of the present invention, residue X12 can be glutamic acid (E), aspartic acid (D), lysine (K), or arginine (R). In additional select embodiments of the present invention, residue X13 can be glycine (G), alanine (A), proline (P), isoleucine (I), leucine (L) or valine (V). In additional select embodiments of the present invention, residue X14 can be aspartic acid (D), glutamic acid (E), lysine (K), or arginine (R). In additional select embodiments of the present invention, residue X15 can be cysteine (C), serine (S), threonine (T), methionine (M), asparagine (N), or glutamine (Q). In additional select embodiments of the present invention, residue X16 can be tryptophan (W), histidine (H), phenylalanine (F), or tyrosine (Y).

The novel peptides of the present invention can serve as at least one CDR of an antibody or antibody fragment that can bind to a specific epitope present on ZIKV. The antibodies of the present invention can be monoclonal or polyclonal. As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term antibody includes fragments of full-length antibodies that specifically bind one or more antigens. Such fragments are also well known in the art and are regularly employed both in vitro and in vivo. Examples of fragments of full length antibodies that are encompassed by the term antibody include but are not limited to F(ab')2, Fab, Fv, Fd fragments, as well as scFv peptides and the like.

In addition to Fabs, smaller antibody fragments and epitope-binding peptides, including the novel peptides of the present invention, that have binding specificity for the epitopes defined by the Zika antibodies are also contemplated by the present invention and can also be used to bind or neutralize the virus. For example, single chain antibodies can be constructed according to the method of U.S. Pat. No. 4,946,778, which is incorporated by reference. Single chain antibodies comprise the variable regions of the light and heavy chains joined by a flexible linker moiety. Another smaller antibody fragment that the invention provides is the antibody fragment known as the single domain antibody or Fd, which comprises an isolated variable heavy chain domain. Techniques for obtaining a single domain antibody with at least some of the binding specificity of the full-length antibody from which they are derived are known in the art.

Complementarity determining regions (CDRs) are peptide regions within the antigen-binding portion of an antibody. CDRs may directly interact with the epitope of the antigen and are the main determinant of antibody specificity. The framework regions (FRs) are peptide regions in the antigen-binding portion of the antibody that maintain the tertiary structure of the paratope. In some embodiments, in both the heavy chain variable region (VH) and the light chain variable region (V), there are four framework regions (FR1 through FR4) separated respectively by three complementarity determining regions (CDR1 through CDR3). The CDRs, and in particular the CDR3 regions, and more particularly the heavy chain CDR3, may be largely responsible for antibody specificity.

In one specific embodiment, the novel peptides of the present invention serve as the CDR1 portion of the heavy chain of an antibody or antibody fragment. In another specific embodiment, the novel peptides of the present invention serve as the CDR2 portion of the heavy chain of an antibody or antibody fragment. In another specific embodiment, the novel peptides of the present invention serve as the CDR3 portion of the heavy chain of an antibody or antibody fragment. In another specific embodiment, the novel peptides of the present invention serve as the CDR1 portion of the light chain of an antibody or antibody fragment. In another specific embodiment, the novel peptides of the present invention serve as the CDR2 portion of the light chain of an antibody or antibody fragment. In another specific embodiment, the novel peptides of the present invention serve as the CDR3 portion of the light chain of an antibody or antibody fragment.

In one embodiment, any of the novel peptides described can serve as a heavy chain CDR3 for an antibody or antibody fragment, with the antibody or antibody fragment further comprising at least one additional heavy chain CDR. In a more specific embodiment, any of the novel peptides described can serve as a heavy chain CDR3 for an antibody or antibody fragment, and a peptide comprising an amino acid sequence disclosed in Table 1 can serve as an additional heavy chain CDR, for example either CDR1 or CDR2. In another embodiment, any of the novel peptides described can serve as a heavy chain CDR3 for an antibody or antibody fragment, with the antibody or antibody fragment further comprising at least two additional heavy chain CDRs. In another specific embodiment, any of the novel peptides described can serve as a heavy chain CDR3 for an antibody or antibody fragment, and peptides comprising an amino acid sequences disclosed in Table 1 can each serve as two additional heavy chain CDRs, for example CDR1 and CDR2, or vice versa.

In additional embodiments, any of the novel peptides described can serve as a heavy chain CDR3 for an antibody or antibody fragment, with the antibody or antibody fragment further comprising at least one light chain CDR, and a peptide comprising an amino acid sequence disclosed in Table 1 can serve as either light chain CDR1, CDR2 or CDR3. In another embodiment, any of the novel peptides described can serve as a heavy chain CDR3 for an antibody or antibody fragment, with the antibody or antibody fragment further comprising at least two additional light chain CDRs. In another specific embodiment, any of the novel peptides described can serve as a heavy chain CDR3 for an antibody or antibody fragment, and peptides comprising any of the amino acid sequences of Table 1 can serve as two additional light chain CDRs, for example light chain CDR1, CDR2 or CDR3. In particular, a peptide with the amino acid sequence of SEQ ID NO: 208 can serve as the light chain CDR1 and a peptide with an amino acid sequence of SEQ ID NO: 209 or SEQ ID NO: 210 can interchangeably serve as the light chain CDR2 or CDR3.

In another specific embodiment, any of the novel peptides described can serve as a heavy chain CDR3 for an antibody or antibody fragment, with the antibody or antibody fragment further comprising at least three additional light chain CDRs. In another specific embodiment, any of the novel peptides described can serve as a heavy chain CDR3 for an antibody or antibody fragment, and peptides comprising the amino acid sequences of SEQ ID NO: 8, SEQ ID NO: 9 or SEQ ID NO: 10 can serve as three additional light chain CDRs, for example light chain CDR1, CDR2 and CDR3. In particular, a peptide with the amino acid sequence of SEQ ID NO: 8 can serve as the light chain CDR1 and a peptide with an amino acid sequence of SEQ ID NO: 9 can serve as the light chain CDR2 and a peptide with an amino acid sequence of SEQ ID NO: 10 can serve as the light chain CDR3.

In additional embodiments, any of the novel peptides described can serve as a heavy chain CDR3 for an antibody or antibody fragment, with the antibody or antibody fragment further comprising at least one, two, three, four or five additional CDRs. In specific embodiments, any of the novel peptides described can serve as a heavy chain CDR for an antibody or antibody fragment, with the antibody or antibody fragment further comprising at least two additional CDRs. In another specific embodiment, any of the novel peptides described can serve as a heavy chain CDR for an antibody or antibody fragment, and peptides comprising the amino acid sequences of SEQ ID NO: 5, SEQ ID NO: 6, SEQ ID NO: 7, SEQ ID NO: 8, SEQ ID NO: 9, or SEQ ID NO: 10 can serve as at least one, two, three, four or five additional CDR(s). In particular, any of the novel peptides described can serve as a heavy chain CDR for an antibody or antibody fragment, and a peptide comprising the amino acid sequences of SEQ ID NO: 5 can serve as a heavy chain CDR1, a peptide comprising the amino acid sequence of SEQ ID NO: 6 can serve as a heavy chain CDR2, a peptide comprising the amino acid sequence of SEQ ID NO: 7 can serve as a heavy chain CDR3, a peptide with the amino acid sequence of SEQ ID NO: 8 can serve as a light chain CDR1, a peptide with an amino acid sequence of SEQ ID NO: 9 can serve as a light chain CDR2, and/or a peptide with an amino acid sequence of SEQ ID NO: 10 can serve as a light chain CDR3.

Any of the series of antibodies or antibody fragments in Table 1 above may or may not include one or more framework regions as well.

In specific embodiments, the antibodies or antibody fragments of the present invention comprise at least one CDR, wherein the amino acid sequence of the CDR comprises, consists essentially of or consist of an amino acid sequence that is at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the amino acid sequence of SEQ ID NO: 5-10, 15-20, 25-30, 35-40, 45-50. 55-60, 65-70, 75-80, 85-90, or 95-100. In more specific embodiments, the antibodies or antibody fragments comprise, consist essentially of or consist of at least two CDRs.

In particular, the present invention provides antibodies or antibody fragments that bind to cross-protomer epitopes on ZIKV. The antibodies may be monoclonal or polyclonal. The primary amino acid structure and the secondary and tertiary structures of the E glycoprotein of the ZIKV are well known.

A polypeptide having an amino acid sequence at least, for example, about 95% "identical" to a reference amino acid sequence, e.g., SEQ ID NO: 1, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to determine identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine identity and similarity are discussed in Michaels (2011) Current Protocols in Protein Science, Vol. 1, John Wiley & Sons.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment−10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query sequence occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "corresponds to" and "corresponding to" as they relate to sequence alignment, are intended to mean enumerated positions within the reference protein and those positions in the modified peptide that align with the positions on the reference protein. Thus, when the amino acid sequence of a subject or query peptide is aligned with the amino acid sequence of a reference peptide, e.g., SEQ ID NO: 3, the amino acids in the subject sequence that "correspond to" certain enumerated positions of the reference sequence are those that align with these positions of the reference sequence, e.g., SEQ ID NO: 3, but are not necessarily in these exact numerical positions of the reference sequence. Methods for aligning sequences for determining corresponding amino acids between sequences are described herein. Accordingly, the invention provides novel peptides whose sequences correspond to the sequence of SEQ ID NO: 3.

Variants resulting from insertion of a polynucleotide encoding the novel peptides into an expression vector system are also contemplated. For example, variants (usually insertions) may arise from when the amino terminus and/or the carboxy terminus of a novel peptide is/are fused to another polypeptide.

In another aspect, the invention provides deletion variants wherein one or more amino acid residues in the novel peptides are removed. Deletions can be effected at one or both termini of the peptides, or with removal of one or more non-terminal amino acid residues.

Within the confines of the disclosed percent identities, the invention also relates to substitution variants of disclosed peptides of the invention. Substitution variants include those polypeptides wherein one or more amino acid residues of an amino acid sequence are removed and replaced with alternative residues. Knowledge of the three-dimensional structure of an antibody, as disclosed herein, as well as the structures of the Zika virus, the Zika virus E glycoprotein, and the Zika virus E glycoprotein in complex with monoclonal antibodies (Dai, Cell Host and Microbe 19(5) 2016, pp 696-704; Sirohi, Science 352(6284) 2016 pp 467-470; Zhau, Cell 166(4) 2-16, pp 1016-1027) provides guidance regarding which positions within the amino acid sequences of the antibodies disclosed herein can be substituted without loss of binding or neutralization activity.

In one aspect, the substitutions are conservative in nature; however, the invention embraces substitutions that are also non-conservative. Conservative substitutions for the purposes of the present invention may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2.

TABLE 2

Conservative Substitutions

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE 3

Conservative Substitutions

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE 4

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |

TABLE 4-continued

Conservative Substitutions

| Original Residue | Exemplary Substitution |
|---|---|
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human framing regions (FRs) and/or Fc/pFc' regions to produce a functional antibody or antibody fragment. For example, PCT International Publication Number WO 92/04381 teaches the production and use of humanized murine RSV antibodies in which at least a portion of the murine FR regions have been replaced by FR regions of human origin. It is also possible, in accordance with the present invention, to produce chimeric antibodies including non-human sequences. For example, murine, ovine, equine, bovine, non-human primate or other mammalian Fc or FR sequences can be used to replace some or all of the Fc or FR regions of Zika antibodies.

The present invention also provides for F(ab')2, Fab, Fv and Fd fragments of Zika antibodies, as well as chimeric antibodies or antibody fragments in which the Fc and/or FR and/or, CDR1 and/or CDR2 and/or CDR3 light chain or heavy chain regions of the Zika monoclonal have been replaced by homologous human or non-human sequences. For example, the invention provides chimeric Fab and/or F(ab')2 fragments in which the FR and/or CDR1 and/or CDR2 and/or CDR3 light chain or heavy chain regions of the Zika antibodies have been replaced by homologous human or non-human sequences. The invention also provides for chimeric Fd fragment antibodies in which the FR and/or CDR1 and/or CDR2 and/or CDR3 heavy chain regions have been replaced by homologous human or non-human sequences. Such CDR grafted or chimeric antibodies or antibody fragments can be effective in prevention and treatment of ZIKV infection.

In select embodiments, the chimeric antibodies or antibody fragments of the invention are fully human monoclonal antibodies including at least the novel peptides of the present invention, which can be used as heavy chain CDR3 regions in the antibodies or antibody fragments. As noted above, such chimeric antibodies may be produced in which some or all of the FR regions of the Zika antibodies or antibody fragments have been replaced by other homologous human FR regions. In addition, the Fc portions may be replaced so as to produce IgA or IgM as well as IgG antibodies bearing some or all of the CDRs of the Zika antibodies or antibody fragments. In select embodiments, administration of the antibodies, antibody fragments, chimeric antibodies or chimeric antibody fragments will not evoke an immune response.

It is possible to determine, without undue experimentation, if any of the antibodies or antibody fragments described herein have specificity towards at least a portion of the ZIKV using standard techniques well known to one of skill in the art. For example, the antibody or antibody fragment can be tested for its ability to can compete with known ZIKV antibodies to bind to ZIKV, e.g., as demonstrated by a decrease in binding of the known ZIKV antibodies. Screening of ZIKV antibodies or antibody fragments can also be carried out by utilizing ZIKV and determining whether the test antibodies or antibody fragments neutralize the virus.

By using the antibodies or antibody fragments of the invention, it is also possible to produce anti-idiotypic antibodies which can be used to screen other antibodies to identify whether the antibody has the same binding specificity as an antibody of the invention. In addition, such antiidiotypic antibodies can be used for active immunization (Herlyn, 1986 Science 232:100-102). Such anti-idiotypic antibodies can be produced using well-known hybridoma techniques (Kohler, 1975 Nature 256:495-497). An anti-idiotypic antibody is an antibody which recognizes unique determinants present on an antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

The present invention also provides nucleic acids encoding the novel peptides of the present invention as well as proteins and peptides comprising the novel peptides of the present invention. Such nucleic acids may or may not be operably joined to other nucleic acids forming a recombinant vector for cloning or for expression of the peptides of the present invention. The present invention thus includes any recombinant vector containing coding sequences of the novel peptides of the present invention, or part thereof, whether for prokaryotic or eukaryotic transformation, transfection or gene therapy. Such vectors may be prepared using conventional molecular biology techniques, known to those with skill in the art. Recombinant techniques would include but are not limited to utilizing DNA coding sequences for the immunoglobulin V-regions of the flavivirus antibodies or antibody fragments, including framework and CDRs or parts thereof, and a suitable promoter either with (Whittle 1987 Protein Eng 1:499-505 and Burton 1994 Science 266:1024-1027) or without (Marasco, 1993. Proc Natl Acad Sci USA 90:7889-7893 and Duan, 1994 Proc Natl Acad Sci USA 91:5075-5079) a signal sequence for export or secretion. Such vectors may be transformed or transfected into prokaryotic (Huse, 1989 Science 246:1275-1281; Ward, 1989 Nature 341:544-546; Marks, 1991 J Mol Biol 222:581-597; and Barbas, 1991 Proc Natl Acad Sci USA 88:7978-7982) or eukaryotic (Whittle, 1987 Protein Eng 1:499-505 and Burton, 1994 Science 266:1024-1027) cells or used for gene therapy (Marasco, 1993 Proc Natl Acad Sci USA 90:7889-7893 and Duan, 1994 Proc Natl Acad Sci USA 91:5075-5079) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques. Some vectors that may be utilized include but are not limited to vectors that are capable of autonomous replication and expression of the structural gene products present in the DNA segments to which they are operably joined.

As used herein, a coding sequence and regulatory sequences are said to be "operably joined" or "operably connected" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but in general include but are not limited to 5' non-transcribing and 5' non-translating sequences involved with initiation of transcription and translation respectively, such as a TATA box, capping sequence, CAAT sequence, and the like. In particular, a 5' non-transcribing regulatory sequence may include a promoter region which includes a promoter sequence for transcriptional control of the operably joined coding sequence. Regulatory sequences may also include enhancer sequences or upstream activator sequences, as desired.

The vectors of the present invention may or may not be expression vectors. Expression vectors include regulatory sequences operably joined to a nucleotide sequence encoding one of the novel peptides, antibodies or antibody fragments of the invention. As used herein, the term "regulatory sequences" means nucleotide sequences necessary for or conducive to the transcription of a nucleotide sequence encoding a desired peptide and/or which are necessary for or conducive to the translation of the resulting transcript into the desired peptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

The present invention also provides for host cells, both prokaryotic and eukaryotic comprising at least one nucleic acid encoding the novel peptides of the present invention, including but not limited to the vectors of the present invention.

In one embodiment using a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art.

One method of achieving high levels of gene expression in *E. coli* includes but is not limited to the use of strong promoters to generate large quantities of mRNA and also ribosome binding sites to ensure that the mRNA is efficiently translated. For example, ribosome binding sites in *E. coli* include an initiation codon (AUG) and a sequence 3-9 nucleotides long located 3-11 nucleotides upstream from the initiation codon (Shine 1975 Nature 254:34-38). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA, the spacing lying between the SD sequence and the AUG and even the nucleotide sequence following the AUG, which affects ribosome binding. The 3' regulatory sequences may or may not define at least one termination (stop) codon in frame with and operably joined to the heterologous fusion polypeptide.

In addition, those embodiments that include a prokaryotic replicon may or may not include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those that are commercially available.

The antibodies or antibody fragments of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding one or more peptides of the present invention. The design and selection of an appropriate eukaryotic vector is within the ability and discretion of one of ordinary skill in the art. The subsequent purification of the antibodies may be accomplished by any of a variety of standard means known in the art.

The antibodies or antibody fragments of the present invention may furthermore, of course, be produced in plants. In 1989, Hiatt et al. (Nature 342:76-78 (1989)) first demonstrated that functional antibodies could be produced in transgenic plants. Since then, a considerable amount of effort has been invested in developing plants for antibody (or "plantibody") production (for reviews see Giddings, 2000 Nat. Biotechnol., 18:1151-1155; Fischer, 2000 Transgenic Res., 9:279-299).

One vector useful for screening monoclonal antibodies is a recombinant DNA molecule containing a nucleotide sequence that codes for and is capable of expressing a fusion polypeptide containing, in the direction of amino- to carboxy-terminus, (1) a prokaryotic secretion signal domain, (2) a peptide of the invention, and, optionally, (3) a fusion protein domain. The vector includes DNA regulatory sequences for expressing the fusion polypeptide, for example prokaryotic regulatory sequences. Such vectors can be constructed by those of ordinary skill in the art and have been described by Smith, 1985 Science 228:1315-1317; Clackson, 1991 Nature 352:624-628; Batbas 1991 Proc Natl Acad Sci USA 88:7978-7982; Roberts, 1992 Proc Natl Acad Sci USA 89:2429-2433.

A fusion polypeptide may be useful for purification of the antibodies of the invention. The fusion domain may, for example, include a His tag that allows for purification of the peptide, or a maltose binding protein of the commercially available vector pMAL (New England BioLabs). A fusion domain that may be useful is a filamentous phage membrane anchor that is particularly useful for screening phage display libraries of monoclonal antibodies.

A secretion signal is a leader peptide domain of a protein that targets the protein to a region, such as the plasma membrane, of the host cell. For example, one secretion signal is the *E. coli* is a pelB secretion signal. The leader sequence of the pelB protein has previously been used as a secretion signal for fusion proteins (Better, 1988 Science 240:1041-1043; Sastry, 1989 Proc Natl Acad Sci USA 86:5728-5732; and Mullinax, 1990 Proc Natl Acad Sci USA 87:8095-8099. Amino acid residue sequences for other secretion signal polypeptide domains from *E. coli* useful in this invention can be found in Neidhard, (ed.), 1987 in *Escherichia coli* and *Salmonella typhimurium: Typhimurium Cellular and Molecular Biology*, American Society for Microbiology.

When the antibodies or antibody fragments of the invention include heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as full-length antibodies or antibody fragments of the invention, is a recombinant DNA molecule adapted for receiving and expressing translatable first and second DNA sequences. That is, a DNA expression vector for expressing a heterodimeric antibody or antibody fragment provides a system for independently cloning (inserting) two or more translatable DNA sequences into two or more separate cassettes present in the vector, to form two or more separate cistrons for expressing the first and second polypeptides of a heterodimeric antibody or antibody fragment. The DNA expression vector for expressing two cistrons is referred to as a dicistronic expression vector.

In general, a dicistronic expression vector comprises a first cassette that includes upstream and downstream DNA regulatory sequences operably joined via a sequence of nucleotides adapted for directional ligation to an insert DNA. The upstream translatable sequence may encode the secretion signal as described above. The cassette also may include DNA regulatory sequences for expressing the first peptide that is produced when an insert translatable DNA sequence (insert DNA) is directionally inserted into the cassette via the sequence of nucleotides adapted for directional ligation.

The dicistronic expression vector may also contain a second cassette for expressing the second peptide. The second cassette may also include a second translatable DNA sequence that encodes a secretion signal, as described above, that may be operably joined at its 3' terminus via a sequence of nucleotides adapted for directional ligation to a downstream DNA sequence of the vector that typically defines at least one stop codon in the reading frame of the cassette. The second translatable DNA sequence can be operably joined at its 5' terminus to DNA regulatory sequences forming the 5' elements. Upon insertion of a translatable DNA sequence (insert DNA), the second cassette is capable of expressing the second fusion polypeptide comprising a secretion signal with a polypeptide coded by the insert DNA.

The invention also provides for methods of making any of the novel, inventive peptides of the present invention. In certain embodiments, the methods of making the novel peptides of the present invention include making antibodies or antibody fragments that comprise at least one novel peptide of the present invention. The methods of making the novel peptides, or making antibodies or antibody fragments comprising the novel peptides, include but are not limited to culturing the novel, inventive host cells of the present invention under conditions suitable for protein expression and isolating the peptides from culture. The host cells used in the methods of making peptides of the present invention may or may not include nucleic acids that encode antibodies or antibody fragments comprising the novel peptides of the present invention. The produced peptides or produced antibodies or antibody fragments may or may not be substantially pure.

As used herein with respect to polypeptides, the term "substantially pure" is used to mean that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Methods of culturing host cells to produce proteins, including antibodies or antibody fragments comprising the novel peptides of the present invention, are well known in the art and such methods need not be repeated herein. One of skill in the art will readily recognize that the culture conditions necessary for protein production depend upon, among other things, the type of host cell being cultured, the nature of the protein or peptide being produced and the quantity desired.

The invention also provides methods for preparing diagnostic or pharmaceutical compositions comprising the peptides of the present invention, which may or may not be part of an antibody or antibody fragment. The invention also provides methods for preparing diagnostic or pharmaceutical compositions comprising the novel nucleic acid sequences encoding the novel peptides of the invention or part thereof. The pharmaceutical compositions of the present invention can be used for treating symptoms of ZIKV Disease in a subject in need thereof, or can be used for treating Zika Disease itself in a subject in need thereof.

Accordingly, the present invention provides methods of treating a subject with a ZIKV infection comprising administering a therapeutically effective amount of at least one peptide of the present invention to a subject in need thereof. In a more specific embodiment, the invention provides for methods of treating a subject with a ZIKV infection comprising administering a therapeutically effective amount at least one antibody or antibody fragment, wherein the antibody or antibody fragment comprises, consists essentially of or consists of at least one novel peptide of the present invention to a subject in need thereof.

As used herein, a "therapeutically effective amount" of the peptides, antibodies or antibody fragments of the invention is a dosage large enough to produce the desired effect in which the symptoms of Zika Disease are ameliorated or the likelihood of infection is decreased. A therapeutically effective amount is generally not a dose so large as to cause adverse side effects, such as but not limited to hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, specifically from about 0.1 mg/kg to about 20 mg/kg, more specifically from about 0.2 mg/kg to about 2 mg/kg. The peptides, antibodies or antibody fragments may be administered once or more than once in a single day or over a period of days. When administered to a pregnant female, a therapeutically effective amount of the peptides, antibodies or antibody fragments of the invention prevents transmission, or reduces the extent of transmission, from an infected mother to her unborn child.

The present invention also provides prophylactic methods as well. Indeed, the present invention provides methods of preventing or reducing the likelihood of acquiring a ZIKV infection and preventing or reducing the likelihood of acquiring a disease or condition associated with ZIKV infection. The prevention methods comprise administering a prophylactically effective amount of at least one peptide of the present invention to a subject. In a more specific embodiment, the invention provides for methods of reducing the likelihood of acquiring a condition or disease associated with ZIKV infection comprising administering a prophylactically effective amount of at least one antibody or antibody fragment, wherein the antibody or antibody fragment comprises, consists essentially of or consists of at least one novel peptide of the present invention to a subject. The subject on which the prevention or prophylactic methods are practiced may or may not be a higher risk of acquiring a condition or disease associated with ZIKV infection than another subject from a different population.

As used herein, a "prophylactically effective amount" of the peptides, antibodies or antibody fragments of the invention is a dosage large enough to produce the desired effect in the protection of individuals against flavivirus infection for a reasonable period of time, such as one to two months or longer following administration. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, specifically from about 0.1 mg/kg to about 20 mg/kg, more specifically from about 0.2 mg/kg to about 2 mg/kg, in one or more administrations (priming and boosting). When administered to a pregnant female, a prophylactically effective amount of the peptides, antibodies or antibody fragments of the invention prevents infection, or reduces the severity of infection, of the mother and her unborn child.

The treatment and prevention methods herein may or may not include screening a subject to determine if the subject has been infected with ZIKV or is at risk of being infected with ZIKV.

As used herein, "administer" or variations thereof is used to mean bringing the one or more novel peptides into proximity with a cell or group of cells, including cells comprised within a living, whole organism, such that the one or more novel peptides can exert a biological effect on the cells. Of course, "administering" the novel peptides of the present invention can be achieved by administering an antibody or antibody fragment comprising one or more novel peptides to a subject in need thereof. Thus, in one embodiment of the present invention, "administer" can mean a stable or transient transfection of DNA or RNA molecule(s) into cells, where the cells may or may not be part of a living, whole organism. In another embodiment, the peptides or antibodies or antibody fragments comprising the novel peptides can be administered repeatedly to the subject.

As used herein, the term "Zika Virus Disease" refers to diseases or conditions caused, directly or indirectly, by infection from ZIKV. Symptoms of Zika Virus Disease include congenital and neurological complications such as microcephaly and Guillain-Barre syndrome.

The pharmaceutical preparation includes a pharmaceutically acceptable carrier. Such carriers, as used herein, means a material that does not interfere with the effectiveness of the biological activity of the active ingredients. The term "physiologically acceptable" refers to a material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The peptides, antibodies or antibody fragments of the invention can be administered by injection or by gradual infusion over time. The administration of the peptides, antibodies or antibody fragments of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the peptides, antibodies or antibody fragments such as the paratope binding capacity (see, for example, Remington's Pharmaceutical Sciences, 2017, Mack Publishing). Those of skill in the art can readily determine the various parameters and conditions for producing injectates or infusates without resort to undue experimentation.

For example, preparations for parenteral administration include sterile aqueous or non-aqueous solutions, suspensions, and emulsions. Examples of non-aqueous solvents include but are not limited to propylene glycol, polyethylene glycol, vegetable oils such as olive oil, and injectable organic esters such as ethyl oleate. Aqueous carriers include but are not limited to water, alcoholic/aqueous solutions, emulsions or suspensions, including saline and buffered media. Parenteral vehicles include but are not limited to sodium chloride solution, Ringer's dextrose, dextrose and sodium chloride, lactated Ringer's or fixed oils. Intravenous vehicles include but are not limited to fluid and nutrient replenishers, electrolyte replenishers (such as those based on Ringer's dextrose), and the like. Preservatives and other additives may also be present such as, for example, antimicrobials, anti-oxidants, chelating agents, and the like.

The peptides, antibodies or antibody fragments of the invention are suited for in vitro use, for example, in immunoassays in which they can be utilized in liquid phase or bound to a solid phase carrier. In addition, the peptides, antibodies or antibody fragments in these immunoassays can be detectably labeled in various ways. Examples of types of immunoassays which can utilize the peptides, antibodies or antibody fragments of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The anti-Zika peptides, antibodies or antibody fragments of the invention may be labeled by a variety of means for use in diagnostic and/or pharmaceutical applications. There are many different labels and methods of labeling known to those of ordinary skill in the art. Examples of the types of labels which can be used in the present invention include but are not limited to enzymes, radioisotopes, fluorescent compounds, colloidal metals, chemiluminescent compounds and bioluminescent compounds. One of ordinary skill in the art will readily be able to determine suitable labels for binding to the peptides, antibodies or antibody fragments of the invention. Furthermore, the binding of these labels to the peptides, antibodies or antibody fragments of the invention can be done using standard techniques common to those of ordinary skill in the art.

Another labeling technique which may result in greater sensitivity consists of coupling the peptides, antibodies or antibody fragments to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

The peptides, antibodies or antibody fragments of the invention can be bound to many different carriers and used to detect the presence of flavivirus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding peptides, antibodies or antibody fragments, or will be able to ascertain such, using routine experimentation.

For purposes of the invention, ZIKV may be detected by the peptides, antibodies or antibody fragments of the invention when present in biological fluids and tissues. Any sample containing a detectable amount of ZIKV can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

The invention also provides for methods of diagnosis and in vivo detection of ZIKV using the peptides, antibodies or antibody fragments of the present invention. In using the peptides, antibodies or antibody fragments of the invention for the in vivo detection of antigen, the detectably labeled peptides, antibodies or antibody fragments are given in a dose which is diagnostically effective. The term "diagnostically effective" means that the amount of detectably labeled peptides, antibodies or antibody fragments are administered in sufficient quantity to enable detection of the site having the flavivirus antigen for which the peptides, antibodies or antibody fragments are specific.

The concentration of detectably labeled peptide, antibody or antibody fragment which is administered should be sufficient such that the binding to flavivirus is detectable compared to the background.

As a rule, the dosage of detectably labeled peptides, antibodies or antibody fragments for in vivo diagnosis will vary depending on such factors as age, sex, and extent of disease of the individual. The dosage of peptides, antibodies or antibody fragments can vary from about 0.01 mg/kg to about 50 mg/kg, specifically from about 0.1 mg/kg to about 20 mg/kg, more specifically from about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a one factor in selecting an appropriate label, such as but not limited to a radioisotope. For example, the radioisotope chosen must have a type of decay which is detectable for the given type of instrument. Still another factor in selecting an appropriate label for in vivo diagnosis is that the half-life of the label must be long enough such that it is still detectable at the time of maximum uptake by the target, but short enough such that any deleterious effect to the host is acceptable.

For in vivo diagnosis, the label(s) may be bound to the peptides, antibodies or antibody fragments of the invention either directly or indirectly by using an intermediate functional group. Intermediate functional groups which often are used to bind labels, such as for example radioisotopes, can exist as metallic ions and may be bifunctional chelating agents such as diethylenetriaminepentacetic acid (DTPA) and ethylenediaminetetra-acetic acid (EDTA) and similar molecules. Typical examples of metallic ions which can be bound to the peptides, antibodies or antibody fragments of the invention are 111In, 97Ru, 67Ga, 68Ga, 72As, 89Zr and 201Tl to name a few.

The peptides, antibodies or antibody fragments of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include but are not limited to 157Gd, 55Mn, 162Dy, 52Cr and 56Fe.

The peptides, antibodies or antibody fragments of the invention can be used in vitro and in vivo to monitor the course of flavivirus disease therapy. Thus, for example, by measuring the increase or decrease in the number of cells infected with ZIKV over time, i.e., measuring at a first and second time point, or changes in the concentration of ZIKV present in the body or in various body fluids over time, it would be possible to determine whether a particular therapeutic regimen aimed at ameliorating flavivirus disease is effective.

The materials for use in the diagnostic assays that the invention provides are ideally suited for the preparation of a kit. Such a kit may comprise a carrier that is compartmentalized to receive in close confinement one or more containers such as vials, tubes, and the like, with each of the container comprising one of the separate elements to be used in the method. For example, one of the containers may comprise a peptide, antibody or antibody fragment of the invention that is, or can be, detectably labeled. The kit may also have containers containing buffer(s) and/or a container comprising a reporter, such as but not limited to a biotin-binding protein, such as avidin or streptavidin, bound to a reporter molecule, such as an enzymatic or fluorescent label.

Measuring the ability of the peptides, antibodies or antibody fragments of the present invention to inhibit fusion mediated by HeV envelope glycoprotein (Env) expressing cells with cells that we had previously identified as fusion-competent can be used to test the neutralizing activity of the peptides, antibodies or antibody fragments of the present invention. Fusion can be measured by two assays—a reporter gene assay and a syncytia formation assay. Methods of measuring fusion of a virus are reported in U.S. Pat. No. 7,988,971, which is incorporated by reference in its entirety.

Neutralization assays utilizing infectious Zika and Dengue viruses can also be used to test the inhibitory activity of the peptides, antibodies or antibody fragments. Such neutralization assays are reported in U.S. Pat. No. 7,988,971.

One aspect of the present application relates to an antibody or fragment thereof that selectively binds whole Zika virus, wherein said antibody comprises: (a) a heavy chain variable region comprising complementarily-determining regions (CDRs) having amino acid sequences SEQ ID NO: 5 for CDR1, SEQ ID NO: 6 for CDR2, and SEQ ID NO: 7 for CDR3; and a light chain variable region comprising CDRs having amino acid sequences of SEQ ID NO: 8 for CDR1, SEQ ID NO: 9 for CDR2 and SEQ ID NO: 10 for CDR3; or (b) a heavy chain variable region comprising CDRs having amino acid sequences SEQ ID NO: 15 for CDR1, SEQ ID NO: 16 for CDR2, and SEQ ID NO: 17 for CDR3; and a light chain variable region comprising CDRs having amino acid sequences of SEQ ID NO: 18 for CDR1, SEQ ID NO: 19 for CDR2 and SEQ ID NO: 20 for CDR3; or (c) a heavy chain variable region comprising CDRs having amino acid sequences SEQ ID NO: 25 for CDR1, SEQ ID NO: 26 for CDR2, and SEQ ID NO: 27 for CDR3; and a light chain variable region comprising CDRs having amino acid sequences of SEQ ID NO: 28 for CDR1, SEQ ID NO: 29 for CDR2 and SEQ ID NO: 30 for CDR3; or (d) a heavy chain variable region comprising CDRs having amino acid sequences SEQ ID NO: 35 for CDR1, SEQ ID NO: 36 for CDR2, and SEQ ID NO: 37 for CDR3; and a light chain variable region comprising CDRs having amino acid sequences of SEQ ID NO: 38 for CDR1, SEQ ID NO: 39 for CDR2 and SEQ ID NO: 40 for CDR3; or (e) a heavy chain variable region comprising CDRs having amino acid sequences SEQ ID NO: 45 for CDR1, SEQ ID NO: 46 for CDR2, and SEQ ID NO: 47 for CDR3; and a light chain variable region comprising CDRs having amino acid sequences of SEQ ID NO: 48 for CDR1, SEQ ID NO: 49 for CDR2 and SEQ ID NO: 50 for CDR3; or (f) a heavy chain variable region comprising CDRs having amino acid sequences SEQ ID NO: 55 for CDR1, SEQ ID NO: 56 for CDR2, and SEQ ID NO: 57 for CDR3; and a light chain variable region comprising CDRs having amino acid sequences of SEQ ID NO: 58 for CDR1, SEQ ID NO: 59 for CDR2 and SEQ ID NO: 60 for CDR3; or (g) a heavy chain variable region comprising CDRs having amino acid sequences SEQ ID NO: 65 for CDR1, SEQ ID NO: 66 for CDR2, and SEQ ID NO: 67 for CDR3; and a light chain variable region comprising CDRs having amino acid sequences of SEQ ID NO: 68 for CDR1, SEQ ID NO: 69 for CDR2 and SEQ ID NO: 70 for CDR3; or (h) a heavy chain variable region comprising CDRs having amino acid sequences SEQ ID NO: 75 for CDR1, SEQ ID NO: 76 for CDR2, and SEQ ID NO: 77 for CDR3; and a light chain variable region comprising CDRs having amino acid sequences of SEQ ID NO: 78 for CDR1, SEQ ID NO: 79 for CDR2 and SEQ ID NO: 80 for CDR3; or (i) a heavy chain variable region comprising CDRs having amino acid sequences SEQ ID NO: 85 for CDR1, SEQ ID NO: 86 for CDR2, and SEQ ID NO: 87 for CDR3; and a light chain variable region comprising CDRs having amino acid sequences of SEQ ID NO: 88 for CDR1, SEQ ID NO: 89 for CDR2 and SEQ ID NO: 90 for CDR3; or (j) a heavy chain variable region comprising CDRs having amino acid sequences SEQ ID NO: 95 for CDR1, SEQ ID NO: 96 for CDR2, and SEQ ID NO: 97 for CDR3; and a light chain variable region comprising CDRs having amino acid sequences of SEQ ID NO: 98 for CDR1, SEQ ID NO: 99 for CDR2 and SEQ ID NO: 100 for CDR3; or (k) a heavy chain variable region comprising CDRs having amino acid sequences SEQ ID NO: 105 for CDR1, SEQ ID NO: 106 for CDR2, and SEQ ID NO: 107 for CDR3; and a light chain variable region comprising CDRs having amino acid sequences of SEQ ID NO: 108 for CDR1, SEQ ID NO: 109 for CDR2 and SEQ ID NO: 110 for CDR3; or (l) a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3; or (m) a heavy chain variable region comprising CDRs having amino acid sequences SEQ ID NO: 125 for CDR1, SEQ ID NO: 126 for CDR2, and SEQ ID NO: 127 for CDR3; and a light chain variable region comprising CDRs having amino acid sequences of SEQ ID NO: 128 for CDR1, SEQ ID NO: 129 for CDR2 and SEQ ID NO: 130 for CDR3; or (n) a heavy chain variable region comprising CDRs having amino acid sequences SEQ ID NO: 135 for CDR1, SEQ ID NO: 136 for CDR2, and SEQ ID NO: 137 for CDR3; and a light chain variable region comprising CDRs having amino acid sequences of SEQ ID NO: 138 for CDR1, SEQ ID NO: 139 for CDR2 and SEQ ID NO: 140 for CDR3; or (o) a heavy chain variable region comprising CDRs having amino acid sequences SEQ ID NO: 145 for CDR1, SEQ ID NO: 146 for CDR2, and SEQ ID NO: 147 for CDR3; and a light chain variable region comprising CDRs having amino acid sequences of SEQ ID NO: 148 for CDR1, SEQ ID NO: 149 for CDR2 and SEQ ID NO: 150 for CDR3; or (p) a heavy chain variable region comprising CDRs having amino acid sequences SEQ ID NO: 155 for CDR1, SEQ ID NO: 156 for CDR2, and SEQ ID NO: 157 for CDR3; and a light chain variable region comprising CDRs having amino acid sequences of SEQ ID NO: 158 for CDR1, SEQ ID NO: 159 for CDR2 and SEQ ID NO: 160 for CDR3; or (q) a heavy chain variable region comprising CDRs having amino acid sequences SEQ ID NO: 165 for CDR1, SEQ ID NO: 166 for CDR2, and SEQ ID NO: 167 for CDR3; and a light chain variable region comprising CDRs having amino acid sequences of SEQ ID NO: 168 for CDR1, SEQ ID NO: 169 for CDR2 and SEQ ID NO: 170 for CDR3; or (r) a heavy chain variable region comprising CDRs having amino acid sequences SEQ ID NO: 175 for CDR1, SEQ ID NO: 176 for CDR2, and SEQ ID NO: 177 for CDR3; and a light chain variable region comprising CDRs having amino acid sequences of SEQ ID NO: 178 for CDR1, SEQ ID NO: 179 for CDR2 and SEQ ID NO: 180 for CDR3; or (s) a heavy chain variable region comprising CDRs having amino acid sequences SEQ ID NO: 185 for CDR1, SEQ ID NO: 186 for CDR2, and SEQ ID NO: 187 for CDR3; and a light chain variable region comprising CDRs having amino acid sequences of SEQ ID NO: 188 for CDR1, SEQ ID NO: 189 for CDR2 and SEQ ID NO: 190 for CDR3; or (t) a heavy chain variable region comprising CDRs having amino acid sequences SEQ ID NO: 195 for CDR1, SEQ ID NO: 196 for CDR2, and SEQ ID NO: 197 for CDR3; and a light chain variable region comprising CDRs having amino acid sequences of SEQ ID NO: 198 for CDR1, SEQ ID NO: 199 for CDR2 and SEQ ID NO: 200 for CDR3; or (u) a heavy chain variable region comprising complementarily-determining regions (CDRs) having amino acid sequences SEQ ID NO: 205 for CDR1, SEQ ID NO: 206 for CDR2, and SEQ ID NO: 207 for CDR3; and a light chain variable region comprising CDRs having amino acid sequences of SEQ ID NO: 208 for CDR1, SEQ ID NO: 209 for CDR2 and SEQ ID NO: 210 for CDR3; or (v) a heavy chain variable region comprising complementarily-determining regions (CDRs) having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

In some embodiments, said antibody comprises: (a) a heavy chain variable region comprising complementarily-determining regions (CDRs) having amino acid sequences SEQ ID NO: 5 for CDR1, SEQ ID NO: 6 for CDR2, and SEQ ID NO: 7 for CDR3; and a light chain variable region comprising CDRs having amino acid sequences of SEQ ID NO: 8 for CDR1, SEQ ID NO: 9 for CDR2 and SEQ ID NO: 10 for CDR3; or (b) a heavy chain variable region comprising CDRs having amino acid sequences SEQ ID NO: 15 for CDR1, SEQ ID NO: 16 for CDR2, and SEQ ID NO: 17 for CDR3; and a light chain variable region comprising CDRs having amino acid sequences of SEQ ID NO: 18 for CDR1, SEQ ID NO: 19 for CDR2 and SEQ ID NO: 20 for CDR3; or (c) a heavy chain variable region comprising CDRs having amino acid sequences SEQ ID NO: 25 for CDR1, SEQ ID NO: 26 for CDR2, and SEQ ID NO: 27 for CDR3; and a light chain variable region comprising CDRs having amino acid sequences of SEQ ID NO: 28 for CDR1, SEQ ID NO: 29 for CDR2 and SEQ ID NO: 30 for CDR3; or (d) a heavy chain variable region comprising CDRs having amino acid sequences SEQ ID NO: 35 for CDR1, SEQ ID NO: 36 for CDR2, and SEQ ID NO: 37 for CDR3; and a light chain variable region comprising CDRs having amino acid sequences of SEQ ID NO: 38 for CDR1, SEQ ID NO: 39 for CDR2 and SEQ ID NO: 40 for CDR3; or (e) a heavy chain variable region comprising CDRs having amino acid sequences SEQ ID NO: 45 for CDR1, SEQ ID NO: 46 for CDR2, and SEQ ID NO: 47 for CDR3; and a light chain variable region comprising CDRs having amino acid sequences of SEQ ID NO: 48 for CDR1, SEQ ID NO: 49 for CDR2 and SEQ ID NO: 50 for CDR3; or (f) a heavy chain variable region comprising CDRs having amino acid sequences SEQ ID NO: 55 for CDR1, SEQ ID NO: 56 for CDR2, and SEQ ID NO: 57 for CDR3; and a light chain variable region comprising CDRs having amino acid sequences of SEQ ID NO: 58 for CDR1, SEQ ID NO: 59 for CDR2 and SEQ ID NO: 60 for CDR3; or (g) a heavy chain variable region comprising CDRs having amino acid sequences SEQ ID NO: 65 for CDR1, SEQ ID NO: 66 for CDR2, and SEQ ID NO: 67 for CDR3; and a light chain variable region comprising CDRs having amino acid sequences of SEQ ID NO: 68 for CDR1, SEQ ID NO: 69 for CDR2 and SEQ ID NO: 70 for CDR3; or (h) a heavy chain variable region comprising CDRs having amino acid sequences SEQ ID NO: 75 for CDR1, SEQ ID NO: 76 for CDR2, and SEQ ID NO: 77 for CDR3; and a light chain variable region comprising CDRs having amino acid sequences of SEQ ID NO: 78 for CDR1, SEQ ID NO: 79 for CDR2 and SEQ ID NO: 80 for CDR3; or (i) a heavy chain variable region comprising CDRs having amino acid sequences SEQ ID NO: 85 for CDR1, SEQ ID NO: 86 for CDR2, and SEQ ID NO: 87 for CDR3; and a light chain variable region comprising CDRs having amino acid sequences of SEQ ID NO: 88 for CDR1, SEQ ID NO: 89 for CDR2 and SEQ ID NO: 90 for CDR3; or (j) a heavy chain variable region comprising CDRs having amino acid sequences SEQ ID NO: 95 for CDR1, SEQ ID NO: 96 for CDR2, and SEQ ID NO: 97 for CDR3; and a light chain variable region comprising CDRs having amino acid sequences of SEQ ID NO: 98 for CDR1, SEQ ID NO: 99 for CDR2 and SEQ ID NO: 100 for CDR3; or (k) a heavy chain variable region comprising CDRs having amino acid sequences SEQ ID NO: 105 for CDR1, SEQ ID NO: 106 for CDR2, and SEQ ID NO: 107 for CDR3; and a light chain variable region comprising CDRs having amino acid sequences of SEQ ID NO: 108 for CDR1, SEQ ID NO: 109 for CDR2 and SEQ ID NO: 110 for CDR3.

In some embodiments, said antibody comprises: (a) a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3; or (b) a heavy chain variable region comprising CDRs having amino acid sequences SEQ ID NO: 125 for CDR1, SEQ ID NO: 126 for CDR2, and SEQ ID NO: 127 for CDR3; and a light chain variable region comprising CDRs having amino acid sequences of SEQ ID NO: 128 for CDR1, SEQ ID NO: 129 for CDR2 and SEQ ID NO: 130 for CDR3; or (c) a heavy chain variable region comprising CDRs having amino acid sequences SEQ ID NO: 135 for CDR1, SEQ ID NO: 136 for CDR2, and SEQ ID NO: 137 for CDR3; and a light chain variable region comprising CDRs having amino acid sequences of SEQ ID NO: 138 for CDR1, SEQ ID NO: 139 for CDR2 and SEQ ID NO: 140 for CDR3; or (d) a heavy chain variable region comprising CDRs having amino acid sequences SEQ ID NO: 145 for CDR1, SEQ ID NO: 146 for CDR2, and SEQ ID NO: 147 for CDR3; and a light chain variable region comprising CDRs having amino acid sequences of SEQ ID NO: 148 for CDR1, SEQ ID NO: 149 for CDR2 and SEQ ID NO: 150 for CDR3; or (e) a heavy chain variable region comprising CDRs having amino acid sequences SEQ ID NO: 155 for CDR1, SEQ ID NO: 156 for CDR2, and SEQ ID NO: 157 for CDR3; and a light chain variable region comprising CDRs having amino acid sequences of SEQ ID NO: 158 for CDR1, SEQ ID NO: 159 for CDR2 and SEQ ID NO: 160 for CDR3; or (f) a heavy chain variable region comprising CDRs having amino acid sequences SEQ ID NO: 165 for CDR1, SEQ ID NO: 166 for CDR2, and SEQ ID NO: 167 for CDR3; and a light chain variable region comprising CDRs having amino acid sequences of SEQ ID NO: 168 for CDR1, SEQ ID NO: 169 for CDR2 and SEQ ID NO: 170 for CDR3; or (g) a heavy chain variable region comprising CDRs having amino acid sequences SEQ ID NO: 175 for CDR1, SEQ ID NO: 176 for CDR2, and SEQ ID NO: 177 for CDR3; and a light chain variable region comprising CDRs having amino acid sequences of SEQ ID NO: 178 for CDR1, SEQ ID NO: 179 for CDR2 and SEQ ID NO: 180 for CDR3; or (h) a heavy chain variable region comprising CDRs having amino acid sequences SEQ ID NO: 185 for CDR1, SEQ ID NO: 186 for CDR2, and SEQ ID NO: 187 for CDR3; and a light chain variable region comprising CDRs having amino acid sequences of SEQ ID NO: 188 for CDR1, SEQ ID NO: 189 for CDR2 and SEQ ID NO: 190 for CDR3; or (i) a heavy chain variable region comprising CDRs having amino acid sequences SEQ ID NO: 195 for CDR1, SEQ ID NO: 196 for CDR2, and SEQ ID NO: 197 for CDR3; and a light chain variable region comprising CDRs having amino acid sequences of SEQ ID NO: 198 for CDR1, SEQ ID NO: 199 for CDR2 and SEQ ID NO: 200 for CDR3; (j) a heavy chain variable region comprising complementarily-determining regions (CDRs) having amino acid sequences SEQ ID NO: 205 for CDR1, SEQ ID NO: 206 for CDR2, and SEQ ID NO: 207 for CDR3; and a light chain variable region comprising CDRs having amino acid sequences of SEQ ID NO: 208 for CDR1, SEQ ID NO: 209 for CDR2 and SEQ ID NO: 210 for CDR3; or (k) a heavy chain variable region comprising complementarily-determining regions (CDRs) having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

In particular embodiments, said antibody or antibody fragment comprises a heavy chain variable region comprising CDRs having amino acid sequences SEQ ID NO: 55 for CDR1, SEQ ID NO: 56 for CDR2, and SEQ ID NO: 57 for CDR3; and a light chain variable region comprising CDRs having amino acid sequences of SEQ ID NO: 58 for CDR1, SEQ ID NO: 59 for CDR2 and SEQ ID NO: 60 for CDR3.

In particular embodiments, said antibody or antibody fragment comprises a heavy chain variable region comprising CDRs having amino acid sequences SEQ ID NO: 95 for CDR1, SEQ ID NO: 96 for CDR2, and SEQ ID NO: 97 for CDR3; and a light chain variable region comprising CDRs having amino acid sequences of SEQ ID NO: 98 for CDR1, SEQ ID NO: 99 for CDR2 and SEQ ID NO: 100 for CDR3.

In particular embodiments, said antibody or antibody fragment comprises a heavy chain variable region comprising CDRs having amino acid sequences SEQ ID NO: 105 for CDR1, SEQ ID NO: 106 for CDR2, and SEQ ID NO: 107 for CDR3; and a light chain variable region comprising CDRs having amino acid sequences of SEQ ID NO: 108 for CDR1, SEQ ID NO: 109 for CDR2 and SEQ ID NO: 110 for CDR3.

In particular embodiments, said antibody or antibody fragment comprises a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3.

In particular embodiments, said antibody or antibody fragment comprises a heavy chain variable region comprising CDRs having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

Another aspect of the present application relates to an antibody or fragment thereof that selectively binds Zika virus wherein, the heavy chain CDR1 sequence differs from SEQ ID NO: 55 by four or less substitutions, the heavy chain CDR2 sequence differs from SEQ ID NO: 56 by two or less substitutions, the heavy chain CDR3 sequence differs from SEQ ID NO: 57 by five or less substitutions, the light chain CDR1 sequence differs from SEQ ID NO: 58 by one or less substitutions, the light chain CDR2 sequence differs from SEQ ID NO: 59 by three or less substitutions, and the light chain CDR3 sequence differs from SEQ ID NO: 60 by one or less substitutions.

Another aspect of the present application relates to an antibody or fragment thereof that selectively binds Zika virus wherein, the heavy chain CDR1 sequence differs from SEQ ID NO: 95 by four or less substitutions, the heavy chain CDR2 sequence differs from SEQ ID NO: 96 by two or less substitutions, the heavy chain CDR3 sequence differs from SEQ ID NO: 97 by five or less substitutions, the light chain CDR1 sequence differs from SEQ ID NO: 98 by one or less substitutions, the light chain CDR2 sequence differs from SEQ ID NO: 99 by three or less substitutions, and the light chain CDR3 sequence differs from SEQ ID NO: 100 by one or less substitutions.

Another aspect of the present application relates to an antibody or fragment thereof that selectively binds Zika virus wherein, the heavy chain CDR1 sequence differs from SEQ ID NO: 105 by four or less substitutions, the heavy chain CDR2 sequence differs from SEQ ID NO: 106 by two or less substitutions, the heavy chain CDR3 sequence differs from SEQ ID NO: 107 by five or less substitutions, the light chain CDR1 sequence differs from SEQ ID NO: 108 by one or less substitutions, the light chain CDR2 sequence differs from SEQ ID NO: 109 by three or less substitutions, and the light chain CDR3 sequence differs from SEQ ID NO: 110 by one or less substitutions.

Another aspect of the present application relates to an antibody or fragment thereof that selectively binds Zika virus wherein, the heavy chain CDR1 sequence differs from SEQ ID NO: 115 by four or less substitutions, the heavy chain CDR2 sequence differs from SEQ ID NO: 116 by two or less substitutions, the heavy chain CDR3 sequence differs from SEQ ID NO: 117 by five or less substitutions, the light chain CDR1 sequence differs from SEQ ID NO: 118 by one or less substitutions, the light chain CDR2 sequence differs from SEQ ID NO: 119 by three or less substitutions, and the light chain CDR3 sequence differs from SEQ ID NO: 120 by one or less substitutions.

In some embodiments, an antibody or antibody fragment as described herein inhibits Zika virus infection.

In some embodiments, an antibody or antibody fragment as described herein inhibits Dengue virus infection.

In some embodiments, an antibody or antibody fragment as described herein inhibits infection by Dengue virus serotype 2.

In some embodiments, an antibody or antibody fragment as described herein inhibits infection by Dengue virus serotype 3.

In some embodiments, an antibody or antibody fragment as described herein inhibits Zika virus transmission from a pregnant female to a fetus.

In some embodiments, an antibody or antibody fragment as described herein inhibits sexual transmission of Zika virus.

In some embodiments, an antibody or antibody fragment as described herein inhibits or prevents infection of human testes.

In some embodiments, an antibody or antibody fragment as described herein has an ED50 for neutralizing Zika infection of less than less than 10 mg kg-1, less than 5 mg kg-1, less than 1 mg kg-1, less than 0.5 mg kg-1, less than 0.2 mg kg-1, less than 0.1 mg kg-1, less than 0.05 mg kg-1, less than 0.02 mg kg-1, or less than 0.01 mg kg-1.

In some embodiments, an antibody or antibody fragment as described herein has an IC50 for neutralizing Zika infection of less than 10 µM, less than 5 µM, less than 2 µM, less than 1 µM, less than 500 nM, less than 200 nM, or less than 100 nM.

In some embodiments, 100 ag/ml of an antibody or antibody fragment as described herein does not neutralize infection by a flavivirus selected from the group of Dengue virus, Japanese Encephalitis virus, West Nile virus, or Yellow Fever virus.

In some embodiments, an antibody or antibody fragment as described herein has an equilibrium dissociation constant (KD) is in the range from $10^{-7}$ to $10^{-9}$ molar.

In some embodiments, an antibody or antibody fragment as described herein has an equilibrium dissociation constant (KD) of less than $10^{-7}$ molar.

In some embodiments, an antibody or antibody fragment as described herein comprises an Fd fragment.

In some embodiments, an antibody fragment as described herein is a Fab fragment.

In some embodiments, an antibody fragment as described herein is a single chain variable fragment (ScFv).

In some embodiments, an antibody or antibody fragment as described herein is a human antibody, humanized antibody or humanized antibody fragment.

Another aspect of the present application relates to a polynucleotide comprising a nucleotide sequence encoding an antibody or antibody fragment as described herein.

Another aspect of the present application relates to a host cell comprising a polynucleotide comprising a nucleotide sequence encoding an antibody or antibody fragment as described herein.

Another aspect of the present application relates to a method of making an antibody or antibody fragment as described herein comprising isolating antibody secreted by a host cell comprising a polynucleotide comprising a nucleotide sequence encoding an antibody or antibody fragment as described herein.

Another aspect of the present application relates to a pharmaceutical composition comprising a pharmaceutically acceptable carrier and an antibody or antibody fragment as described herein.

Another aspect of the present application relates to a method for the prevention or treatment of a flavivirus infection comprising administering to a patient a therapeutically effective amount of a pharmaceutical composition comprising a pharmaceutically acceptable carrier and an antibody or antibody fragment as described herein.

Another aspect of the present application relates to a method for inhibiting or preventing transmission of a flavivirus infection from a pregnant female to her fetus comprising administering to the pregnant female a therapeutically effective amount of a pharmaceutical composition comprising a pharmaceutically acceptable carrier and an antibody or antibody fragment as described herein.

Another aspect of the present application relates to a method for inhibiting or preventing sexual transmission of a flavivirus infection comprising administering a therapeutically effective amount of a pharmaceutical composition comprising a pharmaceutically acceptable carrier and an antibody or antibody fragment as described herein.

Another aspect of the present application relates to a method of reducing the likelihood of a subject developing a disease caused by Zika virus or a flavivirus, the method comprising administering a pharmaceutical composition comprising a pharmaceutically acceptable carrier and an antibody or antibody fragment as described herein to a subject prior to a flavivirus infection.

Another aspect of the present application relates to a method of detecting the presence of a flavivirus in a biological sample, the method comprising contacting an antibody or antibody fragment as described herein with the biological sample and detecting the binding of the antibody or antibody fragment to a flavivirus.

Another aspect of the present application relates to a kit for detecting the presence of a flavivirus in a biological sample, the kit comprising an antibody or antibody fragment as described herein.

Another aspect of the present application relates to a method of diagnosing infection by a flavivirus, the method comprising: obtaining a biological sample for a subject at risk of a flavivirus infection; contacting the biological sample with an antibody or antibody fragment as described herein; and determining if the antibody or antibody fragment has bound to a flavivirus antigen; wherein binding of the antibody or antibody fragment to a flavivirus antigen indicates that the subject is infected with a flavivirus.

Another aspect of the present application relates to a method of detecting a latent infection by a flavivirus, the method comprising: obtaining a biological sample for a subject at risk of a flavivirus infection; stimulating the biological sample to induce viral outgrowth; contacting the biological sample with an antibody or antibody fragment as described herein; and determining if the antibody or antibody fragment has bound to a flavivirus antigen; wherein binding of the antibody or antibody fragment to a flavivirus antigen indicates that the subject is infected with a flavivirus.

Another aspect of the present application relates to a method of inducing immunity to a flavivirus in a human subject at risk of flavivirus infection comprising, administering a single dose of Zika virus purified inactivated vaccine in the human subject, wherein the subject was previously infected by a flavivirus.

In some embodiments, the flavivirus is a Zika virus.

In some embodiments, the flavivirus is a Dengue virus.

In some embodiments, the flavivirus is Dengue virus serotype 2.

In some embodiments, the flavivirus is Dengue virus serotype 3.

In some embodiments, the flavivirus is a West Nile virus.

In some embodiments, the flavivirus is a Japanese Encephalitis virus.

In other embodiments, the flavivirus that the human subject was previously exposed to was not a Zika virus.

Another aspect of the present application relates to a method of measuring the efficacy of a vaccine batch comprising contacting an aliquot of the vaccine batch with an antibody or antibody fragment as described herein, and detecting the binding of the antibody or antibody fragment.

A method of determining whether a flavivirus vaccine comprises a DI/DIII linker domain comprising contacting the vaccine with an antibody or antibody fragment antibody comprising: (a) a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3; or (b) a heavy chain variable region comprising CDRs having amino acid sequences SEQ ID NO: 125 for CDR1, SEQ ID NO: 126 for CDR2, and SEQ ID NO: 127 for CDR3; and a light chain variable region comprising CDRs having amino acid sequences of SEQ ID NO: 128 for CDR1, SEQ ID NO: 129 for CDR2 and SEQ ID NO: 130 for CDR3; or (c) a heavy chain variable region comprising CDRs having amino acid sequences SEQ ID NO: 135 for CDR1, SEQ ID NO: 136 for CDR2, and SEQ ID NO: 137 for CDR3; and a light chain variable region comprising CDRs having amino acid sequences of SEQ ID NO: 138 for CDR1, SEQ ID NO: 139 for CDR2 and SEQ ID NO: 140 for CDR3; or (d) a heavy chain variable region comprising CDRs having amino acid sequences SEQ ID NO: 145 for CDR1, SEQ ID NO: 146 for CDR2, and SEQ ID NO: 147 for CDR3; and a light chain variable region comprising CDRs having amino acid sequences of SEQ ID NO: 148 for CDR1, SEQ ID NO: 149 for CDR2 and SEQ ID NO: 150 for CDR3; or (e) a heavy chain variable region comprising CDRs having amino acid sequences SEQ ID NO: 155 for CDR1, SEQ ID NO: 156 for CDR2, and SEQ ID NO: 157 for CDR3; and a light chain variable region comprising CDRs having amino acid sequences of SEQ ID NO: 158 for CDR1, SEQ ID NO: 159 for CDR2 and SEQ ID NO: 160 for CDR3; or (f) a heavy chain variable region comprising CDRs having amino acid sequences SEQ ID NO: 165 for CDR1, SEQ ID NO: 166 for CDR2, and SEQ ID NO: 167 for CDR3; and a light chain variable region comprising CDRs having amino acid sequences of SEQ ID NO: 168 for CDR1, SEQ ID NO: 169 for CDR2 and SEQ ID NO: 170 for CDR3; or (g) a heavy chain variable region comprising CDRs having amino acid sequences SEQ ID NO: 175 for CDR1, SEQ ID NO: 176 for CDR2, and SEQ ID NO: 177 for CDR3; and a light chain variable region comprising CDRs having amino acid sequences of SEQ ID NO: 178 for CDR1, SEQ ID NO: 179 for CDR2 and SEQ ID NO: 180 for CDR3; or (h) a heavy chain variable region comprising CDRs having amino acid sequences SEQ ID NO: 185 for CDR1, SEQ ID NO: 186 for CDR2, and SEQ ID NO: 187 for CDR3; and a light chain variable region comprising CDRs having amino acid sequences of SEQ ID NO: 188 for CDR1, SEQ ID NO: 189 for CDR2 and SEQ ID NO: 190 for CDR3; or (i) a heavy chain variable region comprising CDRs having amino acid sequences SEQ ID NO: 195 for CDR1, SEQ ID NO: 196 for CDR2, and SEQ ID NO: 197 for CDR3; and a light chain variable region comprising CDRs having amino acid sequences of SEQ ID NO: 198 for CDR1, SEQ ID NO: 199 for CDR2 and SEQ ID NO: 200 for CDR3; (j) a heavy chain variable region comprising complementarily-determining regions (CDRs) having amino acid sequences SEQ ID NO: 205 for CDR1, SEQ ID NO: 206 for CDR2, and SEQ ID NO: 207 for CDR3; and a light chain variable region comprising CDRs having amino acid sequences of SEQ ID NO: 208 for CDR1, SEQ ID NO: 209 for CDR2 and SEQ ID NO: 210 for CDR3; or (k) a heavy chain variable region comprising complementarily-determining regions (CDRs) having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

Another aspect of the present application relates to a method of purifying a flavivirus E glycoprotein comprising contacting the flavivirus E glycoprotein with an antibody or antibody fragment as described herein.

Another aspect of the present application relates to an antibody or antibody fragment as described herein, wherein the antibody or antibody fragment binds to the DI-DIII linker domain of a Zika virus.

In some embodiments, 100 ng, 50 ng, 20 ng, 10 ng, 5 ng, 2 ng, 1 ng, 0.5 ng, 0.2 ng or 0.1 ng of the antibody or fragment thereof can neutralize at least 50% of the infectious activity of 100 PFU of Zika virus in a microneutralization assay.

In some embodiments, binding to Zika virus is reduced by at least 70% when Zika virus E glycoprotein residue Tyrosine 305 is substituted with alanine.

Another aspect of the present application relates to a method for isolating an antibody that binds to cross-protomer epitopes of a virus comprising: (a) immunizing a subject with a viral immunogen, (b) isolating peripheral blood mononuclear cells (PBMCs) from the subject, (c) contacting the PBMCs with intact virus to create PBMC-virus complexes, (d) contacting the PBMC-virus complexes with a fluorescently-labeled antibody that binds the virus, (e) isolating a fluorescent PBMC, (f) isolating polynucleotides encoding the heavy and light chains of an antibody from the fluorescent PBMC, (g) expressing the isolated polynucleotides in a host cell, and (h) isolating an antibody expressed by the host cell.

In some embodiments, the subject is a primate.

In some embodiments, the viral immunogen is an intact virus.

In some embodiments, the viral immunogen is a flavivirus immunogen. In some further embodiments, the flavivirus immunogen is a Zika virus immunogen. In other further embodiments, the flavivirus immunogen is a Dengue virus immunogen. In still other further embodiments, the flavivirus immunogen is a West Nile virus immunogen.

Another aspect of the present application relates to a multispecific antibody comprising a first binding site that binds to a flavivirus and a second binding site that binds to a flavivirus, wherein the first binding site binds to a different epitope than the second binding site.

In some embodiments, the multispecific antibody comprises a plurality of first binding sites and a plurality of second binding sites.

In some embodiments, the multispecific antibody comprises a third binding site that binds to a different flavivirus epitope than the first binding site or the second binding site. In some still further embodiments, the multispecific antibody comprises a fourth binding site that binds to a different flavivirus epitope. In some still further embodiments, the multispecific antibody comprises a fifth binding site that binds to a different flavivirus epitope. In some still further embodiments, the multispecific antibody comprises a sixth binding site that binds to a different flavivirus epitope. In some still further embodiments, the multispecific antibody comprises a seventh binding site that binds to a different flavivirus epitope. In some still further embodiments, the multispecific antibody comprises an eighth binding site that binds to a different flavivirus epitope. In some still further embodiments, the multispecific antibody comprises a ninth binding site that binds to a different flavivirus epitope. In some still further embodiments, the multispecific antibody comprises a tenth binding site that binds to a different flavivirus epitope.

In some embodiments, the first binding site comprises CDR sequences of a heavy chain variable domain or a fragment thereof and CDR sequences of a light chain variable domain or a fragment thereof.

In some embodiments, the second binding domain comprises CDR sequences of a single chain variable fragment (ScFv).

In some embodiments, the constant region of a heavy chain polypeptide comprising CDR sequences of the first binding site comprises a Threonine 366 to Tyrosine substitution and the constant region of a heavy chain polypeptide comprising CDR sequences of the second binding site comprises a Tyrosine 407 to Threonine substitution.

In some embodiments, a ScFv comprising the second binding site is inserted into the hinge region of a heavy chain polypeptide comprising CDR sequences of the first binding site.

In some embodiments, a ScFv comprising the second binding site is inserted within a constant region of a heavy chain polypeptide comprising CDR sequences of the first binding site.

In some embodiments, the first binding site has relatively higher affinity for a Zika virus E glycoprotein than for a Dengue virus E glycoprotein and the second binding site has relatively higher affinity for a Dengue virus E glycoprotein than for a Zika virus E glycoprotein.

In some embodiments, wherein the first binding site comprises CDR sequences from an antibody selected from the group comprising MZ4, MZ20, EDE2-A11 and Ab513.

In some embodiments, the second binding site comprises CDR sequences from an antibody selected from the group comprising MZ4, MZ20, EDE2-A11 and Ab513.

In some embodiments, wherein the mean binding response as measured by BioLayer Interferometry for ZIKV, DENV1, DENV2, DENV3, and DENV4 is less than the mean binding response as measured by BioLayer Interferometry for ZIKV, DENV1, DENV2, DENV3, and DENV4 of an antibody comprising only a first binding site or only a second binding site.

In some embodiments, the mean of $IC_{50}$ values for neutralization of ZIKV, DENV1, DENV2, DENV3, and DENV4 is less than the mean of $IC_{50}$ values for neutralization of ZIKV, DENV1, DENV2, DENV3, and DENV4 of an antibody comprising only a first binding site or only a second binding site.

In some embodiments, the multispecific antibody comprises a first polypeptide comprising an MZ4 heavy chain variable domain and an MZ4 light chain variable domain and a second polypeptide comprising an EDE2-A11 heavy chain variable domain and an EDE2-A11 light chain variable domain.

In some embodiments, the multispecific antibody comprises a polypeptide comprising an MZ4 heavy chain variable domain, an MZ4 light chain variable domain, an EDE2-A11 heavy chain variable domain and an EDE2-A11 light chain variable domain.

Unless otherwise defined, all technical and scientific terms used herein have the same meaning as commonly understood by one of ordinary skill in the art. All publications, patent applications, patents, and other references mentioned herein are incorporated by reference in their entirety. In case of conflict, the present specification, including definitions, will control.

Aspects and embodiments of the present application are further illustrated by the following non-limiting examples.

Example 1. General Methods

Cell lines: D1-4G2-4-15 mouse hybridoma (ATCC #HB-112), C6/36 (ATCC #CRL-1660), Vero (ATCC #CCL-81), Expi293F (ThermoFisher Scientific), DS-2 (ThermoFisher Scientific), and U937-DC-SIGN (ATCC) cell lines were utilized in this study. These lines were verified to be authentic, using short tandem repeat profiling, morphology, and cytochrome C oxidase I testing, and free of contamination by *Mycoplasma* prior to use.

Preparation of ZIKV and DENV: C6/36 mosquito cells were grown in T75 flasks and infected with ZIKV strain (Paraiba_01 strain, GenBank KX280026) or DENV-2 (S16803, GenBank GU289914) at a multiplicity of infection of approximately 0.1 PFU/cell. The infected cell culture supernatant was harvested on day 5 postinfection. Cell debris was removed by centrifugation at 5,000 rpm for 30 min at 4° C. The supernatant was layered on top of a 30% sucrose solution containing 10 mM Tris, 100 mM NaCl, and 1 mM EDTA. The virus was pelleted by ultracentrifugation in a swinging-bucket rotor at 26,000 rpm for 4 hr at 4° C. to remove low-molecular-weight contaminants such as soluble proteins. The supernatant was removed, and the tubes were briefly left upside down on chromatography paper in order to remove excess liquid from the side of the tubes. The virus pellet was resuspended in phosphate-buffered saline. The purity of the viral preparations was verified by sodium dodecyl sulfate-polyacrylamide gel electrophoresis.

Sorting of whole ZIKV positive B cells from non-human primates: Approximately 10 million cryopreserved peripheral blood mononuclear cells (PBMCs) were obtained from a flavivirus-naïve, five-year-old male, rhesus macaque previously described in McCracken, 2017. This animal was not previously infected and confirmed by testing for ZIKV, JEV, WNV, YFV, and DENV1-4 antibodies by a sensitive screening virus neutralization assay prior to initial infection (McCracken, 2017. The PBMC sample was collected 14 days following challenge with ZIKV (Brazil-ZKV2015 strain, GenBank KU497555). PBMCs were thawed in warm medium containing benzonase, then washed with phosphate-buffered saline (PBS) and stained for viability using Invitrogen Aqua Live/Dead stain. Cells were incubated at 4° C. for 30 minutes with a cocktail of antibodies including CD3 BV510, CD14 BV510, and CD56 BV510 (BioLegend) as dump channel markers, and CD19 ECD (Beckman Coulter), CD20 APC-Cy7 (BioLegend), CD38 PE (NHP Reagent Resource) and CXCR5 PE-Cy7 (eBioscience) as positive gating markers. To obtain monoclonal antibodies that target quaternary epitopes, primary staining also included a 1/10 dilution of live whole ZIKV (Paraiba_01) produced in C6/36 cells (see above). ZIKV-reactive B cells were identified by secondary staining using 4G2 (Biovest) conjugated to APC (Thermofisher). Cells were selected by sorting based on negative expression of CD3, CD14 and CD56, positive expression of CD19, mid to high expression of CD38, and positive sequential staining with 4G2. Cells were sorted directly into lysis buffer (murine RNAse inhibitor (New England Biolabs), DTT and SuperScript III First Strand Buffer (ThermoFisher), Igepal (Sigma) and carrier RNA (Qiagen) at one cell per well into polypropylene PCR plates using a FACSAria (Becton Dickinson) and stored at −80° C. until subsequent reverse transcription.

Antibody sequencing and production: RNA from single B cells was reverse-transcribed using random primers and the SuperScriptIII kit (ThermoFisher). Antibody V (D) J genes were amplified from the cDNA by nested PCR, using the HotStar Taq DNA Polymerase kit (Qiagen) and a combination of primer. V (D) J gene assignment, somatic hypermutation and CDR3 determinations was performed with IgBlast (Ye, 2013). For the non-human primate experiments, antibody variable regions were synthesized and cloned (Genscript) into CMVR expression vectors (a gift from Kevin Saunders) between a murine Ig leader (GenBank DQ407610) and the constant regions of rhesus macaques IgG1 (GenBank AAF14058), Ig K light chain (GenBank AAD02577) or Igλ light chain (GenBank ADX62855) (Saunders, 2015. Variable regions for control antibodies EDE1-C8, Z3L1 (Wang, 2016), 2A10G6 (Deng, 2011) and Z004 were synthesized as above and cloned into CMVR expression vectors carrying human IgG1, Igκ and Igλ constant regions. For human antibodies, antibody variable regions were synthesized and cloned (Genscript) into CMVR expression vectors (NIH AIDS reagent program) between a murine Ig leader (GenBank DQ407610) and the constant regions of human Igy1 (GenBank AAA02914), Igκ (GenBank AKL91145) or IgλGenBank AAA02915). Plasmids encoding heavy and light chains were co-transfected into Expi293F cells (ThermoFisher) according to the manufacturer's instructions. After 5 days, antibodies were purified from cleared culture supernatants with Protein A agarose (ThermoFisher) using standard procedures, buffer exchanged to Phosphate-buffered saline (PBS) and quantified from A280 measurements. SDS-PAGE and Coomassie staining in both reducing and non-reducing conditions assessed purity and stability of the purified antibodies.

Fab production: Freshly prepared Fab digestion buffer containing 20 mM sodium phosphate, 10 mM EDTA and 20 mM of cysteine-HCl, pH 7.4 was added to papain slurry (Thermo Scientific) and incubated with MZ antibodies (IgGs) at 20 mg/ml. Reaction was allowed to proceed for five hours to overnight in a shaker incubator at 37° C. temperature and 100 rpm shaking speed. Resin was separated from the supernatant by centrifugation at 3000×g. Digestion was assessed by SDS-PAGE and upon completion, the reaction mixture was passed through protein-A beads (0.5-1 ml beads) 3 times and the final flow through was assessed by SDS-PAGE for purity.

Production of recombinant proteins: Recombinant ZIKV soluble E (sE) protein (1-404) from strain PRVABC59 (GenBank KX087101) and DENV-2 sE (1-396) from strain 16681-PDK53 (GenBank M84728) were produced with C-terminal AviTag and poly-histidine tags from Expi293F cells. The coding sequence for prM/sE was synthesized (Genscript) and cloned into the pcDNA3.4 vector (ThermoFisher) downstream a murine Ig leader sequence. Following transient co-transfection with a furin (Genbank BC012181) expression vector, mature sE proteins were purified from cell culture supernatants using a Ni-NTA (Qiagen) affinity column. An isolated E domain III (303-404) was expressed by deleting the prM and domains I-II from the full-length prM/sE pcDNA3.4 construct. A cleavable twin-strep-tagged ZIKV sE version was also expressed from stably transfected S2 cells using the *Drosophila* Expression system (ThermoFisher) according to the manufacturer's instructions. Briefly, a DNA fragment encoding for the first 405 residues of E from strain PRVABC59 was synthesized (Genscript) with a C-terminal HRV-3C cleavage site followed by a twin-strep tag (IBA) and cloned into the pMT-BiP vector (ThermoFisher). The L107C and A319C mutations were introduced using the Quikchange Lightning site-directed mutagenesis kit (Agilent). S2 cells were co-transfected with the pMT-BiP-ZIKV sE expression vector and the pCoBlast selection vector at a 19:1 (w/w) ratio. Stably transfected cells were selected with Blasticidin and adapted to suspension and serum-free medium (Lonza Insect Xpress). ZIKV E expression was induced with 0.5 mM $CuSO_4$ and culture supernatants were harvested after 7 days. The insect-produced ZIKV sE was purified on a StrepTactin XT column (IBA) following the manufacturer's instructions followed by gel filtration on an Enrich SEC 650 column (Bio-Rad) or GE Sephadex S200 column to obtain pure monomeric (WT sE) or dimeric (mutant sE) ZIKV sE proteins. ZIKV (Suriname) NS1 was purchased from The Native Antigen Company.

Biolayer interferometry binding and competition assays: Real-time interactions between purified sE proteins and antibodies were monitored on an Octet RED96 instrument (Pall ForteBio) at 30° C. Avi-tagged purified ZIKV or DENV-2 sE proteins, biotinylated with the BirA biotinylation kit (Avidity), were diluted in kinetics buffer (0.1% [w/v] bovine serum albumin (BSA), 0.02% [v/v] Tween-20 in PBS; Pall ForteBio) and immobilized on streptavidin (SA) biosensors (Pall ForteBio) at ~50% of the sensor maximum binding capacity. Baseline was established in kinetics buffer. In the screening assay for NHP antibodies, loaded biosensors were then dipped into wells containing the antibodies diluted to 400 nM in kinetics buffer. Binding responses were measured after 450 s of association using the Data analysis software 9.0 (Pall ForteBio). For measurement of human antibody binding activities in plasma, loaded biosensors were dipped into wells containing plasma diluted at 1/40 in kinetic buffer for 450 s, to obtain binding responses, followed by a dissociation strep in buffer. Off-rates were calculated by fitting dissociation curves to a 1:1 binding model. For full characterization of Fabs affinity, loaded biosensors were dipped into wells containing serial dilutions of the antibody Fab fragments for 450 s. sE:Fab complexes were then allowed to dissociate for 1200 s in buffer. After reference subtraction, binding kinetic constants were determined, from at least 4 concentrations of Fab, by fitting the curves to a 1:1 binding model using the Data analysis software 9.0 (Pall ForteBio). Finally, in the binding competition assay, sensors loaded with ZIKV sE, as described above, were immersed into wells containing the first competing antibody at a concentration (ranging from 100 to 800 nM) necessary to reach binding saturation after 900 s. Next, biosensors were dipped into wells containing the second antibody, in presence of the first competing antibody, and binding was measured after 900 s of association. Residual binding signal of the second antibody was expressed as a percent of the signal obtained in presence of a non-competing control antibody (VRC01), ran in parallel, and further corrected for the binding signal obtained with the first antibody alone after 1800 s. As some competing antibodies did not reach saturation after the first 900 s association and continue to contribute to binding signal together with the second antibody, a set of controls were run independently with all first competing antibodies alone for a 1800 s association. The difference in signal obtained between t=1800 s and t=900 s was subtracted from the signal obtained in presence of the second antibody to generate a corrected residual binding signal Antibodies were defined as competing when binding signal of the second antibody was reduced to less than 30% of its maximum binding capacity and non-competing when binding was greater than 70%. Intermediate competition was defined by binding levels of 30-70%. Control monoclonal antibodies included the monoclonal 4G2 purified from hybridoma2, A10G6 (Deng, 2011), expressed with a human Fc domain, Z3L1 (Wang, 2016), EDE1-C8 (Dejnirattisai, 2015), and Z004 (Robbiani, 2017), all expressed and purified from Expi293F cells. The HIV-1 specific VRC01 monoclonal antibody (also expressed in Expi293F cells) served as negative control.

Plasma competition assays were performed similarly to the mAb competition assays described above with the following modifications. Sensors loaded with ZIKV sE were immersed into wells containing plasma from ZIKV infected macaques (McCracken, 2017) and humans (Seracare), as well as control naïve plasma from the two species at dilutions (ranging from 1/10 to 1/200) necessary to reach near binding saturation after 900 s. Next, biosensors were dipped into wells containing the indicated monoclonal antibody, in presence of competing plasma, and binding was measured after 30 s of association. Residual binding signal of the monoclonal antibody was expressed as a percent of the signal obtained in presence of a non-competing matrix control of IgG-depleted human serum (BBI solutions), ran in parallel. Binding of monoclonal antibodies was further corrected for the binding signal obtained with plasma-only controls that ran simultaneously. Finally, results were expressed as percentage of binding inhibition defined as the inverse of residual binding.

Measurement of antibody binding affinity: Determination of affinity constant was performed on the Octet RED96 instrument. Disulfide-stabilized ZIKV sE was biotinylated at a 2:1 molar ratio using EZ-link NHS-PEG4-biotin (ThermoFisher), following manufacturer's instructions. A single buffer (1× kinetics buffer [Pall ForteBio]) was used for all dilution, baseline and dissociation steps. Streptavidin biosensors, loaded with ZIKV sE dimer at ~50% of maximum binding capacity, were dipped into wells containing two-fold serial dilutions of the antibody Fab fragments for 450 s with starting concentrations ranging from 1 to 10 µM. ZIKV sE:Fab complexes were then allowed to dissociate for 1200 s in buffer. After reference subtraction, binding kinetic constants were determined, from at least 4 concentrations of Fab, by fitting the curves to a 1:1 binding model using the Data analysis software 9.0 (Pall ForteBio).

Whole virus ELISA assay: Binding of antibodies to whole ZIKV or DENV-2 viruses was measured using a capture ELISA assay. ELISA plates were coated overnight at 4° C. with the capture antibody (4G2) at 100 ng per well in borate saline pH9.0 buffer. After washes in PBS-T (PBS with 0.05% Tween-20), plates were blocked with 1% (v/v) normal goat serum, 0.25% (w/v) BSA, 0.1% (v/v) Tween-20 for 30 min at 37° C. Washes in PBS-T were performed after each subsequent steps and all dilutions were made in blocking buffer. Previously titrated purified viruses (ZIKV/Brazil/2015 or DENV-2 16681) were diluted and added at 50 µl per well and incubated for 2 h at 37° C. Serial 4-fold dilutions of antibodies (starting at 20 µg/ml) were added to the plate and incubated for 2 h at 37° C. Secondary HRP-conjugated antibodies anti-mouse, human and monkey IgG were added for 1 h at 37° C. and plates were developed using 3,3',5,5'-Tetramethylbenzidine (TMB) peroxidase substrate (KPL) and read at 650 nm. After background (average blank+2 standard deviation) subtraction, the binding curves were fitted using a 4-parameter logistic regression model in the Prism 7 software (GraphPad).

Recombinant ZIKV sE binding ELISA assay: Binding of antibodies to recombinant ZIKV sE protein was also performed in a standard ELISA assay. ELISA plates were coated overnight at 4° C. with 100 ng of purified ZIKV sE (produced in DS-2 cells) in sodium bicarbonate/carbonate pH9.4 buffer. Plates were then blocked with 5% (w/v) nonfat dry milk, 1% (w/v) BSA in PBS for 1 h at 37° C. Washes in between each steps were performed with 0.1% (v/v) Triton-X100 in PBS. Serial 4-fold dilutions of antibodies (starting at 20 µg/ml) made in 5% (v/v) Fetal Bovine Serum, 2% (w/v) BSA, 1% (v/v) Triton X-100 in PBS were added to the plate and incubated for 1 hour at RT. Secondary HRP-conjugated antibodies anti-mouse, human and monkey IgG were added for 1 h at 37° C. and plates were developed using TMB peroxidase substrate (KPL) and read at 650 nm. Data were analyzed as described for the whole virus ELISA.

In vivo protection studies: Female Balb/c mice were purchased from commercial vendors and housed at Beth Israel Deaconess Medical Center. Indicated monoclonal macaque antibody was infused intravenously into groups of naïve recipient Balb/c mice (N=5/group) prior to ZIKV-BR challenge. Mice received 100 µl (200 µg) of a 2 mg/ml solution of purified monoclonal antibody and 2 hr after infusion, mice were challenged with 105 viral particles (VP) [102 plaque-forming units (PFU)] ZIKV-BR intravenously. RT-PCR assays were utilized to monitor viral loads, essentially as previously described (Larocca, 2016). RNA was extracted from serum samples with a QIAcube HT (Qiagen). The wildtype ZIKV BeH815744 Cap gene was utilized as a standard. RNA was purified (Zymo Research). Log dilutions of the RNA standard were reverse transcribed and included with each RT-PCR assay. Viral loads were calculated as virus particles (VP) per ml with a sensitivity of 100 copies/ml.

Shotgun Mutagenesis Epitope Mapping: Epitope mapping was performed by shotgun mutagenesis. A ZIKV prM/E expression construct (strain ZikaSPH2015) was subjected to high-throughput alanine scanning mutagenesis to generate a comprehensive library of individual mutations where each residue within prM/E was changed to alanine, with alanine mutated to serine. In total, 672 ZIKV prM/E mutants were generated (100% coverage), sequence confirmed, and arrayed into 384-well plates. Each prM/E mutant was transfected into HEK-293T cells and allowed to express for 22 hrs. Cells were fixed in 4% (v/v) paraformaldehyde (Electron Microscopy Sciences), permeabilized with 0.1% (w/v) saponin (Sigma-Aldrich) in PBS plus calcium and magnesium (PBS++), then incubated with purified mAbs diluted in PBS++, 10% (v/v) normal goat serum (NGS) (Sigma), 0.1% (v/v) saponin. Primary mAb screening concentrations were determined using an independent immunofluorescence titration curve against wild-type ZIKV prM/E to ensure that signals were within the linear range of detection. MAb binding was detected using 3.75 µg/ml AlexaFluor488-conjugated secondary antibody (Jackson ImmunoResearch Laboratories) in 10% NGS/0.1% saponin. Cells were washed 3 times with PBS++/0.1% saponin followed by 2 washes in PBS. Mean cellular fluorescence was detected using a high throughput flow cytometer (HTFC, Intellicyt). MAb reactivities against each mutant prM/E clone were calculated relative to wild-type prM/E reactivity by subtracting the signal from mock-transfected controls and normalizing to the signal from wild-type prM/E-transfected controls. Mutations within clones were identified as critical to the mAb epitope if they did not support reactivity of the test mAb, but supported reactivity of other ZIKV mAbs. This counter-screen strategy facilitates the exclusion of prM/E mutants that are locally misfolded or have an expression defect.

Zika Virus Microneutralization (MN): The method of Larocca et al., 2016 was used to perform microneutralization assays. Plasma or purified antibodies at 1 to 2 mg/ml were serially diluted 3-fold in 96-well micro-plates, and 100 µl of ZIKV containing 100 PFU were added to 100 µl of each serum dilution and incubated at 35° C. for 2 hr. Supernatants were then transferred to microtiter plates containing confluent Vero cell monolayers (World Health Organization, NICSC-011038011038). After incubation for 4 days, cells were fixed with absolute ethanol: methanol for 1 hr at −20° C. and washed three times with PBS. The pan flavivirus monoclonal antibody 6B6-C1 conjugated to HRP was then added to each well, incubated at 35° C. for 2 hr, and washed with PBS. Plates were washed, developed with TMB substrate for 50 min at room temperature, stopped with 1:25 phosphoric acid, and absorbance was read at 450 nm. Assays were validated using the following criteria: the average absorbance at 450 nm of three non-infected control wells had to be ≤0.5, and virus-only control wells had to be ≥0.9. Normalized absorbance values were calculated, and the concentration to achieve 50% neutralization (MN50 or IC50) titer was calculated using a 4-parameter logistic regression analysis in GraphPad Prism 7.

FlowNT50 Zika virus neutralization assay: Serial dilutions of mAb or plasma were mixed with an equal volume of virus, diluted to achieve 10-15% infection of cells/well, and incubated for 1 hr at 37° C. After 1 hr of incubation, an equal volume of medium (RPMI-1640 supplemented with 10% FBS, 1% penicillin/streptomycin, 1% L-glutamine (200 mM), and 1% non-essential amino acids (10 mM)) containing 5×10⁴ U937-DC-SIGN cells were added to each serum-antibody mixture and incubated 18-20 hr overnight in a 37° C., 5% $CO_2$, humidified incubator. Following overnight incubation, the cells were fixed, permeabilized and immunostained with flavivirus group-reactive mouse monoclonal antibody 4G2 (Envigo Bioproducts) and secondary polyclonal goat anti-mouse IgG PE-conjugated antibody. The percentage of infected cells was quantified on a BD Accuri C6 Plus flow cytometer (BD Biosciences). Data were analyzed by nonlinear regression in GraphPad Prism to determine 50% neutralization titers.

PRNT50 Zika Virus neutralization assay: Serial dilutions of mAb were mixed with an equal volume of virus and incubated for 1 hr at 37° C. followed by infection of Vero-cell monolayers in triplicate. Plaques were visualized by staining with neutral red. Data were analyzed by nonlinear regression using asymmetric five-parameter logistic equation in GraphPad Prism to determine 50% neutralization titers.

Reporter Virus Particle (RVP): Neutralization of wildtype and mutant Zika (strain H/PF/2013) by mAbs was measured using a reporter virus particle (RVP) assay as described previously (Dowd et al., 2016). Briefly, mAbs were serially diluted 5-fold from 50 µg and incubated with 100 µl of virus for 1 hr at 37° C., after which 50 µl of target Vero cells (400,000 cells/ml) was added. Input virus dilution was calculated from titration experiments to ensure sufficient luciferase output within the linear portion of the titration curve. Cell only and virus only controls were included on each plate, and all mAbs (and virus-only) were run in triplicate. After a 48 hr incubation, luciferase activity was measured, and neutralization curves were calculated by averaging luciferase units from triplicates, subtracting cell-only control background and calculating the percent difference in serum samples to virus-only controls. Data was fit by nonlinear regression using the asymmetric five-parameter logistic equation in GraphPad Prism. The 50%, 80% and 90% inhibitory dilutions (ID50, ID80 and ID90, respectively) were defined as the reciprocal sera dilution resulting in a 50%, 80% or 90% reduction in infectivity.

Example 2. X-Ray Crystallography Methods for Non-Human Primate Antibodies

Protein Purification: A construct encoding ZikaE glycoprotein spanning residues 1 to 405 with a C-terminal HRV-3c cleavage site followed by a StrepTagII peptide, was expressed in DS-2 insect cells as described above. Protein was purified from cell supernatant by StrepTagII affinity chromatography. The C-terminal StrepTagII peptide was removed using HRV-3c at 4° C. overnight, followed by gel filtration chromatography using a S200 Superdex 16/60 column. Monoclonal antibodies used in crystallization studies were expressed in Expi293F using transient co-transfection of constructs encoding the IgG heavy and light chains, respectively. Cultures were supplemented with fresh 293FreeStyle media (Life Technologies) 4 hr post-transfection and with HyClone SFM4HEK293 enriched medium (HyClone) containing valproic acid (4 mM final concentration) 24 hr after transfection. Cultures were incubated at 33° C. for six days, after which supernatants were harvested. IgG protein was purified from the clarified supernatant using Protein A affinity chromatography and dialyzed against PBS, pH 7.4. The antigen binding fragments (Fab) were proteolytically cleaved from the crystallizable fragment regions (Fc) using Pierce™ Fab Preparation Kit (Thermo Scientific 44985) at 37° C. for 12 hr. The resulting Fc molecules and any remaining uncleaved IgG were removed from the reaction mixture using Protein A or Protein G chromatography.

X-ray crystallography and structure analysis: Purified Fabs were concentrated to 7-10 mg/ml and used for crystallization screening. For complexes, Fabs and ZikaE were mixed in an equimolar ratio at 7 mg/ml and incubated at 4° C. for 1 hr prior to crystallization screening using an Art Robbins Gryphon crystallization robot. A set of 1200 crystal growth conditions prepared using an Art Robbins Scorpion robot, were assessed by mixing 0.2 µl of protein complex with 0.2 µl of reservoir solution using the sitting-drop vapor diffusion method at 20° C. Once initial crystal conditions were observed, further crystallization trials to improve crystal size and shape were carried out by hand, using a 1:1 ratio of protein and reservoir solution. Optimized crystals were briefly soaked in mother liquor supplemented with a cryoprotectant and frozen in liquid nitrogen prior to x-ray diffraction data collection.

Crystals of the rhMZ103-A Fab were obtained at ~8 mg/ml protein concentration and a reservoir solution containing 20% PEG 4000, 0.2M sodium acetate, 0.1 M sodium citrate (pH 5.6). Crystals of the rhMZ107-B Fab were obtained at ~7 mg/ml protein concentration and a reservoir solution containing 23.5% PEG 4K, 0.2 M (NH4)2SO4. Crystals of the rhMZ107-B Fab in complex with Zika E were obtained at 7 mg/ml protein concentration and a reservoir solution of 15% PEG 6000, 5% MPD, 0.1 M MES (pH 6.5). Crystals of the rhMZ100-C Fab were obtained at 8.1 mg/ml protein concentration and a reservoir solution containing 22.5% PEG 4000, 22.5% isopropanol, 0.1 M sodium citrate (pH 5.6). Crystals of the rhMZ100-C Fab in complex with Zika E were obtained using the hanging drop vapor diffusion method at 7.5 mg/ml protein concentration and a reservoir solution of 12% PEG 8000, 0.2 M (NH4)2SO4, 0.1 M Tris (pH 8.5). Crystals of the rhMZ104-D Fab were obtained using the hanging drop vapor diffusion method at 8 mg/ml protein concentration and a reservoir solution containing 26% PEG 8000, 0.2 M zinc acetate, 0.1 M Tris-HCl (pH 8.5). Crystals of the rhMZ104-D Fab in complex with ZikaE were obtained at 7 mg/ml protein concentration and a reservoir solution of 12% PEG 8000, 0.2 M (NH4)2SO4, 0.1 M Tris (pH 8.5). Crystals of the rhMZ119-D Fab were obtained at ~8.5 mg/ml protein concentration and a reservoir solution containing 18% PEG 8000, 0.2 M calcium acetate hydrate, 0.1 M sodium cacodylate trihydrate (pH 6.5). All crystals were cryoprotected with mother liquor supplemented with 25% (v/v) glycerol prior to flash-cooling.

Data for all crystals were collected at 0.97-1.00 Å wavelength at APS, ANL (Advanced Photon Source, Argonne National Laboratory) beamlines 19-BM, 22-BM, 19-ID, 22-ID and 24-ID-E and data collection and refinement statistics are provided in Tables 5 and 6.

TABLE 5

Crystallographic Data Collection and Refinement Statistics (rhMHRPZ Fab Complexes)

| | rhMZ100-C/ ZIKV E | rhMZ104-D/ ZIKV E | rhMZ107-B/ ZIKV E | rhMZ119-D/ ZIKV E |
|---|---|---|---|---|
| Data collection | APS 19-ID | APS 19-ID | APS 22-BM | AMX 17-ID-1 |
| Crystallization conditions | 12% PEG 8000, 0.2M (NH$_4$)$_2$SO$_4$, 0.1M Tris (pH 8.5) | 12% PEG 8000, 0.2M (NH$_4$)$_2$SO$_4$, 0.1M Tris-HCl (pH 8.5) | 15% PEG 6000, 5% MPD, 0.1M MES (pH 6.5) | 0.06M Nitrate Phosphate Sulfate, 0.1M Sodium HEPES and MOPS (acid) pH 7.5, 20% Ethylene glycol, 10% PEG 8000 + 2% w/v Benzamidine hydrochloride |
| Space group | P2$_1$ | P2$_1$ | P1 | P2$_1$2$_1$2 |
| Cell dimensions | | | | |
| a, b, c (Å) | 101.84, 126.68, 140.5 | 85.3, 130.4, 109.7 | 92.0, 105.6, 132.4 | 51.7, 103.7, 196.7 |
| α, β, γ (°) | 90.0, 90.0, 90.0 | 90.0, 104.2, 90.0 | 82.5, 70.5, 81.0 | 90.0, 90.0, 90.0 |
| Resolution (Å) | 50.0-2.8 | 50.0-2.8 | 50.0-3.2 | 29.4-3.58 |
| R$_{sym}$ | 8.3 (68.9) | 8.9 (48.2) | 25.3 (90.6) | 21.1 (104.8) |
| I/σI | 11.7 (1.24) | 14.5 (1.4) | 3.2 (0.8) | 9.97 (2.18) |
| Reflections (tot/uni) | 160,066/62,002 | 233,950/50533 | 148,912/70,659 | 86,432/13,100 |
| Completeness (%) | 70.8 (72.0) | 89.0 (33.6) | 92.3 (74.6) | 98.6 (93.0) |
| Redundancy | 2.6 (2.3) | 4.6 (2.9) | 2.1 (1.8) | — |
| CC(1/2) | 49.9 | 79.8 | 32.2 | 99.5 |
| R$_{pim}$ | 5.8 (52.1) | 4.5 (27.1) | 22.2 (85.7) | — |
| Refinement | | | | |
| Resolution (Å) | 10.0-2.9 | 15.0-2.82 | 50.0-3.5 | 15-3.58 |
| No. reflections | 53,190 | 40,826 | 47, 50 | 12,826 |
| R$_{work}$/R$_{free}$ * | 24.1/29.5 | 23.8/29.0 | 28.8/33.0 | 25.3/31.1 |
| Rfree percentile/ Total entries | 14.5/2792 | 48.6/3177 | 14.5/1159 | 31.4/1163 |
| Ramachandran favored/allowed/ outliers | 92.0/8.0/0.0 | 89.0/9.0/2.0 | 91.9/7.7/0.4 | 93.0/7.0/0.0 |
| B-Factor | | | | |

TABLE 5-continued

Crystallographic Data Collection and Refinement Statistics (rhMHRPZ Fab Complexes)

|  | rhMZ100-C/ ZIKV E | rhMZ104-D/ ZIKV E | rhMZ107-B/ ZIKV E | rhMZ119-D/ ZIKV E |
|---|---|---|---|---|
| Protein/ion/water | 65.6/0.0/– | 69.0/0.0/– | 48.7/0.0/– | 105.4/0.0/- |
| R.m.s deviations Bond lengths (Å) | 0.003 | 0.003 | 0.002 | 0.002 |
| Bond angles (°) | 0.743 | 0.715 | 0.610 | 0.584 |

Values in parentheses are for highest-resolution shells.
* $R_{free}$ was calculated using ~5% randomly selected reflections.

TABLE 6

Crystallographic Data Collection and Refinement Statistics (rhMHRPZ Fabs)

|  | Z100 | Z103 | Z104 | Z107 | Z119 |
|---|---|---|---|---|---|
| Crystallization condition | 22.5% PEG 4K, 22.5% IPA, 0.1M Na Citrate (pH 5.6) | 20.0% PEG 4K, 0.2M NaAc, 0.1M Na Citrate (pH 5.6) | 26% PEG 8K, 0.2M ZnAc, 0.1M Tris-HCl (pH 8.5) | 23.5% PEG 4K, 0.2M $(NH_4)_2SO_4$ | 18% PEG 8K, 0.2M CaAc hydrate, 0.1M Na Cacodylate trihydrate (pH 6.5) |
| Data collection |  |  |  |  |  |
| Space group | $P2_12_12_1$ | $C222_1$ | $P3_2 2 1$ | $P2_12_12_1$ | $P1 2_1 1$ |
| Cell dimensions |  |  |  |  |  |
| a, b, c (Å) | 56.0, 71.2, 114.2 | 71.5, 80.1, 175.5 | 71.7, 71.7, 159.9 | 5 41.2, 118.7, 119. | 70.2, 71.0, 103.7 |
| α, β, γ (°) | 90.0, 90.0, 90.0 | 90.0, 90.0, 90.0 | 90.0, 90.0, 120.0 | 90.0, 90.0, 90.0 | 90.0, 90.0, 102.4 |
| Resolution (Å) | 50.0-2.19 | 19.7-1.87 | 50.0-2.48 | 50.0-2.1 | 50.0-1.67 |
| $R_{sym}{}^a$ | 12.7 (59.2) | 5.2 (43.7) | 19.4 (96.0) | 12.3 (62.9) | 6.2 (111.8) |
| I/σI | 7.6 (1.8) | 11.9 (1.9) | 1.3 (9.2) | 9.4 (1.1) | 21.2 (1.0) |
| Reflections (tot/uni) | 91,755/22,274 | 91,481/37,647 | 102,754/17,381 | 129,620/32,733 | 423,438/114,507 |
| Completeness (%) | 92.5 (83.5) | 90.5 (92.1) | 98.4 (89.1) | 93.2 (84.1) | 99.3 (97.4) |
| Redundancy | 4.1 (3.5) | 2.4 (2.4) | 5.9 (3.9) | 4.0 (2.5) | 3.7 (3.2) |
| CC(1/2) | 98.8 | 99.8 | 46.1 | 54.3 | 35.4 |
| $R_{pim}$ | 9.6 (53.1) | 4.3 (34.5) | 8.2 (52.7) | 6.5 (46.0) | 3.7 (74.1) |
| Refinement |  |  |  |  |  |
| Resolution (Å) | 45.0-2.19 | 15.0-1.87 | 10.0-2.55 | 15.0-2.10 | 35.0-1.67 |
| No. reflections | 20,504 | 37,560 | 14,291 | 32,599 | 106,010 |
| $R_{work}/R_{free}$ * | 20.7/24.8 | 16.4/19.7 | 21.7/27.1 | 17.9/20.8 | 18.2/19.8 |
| Ramachandran favored/allowed/ outliers | 95.0/3.0/2.0 | 96.3/3.0/0.7 | 96.5/3.0/0.5 | 96.6/2.94/0.45 | 95.2/4.2/0.6 |
| B-Factor Protein | 39.5 | 36.5 | 39.8 | 35.2 | 20.9 |
| R.m.s deviations Bond lengths (Å) | 0.003 | 0.006 | 0.009 | 0.007 | 0.003 |
| Bond angles (°) | 0.626 | 0.862 | 0.611 | 1.210 | 0.734 |

All diffraction data were processed with the HKL2000 suite. Diffraction data for all ZikaE complexes was anisotropic and data were corrected using the UCLA Diffraction Anisotropy Server (Strong et al., 2006). Diffraction resolution of the structures are reported as the highest resolution shell with greater than 69% completeness and an I/σI of 1.0 or higher. Structures were solved by molecular replacement using PHASER, and iterative model building and refinement were performed in COOT, and Phenix or BUSTER, respectively. Prior to refinement, a cross validation (Rfree) test set consisting of 5% of the reflections was selected and used to assess the model accuracy throughout the refinement process. For rhMZ103-A Fab, the heavy chain of 4FQQ and light chain of 2J6E PDBs were used as a search model. For all other Fab structures, rhMZ103-A was used as a search model, with ZikaE from PDB 5JHL used as the search model for ZikaE in the complex structures.

The Ramachandran plot as determined by MOLPROBITY showed 91-97% of all residues in favored regions and 97-99% of all residues in allowed regions. Interactive surfaces were analyzed using PISA (www.ebi.ac.uk/pdbe/pisa/). Structure figures were prepared using PyMOL (The PyMOL Molecular Graphics System (DeLano Scientific).

Example 3. Crystallization Methods for Human Antibodies

Crystallization: All proteins were crystallized by hanging-drop vapor diffusion at 273 K. MZ1 Fab (~7.5 mg ml-1), MZ4 Fab (~6.5 mg ml-1), MZ1 Fab+Zika E glycoprotein (~6.0 mg ml-1), MZ4 Fab+Zika E glycoprotein (~6.8 mg ml-1) were screened for crystallization using a set of 1200 conditions using an Art Robbins Gryphon crystallization robot and crystal drops were observed daily using a Jan Scientific UVEX-PS with automated UV and brightfield plate scanning. Initial crystal growth conditions were optimized manually and crystals used for data collection grew as follows. MZ1 Fab crystals were grown in 0.2 M ammonium sulfate, 0.1 M sodium acetate trihydrate (pH 4.6) and 25% (w/v) polyethylene glycol 4,000. Crystals of MZ4 Fab were grown in 0.2 M ammonium sulfate, 0.1 M HEPES (pH 7.5) and 25% (w/v) polyethylene glycol 3,350. Crystals of MZ1-ZikaE complex were grown in 0.1 M magnesium chloride, 0.1 M imidazole (pH 6.5), 0.1 M MES monohydrate (pH 6.5), 20% (v/v) ethylene glycol and 10% (w/v) polyethylene glycol 8000. Crystals of MZ4-ZikaE complex were grown in 1.26 M ammonium sulfate, 0.1 M CHES/NaOH (pH 9.5) and 0.2 M sodium chloride.

Diffraction data collection and processing: Single crystals were transferred to mother liquor containing 22% glycerol, and cryo-cooled inn liquid nitrogen prior to data collection. All diffraction data were collected at Advanced Photon Source, Argonne National Laboratory beamlines. Diffraction data for MZ1 and MZ4 Fabs were collected at beamline 19-ID to a final resolution of 1.95 Å and 2.85 Å, respectively, using a Q315r CCD detector. Diffraction data for MZ1-ZikaE complex were collected at 24-ID-E beamline and measured using a DECTRIS EIGER 16M PIXEL detector to a final resolution of 4.0 Å. Diffraction data for MZ4-ZikaE complex were collected at 19-BM beamline and measured using ADSC Quantum 210r CCD detector to a final resolution of 4.2 Å. Diffraction data for both antibody-E complexes were anisotropic and data were corrected using the UCLA Diffraction Anisotropy Server. Data indexing, integration and scaling were carried out using the HKL2000 suite. Data collection statistics are reported in Table 7.

Structure solution and refinement: All the structures reported here were solved by molecular replacement using the program Phaser. For MZ1 and MZ4 Fab crystal structures, a hybrid search model was prepared using heavy and light chains from two previously reported crystal structures (heavy chain: PDB code 4FQQ light chain: PDB code 26JE). Refinement was carried out with Phenix refine with positional, individual isotropic B-factor refinement and TLS. Manual model building was performed in Coot. One protomer of ZikaE (PDB code 5IRE) was used in combination with either the MZ1 or MZ4 Fab structure to find a molecular replacement solution for the antibody-ZikaE complexes. Refinement was carried out using Phenix with positional, global isotropic B-factor refinement and TLS. Manual model building was performed in Coot. The later stages of refinement were performed with release of all non-crystallographic symmetry (NCS) restraints. Structure quality was assessed with MolProbity (Chen et al., 2010). The final refinement statistics for all the structures are presented in Table 7. Structure figures were prepared using PyMOL (The PyMOL Molecular Graphics System (DeLano Scientific)).

TABLE 7

Crystallographic Data Collection and Refinement Statistics

|  | MZ1 Fab (PDB: 6MTX) | MZ4 Fab (PDB: 6MTY) | MZ24 Fab (PDB: 6NIS) | MZ1 - ZIKV E complex (PDB: 6NIP) | MZ4 - ZIKV E complex (PDB: 6NIU) |
|---|---|---|---|---|---|
| Crystallization conditions | 0.2M ammonium sulfate, 0.1 M sodium acetate trihydrate (pH 4.6) and 25% (w/v) polyethylene glycol 4,000 | 0.2M ammonium sulfate, 0.1M HEPES (pH 7.5), 25% (w/v) polyethylene glycol 3,350 | 0.1M Citric acid/NaOH (pH 4.0), 1M LiCl and 20% polyethylene glycol 6,000 | 0.06M MgCl2, 0.1M Imidazole MES monohydrate (pH 6.5), 20% Ethylene glycol and 10% polyethylene glycol 8,000 | 1.26M ammonium sulfate, 0.1M CHES/NaOH (pH 9.5) and 0.2M sodium chloride |
| Data collection | | | | | |
| Space group | $P2_12_12_1$ | $P2_12_12_1$ | $P2_12_12_1$ | C 1 2 1 | P 1 |
| Cell dimensions | | | | | |
| a, b, c (Å) | 59.6, 66.8, 137.5 | 0 60.4, 67.6, 138. | 63.8, 66.7, 134.4 | 417.4, 69.3, 212.6 | 113.5, 136.7, 137.4 |
| α, β, γ (°) | 90.0, 90.0, 90.0 | 90.0, 90.0, 90.0 | 90.0, 90.0, 90.0 | 90.0, 113.0, 90.0 | 80.4, 65.5, 65.8 |
| Resolution (Å) | 50.0-1.95 (2.2-2.10, 2.10-2.02, 2.02-1.95) | 50.0-2.85 (3.07-2.95, 2.95-2.85) | 28.8-2.11 | 50.0-4.1 (4.42-4.25, 4.25-4.1) | 50.0-4.2 (4.52-4.35, 4.35-4.2) |
| $R_{sym}{}^a$ | 20.3 (76.2, 58.4, 67.4) | 28.6 (69.9, 93.5) | 10.4 (73.5) | 27.1 (59.4,78.2) | 23.9 (34.5,51.5) |
| I/σI | 9.0 (1.4, 2.1, 1.1) | 7.4 (1.6, 1.1) | 12.8 (2.5) | 3.7 (1.6, 1.0) | 2.64 (1.8, 1.2) |
| Reflections (uni/tot) | 39,609/198,398 | 13,145/65,81 2 | 33,620/ 224,335 | 32,942/77,494 | 28,644/46,190 |
| Completeness (%) | 94.8 (94.2, 85.6, 79.6) | 94.4 (84.1, 78.1) | 99.7 (98.9) | 75.6 (77.1, 77.5) | 53.2 (54.5, 54.9) |
| Redundancy | 5.0 (3.3, 2.4 ,2.1) | 5.0 (3.2, 2.8) | —*** | 2.4 (2.3, 2.3) | 1.6 (1.5, 1.5) |
| CC(1/2) | (63.0, 52.2, 39.3)** | (42.4, 44.1) ** | 99.7 (81.5) | (64.1, 39.2) ** | (83.3, 69.3) ** |
| Rpim | 8.1 (34.6, 45.2, 54.4) | 12.4 (42.6,6 0.8) | —*** | 19.5 (43.2, 56.7) | 23.9 (34.5, 51.5) |
| Refinement | | | | | |
| Resolution (Å) | 15.0-2.00 | 15.0-2.85 | 15.0-2.11 | 15.0-4.16 | 15.0-4.20 |
| No. reflections | 32,475 | 10,863 | 33,455 | 28,024 | 16,181 |
| $R_{work}/R_{free}$ * | 18.1/20.8 | 24.0/27.9 | 17.4/19.9 | 21.1/25.8 | 29.3/35.8 |
| $R_{free}$ percentile/ Total entries | 83.0/2220 | 22.0/3791 | 95.0/5449 | 88.0/1004 | 14.0/1006 |

TABLE 7-continued

Crystallographic Data Collection and Refinement Statistics

|  | MZ1 Fab (PDB: 6MTX) | MZ4 Fab (PDB: 6MTY) | MZ24 Fab (PDB: 6NIS) | MZ1 - ZIKV E complex (PDB: 6NIP) | MZ4 - ZIKV E complex (PDB: 6NIU) |
| --- | --- | --- | --- | --- | --- |
| Ramachandran allowed/outliers | 100/0.0 | 100/0.0 | 100/0.0 | 100 /0.0 | 98.5/1.5 |
| B-Factor Protein | 25.2 | 55.0 | 43.4 | 108.5 | 118.4 |
| R.m.s deviations Bond lengths (Å) | 0.003 | 0.002 | 0.004 | 0.002 | 0.004 |
| Bond angles (°) | 0.715 | 0.596 | 0.727 | 0.533 | 1.041 |

Values in parentheses are for highest-resolution shells. *Rfree was calculated using ~5% randomly selected reflections. HKL2000 was used for data reduction and scaling which did not calculate overall CC(1/2) for the listed data sets. *XDS was used for data reduction and scaling, which did not calculate redundancy and Rpim.

Example 4. Isolation of ZIKV Reactive Antibodies from a Flavivirus Naïve ZIKV-Infected Macaque Using Whole ZIKV Monoclonal antibodies were isolated from a flavi-naïve macaque infected Brazil ZK2015 (ZIKA-BR) previously described in McCracken, 2017.

To cast a wide net on ZIKV-reactive B cells and, in particular, capture B cells recognizing quaternary structure neutralizing epitopes, a sequential sorting strategy was developed based on whole ZIKV (FIG. 1A-B). Unlabeled Zika virions were incubated with peripheral blood mononuclear cells (PBMCs) from a flavivirus naïve ZIKV-infected rhesus macaque at day 14 post-infection where high titers of neutralization were observed. None of the flavinaïve macaques within this study developed cross-neutralizing antibodies to DENV 1-4 following ZIKV infection, except one animal that had very low levels of detectable neutralizing antibody to DENV-2 only.

TABLE 8

MN50 titers of flavivirus serologically-naive NHP pre- and post- ZIKV infection.

| | Sample | 10U001 | 10U003 | 10U021 | 10U030 | 10U032 | 10U036 | 10U043 | 10U047 | M230 |
|---|---|---|---|---|---|---|---|---|---|---|
| ZIKV | pre- | <10 | <10 | <10 | <10 | <10 | <10 | <10 | <10 | <10 |
| | day 14 | >7290 | 1867 | 1655 | 810 | >7290 | 3622 | >7290 | >7290 | 1970 |
| | day 28 | N/A | 1659 | 1874 | >7290 | N/A | >7290 | 4122 | 3987 | 5759 |
| YFV | pre- | <10 | <10 | <10 | <10 | <10 | <10 | <10 | <10 | <10 |
| | day 14 | <10 | <10 | <10 | <10 | <10 | <10 | <10 | <10 | <10 |
| | day 28 | N/A | <10 | <10 | <10 | N/A | <10 | <10 | <10 | <10 |
| DENV-1 | pre- | <20 | <20 | <20 | <20 | <20 | <40 | <40 | <20 | ND |
| | day 14 | <20 | <20 | <20 | <20 | <20 | <20 | <20 | <20 | <20 |
| | day 28 | N/A | <20 | <20 | <20 | N/A | <20 | <20 | <20 | <20 |
| DENV-2 | pre- | <20 | <20 | <20 | <20 | <20 | <40 | <40 | <20 | ND |
| | day 14 | <20 | <20 | <20 | <20 | <20 | <20 | <20 | 20 | <20 |
| | day 28 | N/A | <20 | <20 | <20 | N/A | <20 | <20 | 22 | <20 |
| DENV-3 | pre- | <20 | <20 | <20 | <20 | <20 | <40 | <40 | <20 | ND |
| | day 14 | <20 | <20 | <20 | <20 | <20 | <20 | <20 | <20 | <20 |
| | day 28 | N/A | <20 | <20 | <20 | N/A | <20 | <20 | <20 | <20 |
| DENV-4 | pre- | <20 | <20 | <20 | <20 | <20 | <40 | <40 | <20 | ND |
| | day 14 | <20 | <20 | <20 | <20 | <20 | <20 | <20 | <20 | <20 |
| | day 28 | N/A | <20 | <20 | <20 | N/A | <20 | <20 | <20 | <20 |

ZIKV-reactive activated CD19+ B cells (CD19+CD38+, CXCR5hi/lo) were identified by secondary staining using 4G2, a fusion loop targeted monoclonal antibody (FIG. 1A-B). Antibody heavy and light chain V (D) J gene segments were amplified from single B cells using nested RT-PCR and sequenced. Primers for both IgG and IgM were used to generate a total of 40 matched pairs with the majority being IgG. All mAbs were expressed as rhesus macaque IgG1 and screened for binding to recombinant ZIKV soluble E protein (sE) and ZIKV neutralization. Twenty-three mAbs were found to bind to ZIKV sE, and 11 out of the 23 neutralized ZIKV (FIGS. 1C, 2A, 14A). Sequence analysis of the antibody variable regions revealed that the 23 ZIKV sE-reactive antibodies belonged to 19 independent clonal families that displayed low levels of somatic hypermutation (SHM) (FIG. 1C, Table 9).

TABLE 9

Analysis of the sequences of NHP antibodies that bind ZIKV soluble E protein.

| mAb ID | Heavy chain IgBlast | Identity (%) | D gene | J gene | Light chain IgBlast | Identity (%) | J gene | Ig type |
|---|---|---|---|---|---|---|---|---|
| rhMZ100-C | VH3.63 | 95.9 | IGHD1-7*01 | IGHJ6*01 | VL11.42 | 98.4 | JLx1 | IgG |
| rhMZ101-B | VH3.15 | 95.6 | IGHD1-8*01 | IGHJ4*01 | VL11.42 | 99.4 | JL6 | IgG |
| rhMZ103-A | VH4.40 | 94.3 | IGHD3-1*01 | IGHJ4*01 | VL1.27 | 100 | JL3 | IgG |
| rhMZ104-D | VH3.15 | 99.7 | IGHD2-2*01 | IGHJ4*01 | VL11.42 | 100 | JLx1 | IgG |
| rhMZ105 | VH3.31 | 91.2 | IGHD4-2*01 | IGHJ6*01 | VL11.42 | 95.8 | JL6 | IgG |
| rhMZ106 | VH4.26 | 99.3 | IGHD3-2*01 | IGHJ2*01 | VL5.28 | 99 | JLx1 | IgG |
| rhMZ107-B | VH4.34 | 100.0 | IGHD4-1*01 | IGHJ6*01 | VL11.42 | 99.4 | JL6 | IgG |
| rhMZ113 | VH7.21 | 82.3 | IGHD1-7*01 | IGHJ1*01 | VL11.42 | 80.1 | JL2 | IgM |
| rhMZ115 | VH5.7 | 82.1 | IGHD6-1*01 | IGHJ4*01 | VL11.42 | 78.8 | JLx1 | IgN |
| rhMZ118 | VH3.52 | 99.7 | IGHD6-1*01 | IGHJ4*01 | VL5.28 | 92.3 | JLx1 | IgG |
| rhMZ119-D | VH5.7 | 99.3 | IGHD6-3*01 | IGHJ5-2*02 | VL3.4 | 99.3 | JL2 | IgG |
| rhMZ120 | VH3.58 | 95.2 | IGHD3-2*01 | IGHJ5-1*01 | VL5.28 | 92.3 | JLx1 | IgG |
| rhMZ121-A | VH4.34 | 100.0 | IGHD3-2*01 | IGHJ4*01 | VL3.15 | 100 | JLx1 | IgG |
| rhMZ123-A | VH5.7 | 96.9 | IGHD6-1*01 | IGHJ4*01 | VL2.44 | 99 | JL1 | IgG |
| rhMZ124-D | VH4.34 | 95.3 | IGHD6-3*01 | IGHJ4*01 | VL11.42 | 94.6 | JL2 | IgG |
| rhMZ125 | VH4.34 | 96.3 | IGHD3-1*01 | IGHJ4*01 | VL2.13 | 90.2 | JL1 | IgG |
| rhMZ129 | VH5.7 | 94.9 | IGHD2-2*01 | IGHJ5-1*01 | VL11.42 | 99.0 | JL1 | IgM |
| rhMZ130 | VH3.58 | 95.5 | IGHD6-1*01 | IGHJ4*01 | VL11.42 | 99.7 | JL2 | IgM |
| rhMZ132 | VH7.21 | 91.8 | IGHD2-2*01 | IGHJ4*01 | VL2.51 | 100.0 | JL2 | IgM |
| rhMZ133-C | VH3.30 | 99.0 | IGHD2-2*02 | IGHJ6*01 | VL2.44 | 98.6 | JLx1 | IgM |
| rhMZ134-B | VH3.15 | 99.7 | IGHD2-3*01 | IGHJ6*01 | VL3.46 | 97.2 | JL3 | IgG |
| rhMZ136 | VH3.52 | 99.0 | IGHD3-2*01 | IGHJ4*01 | VL11.42 | 100.0 | JL3 | IgM |
| rhMZ140 | VH3.58 | 95.5 | IGHD1-8*01 | IGHJ4*01 | VL11.42 | 99.7 | JLx1 | IgM |

The observation of low somatically hypermutated antibodies were in agreement with previous reports of ZIKV infection in flavivirus-naïve humans (Stettler K 2016, Yu L 2017, Rogers T 2017). A few had unexpectedly high SHM levels over 15%, in particular some of the IgM clones, which is likely the result of incorrect V gene assignment in IgBlast due to the poor coverage of the rhesus V gene database. ZIKV sE-reactive antibodies showed great diversity in VH gene usage and CDRH3 length, ranging from 10 to 30 residues, with the longest CDRH3 lengths correlating with the ability to neutralize ZIKV (FIG. 1C). Interestingly, VL gene usage was strongly biased toward VL11.42, which was present in a majority of the clones. As 90% of the neutralizers derived from IgG-expressing B cells, it is worth noting that only one IgM-derived antibody (rhMZ133-C) demonstrated neutralization activity, when expressed as IgG1 (FIG. 1C).

Figures 2A, 2B:
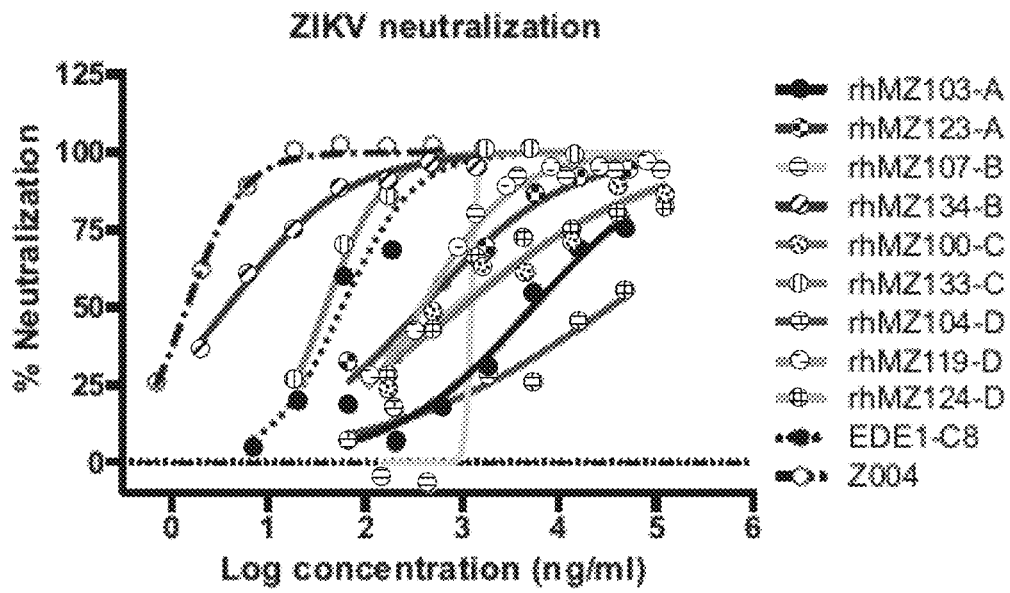
FIG. 2. Neutralizing and binding characteristics define four ZIKV-specific epitopes targeted on the E glycoprotein. (A) Neutralizing activities against ZIKV PR were assessed by micro-neutralization assay in Vero cells (MN50). Shown are neutralization curves compared to the EDE1-C8 and Z004 controls. (B) Summary of binding and neutralization activities. Antibodies were screened for binding to recombinant ZIKV sE by BLI. Values indicate mean binding responses calculated from two independent experiments. Neutralization results from the MN50 and a flow-based assay in U937-DC-SIGN cells (FlowNT50) against ZIKV PR and BR strains, respectively. Shown are mean values for the 50% inhibitory concentration (IC50) in ng/mL averaged from at least two independent experiments. Screening for cross-neutralization was performed against a 7 flavivirus panel (DENV1-4, JEV, WNV and YFV). Shading represents binding or neutralization strength ranging from strong (dark) to weak (light); NT=not tested. (C, D) Binding activities observed against monomeric ZIKV sE (C) and whole ZIKV (D) by ELISA. Antibodies were titrated using 4-fold dilution series starting from 20 μg/ml. Values indicate mean binding responses calculated from two independent experiments. (E) Relative ratio of sE over whole virus binding activities from C, D revealed quaternary targeting. To directly compare binding activities between isolated macaque antibodies and human controls, sE/whole virus relative binding ratios were calculated by using O.D. values obtained at 20 μg/ml with their respective secondary antibodies. Antibodies with low ratio values were considered as targeting quaternary epitopes (such as EDE) whereas ratios closer to 1 would be characteristic of FLE antibody, such as 2A10G6, that bind well to both monomeric E and ZIKV. (F) Binding competition with a set of characterized control antibodies. Lek, control antibody epitopes mapped onto the ZIKV E dimer structure. Right, 4 groups of neutralizing antibodies were identified in a BLI-based competition assay for ZIKV sE glycoprotein. Values represent the % of residual binding of the indicated second antibody aker prior saturation of ZIKV sE with the indicated first antibody. Shading from dark to light indicates competition strength ranging from strong (0-30%), intermediate (31-69%), to weak/none (70-100%). The negative control mAb, used as a non-ZIKV sE reactive antibody, was VRC01, an HIV-1-specific antibody.
Figure 14B:
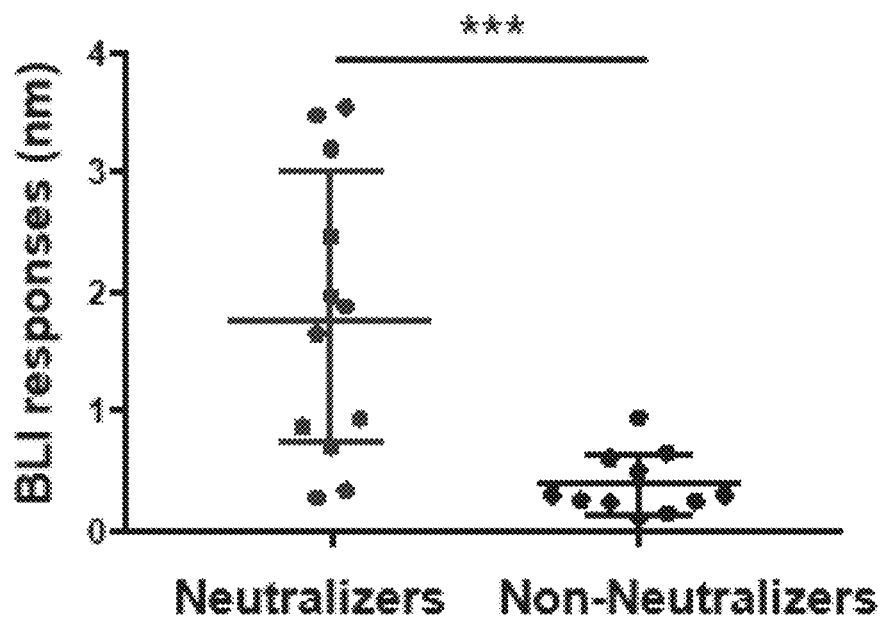
FIG. 14. Binding and neutralization of 23 ZIKV-reactive mAbs isolated in this study. (A) Summary of all mAbs isolated in this study that were found to bind to ZIKV E or ZIKV. Highlighted in grey are mAbs that neutralized ZIKV that were further studied. Binding to ZIKV and DENV-2 E glycoproteins was assessed using both Biolayer Interference (BLI) and ELISA. Both E monomeric and dimeric epitopes were available using BLI which resulted in increased binding activity. Modest, if any, binding of was found to ZIKV monomeric sE using ELISA. The magnitude of binding obtained by BLI assays to ZIKV and DENV-2 immobilized E glycoproteins are indicated as follows: 0-1 nM (+); 1-2 nM (++); 2-3 nM (+++); >3 nM (++++). For ZIKV and DENV E and whole virus ELISA, antibodies were used at 10 or 20 µg/ml. Background nonspecific binding was obtained using an HIV-1 specific antibody, VRC01, and this background was subtracted from all values. The magnitude of binding measured in ELISA is indicated as follows: OD650 0-0.5 (+); 0.5-1.0 (++); 1.0-2.0 (+++); >2.0 (++++). Also shown are micro-neutralization activities obtained for antibodies at >100 µg/ml against ZIKV, DENV1-4, JEV, WNV and YFV. Magnitude of neutralization is indicated as follows: IC50>10 µg/ml (+); 1-10 µg/ml (++), 0.1-1 µg/ml (+++), <100 ng/ml (++++). In all cases, (−) indicates a lack of binding or neutralization in the assays tested. No binding or neutralization was detected against DENV-2 or other flaviviruses for the mAbs that neutralized ZIKV. *: Deng et al., 2011; **: Robbiani et al., 2017. (B) Among E binders, neutralizing mAbs demonstrated significantly higher binding responses than non-neutralizing mAbs (Mann-Whitney t test, p=0.0005). (C) Among neutralizers, no significant correlation in the magnitude of E binding and neutralization potency was observed (Spearman correlation, r=−0.19).
Figure 14C:
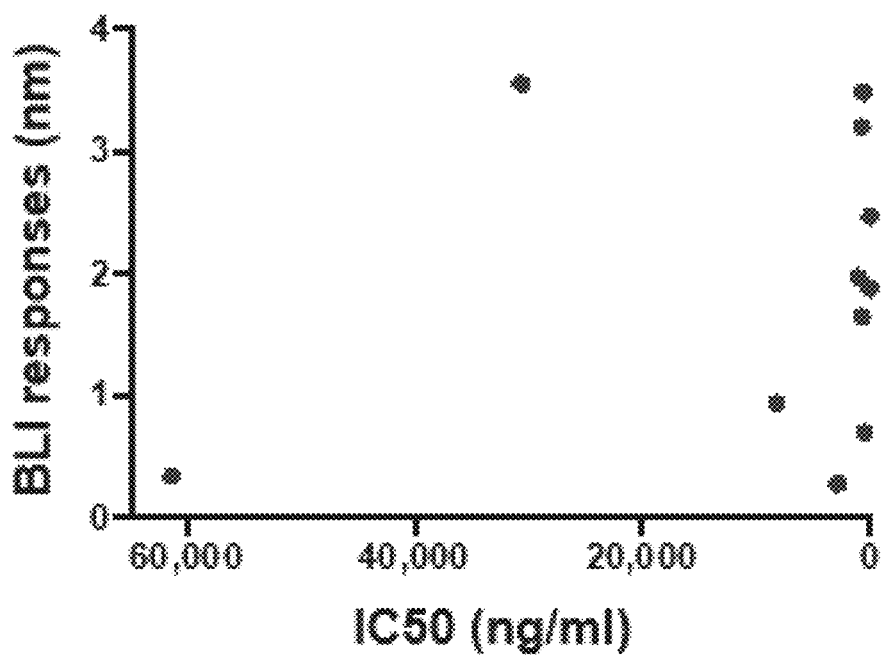
Figure 15A:
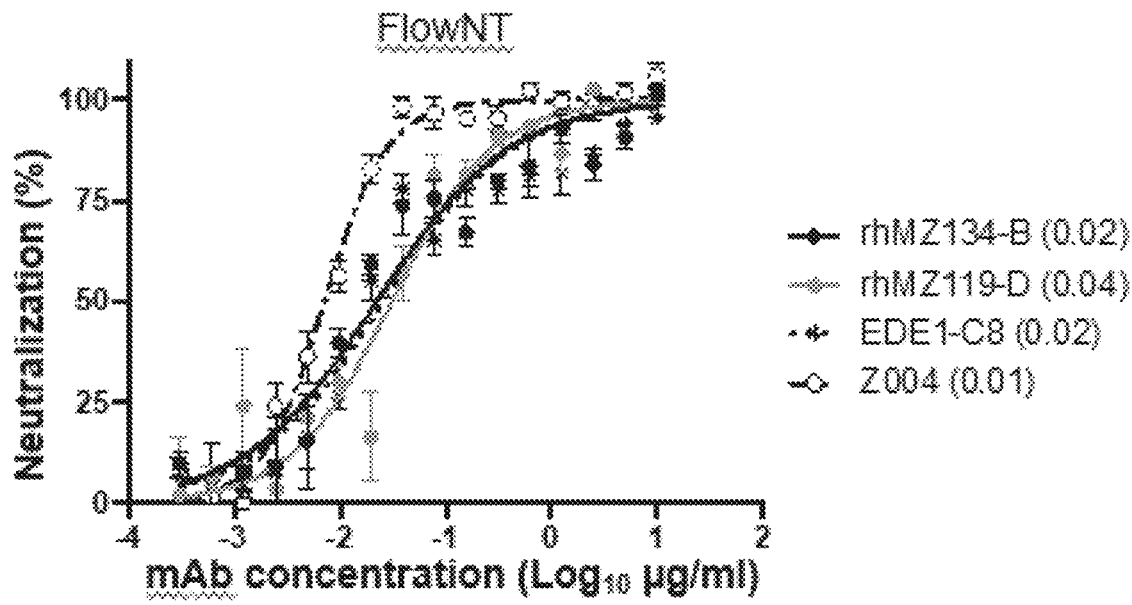
FIG. 15. Characterization of isolated mAbs using FlowNT, PRNT, and ELISA. (A) Neutralization of ZIKV BR strain measured in the FlowNT assay of rhMZ134-B and rhMZ119-D compared to EDE1-C8 and Z004 controls. The 50% inhibitory concentration (IC50) in µg/ml is indicated in parenthesis for each mAb. (B) PRNT neutralization of ZIKV BR using the 5 most potent antibodies identified by MN and FlowNT assays compared to the Z004 control. The 50% inhibitory concentration (IC50) in µg/ml is indicated in parenthesis for each mAb. (C) PRNT neutralization of ZIKV Brazil, Thailand and Uganda strains using rhMZ134-B. In each graph, neutralization curves are shown with mean±s.e.m. values from at least two independent experiments. The 50% inhibitory concentration (IC50) in µg/ml is indicated in parenthesis for each mAb. (D) Binding of control antibodies 2A10G6 (FLE) and EDE1-C8 (EDE1) to ZIKV E (left) and whole ZIKV (right) measured by ELISA. Antibodies were titrated using 4-fold dilution series starting from 20 µg/ml. Values indicate mean binding responses calculated from two independent experiments. An anti-human secondary antibody was used to detect binding of 2A10G6 (humanized Fc domain) and EDE1-C8. These curves were not plotted on the same graph as the rhMZ mAbs due to difference in secondary Ab detection reagent.
Figure 15B:
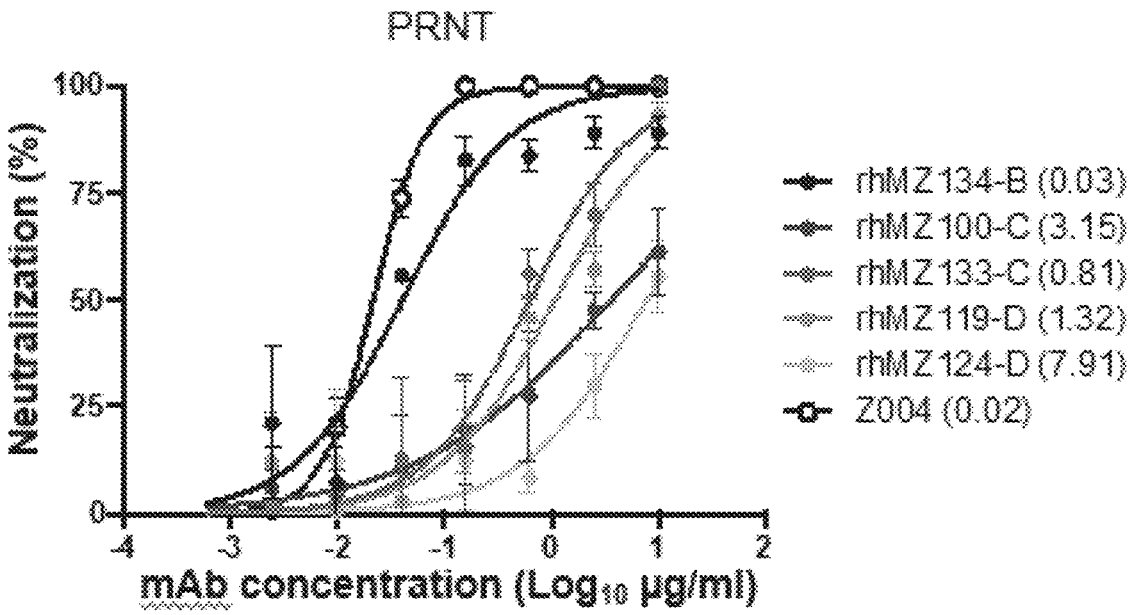
Figure 15C:
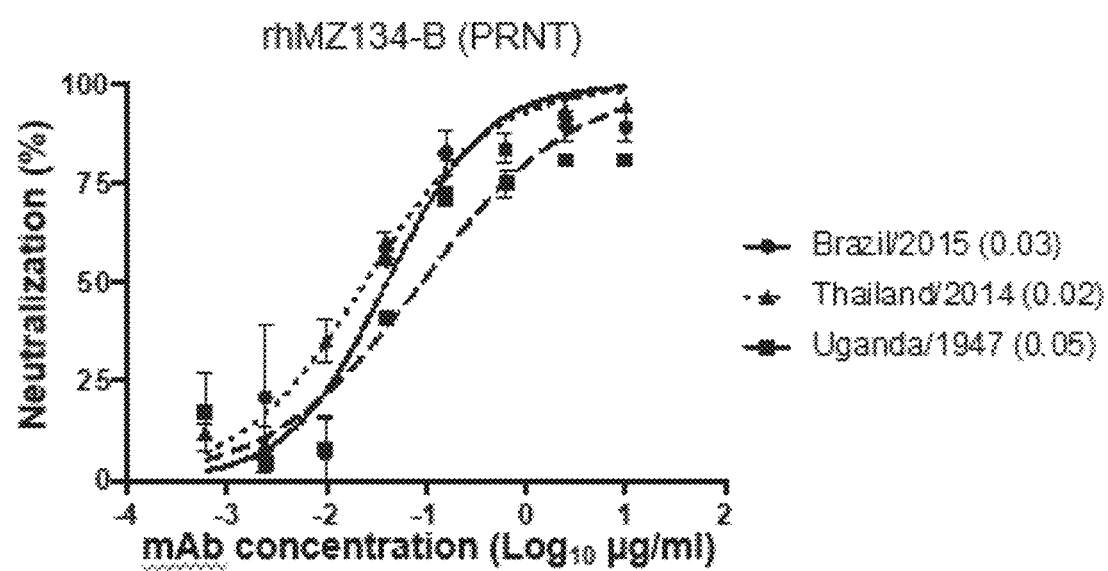

Example 5. Neutralizing and Binding Characteristics Define Four ZIKV-Specific Epitopes Targeted on the E Glycoprotein Eleven mAbs were identified as capable of ZIKV neutralization by screening in a micro-neutralization (MN) assay using Vero-produced ZIKV and Vero cells as target cells (FIG. 1C, 14A). Although neutralizers showed significantly higher binding responses than non-neutralizers in the BLI assay (P=0.0005, Mann Whitney test), binding and neutralizing activities did not significantly correlate among the mAbs that neutralized (FIG. 14 B-C). While most mAbs displayed modest micro-neutralization activity against a Puerto Rican strain with IC50 in the µg/ml range, two mAbs, rhMZ133-C and rhMZ134-B (short for rhesus macaque MHRP Zika 133-C and 134-B, respectively), demonstrated greater potencies matching or surpassing the EDE1-C8 control, a potent DENV cross-neutralizing antibody (Dejnirattisai, 2015; Barba-Spaeth, 2016) (FIG. 2A-B). Of note, rhMZ134 was also on par with Z004, one of the most potent ZIKV neutralizing antibodies reported to date (Robbiani 2017) with IC50s of 3.8 ng/mL and 1.4 ng/mL, respectively (FIG. 2A-B). To further confirm the observed neutralization properties in an assay that would better reflect the initial ZIKV infection events, we employed a flow cytometry-based assay (FlowNT50) measuring single cell infection of human monocytes by a Brazilian strain of ZIKV produced in mosquito cells. Comparable to the results of the Vero-based MN assays, the majority of antibodies performed similarly in the FlowNT50 assay (FIG. 2B). rhMZ134-B was again the best neutralizing antibody with an IC50 of 22 ng/ml (FIG. 2B, 15A), rhMZ119 was the second most potent antibody with an IC50 of 31 ng/ml, while rhMZ133-C did not perform as well in this FlowNT50 neutralization assay (FIG. 2B, 15A). To compare to other mAbs previously published in the literature, a third neutralization assay was performed using the plaque reduction neutralization test (PRNT) with the top 5 neutralizers identified by MN or FlowNT50 neutralization assays, where similar trends were obtained and rhMZ134 potency was again similar to Z004 (FIG. 14B). When tested against non-American ZIKV strains, rhMZ134-B demonstrated broad neutralization activities against Ugandan and Thai strains (FIG. 14C). Finally, to investigate whether the isolated neutralizing antibodies recognize ZIKV-specific or flavivirus cross-reactive epitopes, we performed a neutralization screen against a panel of 7 flaviviruses, including all 4 DENV serotypes, JEV, WNV and YFV. None of the isolated antibodies, displayed neutralization activity in this assay even when starting at a high concentration (≥100 µg/ml), indicating that all antibodies neutralized ZIKV specifically (FIG. 2B). Consistent with these results, weak to no binding to DENV-2 sE or whole DENV-2 was detected by BLI and ELISA, respectively, confirming the mAb specificity for ZIKV (FIG. 14).

To gain insight into the epitopes targeted with this set of neutralizing mAbs, the mAbs were titrated in binding assays using ELISA to monomeric sE glycoprotein and whole ZIKV. Binding to an immobilized ZIKV sE was performed in conditions where quaternary antibodies, such as EDE1-

Figure 1B:
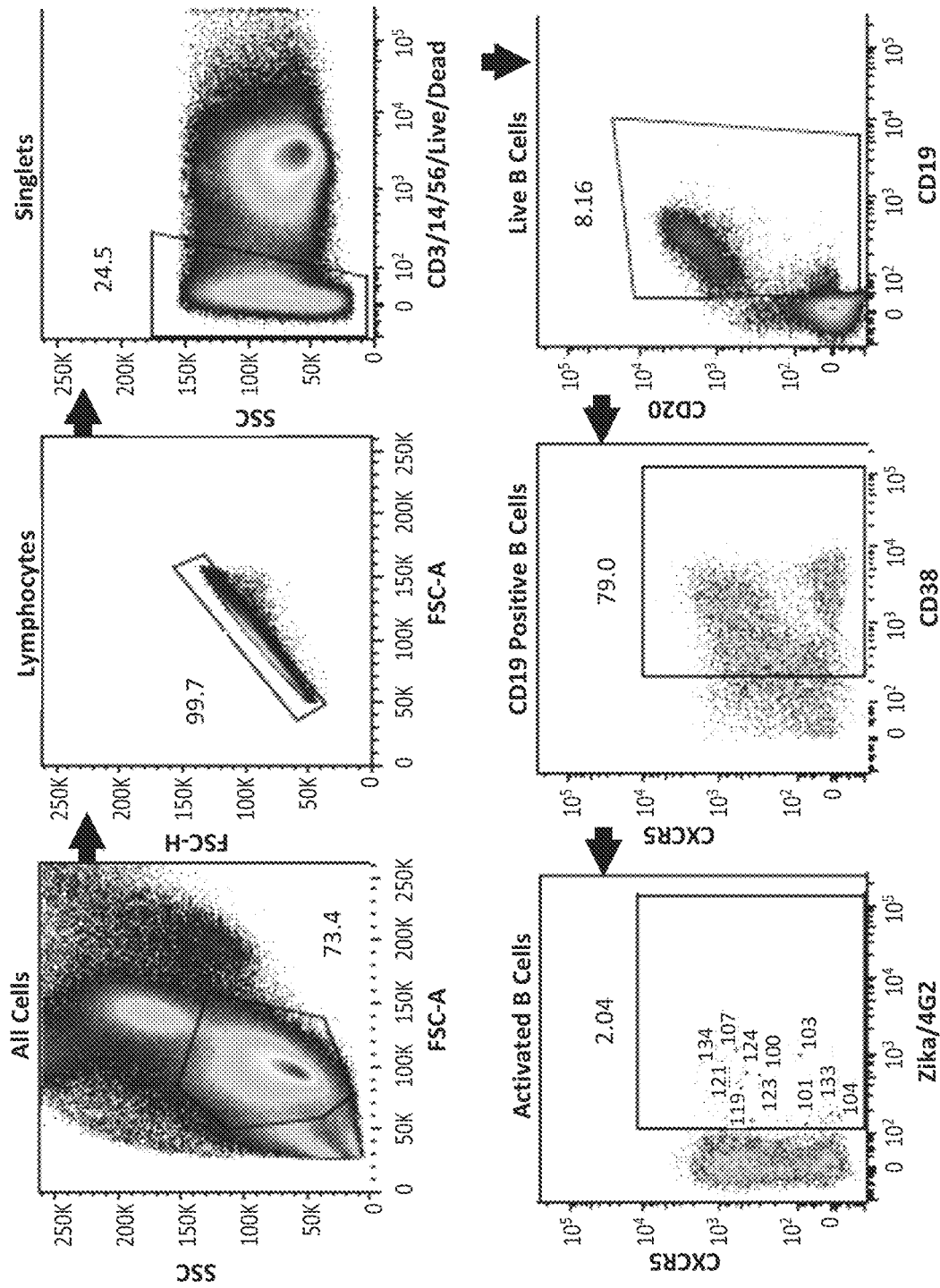
Figure 2C:
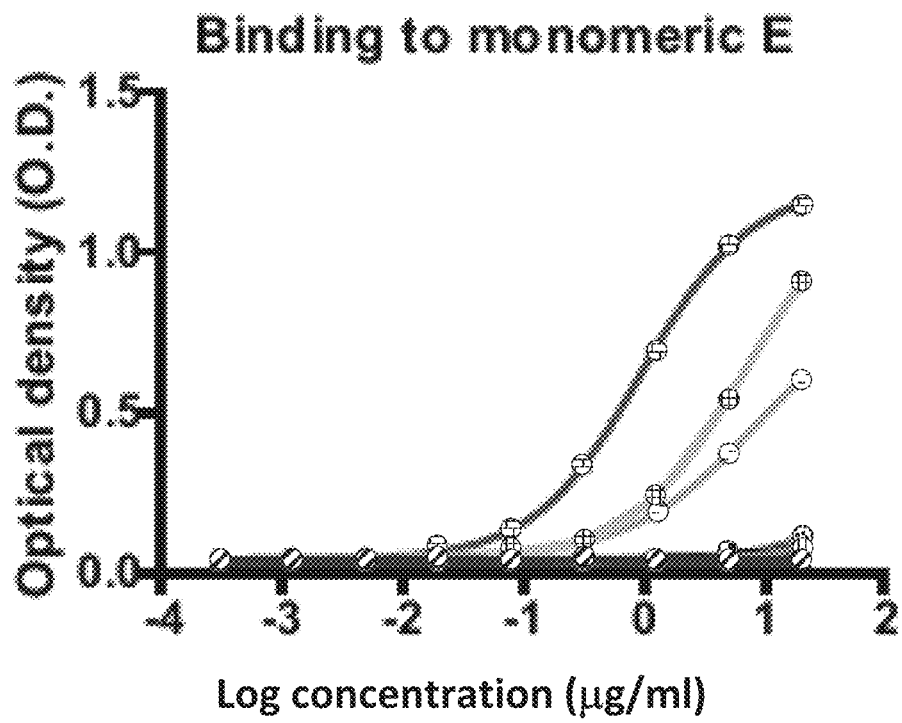
Figure 2D:
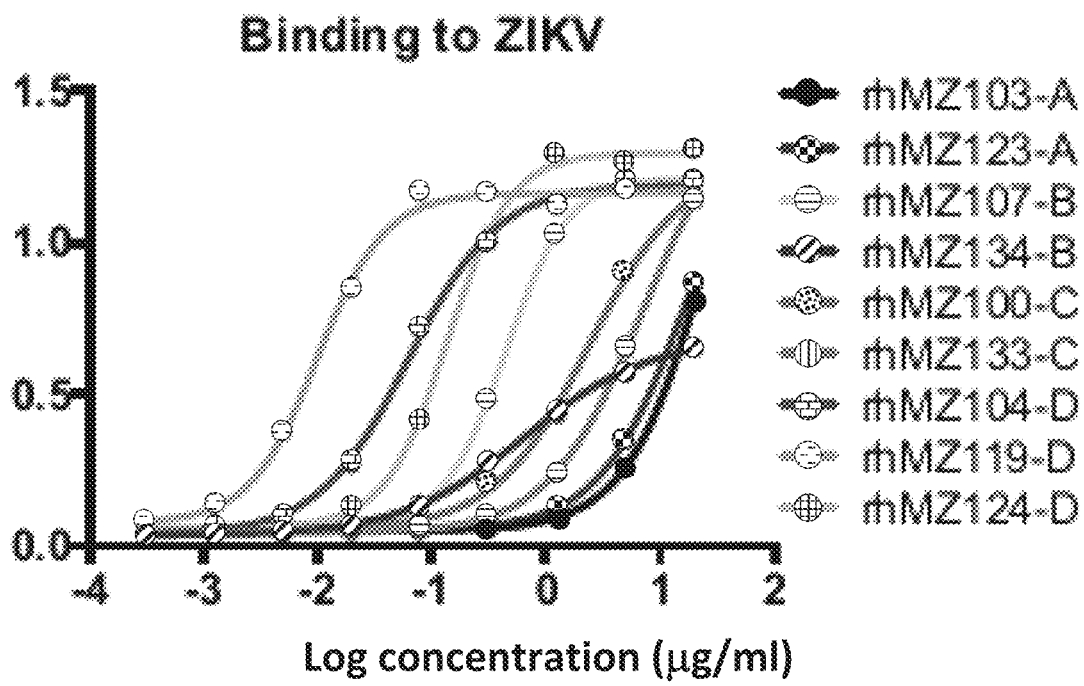
Figure 2E:
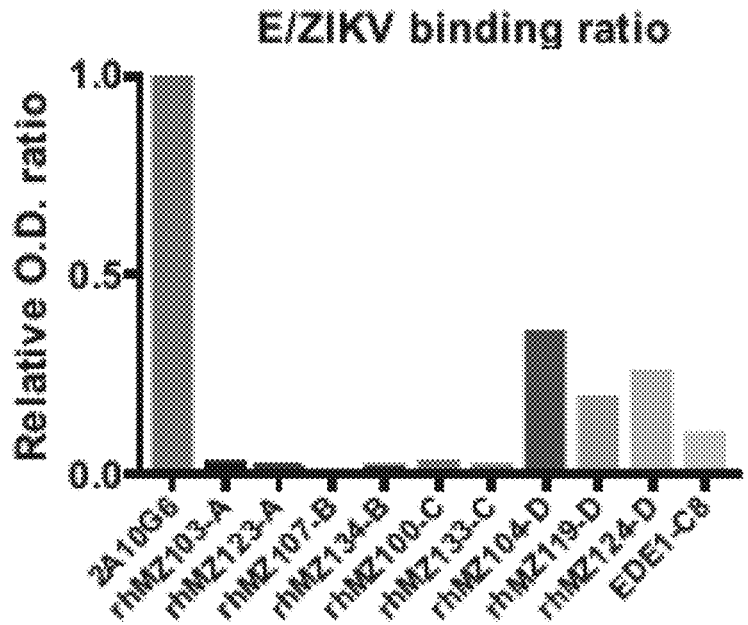
Figure 15D:
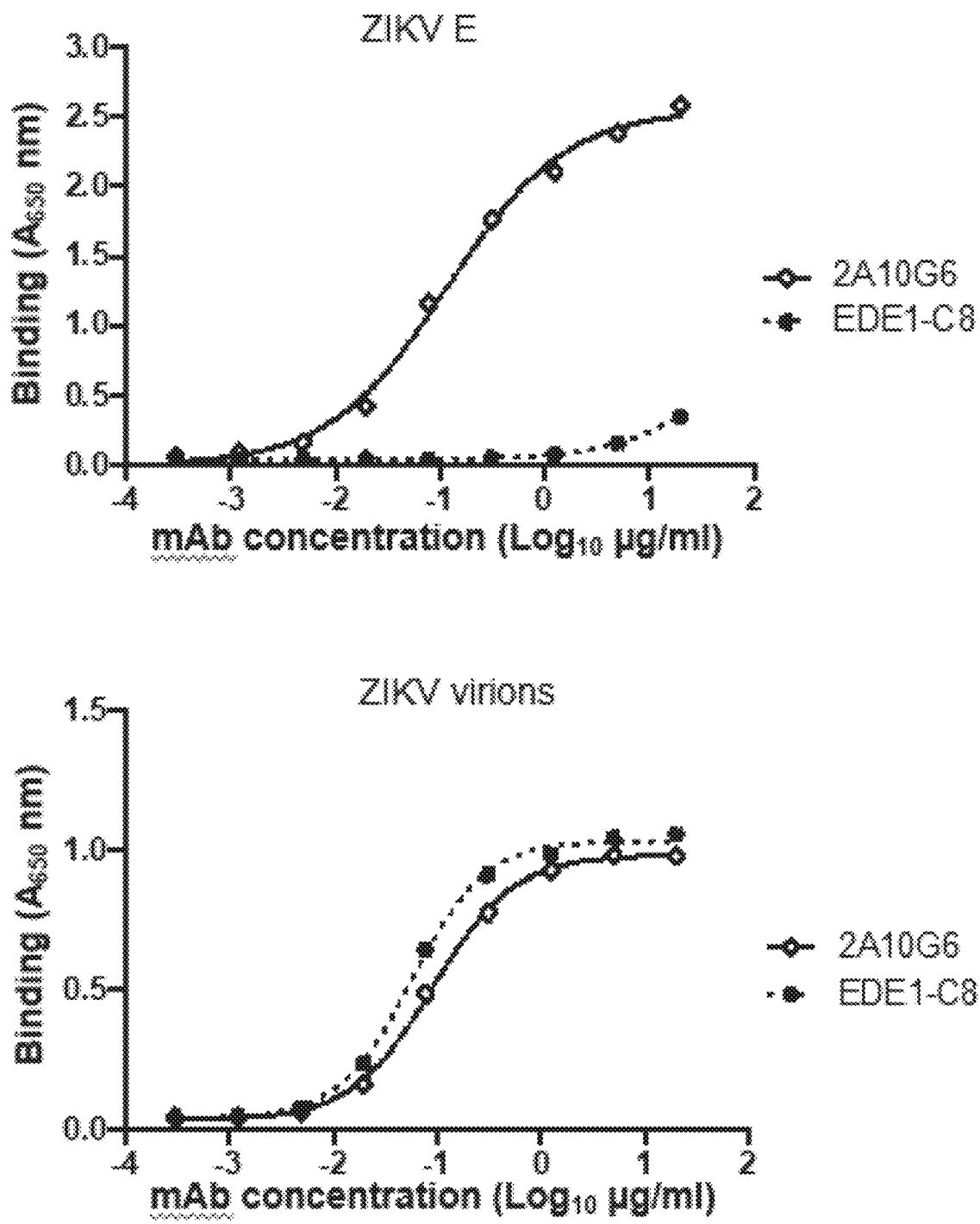

C8, are poorly reactive (Rouvinski 2017) while antibodies to the monomeric E protein, such as the FLE-directed mAb 2A10G6, bound robustly (FIG. 15D left). However, since whole ZIKV displays both monomeric and quaternary epitopes, both EDE1-C8 and 2A10G6 bound robustly in the ELISA (FIG. 15D right). When testing the isolated ZIKV-specific macaque mAbs, the majority of them did not demonstrate detectable binding monomeric ZIKV sE in ELISA (FIG. 2C). Some reactivity was observed for rhMZ104-D, rhMZ119-D and rhMZ124-D, which were also identified as the strongest binders by BLI (FIG. 2B-C). Next, binding was assessed in the context of the native viral particle by capture ELISA using whole purified ZIKV. All neutralizing antibodies bound to the whole ZIKV, suggesting that they recognized quaternary epitopes (FIG. 2D). This was not surprising, as whole ZIKV was used to isolate antigen-specific B cells (FIG. 1B). The differences in binding observed between the mAbs mirrored binding responses to sE obtained in the BLI assay (FIG. 14A), suggesting that both monomeric and E dimer epitopes are available using the BLI binding assay. Interestingly, rhMZ104-D, rhMZ119-D and rhMZ124-D were again the strongest binders, reaching saturation at lower concentrations than their counterparts. In contrast, the most potent neutralizer, rhMZ134-B, bound ZIKV rather poorly and appeared to reach saturation at much lower optical density, suggesting that fewer rhMZ134-B epitopes might be present on ZIKV. To compare these binding responses to control mAbs 2A10G6 and EDE1-C8 where each had different secondary antibodies, we calculated ZIKV sE/whole virus binding ratios to assess the ability of these mAbs to recognize quaternary epitopes relative to the FLE control antibody (2A10G6), in which a ratio of 1 reflected a strong affinity for monomeric sE glycoprotein (FIG. 2E). In contrast, the binding of the EDE1-C8 control, with a ratio of 0.1, was strongly biased towards whole virus, consistent with its quaternary epitope specificity. Intermediate binding ratios of approximately 0.2-0.4 were obtained for rhMZ104-D, rhMZ119-D and rhMZ124-D, which indicated that they were not as potent as the FLE control antibody in engaging monomeric sE. This data suggested that their epitopes may include a quaternary component. All the other neutralizing antibodies had a ratio less than 0.1 (FIG. 2E), indicating that they exclusively targeted quaternary epitopes found on the whole ZIKV.

Figure 2F:
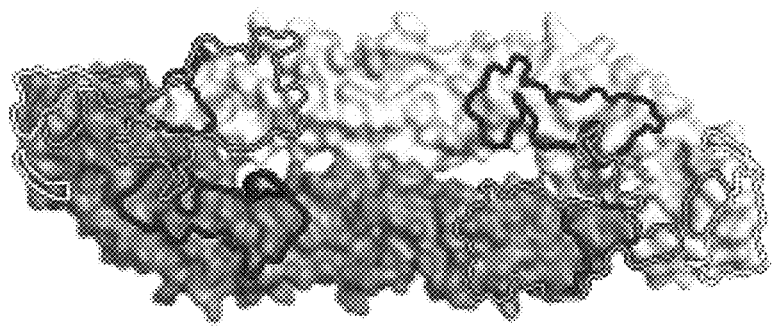

Next, binding competition experiments were performed to delineate the antigenic sites targeted by these neutralizing antibodies (FIG. 2F). Control antibodies directed against previously identified sites of vulnerability such as the fusion loop epitope (FLE, mAb 2A10G6), domain I/II (DI/II, mAb Z3L1), the E-dimer epitope-1 (EDE1, mAb EDE1-C8) and domain III (DIII, mAb Z004) were used in competition assays for real-time binding to ZIKV sE. When the eleven ZIKV-specific macaque neutralizing mAbs were used in these competition assays, their pattern of competition fell into four groups with overlapping, but discrete features (FIG. 2F). As such, we labeled these mAbs accordingly with the letter of the group within the nomenclature of each neutralizing mAb (FIG. 1C, 14A). Antibodies within group A was competed by all 4 control mAbs to varying degrees. Group B resembled the competition profile obtained with the EDE1 control, suggesting that these antibodies might represent new ZIKV-specific EDE members. Group C was competed by EDE1 and DIII mAbs, whereas group D was only sensitive to EDE1 mAb competition. Group C and D antibodies were of particular interest as their unique competition profiles indicated that they might target uncharacterized neutralizing epitopes. All together, these eleven neutralizing mAbs defined 4 ZIKV-specific epitopes that targeted quaternary epitopes on the E glycoprotein surface.

Figure 16A:
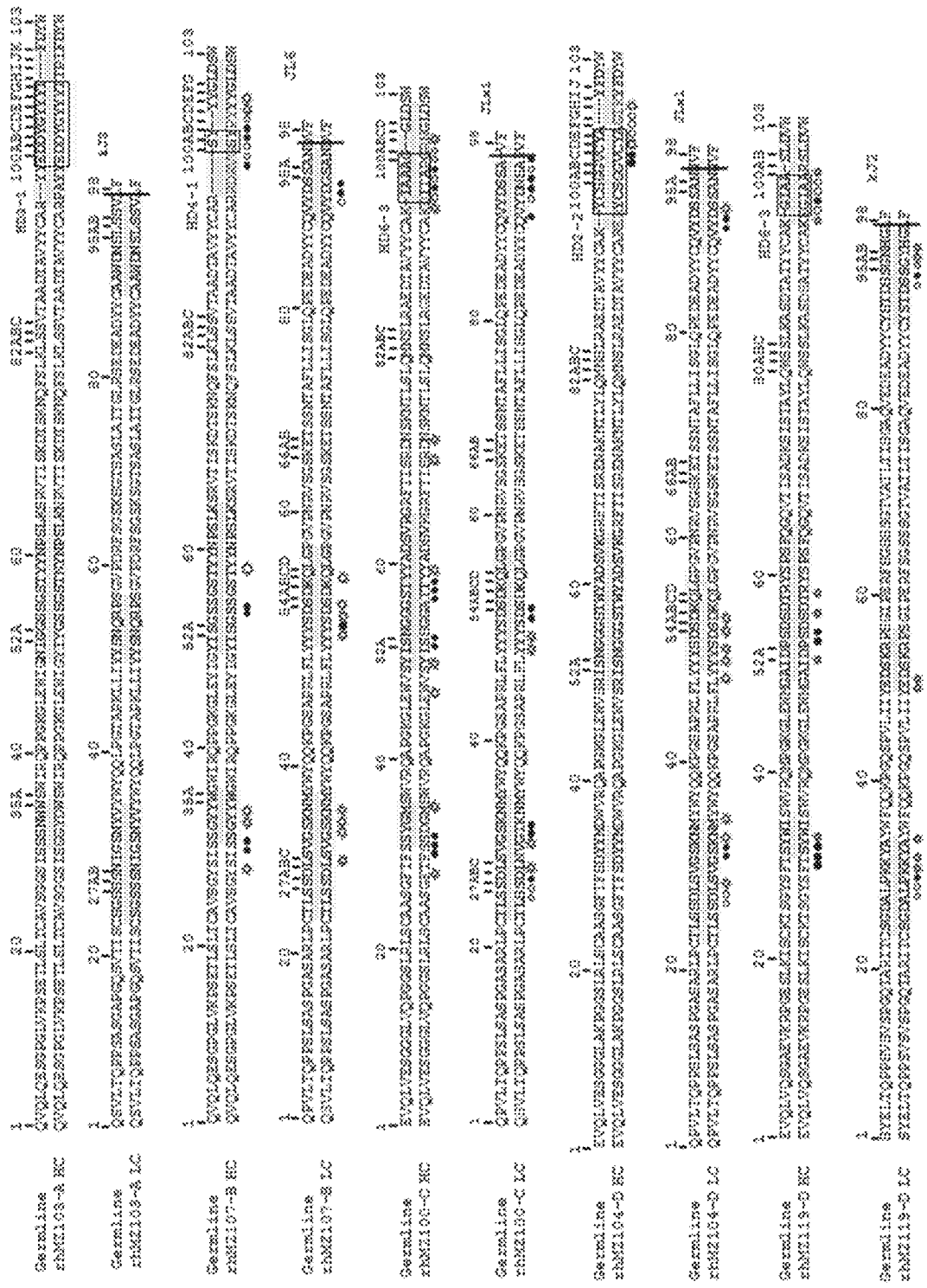
FIG. 16. Antibody somatic hypermutation, and structure analysis. (A) Alignment of rhMZ103-A, rhMZ107-B, rhMZ100-C, rhMZ104-D, and rhMZ119-D Ig heavy and light chain sequences with germline gene-encoded sequences. Junction-encoded residues are colored blue and residues that have undergone somatic hypermutation are colored red. HD-encoded residues are boxed. Heavy and light chain CDR loop residues are highlighted in gray. Antibody-ZIKV E contact residues are indicated below the sequences. (B-F) Crystal structures of rhMZ103-A, rhMZ107-B, rhMZ100-C, rhMZ104-D, and rhMZ119-D are shown in ribbon representation with spheres indicating residues that have undergone somatic hypermutation.

Example 6. Crystal Structure of ZIKV-Specific EDE Antibody rhMZ107-B Fab in Complex with ZikaE Glycoprotein To understand the structural basis for the recognition of the ZIKV-specific EDE-like antibodies, crystal structures of representative mAbs from each group were determined alone in and complex with the Zika sE glycoprotein. From antigenic specificity group B, the crystal structure of rhMZ107-B alone (2.1 Å resolution), and in complex with Zika sE glycoprotein at 3.2 Å resolution were determined (FIGS. 3A-D; FIG. 16; Tables 9-10). Within the asymmetric unit, four rhMZ107-B, and four Zika sE glycoproteins were observed, with each Fv binding an epitope that spans three protomers with a contact region of X, X, and X Å$^2$ buried surface area (BSA), within the site of recognition. The largest antibody contact area was on the DII of one protomer, followed by recognition of the DIII of a second protomer, adjacent to the glycan-154, with minor contacts on the DI of a third protomer (FIG. 3A-B). The heavy chain and light chain of the antibody shared approximately the same BSA (X Å heavy chain; X Å light chain). In the context of the mature ZIKV (PDB: 5IRE), rhMZ107-B was able to bind 180 sites with no structural rearrangement required of the E glycoproteins (FIG. 3C). Antibody rhMZ107-B recognition of ZikaE used 100% of germline-encoded residues in both the HV, and HD,HJ encoded regions while in the light chain a single complementarity-determining region CDR L3 residue glycine94 which made a single main chain contact was mutated from the VL11.42 gene-encoded serine (FIG. 3D).

Figure 3E:
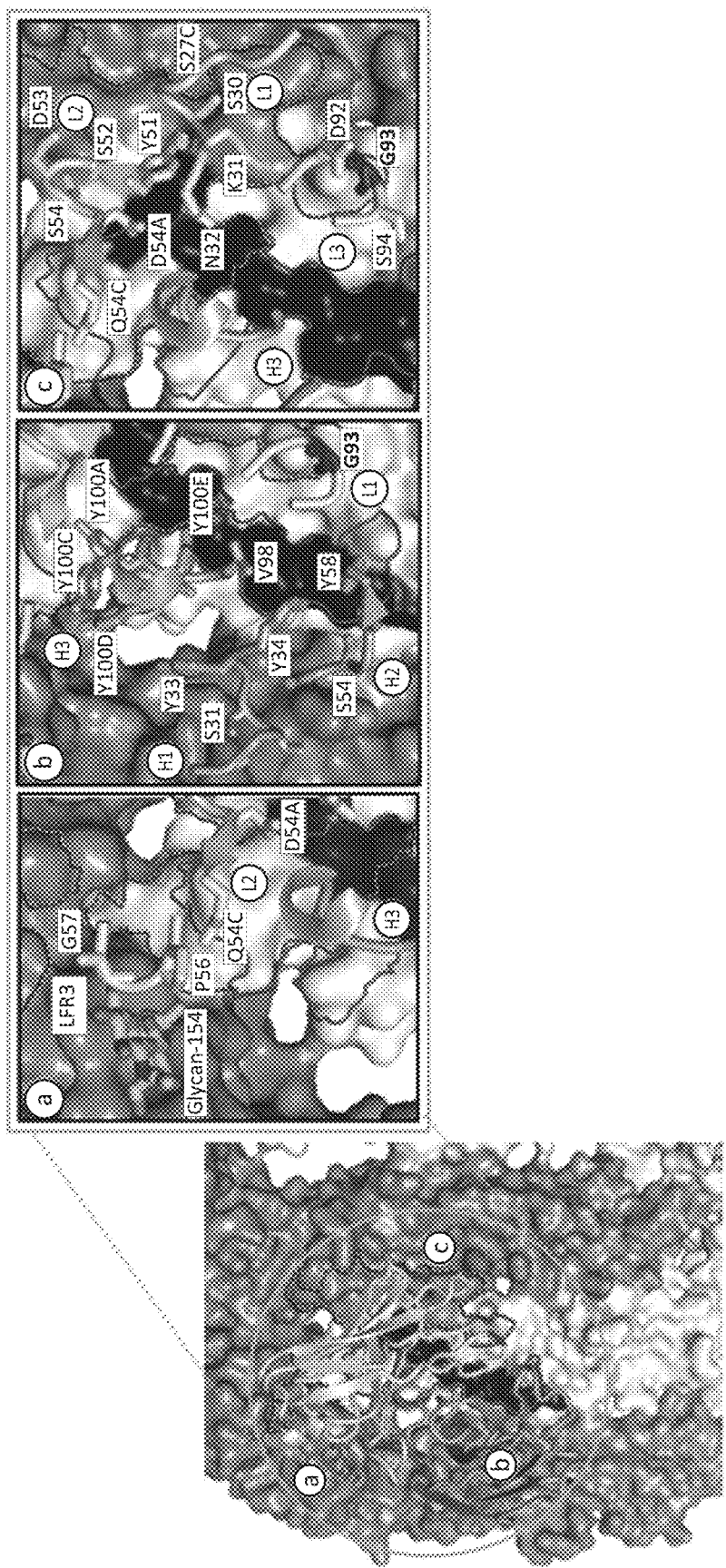
FIG. 3. Crystal structure of ZIKV-specific EDE antibody rhMZ107-B Fab in complex with Zika E glycoprotein. (A) Top view of the co-crystal structure of rhMZ107-B in complex with Zika E (PRVABC59). rhMZ107-B Fv heavy and light chains are colored dark, and light green respectively, and are shown in surface representation, while four Zika E protomers are shown in ribbon representation, and colored blue, and gray, with glycan-154 shown in stick representation. (B) Antibody epitope footprint of rhMZ107-B heavy and light chain binding is shown as solid, and dashed lines, respectively, displayed on four Zika E protomers in surface representation with glycan-154 represented as above. (C) rhMZ107-B antibody recognition is modeled in the context of the mature ZIKV (PDB: 5IRE). Individual protomers of ZIKV are depicted in smooth surface colored green, blue, and gray, with rhMZ107-B Fv shown in atomic surface representation colored dark, and light green. (D) rhMZ107-B amino-acid sequence alignment with immunoglobulin heavy (HC) (VH3.63, HD4-1*01, and HJ6*01) and light (VL) chains (VL11.42 and JL6) germline gene-encoded sequences. Junction-encoded residues are colored light blue and residues that have undergone somatic hypermutation are colored red with HD-encoded residues boxed. Heavy and light chain CDR loop residues are highlighted in gray. Antibody heavy and light chain contacts are indicated with open circles (○) denoting antibody main-chain-only contacts, open circle with rays (¤) denoting antibody side-chain-only contacts, and filled circles (●) denoting both main-chain and side-chain contacts. (E) Co-crystal structure of rhMZ107-B antibody in complex with Zika E glycoprotein. Inset panels (a-c) show rhMZ107-B antibody residues within 5 Å of Zika E glycoprotein represented as sticks and colored as in (D). Zika E is colored blue and gray with the exception of the B-strand (residues X-Y) which is highlighted in dark blue. (F) Surface representation of antibody rhMZ107-B, and ribbon representation of Zika E glycoprotein contact residues, viewed looking down at the CDRs at a 180° rotation about the horizontal axis from (E). (G) Overlay of the rhMZ107-B Zika E co-crystal structure with the EDE1-C8 Zika E co-crystal structure (PDB: 5LBS). rhMZ107-B and EDE1-C8 are depicted in ribbon representation and colored green and white respectively.

Antibody rhMZ107-B recognized the DII of Zika E utilizing CDRs H2, H3, L1, L2 and L3 with the area of recognition focused on the B strand (residues X-Y) located in the center of the epitope. Additional recognition of the DIII from an adjacent protomer was through the light chain framework 3 (FR3), while recognition of the DI from the third protomer was facilitated by CDR L1, and L2 (FIGS. 3E-F). Features of the antibody recognition were reminiscent of EDE1-C8 recognition, which had broad reactivity against ZIKV, and multiple strains of DENV. Interestingly group B mAbs inclusive of rhMZ107-B were ZIKV-specific (FIG. 3G). Analysis of the epitope-contact residues shows similar contact residues (FIG. 3, and Tables 9-10), with only the interaction with residues adjacent to glycan-67 (DENV) showing major differences (FIG. 3H). In addition to rhMZ107-B, we also screened the group B mAb rhMZ134-B for recognition of Zika E glycoprotein by shotgun alanine/serine-scanning mutagenesis and residues W101, F108, V257, G259, K316, M375 were highlighted as contact residues similar to rhMZ107-B, as well as other EDE1-like antibodies.

TABLE 10 rhMZ107 interface with E glycoprotein of Zika virus.

| rhMZ107 | Zika E glycoprotein | Distance (Å) |
|---|---|---|
| Hydrogen bonds | | |
| H:TYR 34[ OH ] | B:MET 68[ O ] | 3.87 |
| H:SER 56[ OG ] | B:SER 66[ OG ] | 3.19 |
| H:SER 56[ OG ] | B:ASP 67[ N ] | 3.76 |
| H:VAL 98[ O ] | B:SER 70[ N ] | 2.27 |

TABLE 10-continued rhMZ107 interface with E glycoprotein of Zika virus.

| rhMZ107 | Zika E glycoprotein | Distance (Å) |
|---|---|---|
| H:TYR 100A[ OH ] | B:CYS 105[ SG ] | 3.22 |
| H:TYR 100A[ OH ] | B:GLY 104[ O ] | 3.20 |
| H:TYR 100E[ OH ] | B:SER 70[ O ] | 3.55 |
| L:ASN 32[ ND2] | B:ASP 71[ OD1] | 3.73 |
| L:SER 52[ OG ] | B:GLN 77[ NE2] | 3.41 |
| L:ASP 54A[ OD1] | B:CYS 74[ N ] | 3.42 |
| L:ASP 54A[ OD2] | B:CYS 74[ N ] | 3.15 |
| L:ASP 54A[ OD1] | B:CYS 105[ SG ] | 3.04 |
| L:LYS 54B[ N ] | B:GLY 104[ O ] | 3.86 |
| L:LYS 66[ O ] | F:ASN 52[ ND2] | 2.68 |
| L:SER 67[ N ] | F:ASN 52[ OD1] | 3.76 |
| L:SER 67[ OG ] | F:ASN 52[ OD1] | 3.84 |

TABLE 11

Buried surface area of rhMZ107 antibody in complex with Zika virus. Residues that form hydrogen bonds and salt bridges are indicated.

| Residue | Bond type | Accessible Surface Area (Å²) | Buried Surface Area (Å²) |
|---|---|---|---|
| H:SER30 |   | 75.7 | 11.8 |
| H:TYR34 | H | 35.2 | 33.7 |
| H:SER52 |   | 5.9 | 2.3 |
| H:SER53 |   | 74.1 | 14.4 |
| H:SER54 |   | 84.8 | 30.9 |
| H:SER56 | H | 33.4 | 19.4 |
| H:TYR58 |   | 118.0 | 46.8 |
| H:ARG97 |   | 71.9 | 14.1 |
| H:VAL98 | H | 83.1 | 46.3 |
| H:GLY99 |   | 62.5 | 49.5 |
| H:SER100 |   | 63.0 | 46.8 |
| H:TYR100A | H | 155.4 | 127.3 |
| H:PRO100B |   | 70.2 | 20.0 |
| H:TYR100C |   | 151.5 | 1.5 |
| H:TYR100E | H | 64.4 | 28.8 |
| L:SER27 |   | 118.4 | 1.7 |
| L:ASP27A |   | 88.3 | 29.2 |
| L:LEU27B |   | 24.5 | 1.8 |
| L:SER27C |   | 68.3 | 33.7 |
| L:GLY29 |   | 32.2 | 20.4 |
| L:SER30 |   | 71.4 | 40.5 |
| L:LYS31 |   | 36.1 | 11.4 |
| L:ASN32 | H | 49.8 | 35.9 |
| L:TYR49 |   | 49.8 | 4.5 |
| L:TYR51 |   | 64.9 | 46.6 |
| L:SER52 | H | 36.6 | 13.7 |
| L:ASP53 |   | 89.3 | 11.7 |
| L:SER54 |   | 103.8 | 82.4 |
| L:ASP54A | H | 73.1 | 55.5 |
| L:LYS54B | H | 86.5 | 24.7 |
| L:GLN54C |   | 122.9 | 34.9 |
| L:ASN60 |   | 135.7 | 49.3 |
| L:LYS66 | H | 42.9 | 16.6 |
| L:GLU66A |   | 89.4 | 9.5 |
| L:THR66B |   | 89.7 | 53.0 |
| L:SER67 | H | 115.3 | 38.8 |
| L:TYR91 |   | 80.7 | 14.5 |
| L:ASP92 |   | 42.1 | 14.0 |
| L:GLY93 |   | 72.9 | 37.4 |
| L:SER94 |   | 98.2 | 21.2 |
| Zika virus E glycoprotein | | | |
| Residue | Bond type | Accessible Surface Area (Å²) | Buried Surface Area (Å²) |
| B:ILE65 |   | 36.1 | 3.1 |
| B:SER66 | H | 64.0 | 30.6 |
| B:ASP67 | H | 87.0 | 60.8 |
| B:MET68 | H | 130.1 | 87.8 |
| B:ALA69 |   | 49.9 | 31.0 |
| B:SER70 | H | 61.6 | 59.5 |
| B:ASP71 | H | 23.7 | 23.1 |
| B:SER72 |   | 54.4 | 54.4 |
| B:ARG73 |   | 103.1 | 74.3 |
| B:CYS74 | H | 17.9 | 17.9 |
| B:PRO75 |   | 18.5 | 1.8 |
| B:GLN77 | H | 122.9 | 67.6 |
| B:LEU82 |   | 41.0 | 11.1 |
| B:ASP83 |   | 96.9 | 43.6 |
| B:LYS84 |   | 95.7 | 36.0 |
| B:ARG99 |   | 56.7 | 31.0 |
| B:TRP101 |   | 187.2 | 1.0 |
| B:GLY102 |   | 77.9 | 4.9 |
| B:ASN103 |   | 67.7 | 3.0 |
| B:ASN103 |   | 67.7 | 17.8 |
| B:GLY104 | H | 57.9 | 57.9 |
| B:CYS105 | H | 55.5 | 41.3 |
| B:GLY106 |   | 45.5 | 15.6 |
| B:LEU107 |   | 102.2 | 10.3 |
| B:LEU113 |   | 5.0 | 3.4 |
| B:THR115 |   | 6.1 | 0.2 |
| B:LYS118 |   | 78.8 | 3.2 |
| B:LYS251 |   | 61.8 | 37.8 |
| B:ARG252 |   | 53.2 | 14.5 |
| B:GLN253 |   | 16.5 | 1.3 |
| F:ASN52 | H | 140.9 | 82.7 |
| F:MET53 |   | 38.5 | 20.6 |
| F:ALA54 |   | 70.1 | 38.1 |
| F:GLU55 |   | 76.1 | 8.0 |
| F:GLN131 |   | 88.3 | 13.1 |
| F:ASN134 |   | 79.3 | 10.9 |
| F:GLY228 |   | 64.2 | 9.1 |
| F:ALA229 |   | 88.7 | 34.4 |
| F:ASP230 |   | 115.8 | 46.9 |
| F:GLY232 |   | 87.4 | 12.1 |
| F:ALA280 |   | 93.1 | 28.6 |
| C:HIS148 |   | 163.5 | 0.6 |
| C:ASP278 |   | 130.0 | 10.7 |
| C:LYS316 |   | 120.1 | 4.2 |
| C:GLN331 |   | 39.8 | 5.1 |
| C:LYS373 |   | 88.8 | 43.5 |

Figures 5A, 5B, 5C:
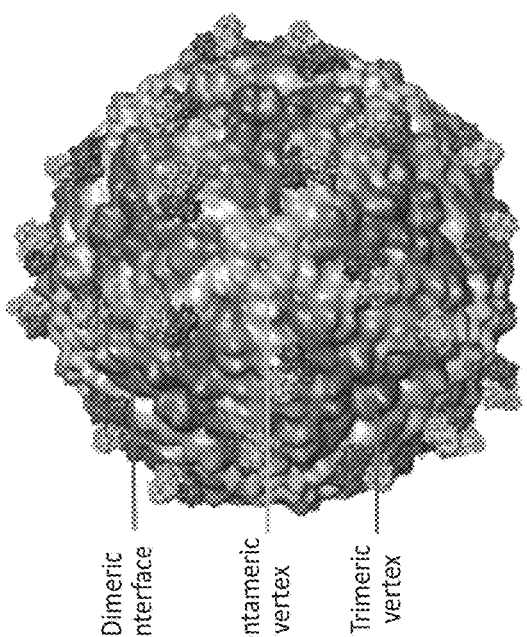
FIG. 5. Crystal structure of Inter-Dimer-Epitope Antibody rhMZ100-C Fab in Complex with ZIKV E Glycoprotein. (A) Co-crystal structure of rhMZ100-C in complex with ZIKV E (PRABC59). rhMZ100-C Fv heavy and light chains are colored dark, and light red respectively, and are shown in surface representation, modeled onto four ZIKV E protomers shown in ribbon representation colored blue, and gray, with glycan-154 shown in stick representation. (B) Antibody epitope footprint of rhMZ100-C heavy and light chain is shown as solid, and dashed lines, respectively displayed on four ZIKV E glycoproteins in surface representation and glycan-154 in stick representation colored as in (A). (C) rhMZ100-C antibody recognition is modeled in the context of the mature ZIKV (PDB: 5IRE). Individual protomers of the ZIKV are depicted in smooth surface, colored blue, dark gray and light gray, with rhMZ100-C Fv shown in atomic surface representation colored dark, and light red. (D) rhMZ100-C amino-acid sequence alignment with immunoglobulin heavy chain (VH3.63, HD6-3*01, and HJ6*01) and light chain (VL11.42 and JLx1) germline genes. Residues that undergo somatic mutation, and junction-encoded residues are colored and highlighted as in FIG. 3D. (E) Co-crystal structure of rhMZ100-C antibody in complex with ZIKV E glycoprotein. Inset panel (a-c) rhMZ100-C antibody residues within 5 Å of ZIKV E glycoprotein are shown as sticks and colored as in (D). The ZIKV E glycoprotein is colored blue, and gray with the exception of the B-strand (residues 63-73) which is highlighted in dark blue. (F) Surface representation of rhMZ100-C and ribbon representation of ZIKV E glycoprotein contact residues, viewed looking down at the CDRs at a 180° rotation about the horizontal axis from (E). Molecule 1 is colored gray, and molecule 2 is colored light blue, with the B strand colored dark blue. (G) Overlay of the rhMZ107-B ZIKV E co-crystal structure with the ZIKV-117 ZIKV E co-crystal structure (PDB: 5UHY). rhMZ100-C and antibody ZIKV-117 are depicted in ribbon representation and colored red, and dark teal respectively.
Figure 5D:
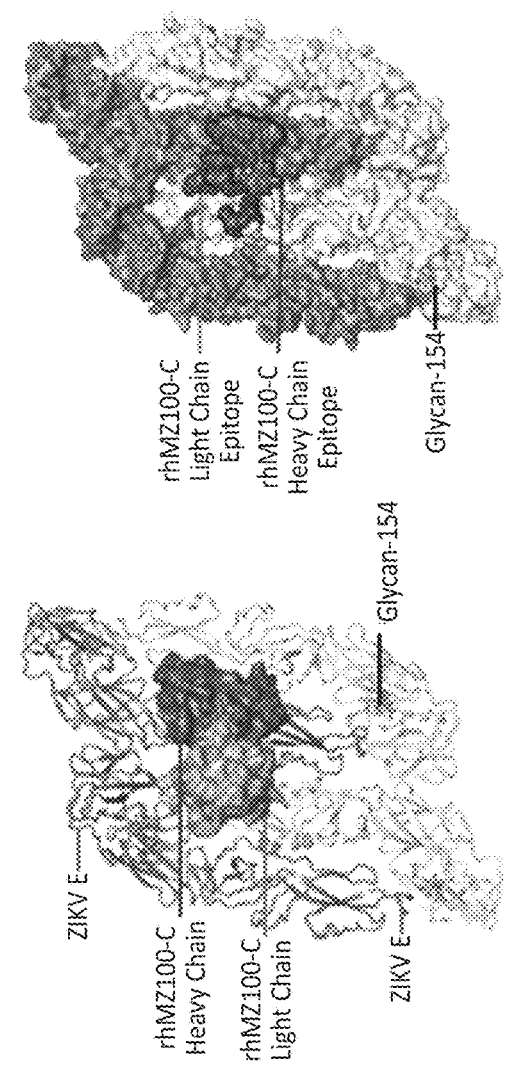

Example 7. Crystal Structure of Inter-Dimer-Epitope Antibody rhMZ100-C Fab in Complex with Zika sE Glycoprotein To understand the structural basis for the recognition of the ZIKV-specific antibodies from antigenic specificity group C, the crystal structure of rhMZ100-C was determined alone (2.1 Å resolution), and in complex with ZikaE glycoprotein at 2.8 Å resolution (FIGS. 5A-D). Within the asymmetric unit, two rhMZ100-C Fab molecules, and four ZikaE glycoprotein protomers were observed, with each Fab binding to a single protomer with a contact region of X Å2 BSA through the light chain and X Å2 from the heavy chain focused on the DI/DII (FIGS. 5A-B). We then modeled rhMZ100-C binding in the context of the mature ZIKV and were able to identify additional significant contacts in the DI/DII of an adjacent Zika E protomer increasing the heavy chain contact region to X Å2. Since this epitope spanned across the center of two dimers, within the context of the ZIKV, only 60 antibody binding sites were accessible since only half of the epitope would be available on the dimers that form the raft-raft interface (FIG. 5C). Antibody rhMZ100-C recognition of ZikaE uses X0% of germline-encoded residues in the heavy chain and 100% in the light chain (FIG. 5D).

Figure 5E:
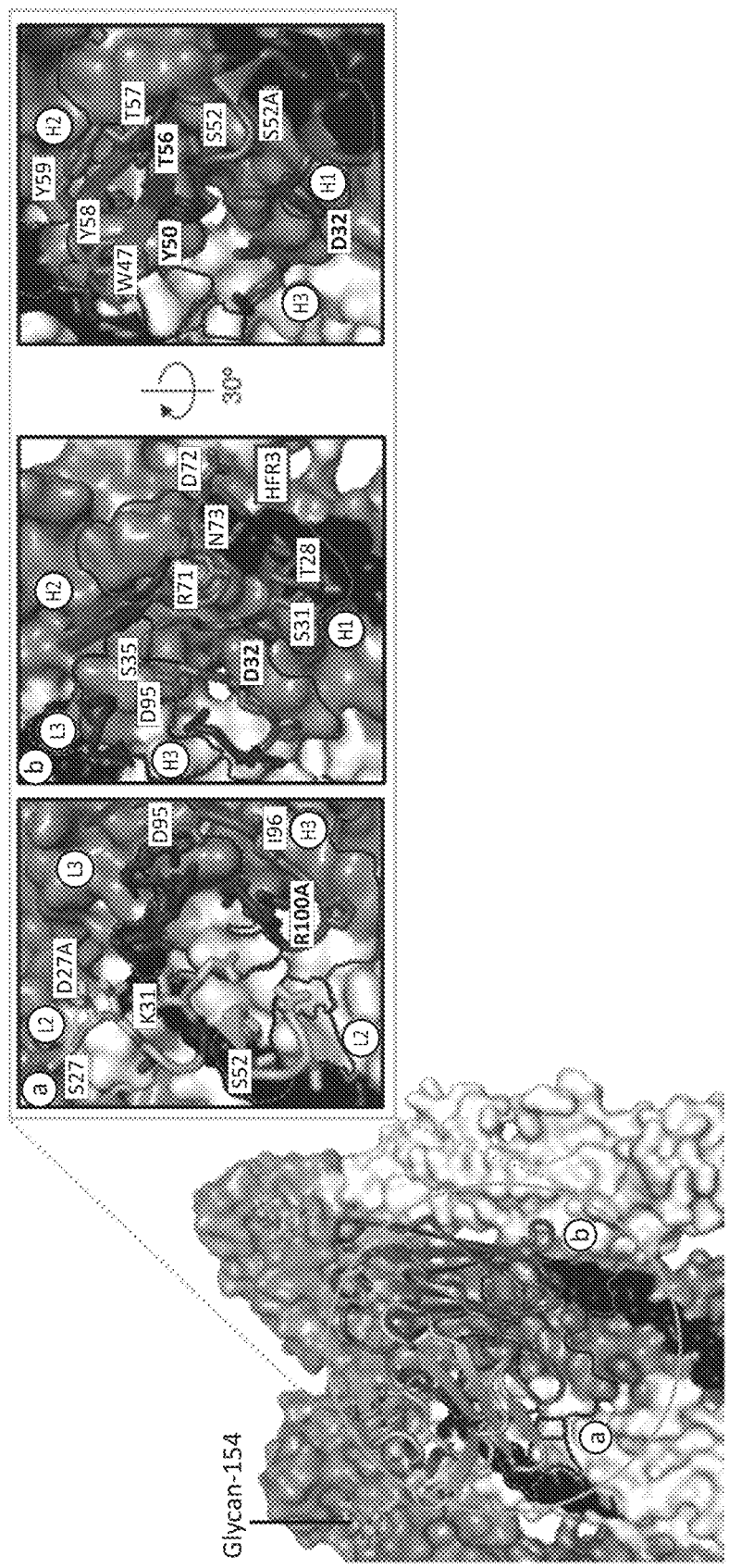
Figure 5F:
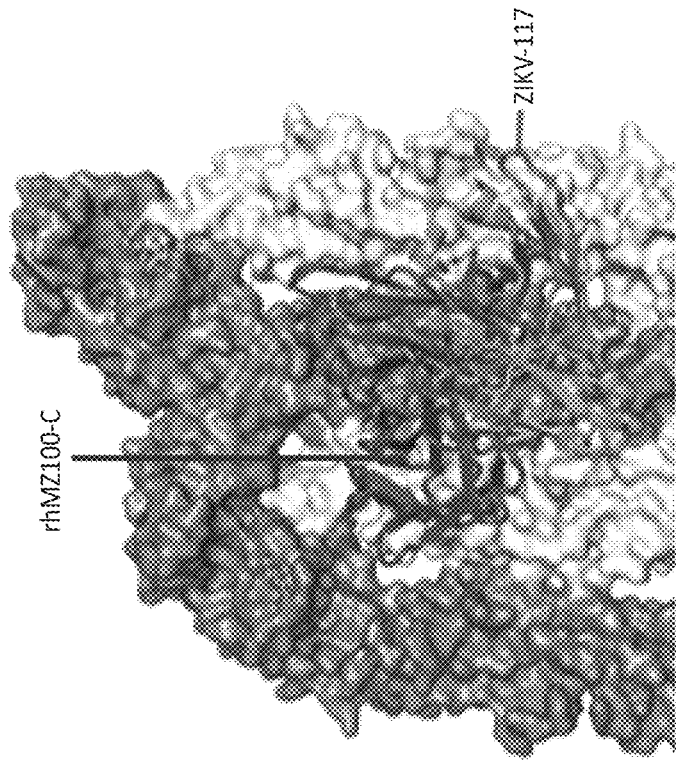
Figure 5G:
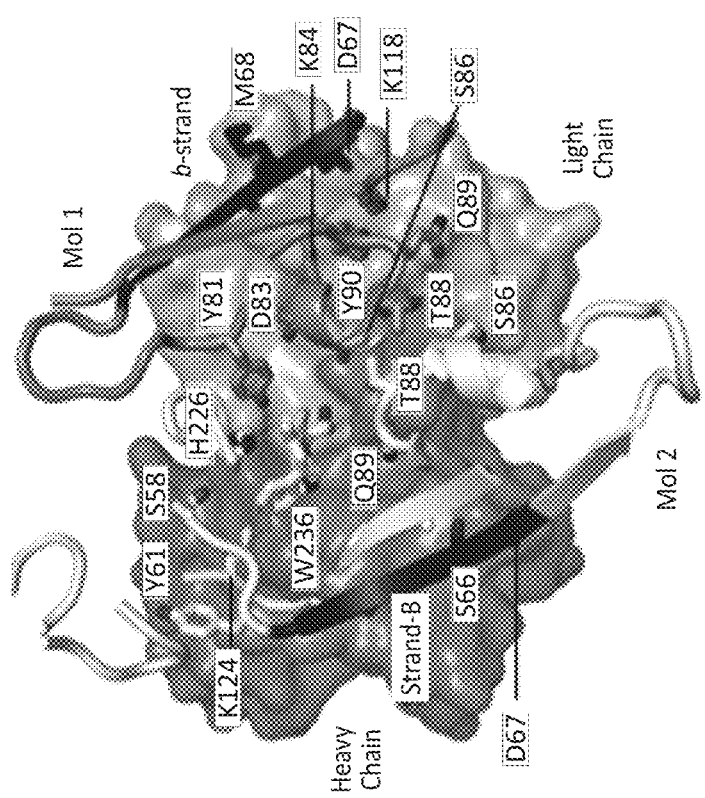
Figure 6C:
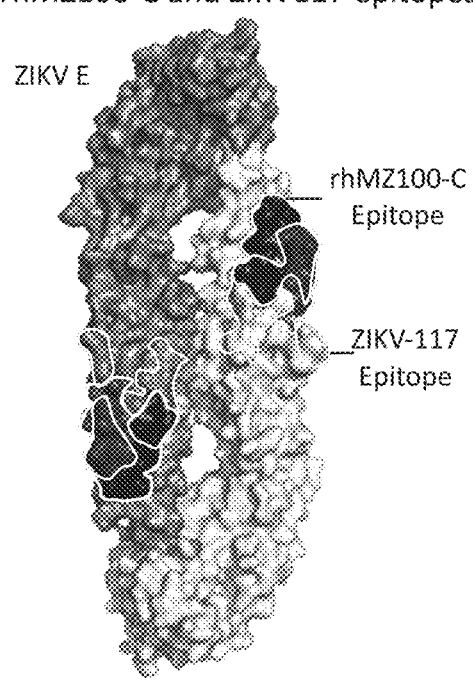
FIG. 6. Crystal Structure of ZIKV-specific EDE Antibody rhMZ100-C in Complex with ZIKV E glycoprotein. (A) Top view of the co-crystal structure of rhMZ100-C in complex with ZIKV E (PRABC59). rhMZ100-C Fv heavy and light chains are shown in surface representation, colored dark, and light red respectively, while two ZIKV E protomers shown in ribbon representation, and colored blue. Antibody epitope footprint of rhMZ107-B is outlined on two ZIKV E protomers shown in surface representation. ZIKV E regions that interact with rhMZ107-B are indicated. (B) rhMZ107-B antibody residues within 5 Å of ZIKV E are shown as sticks and colored as in (A). ZIKV E is colored blue and gray with the b-strand (residues 63-73) highlighted in dark blue. (C) Overlay of the rhMZ107-B epitope and the ZIKV-117 antibody epitope (PDB: 5UHY).

MAb rhMZ100-C recognized the DII of ZikaE utilizing all CDRs with the area of recognition demarcated on either side by the ZikaE B strand (residues X-Y) (FIG. 5E). Additional recognition of chain A, and C form the center of the epitope in an almost perfect mirror image (FIGS. 3E, and 3F). Features of the antibody recognition are reminiscent of the recently described Z117 antibody, which is highly potent against ZIKV (FIG. 5G). However, there were distinct differences between the sites of recognition, with Z117 recognizing an inter-dimer epitope that is less centered across the inter-dimer interface with a predominant recognition of one protomer (X Å2) as compared to rhMZ100-C. Analysis of the epitope-contact residues showed dissimilar contact residues, with the rhMZ100-C epitope centered over the glycan-67 (DENV) site.

TABLE 12 rhMZ100 interface with E glycoprotein of Zika virus.

| | rhMZ100 | Zika E glycoprotein | Distance (Å) |
|---|---|---|---|
| Hydrogen bonds | | | |
| | H:GLY 100[ O ] | G:LYS 84[ NZ ] | 2.93 |
| | L:LYS 31[ NZ ] | G:ASP 83[ OD1] | 3.33 |
| | L:TYR 51[ OH ] | G:TYR 90[ OH ] | 3.86 |
| Salt bridges | | | |
| | L:LYS 31[ NZ] | G:ASP 83[ OD2] | 3.16 |
| | L:LYS 31[ NZ ] | G:ASP 83[ OD1] | 3.33 |

TABLE 13

Buried surface area of rhMZ100 antibody in complex with Zika virus. Residues that form hydrogen bonds and salt bridges are indicated.

| rhMZ100 antibody Residue | Bond type | Accessible Surface Area (Å²) | Buried Surface Area (Å²) |
|---|---|---|---|
| H:THR97 | | 110.71 | 5.35 |
| H:ALA98 | | 28.43 | 2.21 |
| H:PRO99 | | 145.03 | 19.55 |
| H:GLY100 | H | 83.37 | 58.14 |
| H:ARG100A | | 153.22 | 2.76 |
| H:ASN100B | | 106.68 | 14.13 |
| L:ASP27A | | 87.17 | 31.91 |
| L:LEU27B | | 40.61 | 35.04 |
| L:ASN27C | | 85.15 | 10.8 |
| L:GLY29 | | 37.97 | 6.77 |
| L:THR30 | | 88.93 | 74 |
| L:LYS31 | HS | 15.47 | 15.13 |
| L:ASN32 | | 54.93 | 38.35 |
| L:TYR49 | | 45.38 | 6.83 |
| L:TYR51 | H | 75.59 | 65.13 |
| L:SER54 | | 114.79 | 8.79 |
| L:ASP54A | | 58.96 | 26.91 |
| L:TYR91 | | 76.02 | 20.71 |
| L:ASP92 | | 37.98 | 11.04 |
| L:ASN93 | | 136.93 | 78.85 |
| L:SER94 | | 99.1 | 1.31 |
| Zika virus PF E glycoprotein Residue | Bond type | Accessible Surface Area (Å²) | Buried Surface Area (Å²) |
| G:ASP 67 | | 94.31 | 22.06 |
| G:ALA 69 | | 45.29 | 17.41 |
| G:SER 70 | | 34.10 | 1.14 |
| G:ASP 71 | | 74.65 | 47.56 |
| G:ARG 73 | | 88.86 | 45.02 |
| G:GLY 78 | | 57.19 | 1.68 |
| G:GLU 79 | | 117.73 | 18.85 |
| G:ALA 80 | | 6.97 | 0.25 |
| G:TYR 81 | | 127.61 | 97.69 |
| G:LEU 82 | | 34.06 | 28.71 |
| G:ASP 83 | HS | 97.14 | 88.4 |
| G:LYS 84 | H | 89.81 | 89.81 |
| G:SER 86 | | 98.91 | 21.89 |
| G:ASP 87 | | 36.12 | 30.97 |
| G:THR 88 | | 74.75 | 11.40 |
| G:GLN 89 | | 61.77 | 0.88 |
| G:TYR 90 | H | 32.29 | 15.63 |
| G:LYS 118 | | 64.63 | 11.93 |

H: Hydrogen bond
S: Salt bridge

Example 8. Structure of Inter-Dimer-Epitope Antibody rhMZ104-D in Complex with ZikaE Glycoprotein To understand the structural basis for the recognition of the ZIKV-specific antibodies from antigenic specificity group D, we determined the crystal structures of rhMZ119-D (1.7 Å resolution), and rhMZ104-D alone (2.5 Å resolution), and in complex with ZikaE glycoprotein at 3.2 Å resolution (FIGS. 7A-D; FIG. 18). Within the asymmetric unit, one rhMZ104-C Fab, and one Fv molecule, and two ZikaE glycoprotein protomers were observed, with each rhMZ100-C binding to the DII region of a single protomer with a contact region of X Å2 BSA through the light chain and X Å2 from the heavy chain (FIG. 7A-B). We then modeled rhMZ104-D recognition in the context of the mature ZIKV and were able to identify significant additional heavy chain contacts in the DI/DII of two adjacent ZikaE protomers increasing the heavy chain contact region to X Å2. Since this epitope spanned across the center of two dimers similar to rhMZ100-C in the context of the ZIKV (FIG. 5C), only 60 antibody binding sites were accessible since only half of the epitope would be available on the dimers that form the raft-raft interface (FIG. 5C, 7C). Antibody rhMZ104-D recognition of the crystallographic ZikaE protomer utilized 100% germline-encoded residues in the heavy chain and 100% in the light chain (FIG. 7D).

Figure 7E:
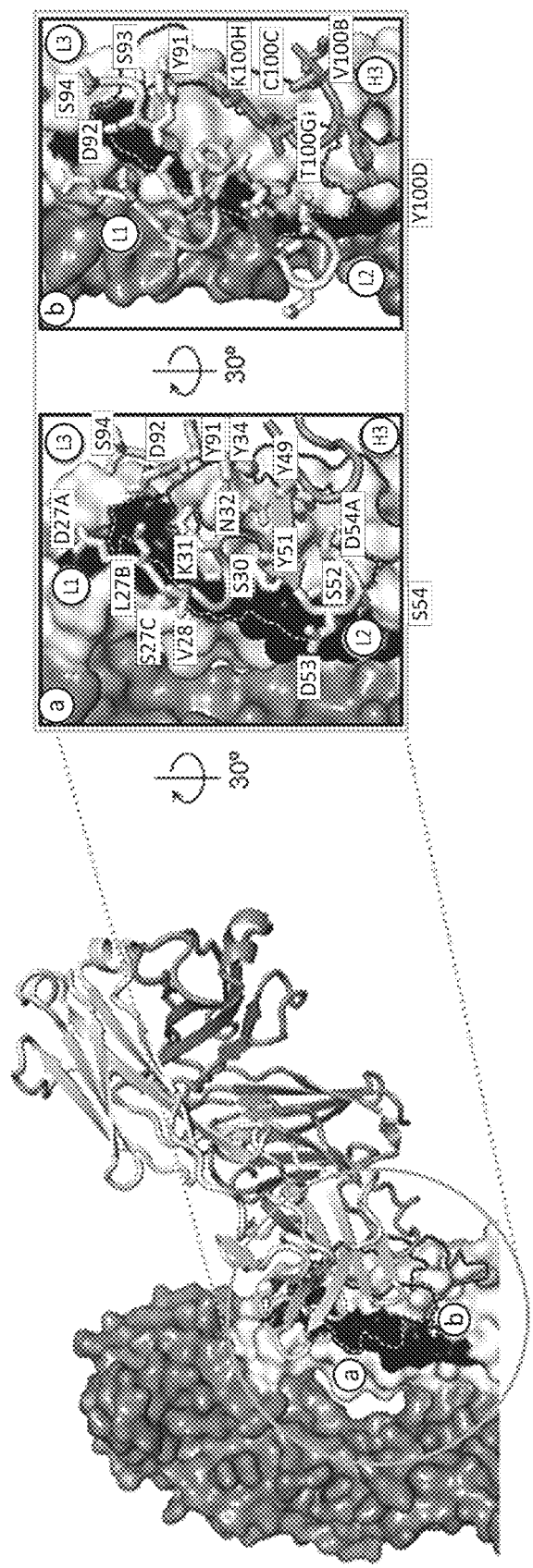
FIG. 7. Structure of Inter-Dimer-Epitope Antibody rhMZ104-D in Complex with ZIKV E Glycoprotein. (A) Top view of the co-crystal structure of rhMZ104-D in complex with ZIKV E (PRABC59). rhMZ104-D Fv heavy and light chains are shown in surface representation and are colored dark, and light orange respectively, while four ZIKV E protomers are shown in ribbon representation, and colored blue, and gray, with glycan-154 shown in stick representation. (B) Antibody epitope footprints of rhMZ104-D heavy, and light chain are shown as solid, and dashed lines, respectively, displayed on four ZIKV E glycoprotein protomers in surface representation with glycan-154 represented as above. (C) rhMZ107-B antibody recognition is modeled in the context of the mature ZIKV (PDB: 5IRE). Individual protomers of the ZIKV are depicted in smooth surface colored blue, dark gray and light gray, with rhMZ104-D Fv shown in atomic surface representation colored dark, and light orange. (D) rhMZ104-D amino-acid sequence alignment with immunoglobulin heavy chain (VH3.15, HD2-2*01, and HJ4*01) and light chain (VL11.42, and JLx1) germline genes. Residues that undergo somatic mutation, and junction-encoded residues are colored and highlighted as in FIG. 3D. (E) Co-crystal structure of antibody rhMZ104-D in complex with ZIKV E glycoprotein. Inset panel (a-b) rhMZ100-C antibody residues within 5 Å of ZIKV E glycoprotein are shown as sticks and colored as in (D). The ZIKV E glycoprotein is colored blue, and gray with the exception of the B-strand (residues 63-73) which is highlighted in dark blue. (F) Surface representation of rhMZ104-D and ribbon representation of ZIKV E glycoprotein contact residues, viewed looking down at the CDRs at a 180° rotation about the horizontal axis from (E). (G) Group D antibodies were assessed for binding using shotgun mutagenesis epitope mapping. Alanine or serine mutations which dramatically impacted group D antibody binding are shown in sphere representation on the ZIKV E structure and indicated on the right. Residues important for binding for all Group D mAb are highlighted in orange.
Figures 7F, 7G:
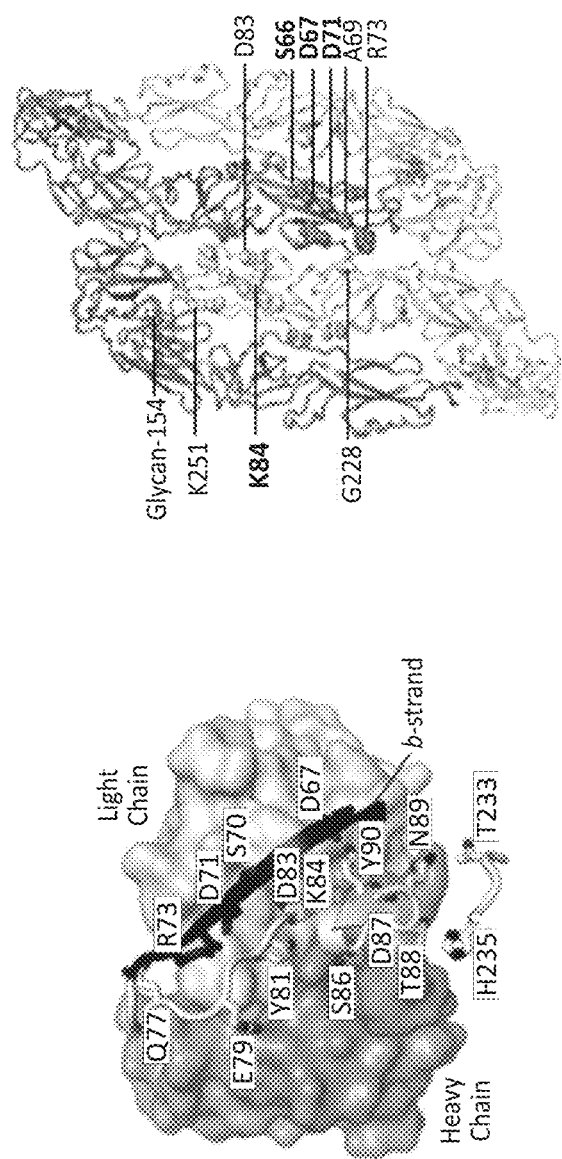
Figure 8A:
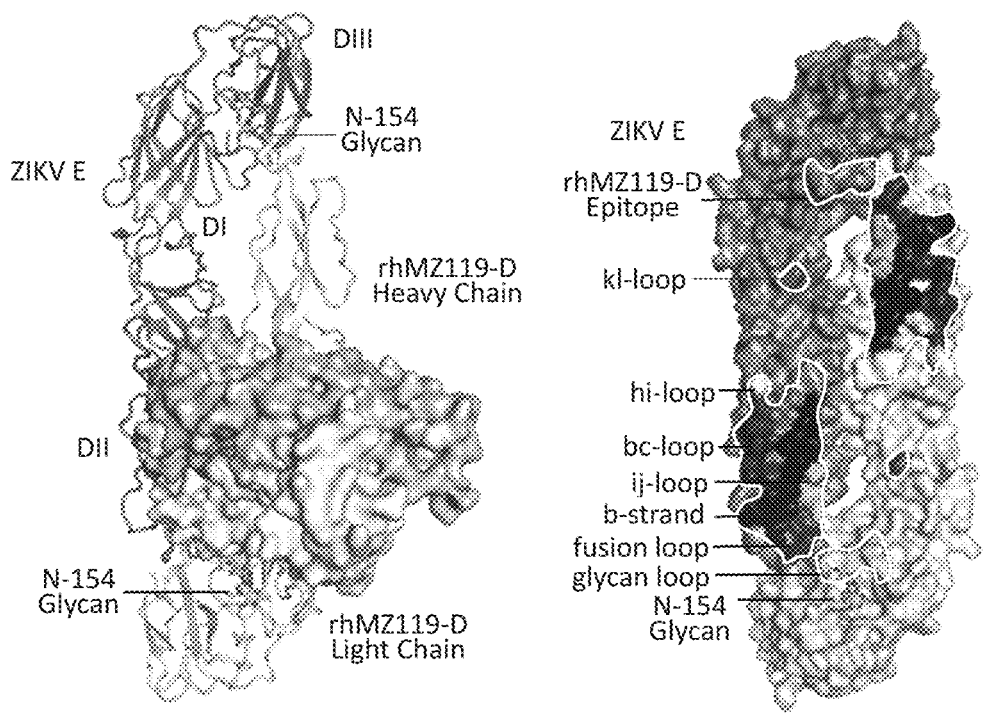
FIG. 8. Structures of Antibodies rhMZ104-D and rhMZ119-D in Complex with ZIKV E Glycoprotein. (A,B) Top view of the co-crystal structures of rhMZ104-D (A) or rhMZ119-D (B) in complex with ZIKV E (PRABC59). Antibody Fv heavy and light chains are shown in surface representation colored tan, and light yellow (rhMZ119-D), dark and light orange (rhMZ119-D), while two ZIKV E protomers are shown in ribbon representation colored blue, and gray, with glycan-154 shown in stick representation. (right panels) Top view of the co-crystal structure of rhMZ119-D in complex with ZIKV E (PRABC59). Fv heavy and light chains are shown in surface representation and are colored dark, and light orange respectively, while two ZIKV E protomers are shown in ribbon representation, and colored blue, and gray, with glycan-154 shown in stick representation. ZIKV E regions that interact with the antibodies are indicated. (C, D) Co-crystal structure of antibody rhMZ104-D in complex with ZIKV E glycoprotein. Inset panel (a-b) rhMZ100-C antibody residues within 5 Å of ZIKV E glycoprotein are shown as sticks and colored as in (A, B). The ZIKV E glycoprotein is colored blue, and gray with the exception of the b-strand (residues 63-73) which is highlighted in dark blue. (E) Comparison of rhMZ104-D, and rhMZ119-D antibody recognition of ZIKV E glycoprotein. (F) Antibody epitope comparisons of rhMZ104-D, ZIKV195, and rhMZ119-D shown on two ZIKV E protomers. ZIKV E regions that interact with the antibodies are indicated as in (A, B). (G) Group D antibodies were assessed for binding using shotgun mutagenesis epitope mapping. Alanine or serine mutations which dramatically impacted group D antibody binding are shown in sphere representation on the ZIKV E structure and indicated on the right. Residues important for binding for all Group D mAb are highlighted in orange.
Figure 8B:
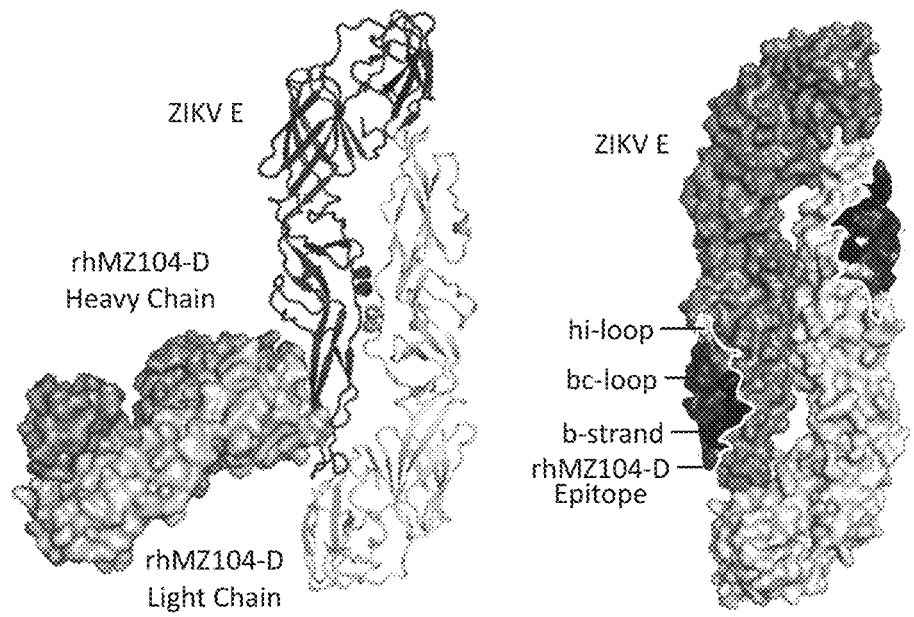
Figure 8C:
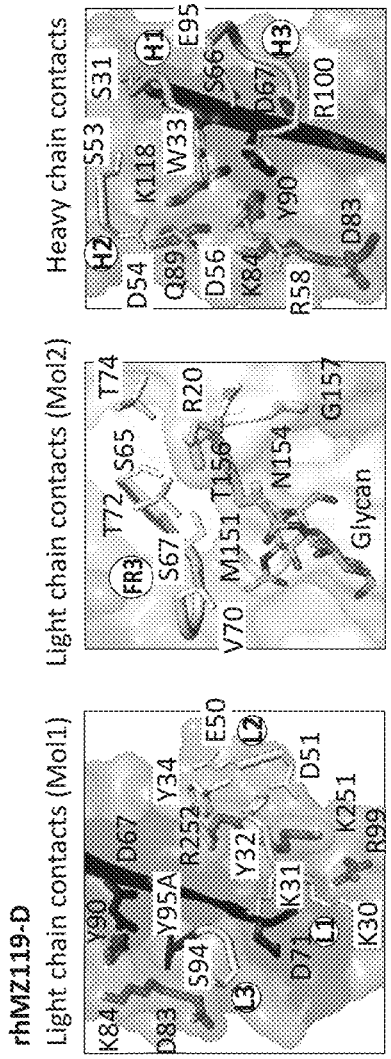
Figure 8D:
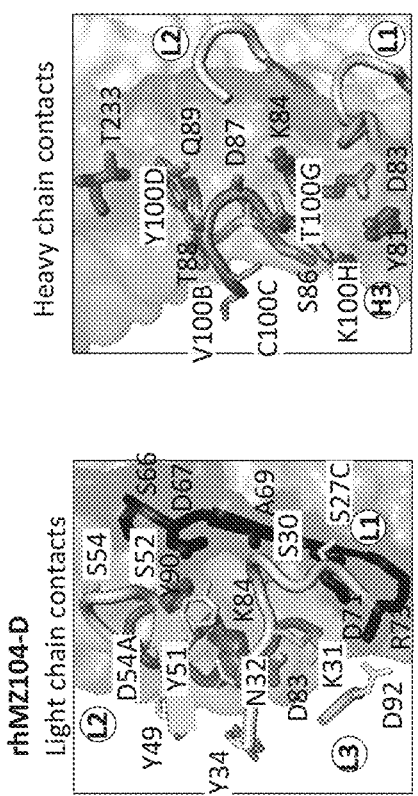
Figure 9A:
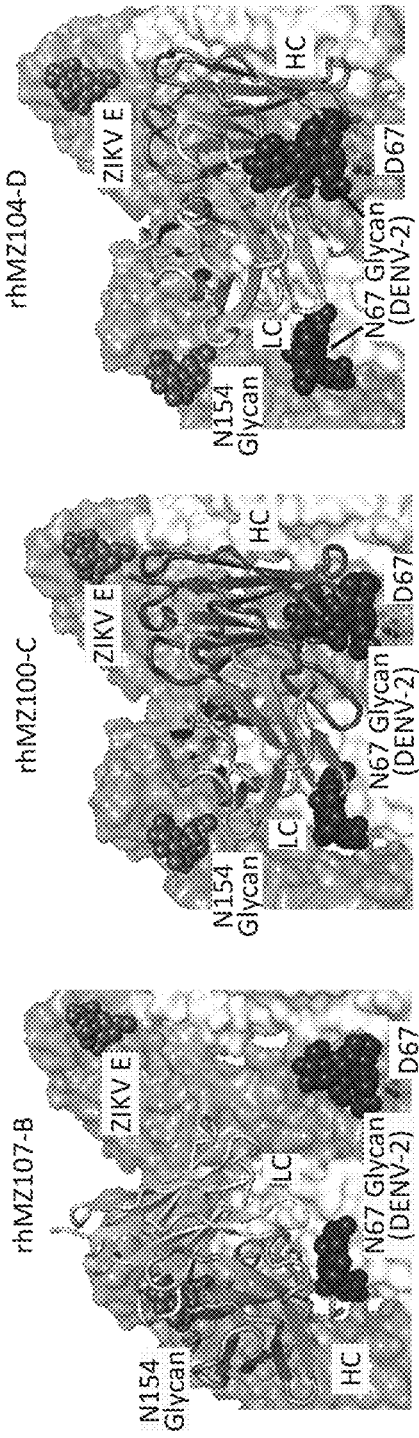
FIG. 9. Sequence differences between ZIKV and DENV. (A) Modeling of rhMZ antibodies in the context of DENV which contains a glycan at residue N67. rhMZ107-B Fab (left, green), rhMZ100-C Fab (middle, raspberry) and rhMZ104-D Fab (right, orange) bound on ZIKV E (PDB: 5IRE). ZIKV E protomers are in blue and white, Glycan-154 is colored brown and the modeled DENV glycan-N67 is shown in red. (B) Control mAbs that have been previously shown to bind to both ZIKV and DENV and can accommodate the glycan-67 are EDE1-C8 Fab (left, grey) and EDE2-A11 Fab (middle, olive). The binding site for antibody ZIKV-117 (right, teal) overlaps significantly with glycan-67. Coloring and labeling scheme for ZIKV E and glycans are as shown in (A). (C) Sequence differences between ZIKV and DENV (−1, −3 and −4) E, are mapped on the ZIKV E structure (PDB: 5IRE). White color indicates 100% identity, while light red indicates sequence differences compared to ZIKV. Glycan-67 and 153 are shown as spheres in raspberry and brown colors, respectively.
Figure 9A:
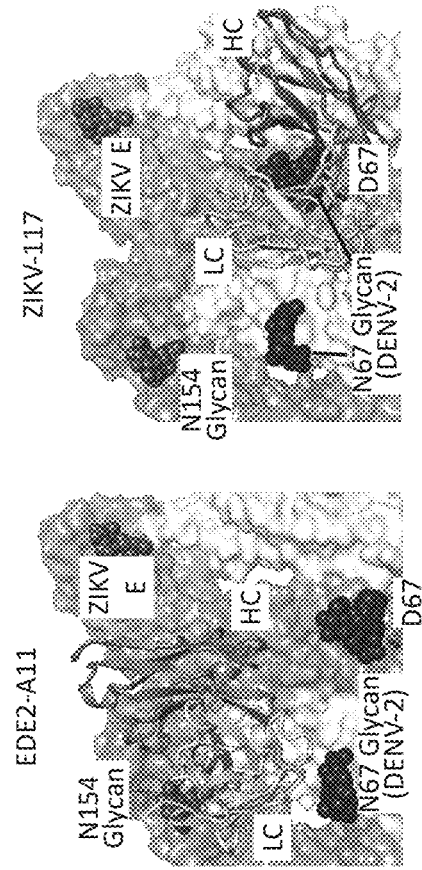
Figure 9B:
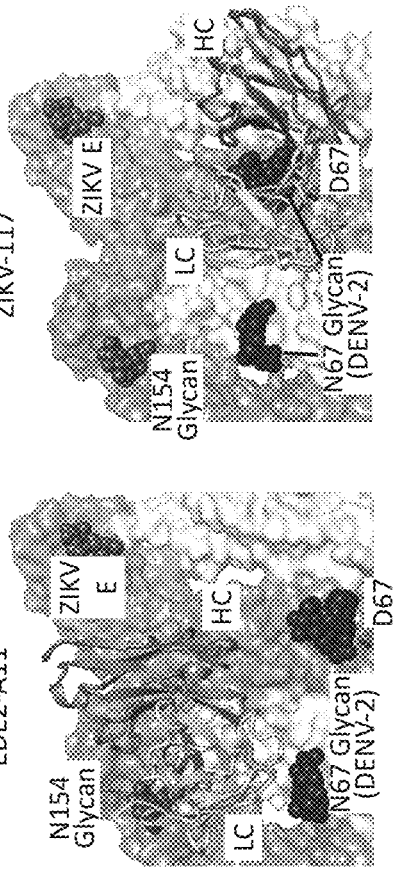
Figure 9C:
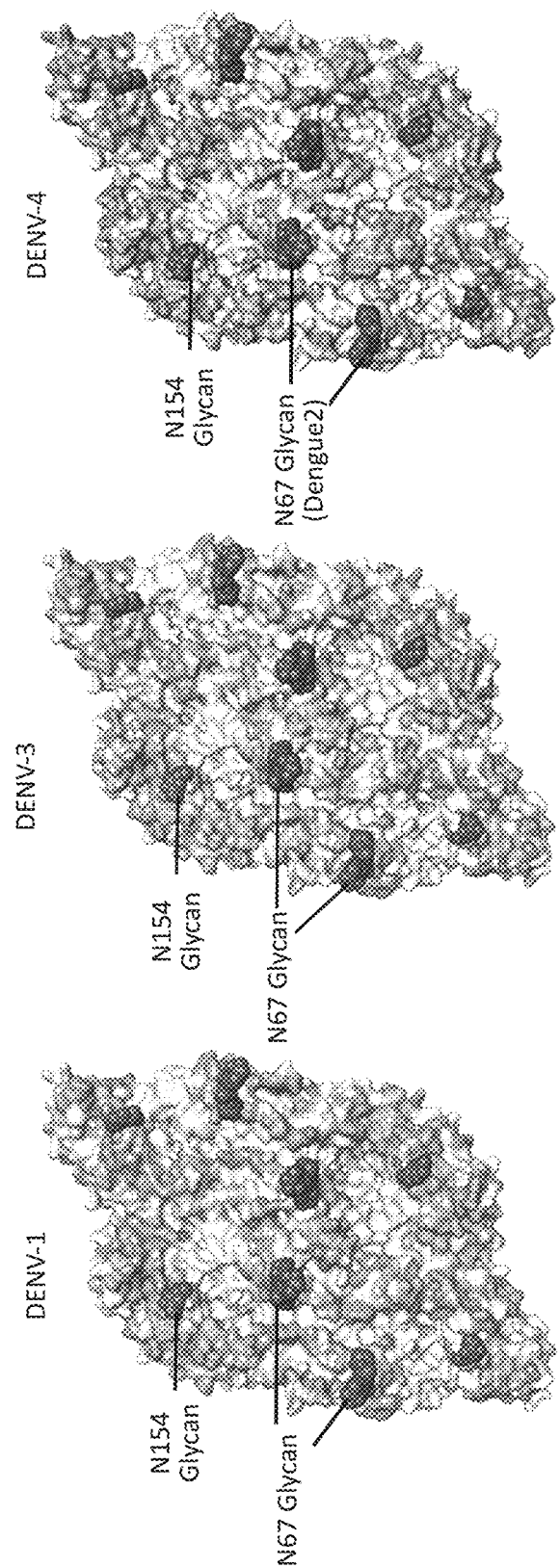
Figure 10A:
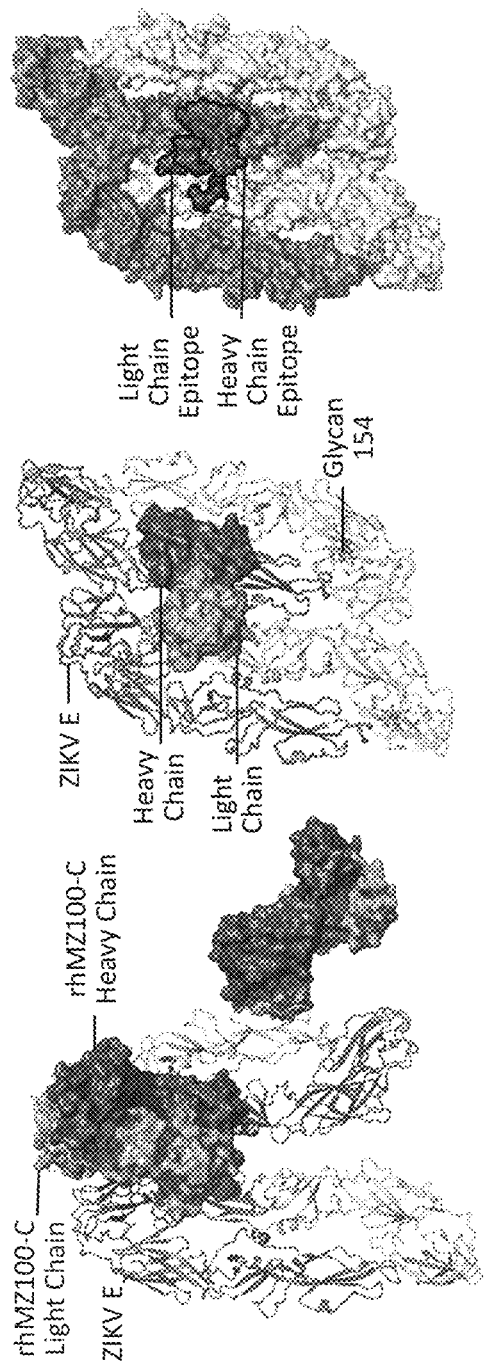
FIG. 10. rhMZ antibody ZIKV E complex structure asymmetric unit contents, and modeling of higher order interactions. (A) Left rhMZ100-C—ZIKV E asymmetric contents. Center rhMZ100-C antibody modeled onto four ZIKV E protomers. Right rhMZ100-C epitope mapped onto four ZIKV E protomers. (B) Left rhMZ104-D—ZIKV E asymmetric contents. Center rhMZ104-D antibody modeled onto four ZIKV E protomers. Right rhMZ104-D epitope mapped onto four ZIKV E protomers. (C) Left rhMZ119-D—ZIKV E asymmetric contents. Center rhMZ119-D antibody binding to two ZIKV E protomers using symmetry related molecules. Right rhMZ119-D epitopes mapped onto two ZIKV E protomers. (D) rhMZ antibodies are modeled in the context of the mature ZIKV virus for the four antibody-E complex structures.
Figure 10B:
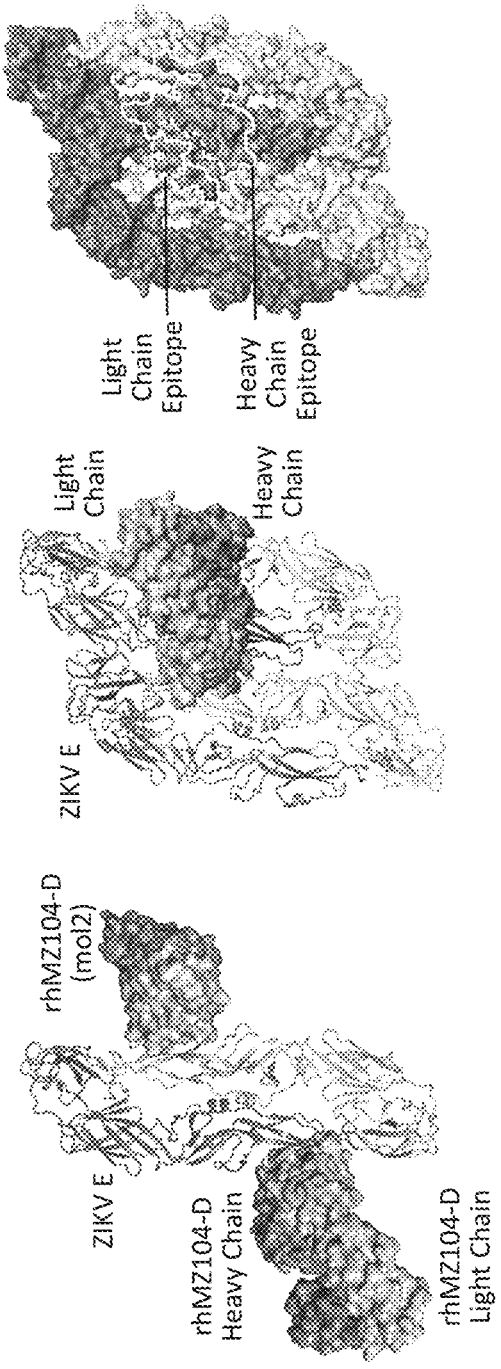
Figure 10C:
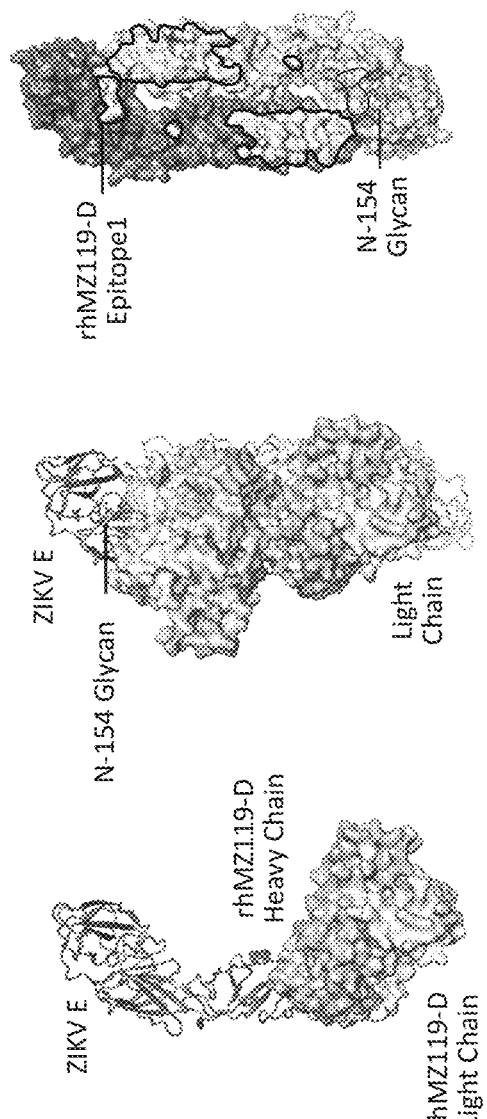
Figure 10D:
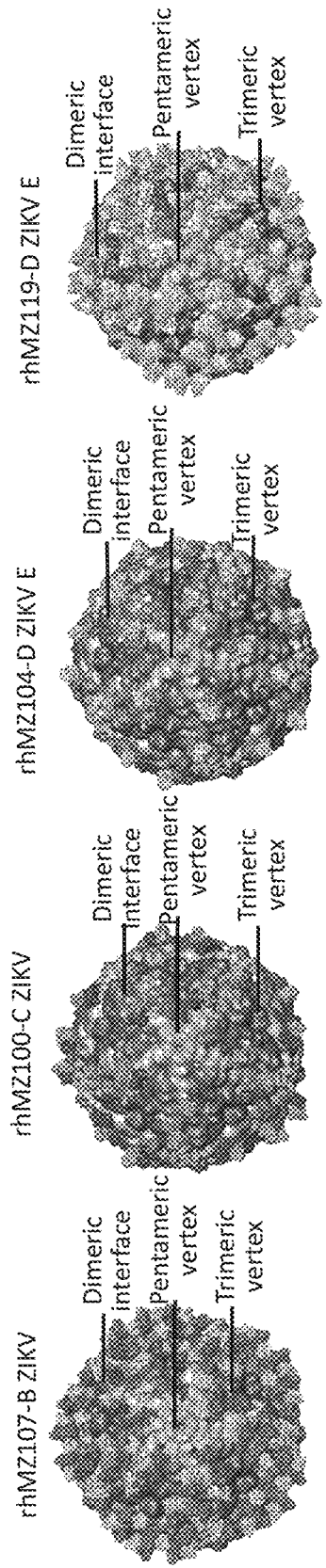
Figure 17:
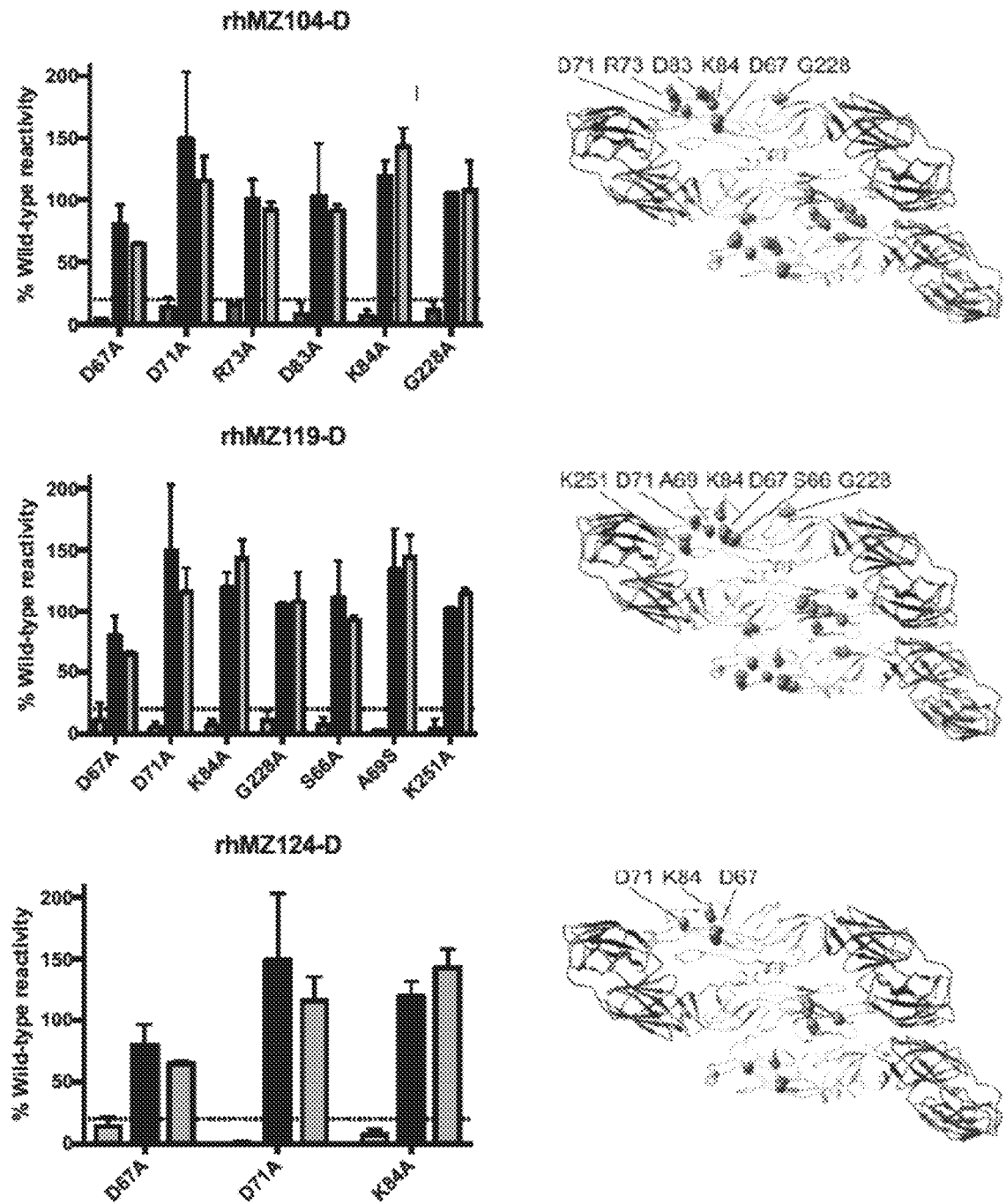
FIG. 17. Shotgun mutagenesis epitope mapping data for group D mAbs.

Antibody rhMZ104-D recognized the DII of ZikaE utilizing all light chain CDRs and CDRH3 with the ZikaE B strand (residues X-Y) the major antigen contact region for the light chain, alongside a continuous stretch of residues from position 77 to position 90 that is recognized by both heavy and light chains (FIGS. 7E and 7F). Comparison of the rhMZ104-B recognition of ZikaE compared to the most related flaviviruses (DENV1-4) highlighted the epitope recognition as focused on a non-conserved region of the glycoprotein distal to the conserved epitope of EDE1-C8 (FIG. 7G). In addition to the structural data describing the rhMZ104-D epitope, we also screened all group D antibodies rhMZ104-D, rhMZ119-D, and rhMZ124-D for recognition of ZikaE glycoprotein by shotgun alanine/serine-scanning mutagenesis (FIGS. 7H and 17). The scanning mutations identified 3-6 residues per antibody that significantly altered ZikaE recognition. In all cases residue D71 was highlighted as a significant contact residue, and D67, D83, D84, and G228 residues knocked out binding of two of the three group D mAbs (FIGS. 7G, and 8G).

TABLE 14 rhMZ104 interface with E glycoprotein of Zika virus.

| rhMZ104 | Zika E glycoprotein | Distance (Å) |
|---|---|---|
| Hydrogen bonds | | |
| H:CYS 100C[ O ] | G:THR 88[ OG1] | 3.83 |
| H:CYS 100C[ O ] | G:THR 88[ N ] | 3.47 |
| H:CYS 100C[ N ] | G:SER 86[ O ] | 3.71 |
| H:CYS 100C[ SG ] | G:SER 86[ O ] | 3.75 |
| H:ALA 100E[ O ] | G:LYS 84[ NZ ] | 3.11 |
| L:LYS 31[ NZ ] | G:ASP 83[ OD2] | 2.36 |
| L:ASN 32[ N ] | G:ASP 83[ OD2] | 3.42 |
| L:TYR 49[ OH ] | G:LYS 84[ NZ ] | 3.25 |
| L:TYR 51[ OH ] | G:TYR 90[ OH ] | 3.65 |
| L:TYR 51[ OH ] | G:ASP 67[ OD1] | 3.05 |
| L:ASP 54A[ OD2] | G:LYS 84[ NZ ] | 2.99 |
| L:ASP 92[ OD1] | G:ARG 73[ NH2] | 2.88 |
| Salt bridges | | |
| L:LYS 31[ NZ ] | G:ASP 83[ OD1] | 3.61 |
| L:LYS 31[ NZ ] | G:ASP 83[ OD2] | 2.36 |
| L:ASP 92[ OD1] | G:ARG 73[ NH2] | 2.88 |
| L:ASP 54A[ OD2] | G:LYS 84[ NZ ] | 2.99 |

TABLE 15

Buried surface area of rhMZ104 antibody in complex with Zika virus. Residues that form hydrogen bonds and salt bridges are indicated

| Residue | Bond type | Accessible Surface Area (Å$^2$) | Buried Surface Area (Å$^2$) |
|---|---|---|---|
| H:CYS 98 | | 31.01 | 1.48 |
| H:GLY 100A | | 69.80 | 17.57 |
| H:VAL 100B | | 102.16 | 34.22 |
| H:CYS 100C | H | 34.52 | 23.91 |
| H:TYR 100D | | 188.90 | 54.79 |
| H:ALA 100E | H | 84.02 | 45.07 |
| H:GLY 100F | | 45.58 | 34.24 |
| H:LYS 100H | | 129.48 | 51.60 |
| L:ASP 27A | | 97.90 | 14.80 |
| L:LEU 27B | | 19.54 | 6.52 |
| L:GLY 29 | | 44.60 | 4.17 |
| L:SER 30 | | 82.48 | 70.48 |
| L:LYS 31 | HS | 31.90 | 20.95 |
| L:ASN 32 | H | 62.93 | 37.50 |
| L:TYR 34 | | 48.02 | 2.81 |
| L:TYR 49 | H | 41.10 | 4.00 |
| L:TYR 51 | H | 73.62 | 65.27 |
| L:SER 52 | | 35.73 | 2.13 |
| L:SER 54 | | 112.56 | 9.85 |
| L:ASP 54A | HS | 55.04 | 19.34 |
| L:TYR 91 | | 103.57 | 38.80 |
| L:ASP 92 | HS | 30.15 | 25.61 |
| L:SER 93 | | 103.98 | 46.23 |
| L:SER 94 | | 90.96 | 3.53 |

| E glycoprotein Residue | Bond type | Accessible Surface Area (Å$^2$) | Buried Surface Area (Å$^2$) |
|---|---|---|---|
| G:ASP 67 | H | 82.67 | 29.98 |
| G:ALA 69 | | 50.73 | 20.85 |
| G:SER 70 | | 34.97 | 2.33 |
| G:ASP 71 | | 29.65 | 5.28 |
| G:ARG 73 | HS | 81.47 | 46.65 |
| G:GLN 77 | | 117.60 | 2.02 |
| G:GLU 79 | | 124.94 | 10.74 |
| G:TYR 81 | | 107.16 | 96.27 |
| G:LEU 82 | | 28.22 | 20.06 |
| G:ASP 83 | HS | 108.11 | 108.11 |
| G:LYS 84 | HS | 92.55 | 92.55 |
| G:GLN 85 | | 62.36 | 0.49 |
| G:SER 86 | H | 102.26 | 84.60 |
| G:ASP 87 | | 33.78 | 28.64 |
| G:THR 88 | H | 84.19 | 58.51 |
| G:GLN 89 | | 59.68 | 21.23 |
| G:TYR 90 | H | 23.54 | 8.13 |
| G:LYS 118 | | 67.11 | 14.60 |
| G:GLY 232 | | 75.04 | 0.61 |
| G:THR 233 | | 89.36 | 18.92 |
| G:HIS 235 | | 86.03 | 3.17 |

H: Hydrogen bond,
S: Salt bridge

Figure 13A:
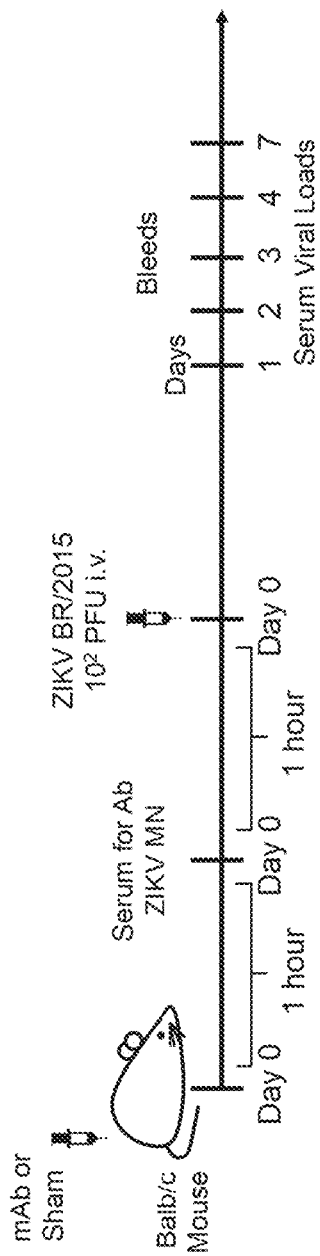
FIG. 13. Protection of ZIKV-specific Neutralizing mAbs. (A) Schematic of passive protection study experimental design. Antibodies were infused intravenously into groups of naïve recipient Balb/c mice (n=5/group) prior to ZIKV-BR challenge. Mice received 200 µg of antibody (10 mg/kg) and were challenged with 105 viral particles (102 plaque-forming units) of ZIKV-BR intravenously, 2 hours after infusion. (B) Complete or partial protection from ZIKV replication were observed for six representative neutralizing mAbs with 1 or 2 from each group. Following infusion with the indicated antibody, or saline (Sham), ZIKV viral loads were measured in serum post-challenge by RT-PCR daily until day 7. Viral load peaked at day 3 or 4. The six antibodies were tested in two sets of experiments, and a representative Sham from one experiment is shown. The most potent neutralizing mAbs completely protected mice from ZIKV replication (top row), while mAbs less potent in neutralization partially protected mice from ZIKV replication (bottom row). (C) Viral dissemination in brain, spleen and lymph nodes (LN) was assessed at day 3 post challenge for 3 of the most potent mAbs (black circles) as compared to the Sham group (red circles). Error bars indicate mean±s.e.m.
Figure 13B:
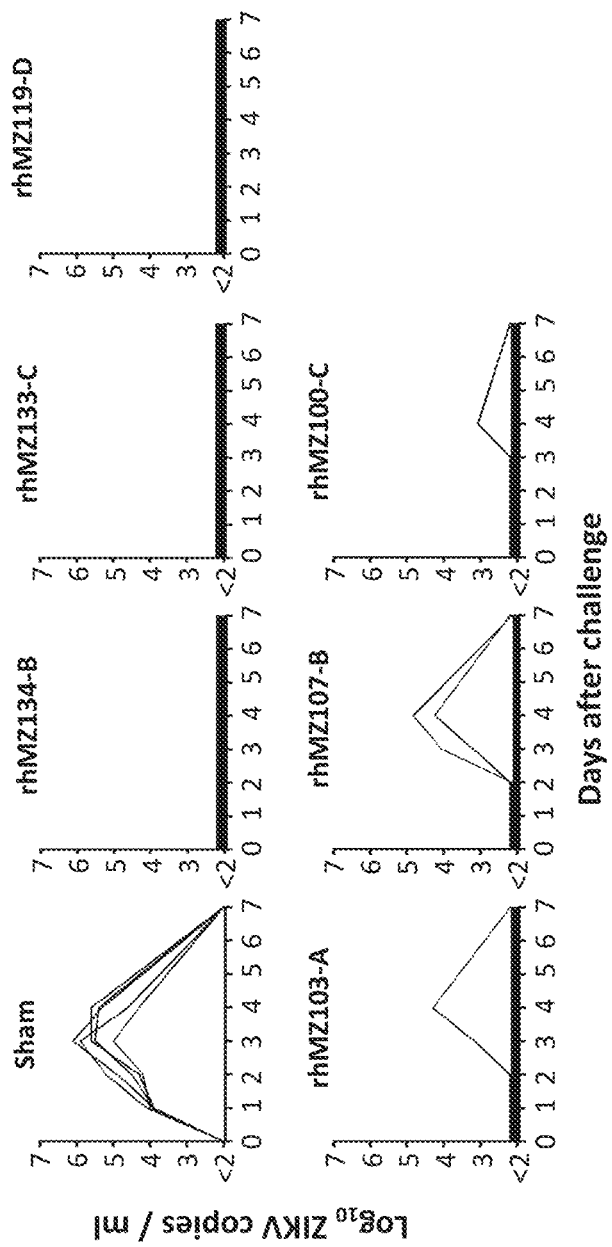
Figure 13C:
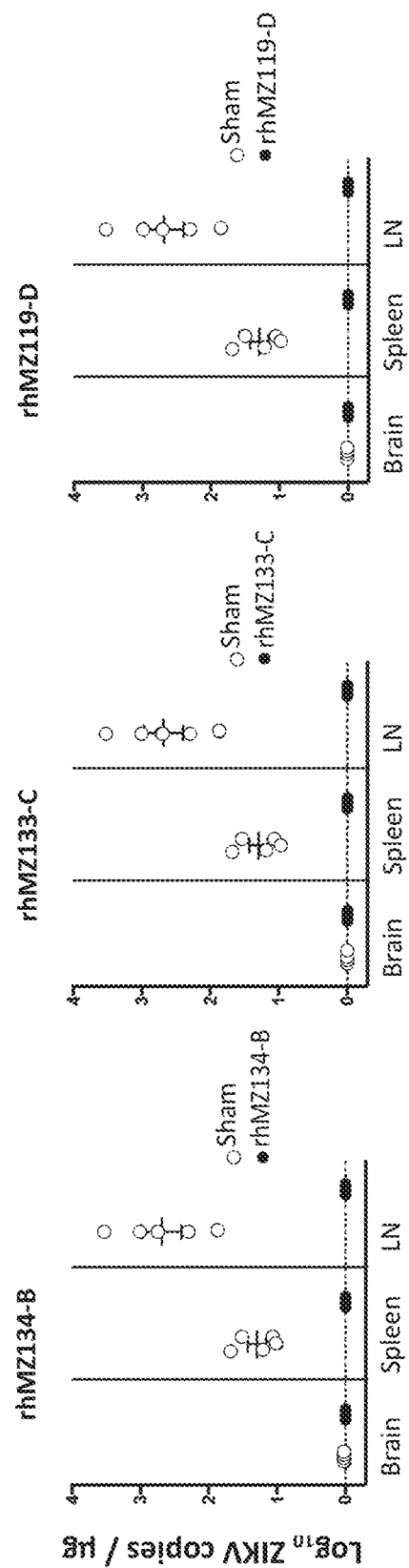

Example 9. Neutralizing Antibodies Afford Complete or Partial Protection from ZIKV Replication in Mice Passive protection experiments were conducted in mice to determine whether representative neutralizing antibodies would confer protection in vivo. Six neutralizing antibodies of various potencies were infused to groups of naïve Balb/c mice (N=5/group) at a single dose (200 μg). Mice were then challenged with 10' viral particles ($10^2$ plaque-forming units) of ZIKV-BR intravenously and viral replication was monitored using a PCR-based assay, as previously described (Larocca R 2016) (FIG. 13A). The top neutralizers, rhMZ134-B, rhMZ133-C and rhMZ119-D, conferred total protection from ZIKV as compared with the SHAM-infused control mice where ZIKV viral load peaked at day 3 post-challenge (FIG. 13B). Partial protection was also observed with the less potent neutralizing antibodies (IC50s within the 1-3 μg/mL range in FlowNT50 assays), with one (rhMZ103-A, rhMZ100-C) or two (rhMZ107-B) mice out of 5 showing detectable viremia.

Example 10. Prevalence and Mapping of ZIKV-Specific Humoral Immune Responses

Figure 11A:
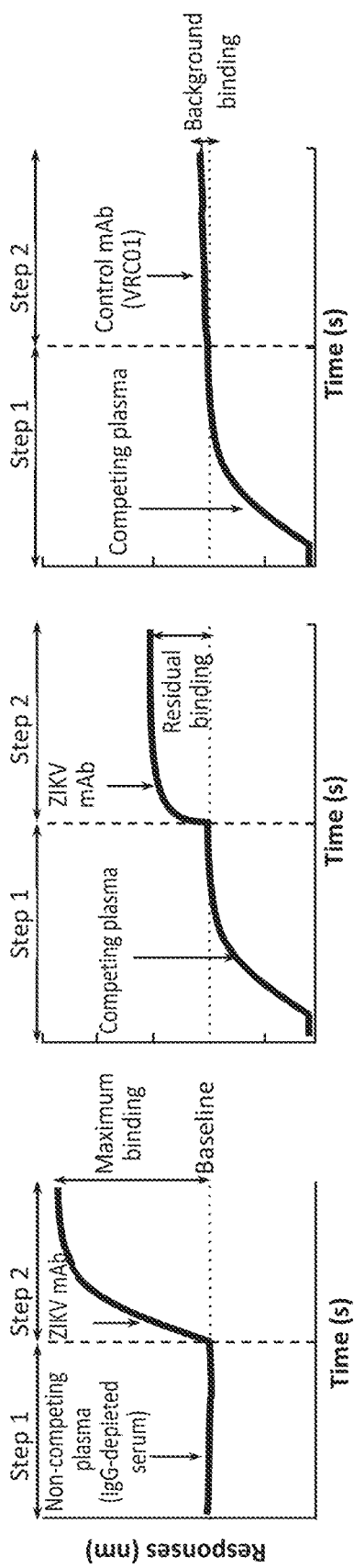
FIG. 11. Prevalence of rhMZ antibody epitope targeting in ZIKV-infected humans and non-human primates. (A) Schematic of the BLI-based competition assay. Streptavidin sensors loaded with biotinylated ZIKV E proteins were incubated with ZIKV-immune or uninfected plasmas (step 1) and then dipped into the mAb of interest diluted in the matching plasma (step 2). For any given plasma, background binding obtained with a E non-reactive control antibody (VRC01, right) was subtracted from residual binding (center) for the rhMZ mAb. The % binding inhibition of rhMZ mAb due to the competing effect of plasma was calculated by taking the reciprocal of the corrected residual binding (center) divided by the maximum binding obtained in presence of a non-competing plasma control (left). (B) Human (left) and macaque (right) ZIKV immune plasmas compete binding of representative mAbs from groups A-D to ZIKV E. Sensors loaded with ZIKV E were incubated with plasmas from ZIKV infected or uninfected macaques prior to binding to the indicated mAb in the BLI-based competition assay. The plotted % binding inhibition was calculated as described in (A). Each dot represents and individual plasma sample, and the geometric mean of all samples is indicated by a red, or black horizontal line.
Figure 11B:
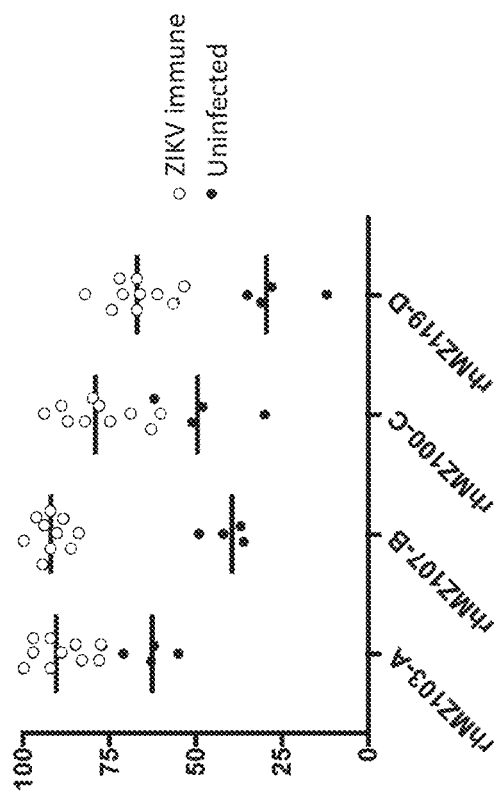
Figure 11B:
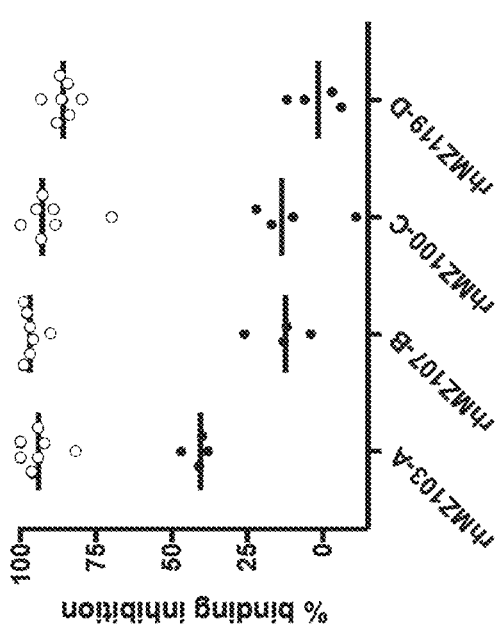
Figure 12A:
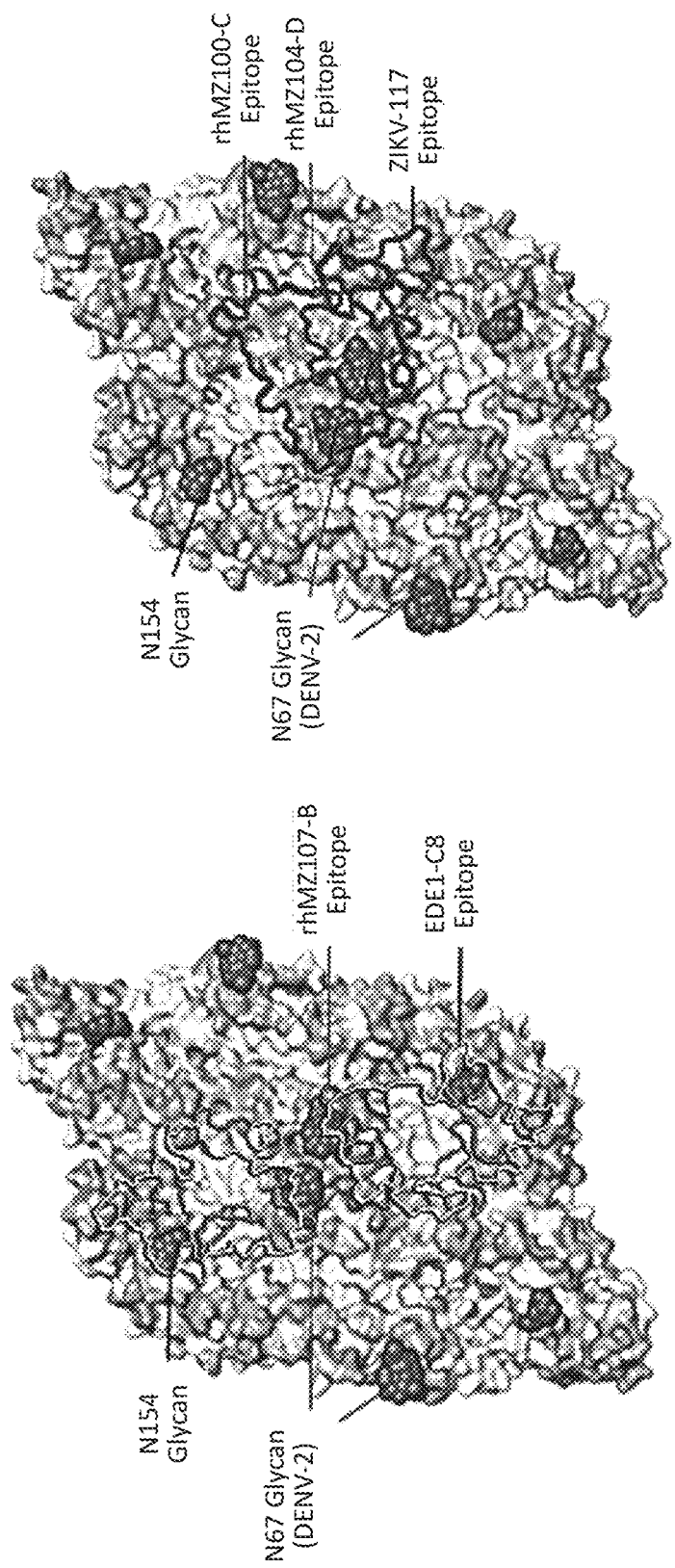
FIG. 12. Comparison of DENV and ZIKV Antibody Specificity. (A) Sequence difference map between ZIKV E and DENV2 E, mapped onto the ZIKV structure shown in surface representation (PDB: 5IRE). Sequence and positional differences between ZIKV and DENV-2 are colored light red, while identical residues are colored white. Glycan-154, and DENV glycan-67 are shown in sphere representation colored brown and raspberry, respectively. The antibody binding footprints of rhMZ107-B, and EDE1-C8 are shown on the left as green and white solid lines, respectively. Antibody binding epitopes of rhMZ100-C, rhMZ104-D, and ZIKV-117 are shown in the center as red, orange, and teal solid lines, respectively. (B) Neutralization (IC50, µg/ml) of wildtype (WT) and D67N-A69T mutant ZIKV performed in the ZIKV/H/PF2013 background using a Reporter Virus Particle (RVP) assay. The addition of glycan-67 found on DENV to ZIKV interfered with epitope recognition and abrogated or eliminated neutralization. (C) Epitope mapping of structurally defined antibodies mapped onto four protomers of DENV (left) and ZIKV (second from left). Residues contacted by previously described mAbs are colored dark gray, and residues not previously identified prior to this study indicated in white. Only previously identified mAb structures with resolution greater than 4 Å were used since the contact residues are clearly interpretable. Newly identified residues contacted by rhMZ mAbs described in this study are colored red (right, and second from right). Glycan sites at positions 67, and 153 or 154 are indicated in rose, and brown color, respectively. (right)

Having identified and characterized new ZIKV-specific neutralizing antibodies, we next evaluated the prevalence of these antibodies in other ZIKV-infected rhesus macaques and humans. To this end, we performed binding competition experiments to the ZIKV sE protein between plasma from infected donors and representative antibodies from each group. Remarkably, plasma response was almost completely ablated in the presence of the group A-D antibodies, as compared to control (non-flavivirus-exposed) sera in humans, suggesting that antibodies with similar specificities are commonly elicited during the course of natural ZIKV infection. Interestingly, most of the human plasma samples were also found to cross-react with DENV, suggesting that these sites are targeted during ZIKV-infection even with prior DENV exposure or other cross reactive antibodies are elicited during ZIKV-infection. Similar observations were also seen with plasma from other ZIKV-infected rhesus macaques at day 14 post-infection (FIG. 11B).

Figure 19B:
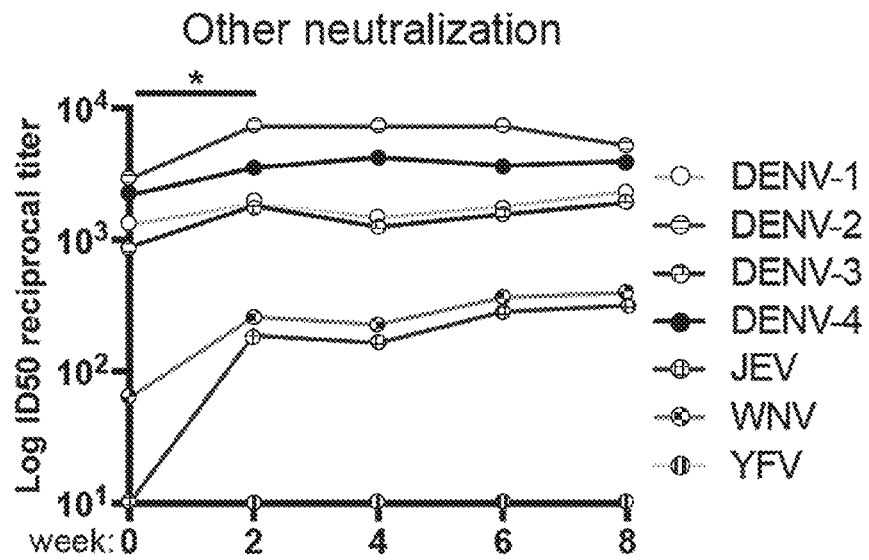
FIG. 19. Isolation of neutralizing antibodies to ZIKV and DENV from a ZPIV-vaccinated individual. a, b, Vaccination schedule and plasma neutralizing antibody titers against (a) ZIKV and (b) other flaviviruses of participant #00015 of the WRAIR trial. ZIKV, ZIKV E and DENV-2 E triple reactive CD19+/IgG+ B cells were sorted at peak ZIKV neutralization, four weeks post second vaccination. c, Characteristics of the binding (ZIKV and DENV-2 virions) and neutralizing (ZIKV and DENV 1-4) monoclonal antibodies isolated at week 8. d, Gene assignment and characteristics of the ZIKV neutralizing antibodies performed with IgBlast (Ye J, 2013). MZ4 family members are shaded in dark grey. e, f, g, Neutralization activities (FlowNT) against ZIKV (Brazil/2015) (e), DENV-2 (S16803) (f), and for MZ4 against ZIKV and DENV 1-4 (g). Shown are neutralization curves obtained by 2-fold serial dilutions of the indicated antibodies and fitted using a 4-parameter logistic regression model. Data are mean±SEM calculated from at least two-independent experiments performed in triplicate. The concentrations (ng/ml) at which 50% neutralization is observed are indicated in parentheses next to antibody names. EDE1-C8, a potent cross-neutralizing antibody (Barba-Spaeth G, 2016) was used as reference. h, Binding competition with a set of characterized control antibodies. Top, identification of domain specificities using a BLI-based competition assay. Values represent the % residual binding of the indicated second antibody after saturation of ZIKV E with the indicated first antibody. Shading from dark to light indicates competition strength ranging from strong (0-30%), to intermediate (31-69%), to weak/none (70-100%). Control indicates a non-ZIKV E reactive antibody. Bottom, control antibody epitopes mapped onto the ZIKV E dimer structure. i, Shotgun mutagenesis epitope mapping. Top, residues critical for binding to ZIKV (black check mark) and DENV-2 (red check mark) prM/E (which substitution to alanine causes >70% loss in binding) are indicated for each mAb. Bottom, same critical residues mapped on the ZIKV E dimer.
Figure 19C:
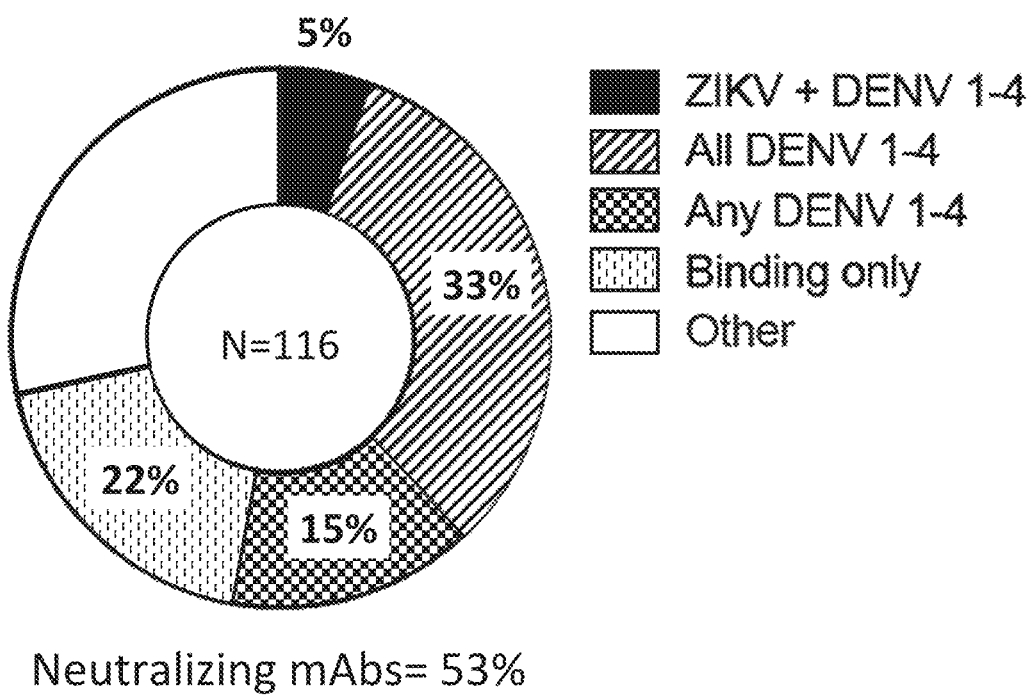
Figure 19H:
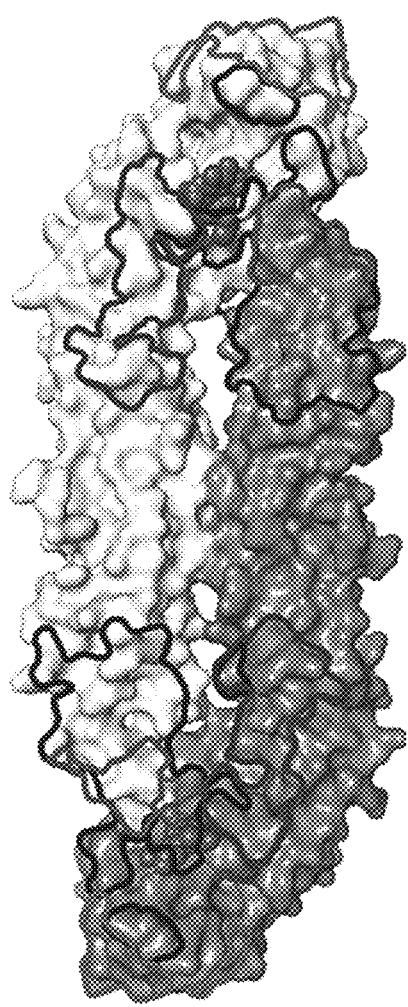
Figure 19I:
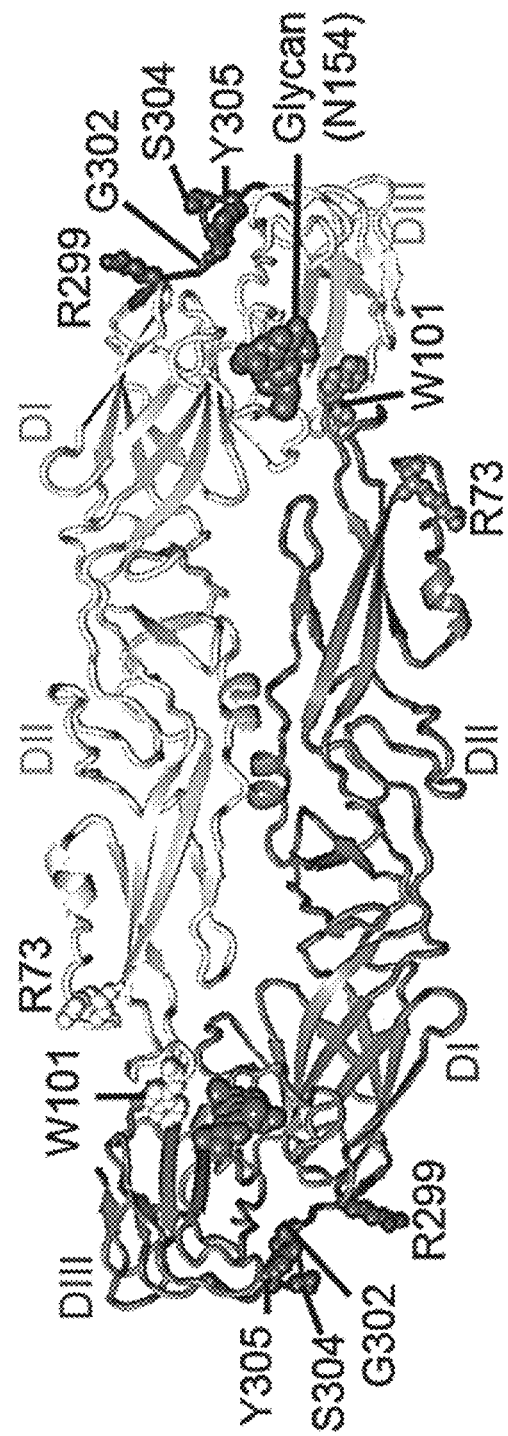
Figure 20A:
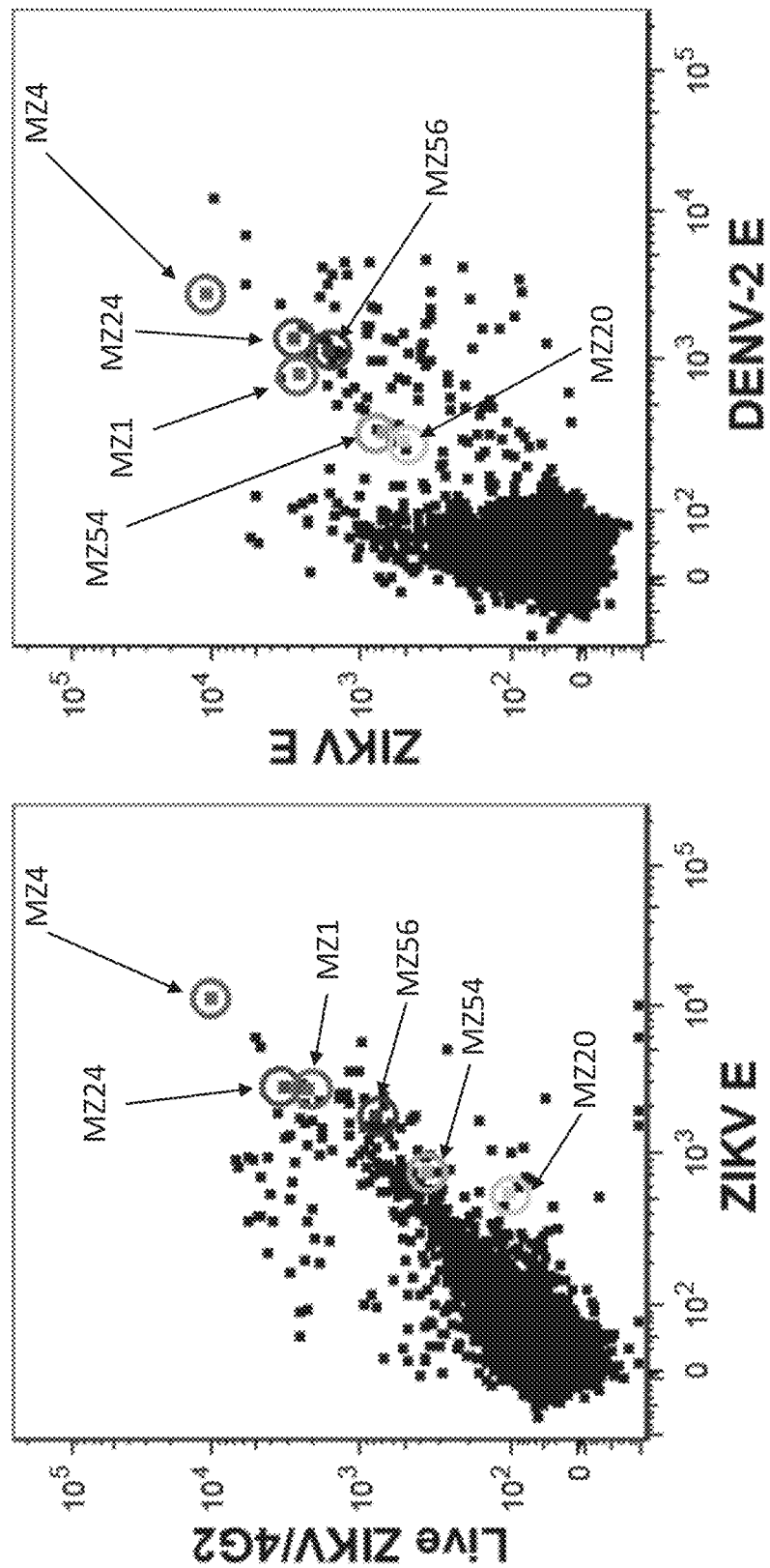
FIG. 20. Additional neutralizing characteristics of MZ4 family antibodies. a, Isolation of ZIKV, ZIKV E and DENV-2 E triple reactive CD19+/IgG+ B cells 4 weeks post second vaccination. Flow plots show the characteristics of individual B cells from which the most potent neutralizing antibodies were isolated. b, Neutralization activities of the MZ4 family antibodies obtained in the microneutralization assay (MN50) against ZIKV PR, DENV1-4, JEV, WNV and YFV. Data were generated from neutralization curves obtained by 3-fold serial dilutions from at least two independent experiments and fitted using a 4-parameter logistic regression model. Shown are the concentrations (ng/ml) at which 50% neutralization is observed. c, d, Neutralization activities (FlowNT) of MZ4 against ZIKV (Brazil/2015) (c) and DENV-2 (S16803) (d) compared to other potent ZIKV/DENV cross-neutralizing antibodies. Shown are neutralization curves obtained by 2-fold serial dilutions of the indicated antibodies and fitted using a 4-parameter logistic regression model. Data are mean±SEM calculated from at least two-independent experiments performed in triplicate. The concentrations (ng/ml) at which 50% neutralization is observed are indicated in parentheses next to antibody names. e, Neutralization activities of MZ4 (PRNT) against ZIKV strains of American, Asian and African lineages. Data were generated as described in c. The concentrations (ng/ml) at which 50% neutralization is observed are indicated in parentheses next to virus names.
Figure 21C:
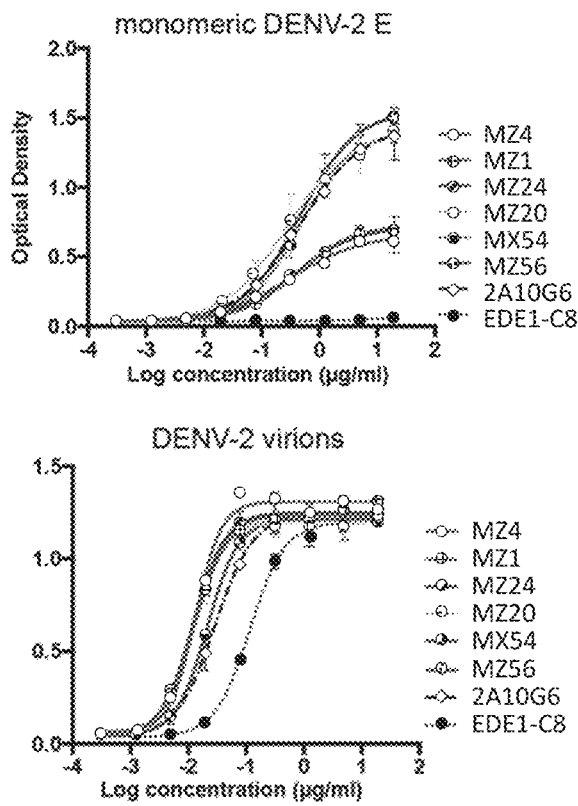
FIG. 21. Additional binding characteristics and epitope mapping of MZ4 family antibodies. a-d, Binding activities to monomeric E proteins and whole virions for ZIKV and DENV-2, assessed by ELISA. a, Binding to ZIKV E (left) and virions (right). Antibodies were titrated using 4-fold dilution series starting from 20 µg/ml. Values indicate mean binding responses calculated from two independent experiments. b, Relative ratio of binding to E over binding to whole ZIKV calculated from (a) at 20 µg/ml. Antibodies with low ratio values indicated targeting of quaternary epitopes (such as EDE) whereas ratios closer to 1 were characteristic of monomeric recognition similar to a FLE antibody, such as 2A10G6, that bind to both monomeric E and ZIKV. c, Binding to DENV-2 E (left) and virions (right), performed as described in (a). d, Relative ratio of binding to E over binding to whole DENV-2 calculated from (c) at 20 µg/ml as described in (b). e, Binding to ZIKV E isolated DIII domain assessed by ELISA. Antibodies were titrated using 4-fold dilution series starting from 20 µg/ml. Values indicate mean binding responses calculated from two independent experiments. f, Shotgun mutagenesis ZIKV E epitope analysis. Relative binding to ZIKV prM/E for individual mutations is plotted. Residues from which substitution to alanine causes >70% loss in binding (dotted line) were considered critical.
Figure 21D:
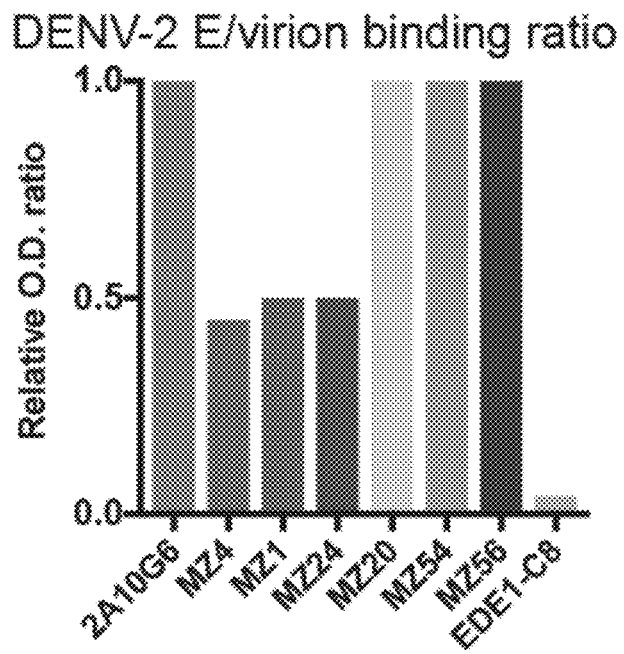

Despite the E glycoprotein sequence differences between ZIKV, and DENV1-4, many of the cross-protomer epitopes targeted by the ZIKV-specific mAbs curiously overlapped with the glycan at position 67 present on DENV E glycoprotein. Therefore, we also wanted to assess the role of the glycan at position 67 on antigenic recognition of ZIKV compared to DENV with the hypothesis that the glycan may cause interference with ZIKV-specific epitope recognition. In the case of DENV, and other flaviviruses, e.g. X and Y, this glycan is highly prevalent even in large sequence datasets. We assessed our full set of eleven NHP mAbs for neutralization of wild-type ZIKV (H/PF/2013), and an E mutant (D67N, A69T) lacking the glycan at position 67. In all cases, the introduction of the glycan at position 67 resulted in loss of neutralization ranging from a two-fold reduction for rhMZ133-C, five-fold reduction for rhMZ103-B, ten-fold for rhMZ134-B, to complete ablation of neutralization for the remaining eight of the eleven antibodies (FIG. 12B). This data suggests that the glycan at position 67 on DENV interferes with antigenic recognition of these mAbs, which in turn yields ZIKV-specificity. To analyze the structural differences in immune responses to ZIKV, compared to DENV and other flaviviruses, we mapped these binding epitopes onto the viral raft in comparison with other previously identified mAbs from DENV-primed individuals that cross-neutralized both DENV and ZIKV. These mAbs were identified as recognizing the ZIKV E glycoprotein DII and DIII regions in areas distal to viral glycan sites (FIG. 12C). However, in the case of ZIKV-infection without prior flavivirus exposure, the antibody response can be seen to target the full length of the Zika E glycoprotein as evident by the newly identified neutralization epitopes described within this study.

Human Antibodies

Monoclonal antibodies were isolated from a flavi-experienced participant of the ZPIV Z001 BIDMC Phase 1 vaccine clinical trial previously described in Modjarrad et al., Lancet 391:563-571, 2018.

Example 11. Isolation of ZIKV and DENV Neutralizing Antibodies

Individuals were administered 5.0 μg doses of the ZPIV vaccine by intramuscular injected at week 0 and week 4 (FIG. 19*a*). Two ZPIV injections elicited neutralizing antibody responses capable of protection in passive transfer studies. Participant #000015 showed remarkably high peak ZIKV neutralization at week 8, four weeks following the second ZPIV vaccination (FIG. 19*a*). Upon further investigation, it was found that this individual had previous exposure to DENV and WNV, as high titers of neutralization to DENV-1-4 and West Nile virus (WNV) were detected prior to ZPIV vaccination (FIG. 19*b*). Following the first ZPIV vaccination, neutralization titers increased to DENV 1-4, WNV, as well as Japanese Encephalitis virus (JEV) and ZIKV, but not Yellow Fever virus (YFV) (FIG. 19*b,c*).

To characterize these neutralizing responses elicited by ZPIV, a unique B cell sorting strategy was performed using a combination of fluorescently-labeled whole ZIKV virions, and ZIKV E and DENV-2 E proteins to isolate antigen-specific B cells (FIG. 20*a*). Viable PBMCs obtained from Participant #000015 at week 8 were incubated with a mixture of Brilliant Violet 510 (BV510) conjugated negative selection antibodies (CD3, CD4, CD8, CD14, CD16 and CD56) and CD19 ECD, CD20 APC-Cy7, ZIKV E PE and DENV-2 E PE-Cy7 positive selection markers. Cells were also sorted for binding to live whole ZIKV stained with a 462-APC secondary stain. Cells were selected by sorting based on negative expression of CD3, CD14 and CD56, positive expression of CD19, mid to high expression of CD38, and positive sequential staining with 4G2, ZIKV E and DENV E. Each positive B cell was sorted directly into lysis buffer in an isolated well of a PCR plate.

Antibody heavy and light chain V(D)J gene segments were amplified from single B cells by nested RT-PCR and sequenced. A total of 116 monoclonal antibodies (mAbs) were isolated and expressed as human IgG1, screened for binding to whole ZIKV and tested for neutralization in a qualified microneutralization assay (MN50). 75% of the mAbs bound to ZIKV and/or DENV, and 53% were found to neutralize at least one DENV serotype (FIG. 20*b*). Six potent ZIKV neutralizing antibodies isolated from B cells that stained positive for all three antigens (FIG. 19*d*) were identified. They belong to four different clonal families, with the VH4-59/VL1-44 family consisting of three members sharing similar CDR3 sequences (FIG. 19*d*). Neutralization of one mAb, termed MZ4 (MHRP ZIKV-1004), demonstrated high potency against both ZIKV and DENV-2 with an $IC_{50}$ of 8.3 and 20.9 ng ml-1, respectively, in a flow-based assay using human monocytes as targets (FIG. 19*e, f*). MZ4 was able to match some of the most potent ZIKV and DENV-2 antibodies described to date and exhibited remarkably strong dual-neutralizing activities against ZIKV and DENV-2 as a single molecule. MZ4 was the most potent antibody against ZIKV, with similar potency as Z004 (FIG. 20*c, d*), a previously identified mAb from a ZIKV-infected individual (Robbiani et al, Cell 169:597-609, 2017). In addition, MZ4 surpassed the related MZ1 and EDE1 control (Barba-Spaeth et al, Nature 536:48-53, 2016), and was on par with other VH4-59 antibodies as well as the EDE2 control for DENV-2 neutralization (FIG. 19*e, f* and FIG. 20*c, e*). Potent activity against DENV-3 was also observed in this assay as well as weak, but detectable, neutralizing capabilities against DENV-1 and -4 (FIG. 19*g*, FIG. 20*c*). MZ4 had broad neutralizing activities against ZIKV strains from American, Asian and African lineages (FIG. 20*f*) but no inhibitory effects against other flaviviruses, such as West Nile (WNV), Yellow Fever (YFV) and Japanese Encephalitis (JEV) viruses (FIG. 20*c*).

Example 12. Characterization and Structural Analysis of ZIPV and DENV Neutralizing Antibodies Epitope-mapping experiments delineated the epitope specificities of these antibodies induced by ZPIV-vaccination. First, binding activities against ZIKV and DENV-2 sE proteins and virions were measured to determine whether neutralizing epitopes were present only on the intact viral particles (FIG. 21*a-d*). Similar to the fusion loop epitope (FLE) control, antibodies such as MZ20, 54 and 56 bound equally well to E and whole virus in this assay, indicating that they recognize an epitope within the E monomer (FIG. 21*a, c*). However, antibodies from the MZ4 family bound better to ZIKV and DENV-2 virions than to their respective E proteins, suggesting that their epitopes have more quaternary characteristics (FIG. 21*b, d*). To gain insights into the target of these antibodies, binding competition experiments were carried out using biolayer interferometry (BLI) with a set of well-characterized controls (FIG. 19*h*). Antibodies within the MZ4 family were only competed by the DIII-directed antibody Z004, indicating that their epitope was within or overlapped with DIII (FIG. 19*h*). However, none of the MZ4 family member mAbs were able to bind to the isolated ZIKV DIII domain by ELISA, suggesting that their epitope lies near but not within DIII (FIG. 21*e*). However, MZ54, 56, and to some extent MZ20, displayed competition profiles consistent with those of FLE antibodies (FIG. 19*h*). A shotgun mutagenesis screen (Davidson E 2014) performed on ZIKV and DENV-2 prM/E proteins identified the FLE to be the target of MZ54 and MZ56, while MZ20 targeted DII (FIG. 19*i*, FIG. 21*f*). MZ4 family of mAbs targeted Interestingly, the MZ4 family of mAbs targeted an epitope within the DI-DIII hinge or linker region in both ZIKV and DENV-2, suggesting a conserved mode of recognition (FIG. 19i, FIG. 21f).

Figure 22A:
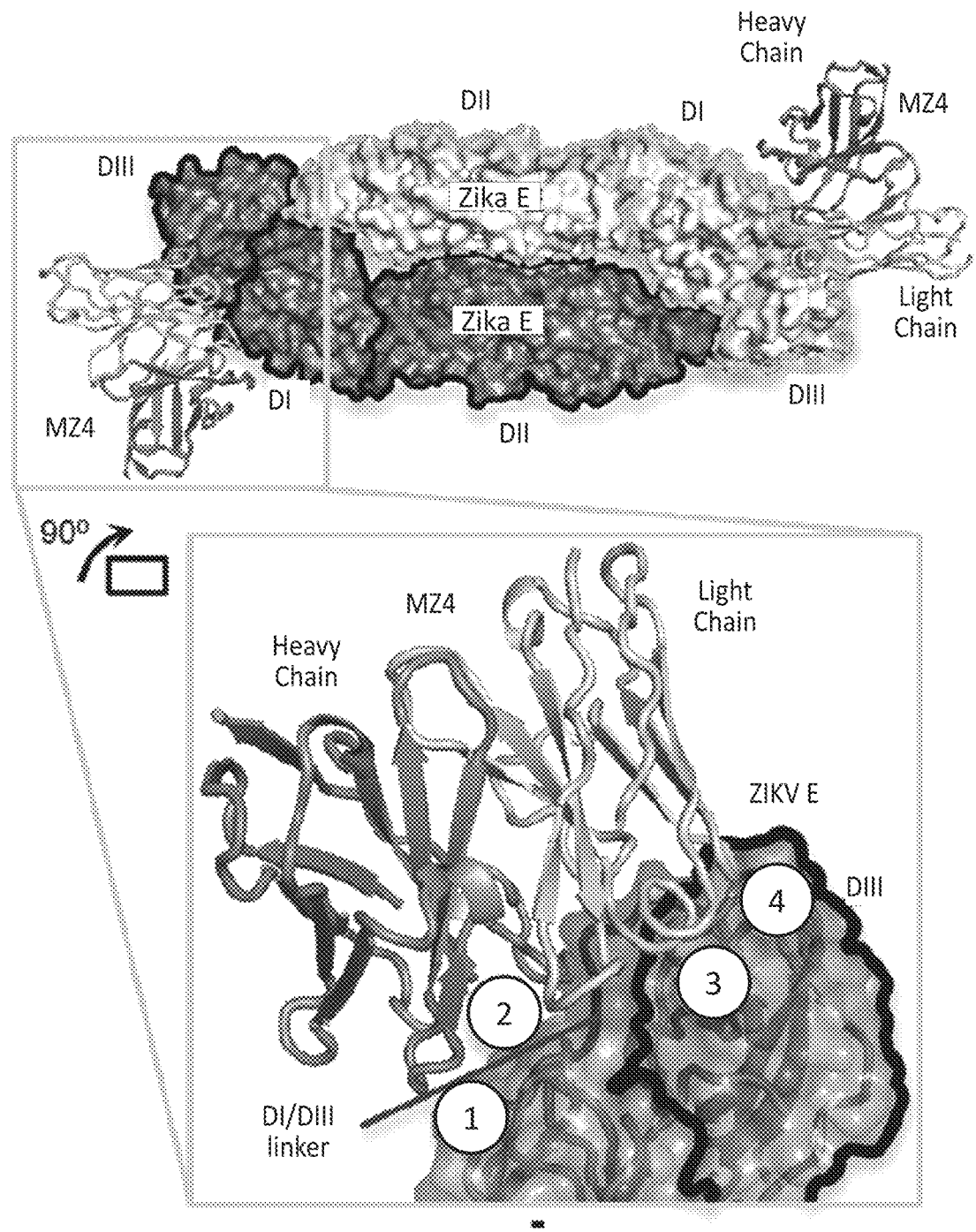
FIG. 22. Crystal structure of human antibody MZ4 in complex with ZIKV E glycoprotein. a, MZ4 recognizes the DI/DIII linker and DIII domain on ZIKV E. MZ4 Fv is shown in ribbon representation (orange), and ZIKV E is shown in surface format (blue and white). Inset highlights the four major areas of contact. DI/DII linker is shown in dark brown color. b, MZ4 contact residues are shown based on 1-CDRs H1, and H2; 2-CDR H3; 3-CDR L1; 4-CDR L2, and FR L3 antibody contacting regions. MZ4 escape mutants G182 and S368 are shown in red. Somatic hyper mutation residues, making contact with ZIKV E, are shown in dark pink color. c, MZ4 shown in surface representation is modeled in the context of the full ZIKV particle (PDB: 5IRE). d, e, Detailed interactions of antibody MZ4 at the 5-fold vertex (d), and inter-raft interface (e) on the mature ZIKV are shown. f, Sequence alignment of ZIKV, and DENV1-4 residues that were identified as MZ4 antibody contacts. Symbols ★, : and ., denote the same, very similar and less similar residues, respectively. Buried surface area (BSA) for contacting residues, calculated using PISA, is shown as bars. g, ZIKV BR/2015 escape from MZ4 neutralization identified two variants which reduced antibody neutralization significantly.
Figure 22B:
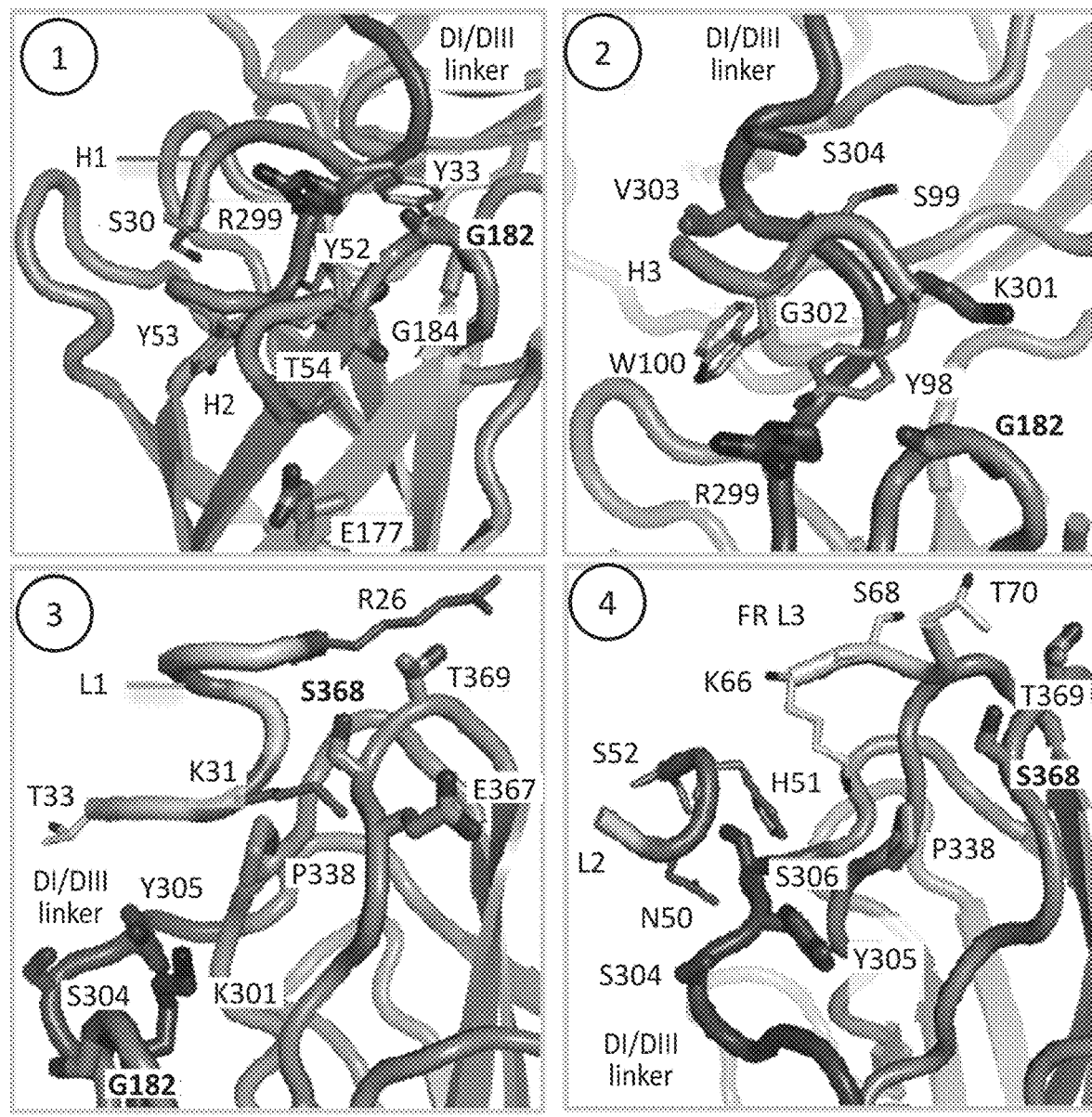

To understand the broad recognition and potent neutralization of MZ4, the structure of MZ4 was determined in complex with the ZIKV E glycoprotein (ZIKV E) at a resolution of 4.2 Å (FIG. 22). The structure was refined to an Rfactor of 27.8% and an Rfree of 35.6% with two ZIKV E dimers, and four antibody Fragment variable (Fv) domains observed in the asymmetric unit (FIG. 22a). MZ4 binds to the E glycoprotein domain I (DI) and DIII centered on the DI-DIII linker region (residues 299-306) with buried surface areas of 472.2 A2 and 137.4 A2 for the antibody heavy and light chains, respectively (FIG. 22a, b). MZ4 interacts with the E glycoprotein at four major sites (FIG. 22b, Table 16). First, the CDR H1 and CDR H2 interact with DI, and the DI-DIII linker via a set of germline gene-encoded Tyr residues that form hydrogen bonds with the main chain atoms of Gly 182 and the side chain of Arg 299. Second, the CDR H3 binds to the full DI-DIII linker with 342.9 A2 of BSA, forming hydrogen bonds with Arg 299, Ser 304, and Tyr 305, while also interacting with the DI Gly 182. Third, the CDR L1 buries 128.3 A2 of surface area of the glycoprotein DIII, utilizing residues that have undergone somatic mutation. And fourth, the CDR L2 residues 50-52 have all undergone somatic hypermutation and bind to the DI-DIII linker and DIII while the FR L3 utilizes germline encoded residues to interact with the DIII BC- and DE-loops.

TABLE 16

Interface of MZ4 with ZIKV E glycoprotein

| MZ4 | Zika E glycoprotein | Distance (Å) |
| --- | --- | --- |
| H:TYR 33 [OH] | G:GLY 182 [O] | 3.73 |
| H:SER 99 [OG] | G:TYR 305 [OH] | 2.88 |
| H:SER 30 [O] | G:ARG 299 [NH1] | 3.42 |
| H:SER 30 [O] | G:ARG 299 [NH2] | 3.28 |
| H:TYR 52 [OH] | ARG 299 [NH1] | 3.62 |
| H:TYR 98 [O] | G:TYR 305 [OH] | 2.89 |
| H:TYR 98 [OH] | G:ARG 299 [NH1] | 2.69 |
| H:SER 99 [O] | G:SER 304 [OG] | 3.02 |
| H:SER 99 [O] | G:SER 304 [N] | 3.62 |
| H:SER 99 [O] | G:VAL 303 [N] | 3.67 |
| L:ASN 50 [ND2] | G:SER 304 [O] | 2.25 |
| L:SER 67 [OG] | G:THR 335 [O] | 2.30 |
| L:GLY 68 [N] | G:THR 335 [O] | 3.03 |
| L:SER 67 [OG] | G:THR 335 [OG1] | 2.45 |
| L:GLY 68 [N] | G:THR 335 [OG1] | 2.31 |
| L:LYS 66 [NZ] | G:PRO 338 [O] | 2.85 |
| L:GLY 29 [O] | G:SER 368 [N] | 3.84 |
| L:ASN 50 [OD1] | G:SER 304 [OG] | 2.69 |
| L:GLY 68 [O] | G:SER 368 [OG] | 3.02 |

TABLE 17A

MZ1 interface with ZIKV E glycoprotein

| Hydrogen bonds MZ1 | ZIKV E PRVABC59 | Distance (Å) |
| --- | --- | --- |
| H:SER 30[ O ] | Z:ARG 299[ NH1] | 3.56 |
| H:ASN 100A[ OD1] | Z:SER 304[ OG ] | 2.34 |
| L:SER 50[ OG ] | Z:SER 304[ O ] | 2.49 |
| L:ARG 53[ NH1] | Z:SER 304[ O ] | 3.60 |
| L:SER 50[ OG ] | Z:SER 306[ OG ] | 3.03 |
| L:LYS 66[ NZ ] | Z:GLY 337[ O ] | 2.44 |
| L:LYS 66[ NZ ] | Z:SER 368[ OG ] | 3.47 |
| L.GLY 29[ O ] | Z:SER 368[ N ] | 3.72 |
| L:SER 50[ O ] | Z:SER 306[ OG ] | 2.29 |

TABLE 17A-continued

MZ1 interface with ZIKV E glycoprotein

| Hydrogen bonds MZ1 | ZIKV E PRVABC59 | Distance (Å) |
| --- | --- | --- |
| L:SER 50[ OG ] | Z:SER 306[ N ] | 3.02 |
| LASN 52[ OD1] | Z:SER 306[ OG ) | 2.76 |

TABLE 17B

Buried surface area of MZ1 antibody in complex with ZIKV E glycoprotein

| MZ1 antibody residues | Bond type | Accessible Surface Area (Å$^2$) | Buried Surface Area (Å$^2$) |
| --- | --- | --- | --- |
| H:SER 30 | H | 37.09 | 9.47 |
| H:ASN 31 |  | 62.75 | 26.21 |
| H:TYR 52 |  | 52.40 | 4.48 |
| H:TYR 53 |  | 86.45 | 31.98 |
| H:THR 54 |  | 90.97 | 7.14 |
| H:PHE 98 |  | 98.68 | 55.53 |
| H:ASN 99 |  | 123.39 | 66.98 |
| H:TRP 100 |  | 170.56 | 128.41 |
| H:ASN 100A | H | 56.63 | 13.61 |
| H:ASP 100B |  | 151.25 | 37.76 |
| H:GLY 100D |  | 29.97 | 1.73 |
| L:LEU 28 |  | 1.35 | 1.35 |
| L:GLY 29 | H | 43.29 | 34.72 |
| L:ARG 30 |  | 179.46 | 26.21 |
| L:ASN 31 |  | 41.02 | 12.03 |
| L:THR 32 |  | 71.68 | 38.45 |
| L:TYR 49 |  | 70.32 | 13.40 |
| L:SER 50 | H | 40.71 | 30.20 |
| L:ASN 51 |  | 22.68 | 20.68 |
| L:ASN 52 | H | 97.88 | 39.46 |
| L:ARG 53 | H | 137.07 | 35.18 |
| L:LYS 66 | H | 76.79 | 58.63 |
| L:SER 67 |  | 88.85 | 45.67 |
| L:ASP 68 |  | 72.79 | 21.05 |

H: Hydrogen bond

TABLE 17C

Buried surface area of ZIKV E glycoprotein in complex with MZ1

| ZIKV E residue | Bond type | Accessible Surface Area (Å$^2$) | Buried Surface Area (Å$^2$) |
| --- | --- | --- | --- |
| Z:GLY 181 |  | 67.66 | 7.97 |
| Z:GLY 182 |  | 40.52 | 33.48 |
| Z:PHE 183 |  | 36.04 | 3.83 |
| Z:GLY 184 |  | 22.61 | 5.71 |
| Z:LYS 297 |  | 113.24 | 32.29 |
| Z:ARG 299 | H | 153.92 | 101.10 |
| Z:LEU 300 |  | 48.30 | 4.84 |
| Z:LYS 301 |  | 91.81 | 34.88 |
| Z:GLY 302 |  | 31.69 | 30.56 |
| Z:VAL 303 |  | 83.30 | 38.74 |
| Z:SER 304 | H | 106.70 | 106.7 |
| Z:TYR 305 |  | 68.46 | 68.46 |
| Z:SER 306 | H | 64.77 | 61.42 |
| Z:LEU 307 |  | 98.17 | 2.29 |
| Z:THR 309 |  | 105.14 | 5.02 |
| Z:THR 335 |  | 127.70 | 55.36 |
| Z:ASP 336 |  | 57.40 | 38.74 |
| Z:GLY 337 | H | 10.22 | 9.71 |
| Z:PRO 338 |  | 59.21 | 59.04 |
| Z:THR 366 |  | 70.38 | 16.40 |

TABLE 17C-continued

Buried surface area of ZIKV E
glycoprotein in complex with MZ1

| ZIKV E residue | Bond type | Accessible Surface Area (Å²) | Buried Surface Area (Å²) |
|---|---|---|---|
| Z:GLU 367 | | 104.85 | 1.48 |
| Z:SER 368 | H | 75.95 | 57.39 |
| Z:THR 369 | | 76.89 | 0.50 |

H: Hydrogen bond

Structure alignment of the MZ4-ZIKV E structure with the Zika virus structure (SIRE), revealed additional quaternary contact sites at the pentamer vertex, and at the inter-raft interface (FIG. 22c). MZ4 binding at the pentamer vertex would generate additional contacts with the domain III and glycan N154 from a second protomer, and with the fusion-loop of a third protomer (FIG. 22d). Both antibody heavy and light chain contacts are involved in the additional recognition, through germline gene encoded residues of the heavy chain FR H3 and H4, and the CDR L2, and FR L3. The additional contacts result in increased contact regions with MZ4 heavy and light chains. This additional recognition also includes interaction with the N154-glycan with x A2 of BSA. In the context of the fully closed mature particle, only two antibodies can bind at the pentameric vertex due to steric hindrance, with the caveat that this vertex has been known to "breath" allowing increased stoichiometric binding (PMID: 28938115). MZ4 binding at the inter-raft interface also allows binding to the domain II of a neighboring protomer (FIG. 22e). These additional contacts result in an increase in the BSA for MZ4 heavy and light chains. These additional contacts are focused on the CDR H1, H3, FR H3, and the CDR L2.

To understand why MZ4 shows ng ml-1 neutralization of ZIKV, and DENV2, but lower values against DENV1, and DENV4, the MZ4 epitope was mapped onto DENV1-4. Analysis of the site conservation, and assessment of critical contact residues indicates that across the five viruses, the MZ4 epitope contact residues are well conserved (9/19 identical; 8/19 similar) with only 2 residues (182 and 336) having significant (FIG. 22f). Critical residues identified in the shotgun mutagenesis experiments, R299 and Y305 are well conserved across viral strains and form five hydrogen bonds with CDR H3 residues. Viral escape analysis of ZIKV in the presence of MZ4 antibody identified escape mutations G182D, and S368N. In the context of the ZIKV, and DENV, residue 182 varies from Gly to Asp/Glu and appears to be critical for MZ4 recognition and viral neutralization potency.

Figures 23A, 23B:
FIG. 23. Structure comparison of human antibody MZ4 with known ZIKV and DENV antibodies. a, MZ4 recognizes the DI/DIII linker and DIII domain on ZikaE. MZ4 Fv is shown in ribbon representation (orange), and ZikaE is shown in surface format (light blue). Other Zika specific DIII domain targeting antibodies (ZV-2, ZV-64, ZV-67 and Z004) are shown in ribbon and are labeled appropriately. b, Dengue E is shown in surface format (gray). Other Dengue E targeting antibodies (EDE1-C8, Ab513, 4E11 and 5H2) are shown in ribbon and are labeled appropriately.

To further understand the MZ4 site of vulnerability, the epitope was compared to previously described ZIKV- or DENV-targeting antibodies (FIG. 23). The majority of the DIII-targeting antibodies have overlapping epitopes with MZ4 to varying degrees, with antibodies ZV64 being the most similar. However, both these antibodies are highly strain specific for ZIKV (ZV64) or DENV2 (5H2) due to the lack of sequence conservation within their epitopes. Structure analysis suggests that one of the factors driving the potent neutralizing activity of MZ4 is its ability to bind to DI, DII, and DIII of the ZIKV (FIG. 22a), and thereby locking the virus in a prefusion form incompatible with viral-cell fusion.

Figure 24A:
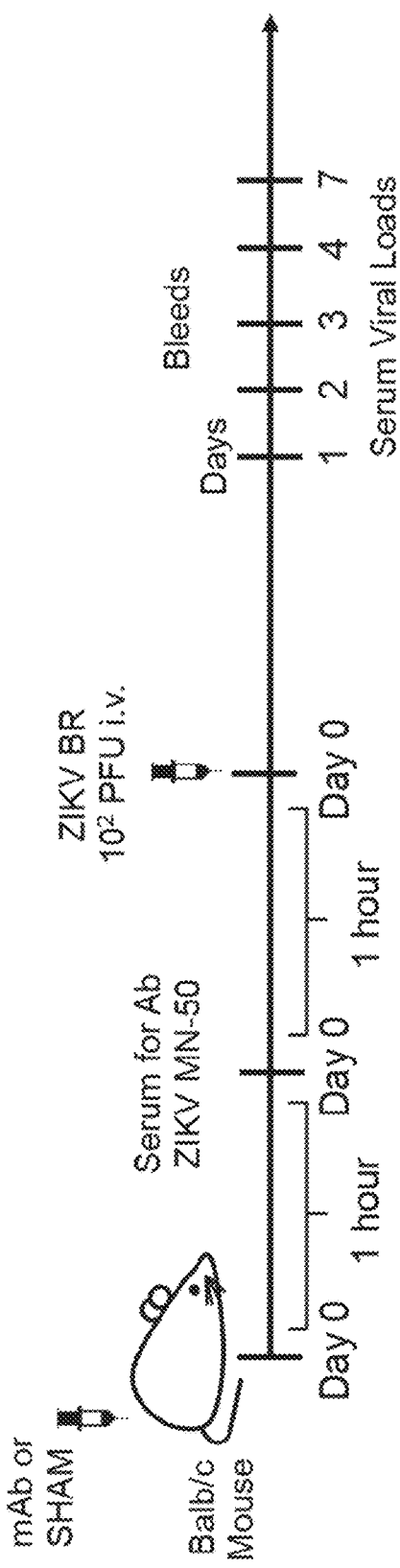
FIG. 24. MZ4 and MZ1 protect mice in vivo from ZIKV replication. a, Schematic of passive protection study experimental design. Antibodies were infused intravenously into groups of naïve recipient Balb/c mice (N=5/group) prior to ZIKV-BR challenge. Mice were infused with antibody or saline (sham) and 2 hours later, mice were challenged with 105 viral particles ($10^2$ plaque-forming units) of ZIKV-BR intravenously. Following infusion with the indicated antibody, or saline (sham), ZIKV viral loads were measured post-challenge by RT-PCR daily until peak viral load (day 4) and at day 7. b, MZ4 and MZ1 afford complete protection from ZIKV viremia at a single dose of 200 µg (10 mg-1 kg-1). c, In vivo titration of MZ4 prophylactic dose. Kaplan-Meier plot of MZ4 dose-dependent protective effects on ZIKV replication. An ED50 of 2.55 µg (95% confidence interval=2.139, 3.262) was calculated as the dose required to protect half of the animals using a 5-parameter non-linear regression analysis.
Figure 24B:
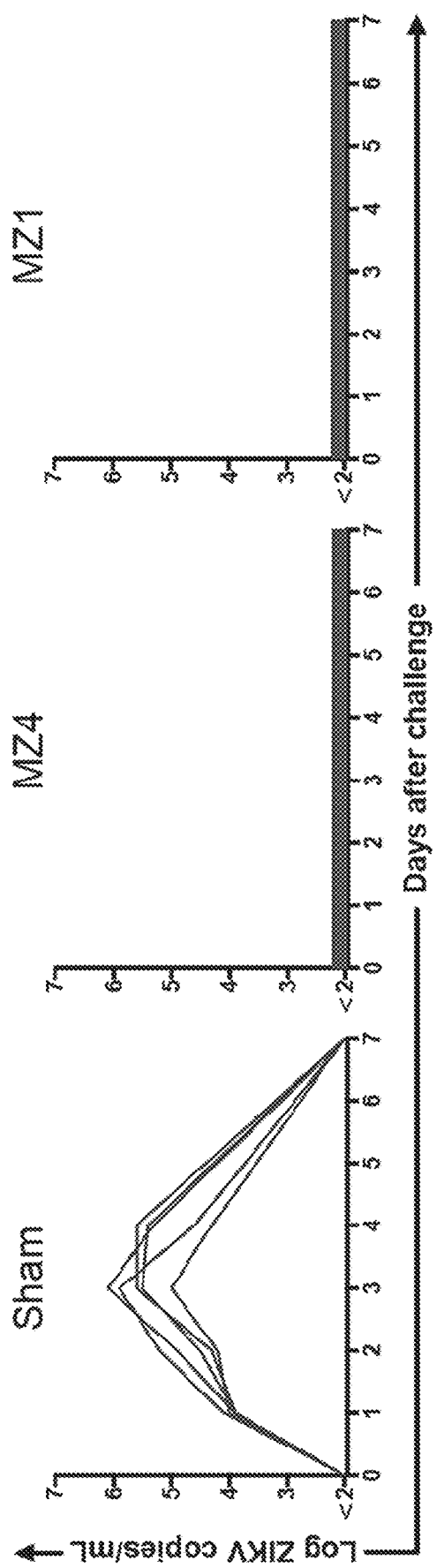
Figure 24C:
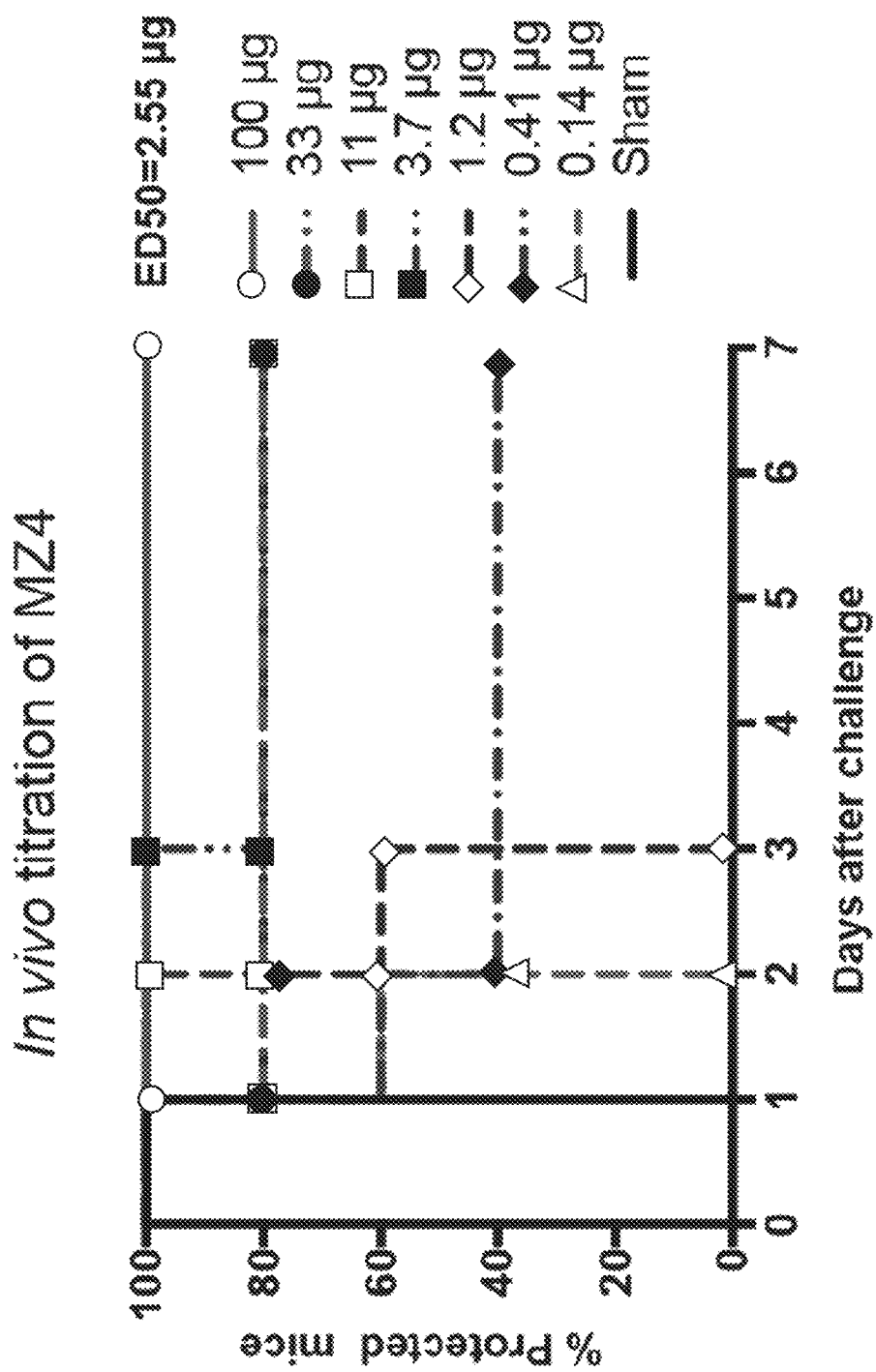
Figure 25:
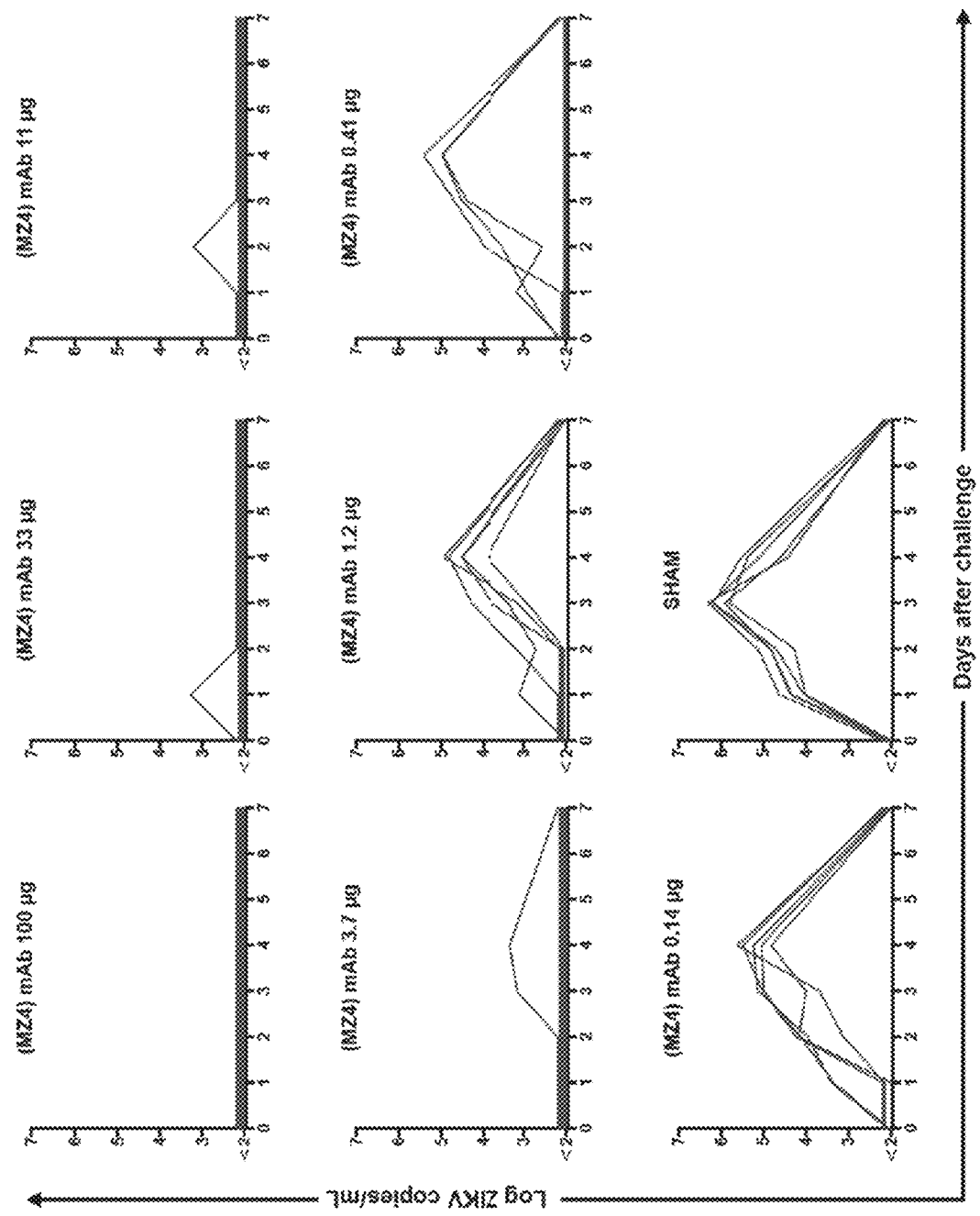
FIG. 25. In vivo titration of MZ4 prophylactic dose. Antibodies were infused intravenously into groups of naïve recipient Balb/c mice (N=5/group) prior to ZIKV-BR challenge. Mice were infused with the indicated dose of MZ4 or saline (sham) and 2 hours later, mice were challenged with 105 viral particles ($10^2$ plaque-forming units) of ZIKV-BR intravenously. Following infusion with the indicated antibody, or saline (sham), ZIKV viral loads were measured post-challenge by RT-PCR daily until peak viral load (day 4) and at day 7.

Example 13. The MZ4 and MZ1 mAbs Provide Passive Immunity Against ZIPV Infection To investigate whether antibodies to the DI/DIII linker would protect from ZIKV replication in vivo, passive protection studies were performed in a wild-type mouse (FIG. 24a). A single dose of 200 μg (10 mg kg-1) of MZ4 or MZ1 fully protected mice from ZIKV viremia, as demonstrated by undetectable viral replication over the course of the experiment while viral loads peaked at three days post-challenge in the sham control group (FIG. 24b). To probe the minimal dose of MZ4 required for sterile protection as well as explore the in vivo effects of low plasma concentration of antibodies, we titrated down the MZ4 dose until protection was lost (FIG. 25). While protection decreased gradually with the antibody dose, eighty percent of the animals (4/5 mice) were still protected from viral replication at the low dose of 3.7 μg (0.185 mg kg-1) giving an estimated ED50 of 2.55 μg (0.1275 mg kg-1).

Figures 26A, 26B:
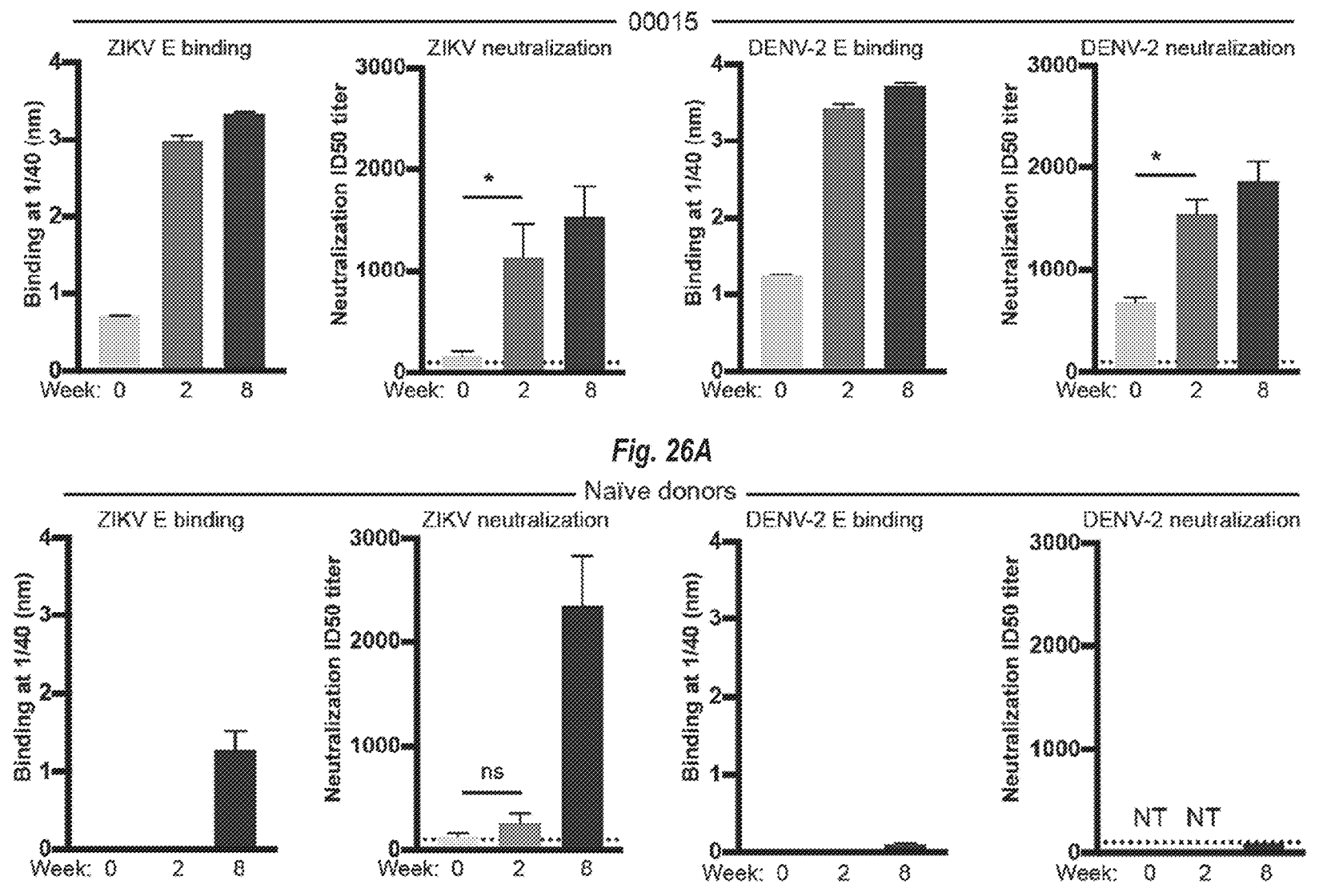
Figures 26E, 26F, 26G:
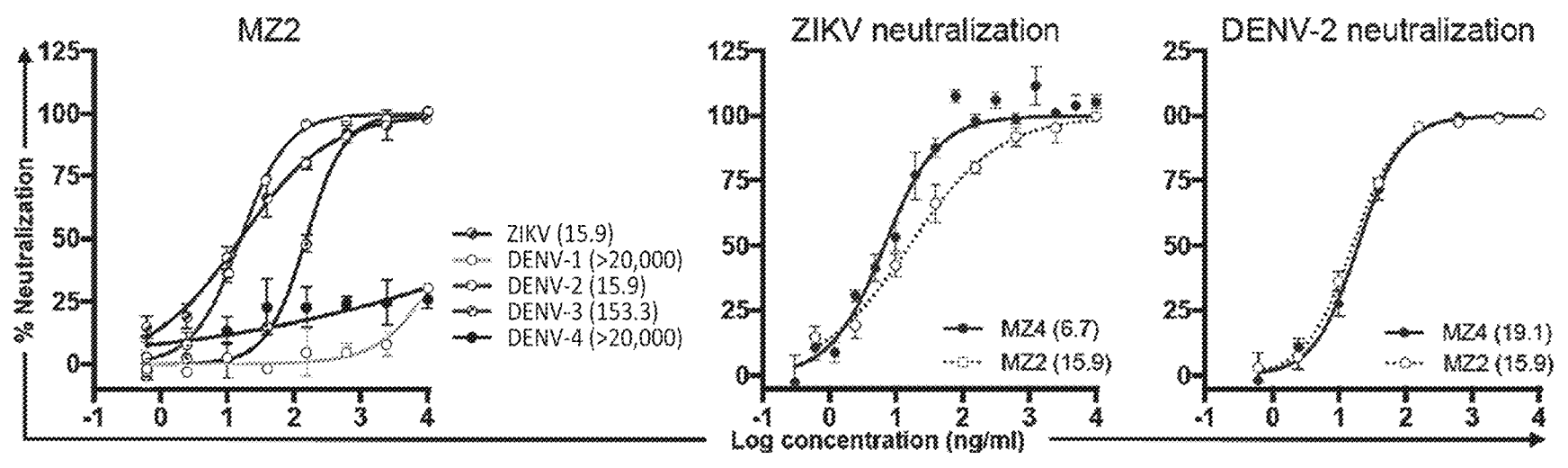
Figures 27D, 27E:
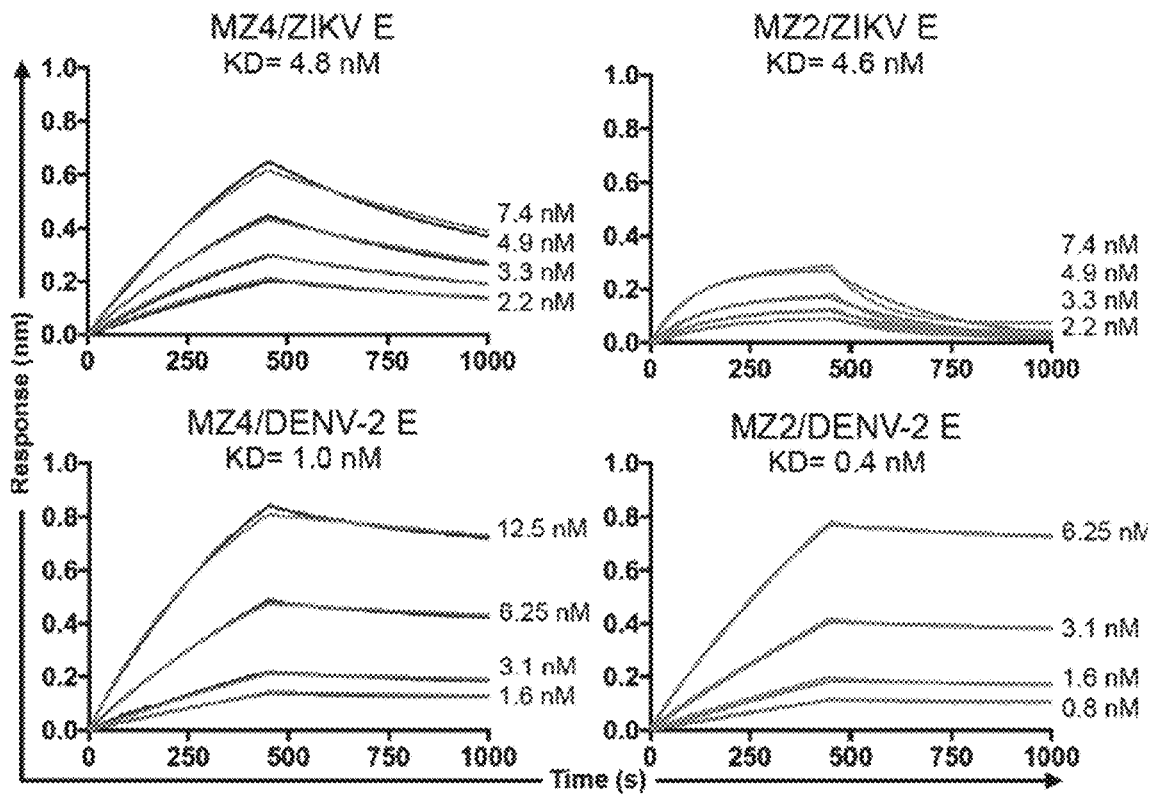
FIG. 27. Additional plasma characteristics and isolation of a MZ4-like antibody, MZ2, two weeks after the first ZPIV vaccination. a, Polyclonal binding responses to ZIKV and DENV-2 E in donor plasma measured by BLI. Off-rates ($s^{-1}$) were calculated after a 1200 s dissociation step and fitted with a 1:1 binding model. Data are mean values±SEM calculated from two independent experiments. b, Longitudinal ZIKV neutralization titers in donor #00015 (red) and 15 flavivirus-naïve donors (blue) during the course of vaccination. Median value with 95% confidence interval is plotted for naïve donors. c, Binding of MZ4 and MZ2 to ZIKV and DENV-2 virions, assessed by ELISA. Antibodies were titrated using 4-fold dilution series starting from 20 µg/ml. d, Binding kinetics of MZ4 and MZ2 to ZIKV (top) and DENV-2 (bottom) E proteins measured by BLI. Kinetic constants (table below) were calculated from binding curves (red [MZ4] and yellow [MZ2]) obtained from 4 serial dilutions of Fabs and fitted (grey curves) using a 1:1 binding model. e, Neutralization activities of the MZ4 and MZ2 antibodies obtained in the microneutralization assay (MN50) against ZIKV PR, DENV1-4, JEV, WNV and YFV. Data were generated from neutralization curves obtained by 3-fold serial dilutions from at least two independent experiments and fitted using a 4-parameter logistic regression model. Shown are the concentrations (ng/ml) at which 50% neutralization is observed.
Figure 28A:
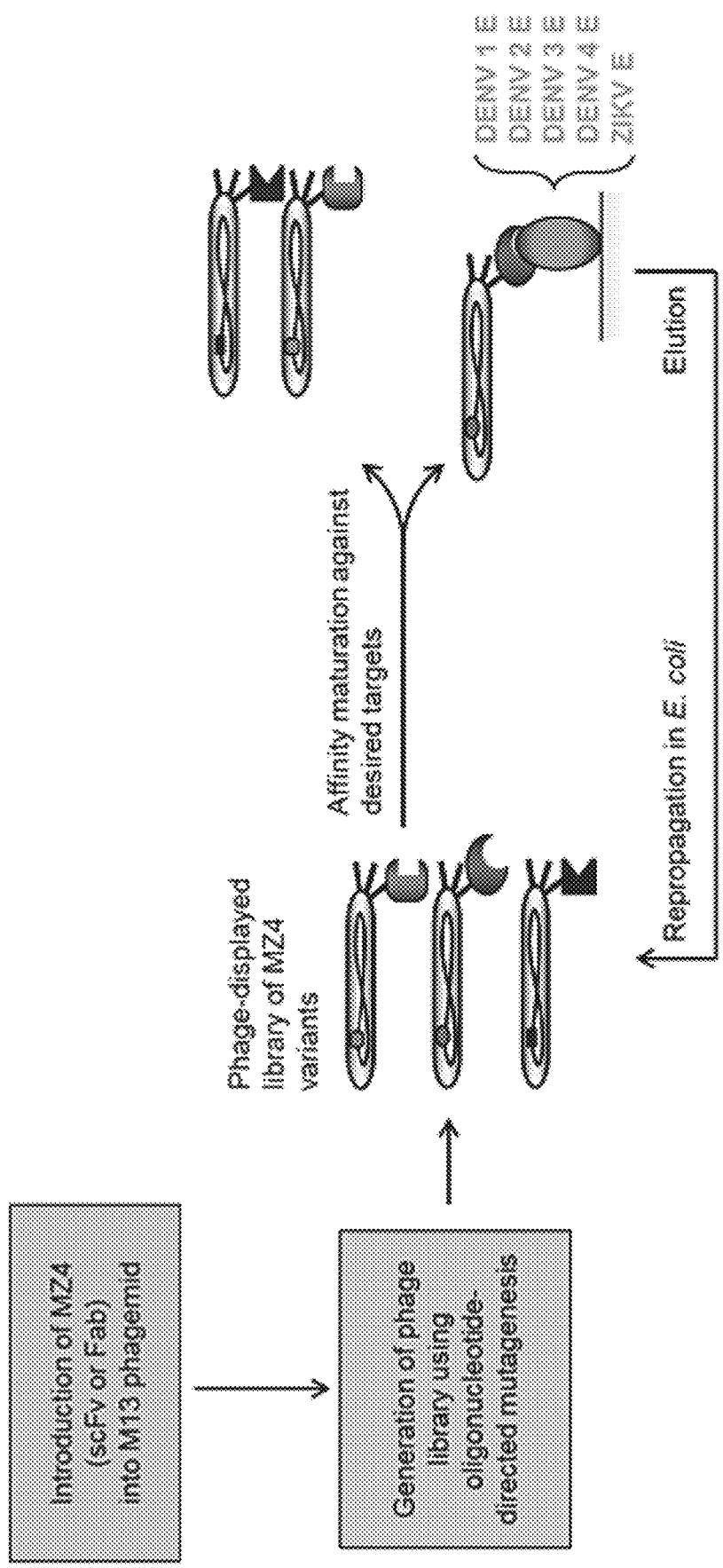
FIG. 28. Schematic of phage-display strategy to increase the neutralization breadth and potency of MZ4. (A) Schematic of structure-based phage display library design and selection of improved MZ4 variants. (B) Description of the two phage-display libraries based on the MZ4-E contact residues. (i) All wildtype (wt) template. MZ4 variants are introduced into a library where wildtype CDR loops will combine with library variants. (ii) All stop4 template. Each displayed MZ4 variant will be made up of combinations of variant CDR loops.
Figure 29:
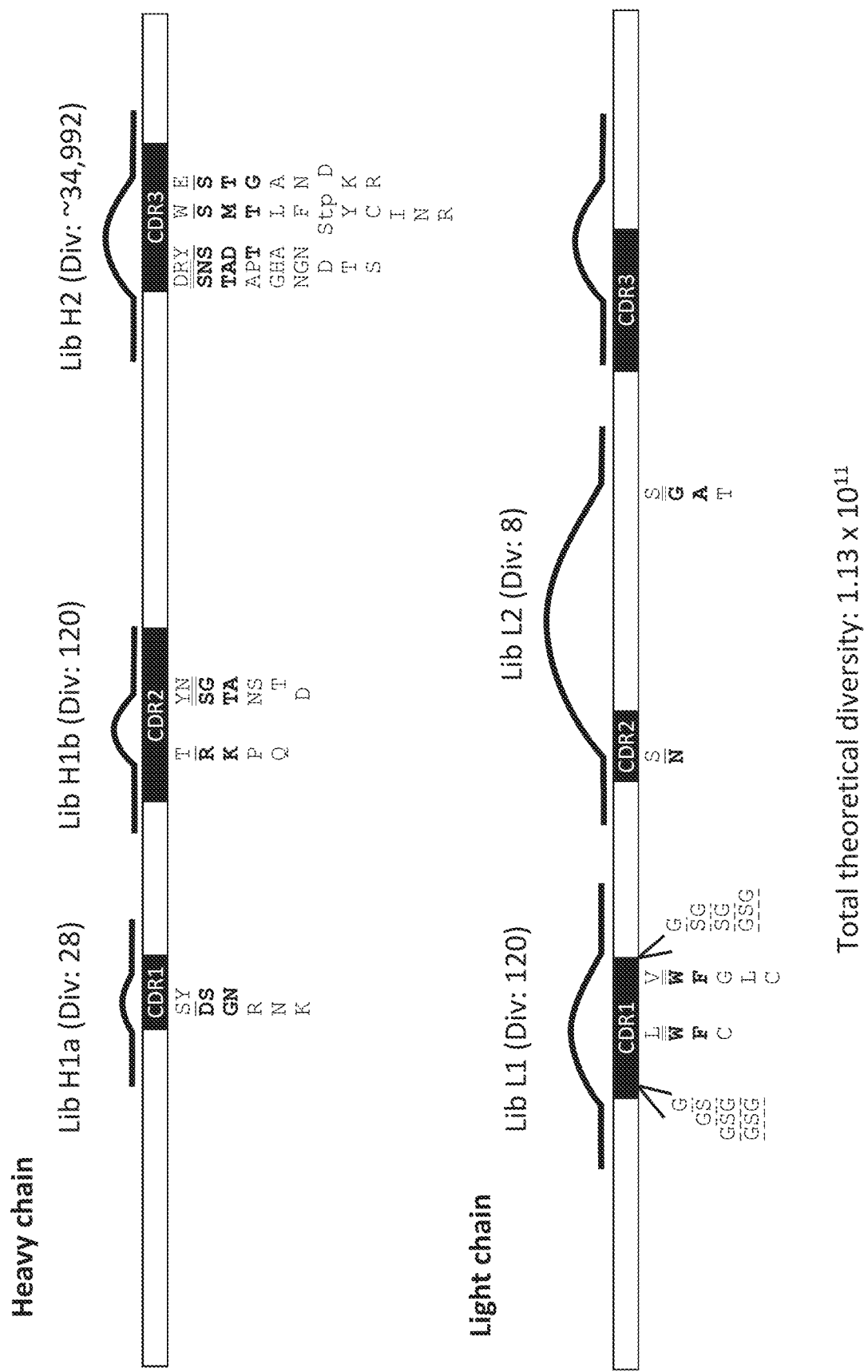
FIG. 29. Structure-based design of MZ4 phage library variants using the MZ4-ZIKV E glycoprotein structure. Analysis of the MZ4-ZIKV E and MZ1-ZIKV E glycoprotein crystal structures allowed identification of critical contact residues. Modeling of MZ4 or MZ1 in complex with DENV1-4 E glycoproteins allowed identification of residue substitutions that may lead to increased affinity to DENV-1, and DENV-4 E glycoprotein and neutralization potency. Residue variants were designed for CDR H1, H2, H3, CDR L1, CDR L2, and FR L3. In addition, a set of insertions in CDR L1 were also designed.
Figure 30:
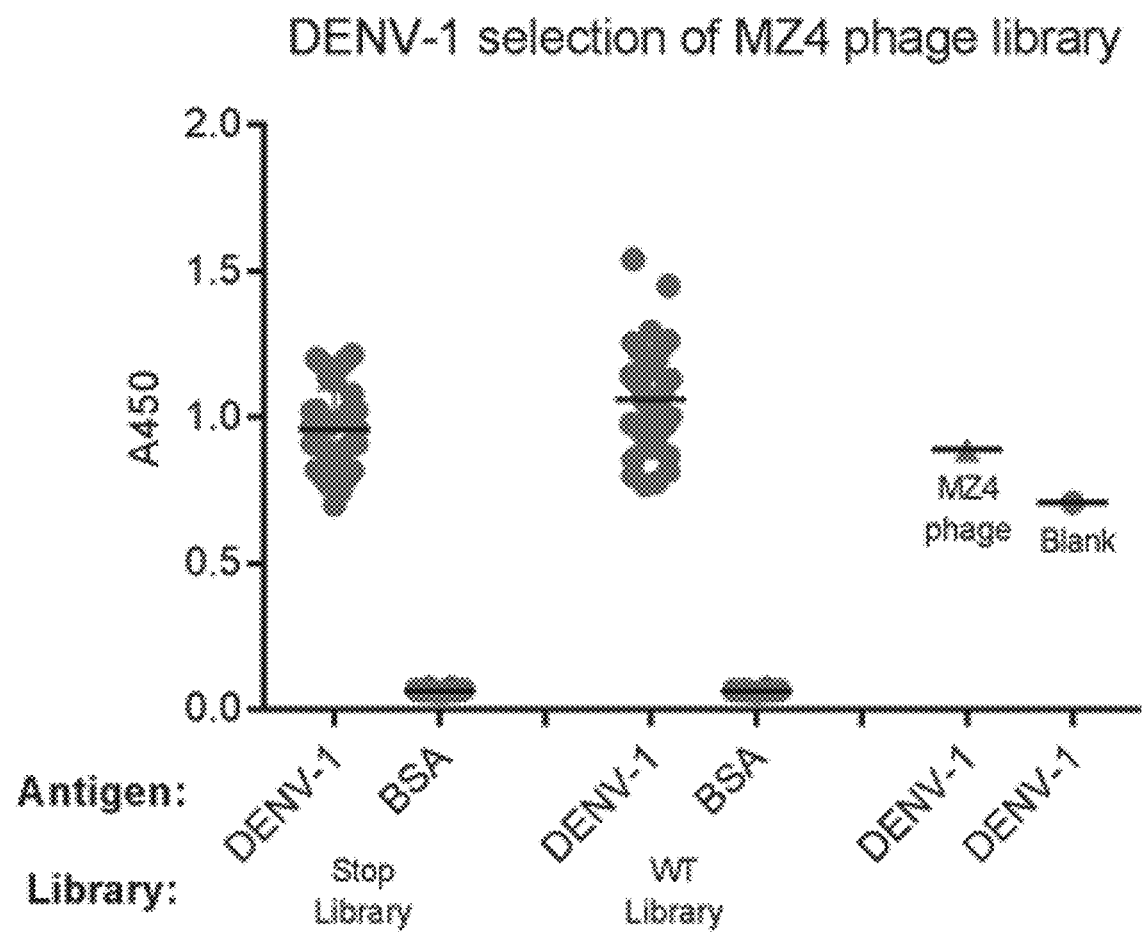
FIG. 30. Selection of MZ4 phage library variants using DENV-1 E glycoprotein. MZ4 variant displaying phage libraries ((i) stop-based and (ii) wild-type-based) were screened for variants with increased binding to DENV-1 E glycoprotein. Phage selection was carried out using increasing concentration of Tween, and increasing number of washes for four rounds. A set of 36 colonies from both libraries were grown overnight in the presence of helper phage. MZ4-displaying phage (MZ4 phage) was grown similarly. *E. coli* cells with no phage were used as a control (Blank). Phage binding to DENV-1 E glycoprotein or BSA was assessed by ELISA. Selected libraries show increased diversity of DENV-1 E glycoprotein binding levels, with some members showing significantly improved binding compared to MZ4.
Figure 31A:
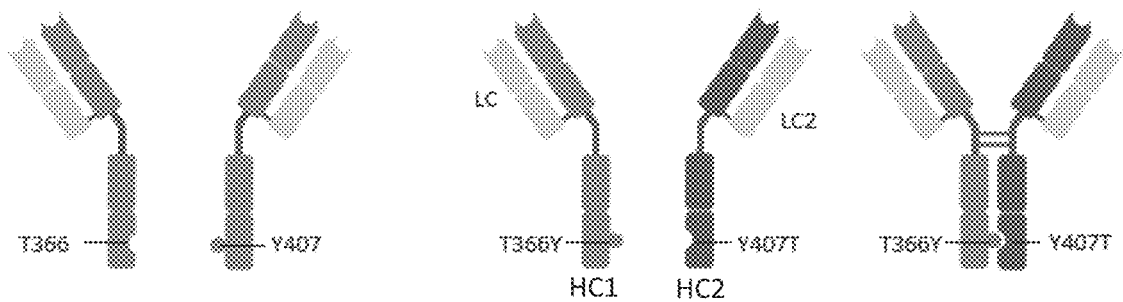
FIG. 31. Design of multi-specific Flavivirus neutralizing antibodies. Development of an immunotherapeutic with broad reactivity and protection against multiple flaviviruses may require combination of a set of antibody domains into a single immunotherapeutic. (A) a set of mutations in the Heavy constant 3 (T366Y, Y407T) create the "knob in hole" approach that allows partnering of two different heavy chains in a single antibody. (B) single-chain Fv design, allows the addition of multiple Fv regions with given specificities into a single antibody. (C) Hinge-insertion approach utilizes the linker region between Fv, and Fc, or between Fc1, and Fc2 to add additional scFvs. (D) Tail addition approach allows addition of either a Fab, or scFv(s) at the C-terminus of an antibody to allow additional specificities. (E) Examples of bi-specific tetravalent and bispecific bivalent antibodies are shown as examples.
Figure 31B:
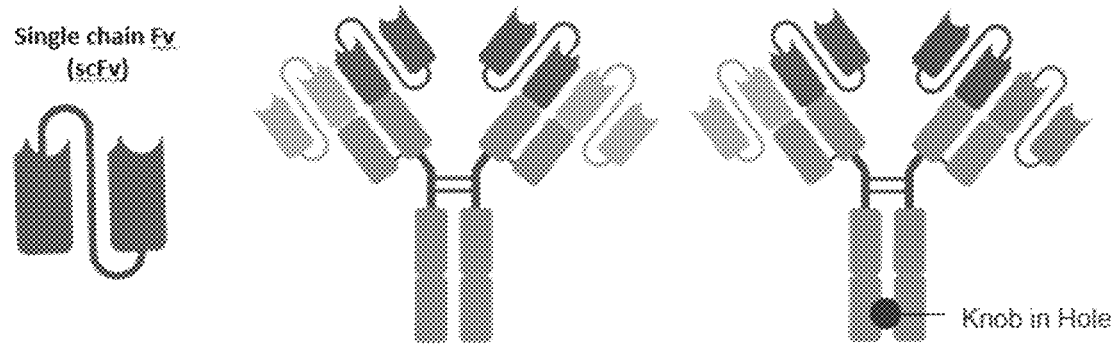
Figure 31C:
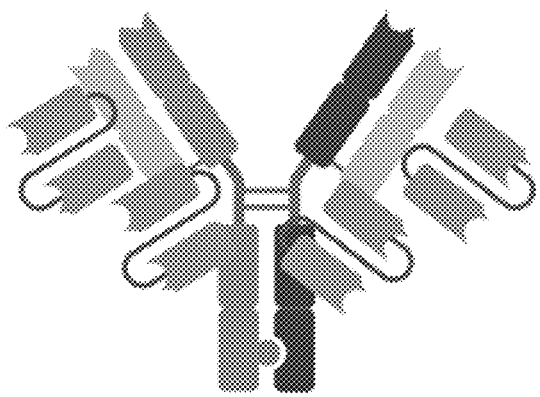
Figure 31D:
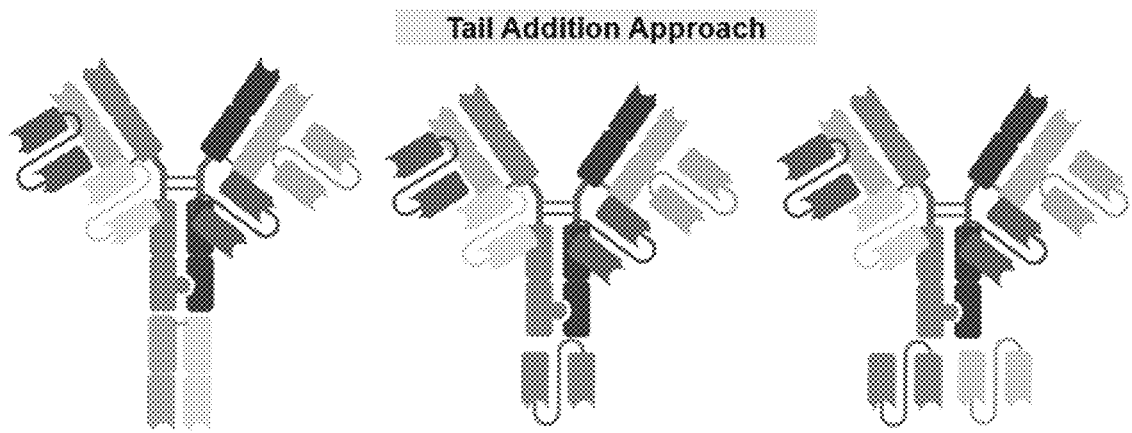
Figure 31E:
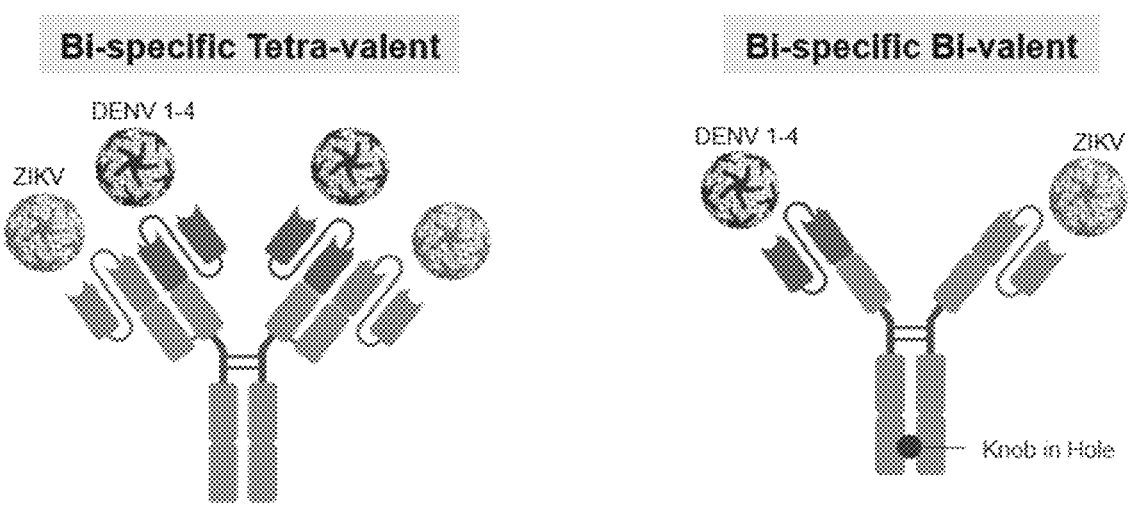
Figure 32A:
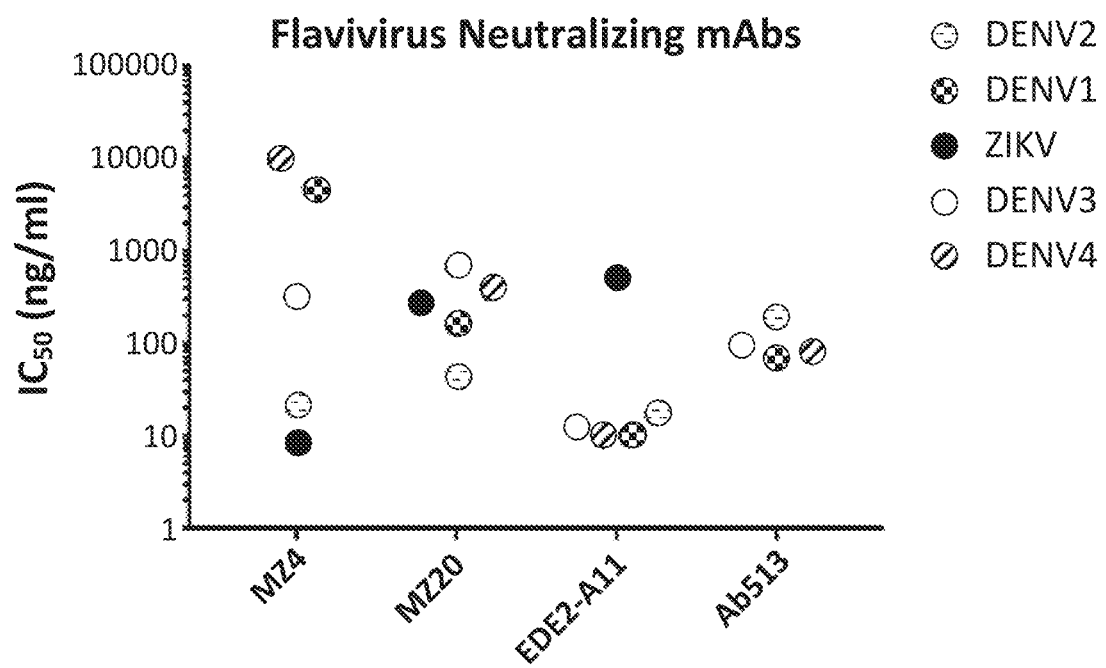
FIG. 32. Design of multi-specific Flavivirus neutralizing antibodies. Development of an immunotherapeutic with broad reactivity and protection against multiple flaviviruses may require combination of a set of antibody domains into a single immunotherapeutic. (A) FlowNT50 of a set of dengue and Zika neutralizing antibodies (MZ4, MZ20, EDE2-A11, and Ab513 (does not neutralize ZIKV). (B) MZ4, Ab513, and EDE2-A11 antibodies have non-overlapping epitopes as shown on a ZIKV E dimer structure. Escape variants in multiple epitopes would be difficult to achieve and increases the protective potential of multi-specific antibodies.
Figure 32B:
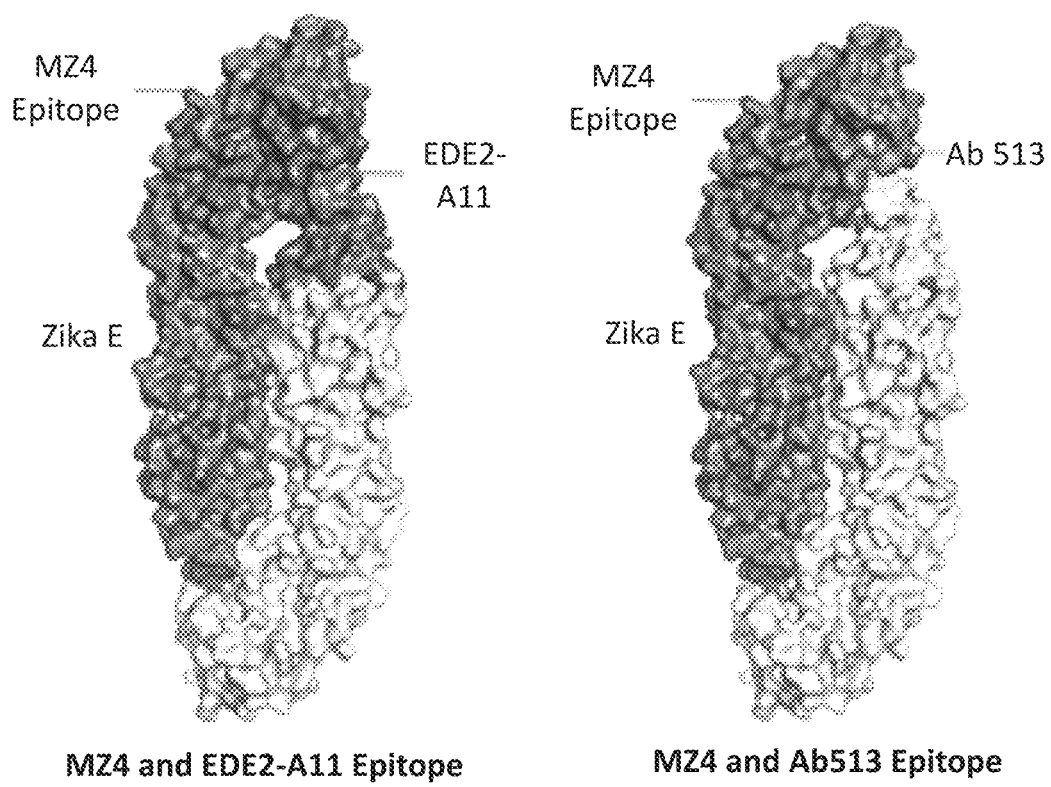
Figure 33A:
FIG. 33. Design and biochemical characterization of bi-specific tetravalent flavivirus neutralizing antibodies. (A) Schematic of Bi-specific tetravalent type A antibodies. Two examples are shown (i) BTA-A11-MZ4 and (ii) BTA-MZ20-MZ4. (B) BTA-A11-MZ4 design schematic, SDS-PAGE profile (reduced and non-reduced), and gel filtration purification profile. (C) BTA-MZ20-MZ4 design schematic, SDS-PAGE profile following expression in 293 Expi cells, and gel filtration profile.
Figure 33A:
Figure 33B:
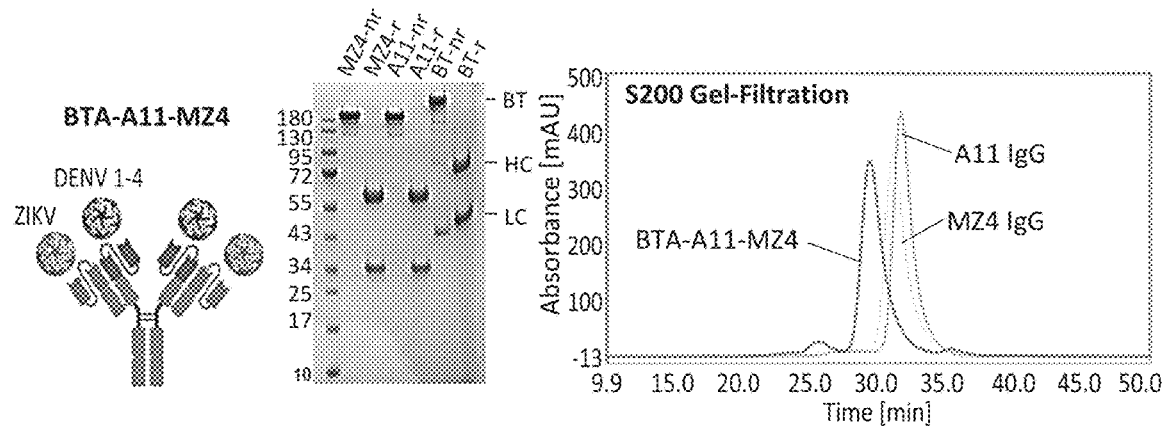
Figure 33C:
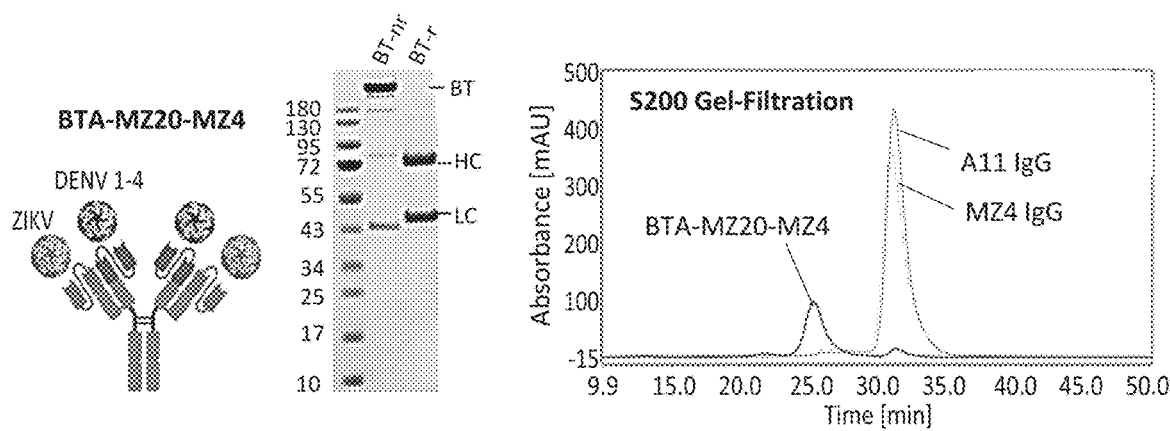
Figure 34A:
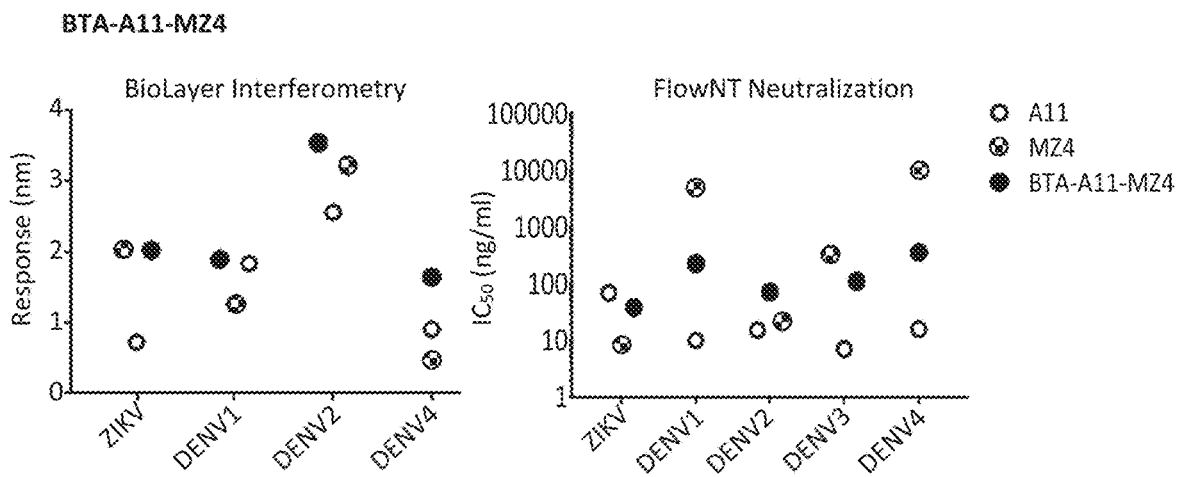
FIG. 34. Antigenic and Neutralization properties of BTA-MZ4-A11 and BTA-MZ20-MZ4 multi-specific antibodies. (A) Binding and Neutralization of BTA-A11-MZ4 against ZIKV, DENV-1, DENV-2, and DENV-4. Binding was measured by biolayer interferometry using E glycoproteins. FlowNT neutralization was used to measure neutralization against ZIKV, and DENV1-4 viruses. EDE2-A11 and MZ4 monoclonal antibodies are included for comparison. (B) Binding and Neutralization of BTA-MZ20-MZ4 against ZIKV, DENV-1, DENV-2, and DENV-4. Binding was measured by biolayer interferometry using E glycoproteins. FlowNT neutralization was used to measure neutralization against ZIKV, and DENV1-4 viruses. EDE2-A11 and MZ4 monoclonal antibodies are included for comparison.
Figure 34B:
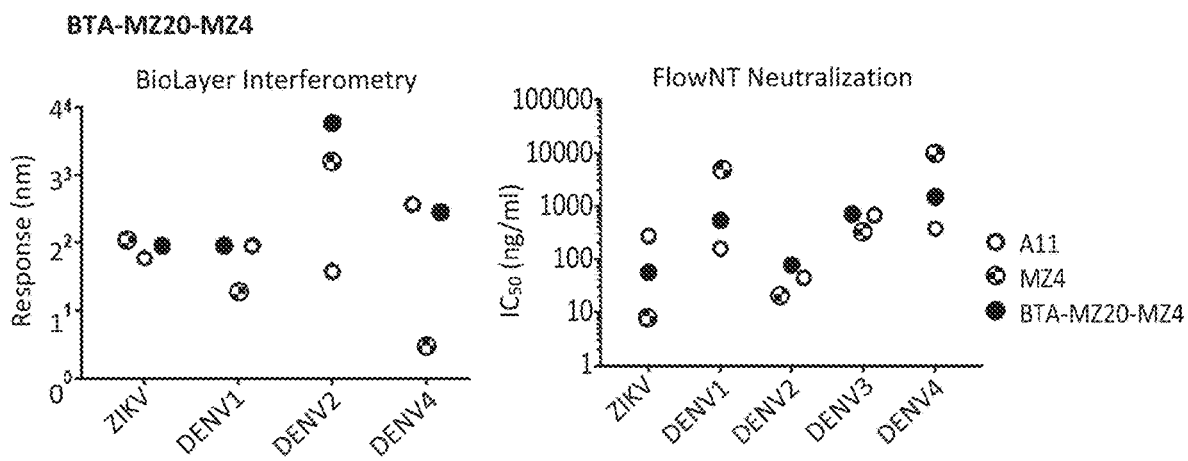
Figure 36A:
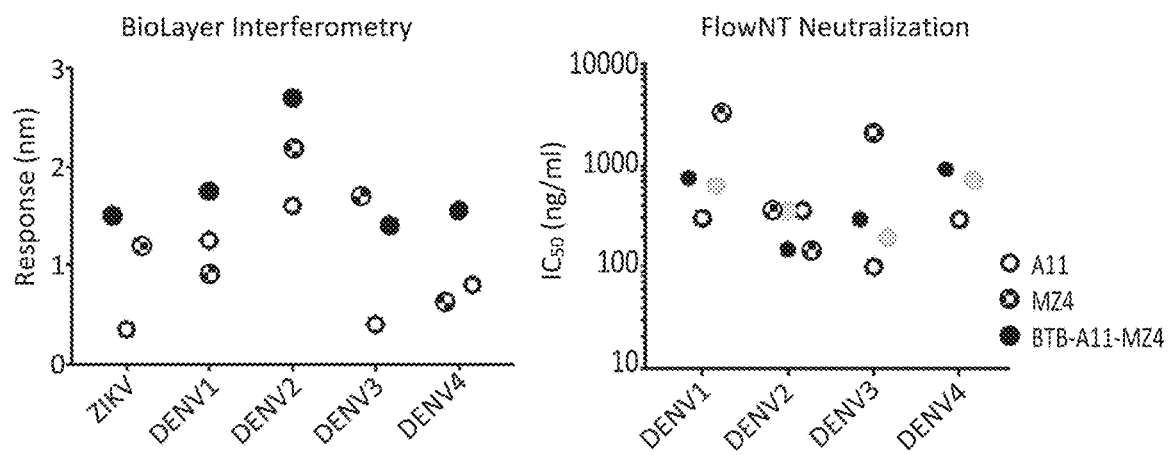
FIG. 36. Antigenic and Neutralization properties of BTB-MZ4-A11 and BTB-MZ20-MZ4 multi-specific antibodies. (A) Binding and Neutralization of BTB-A11-MZ4 against ZIKV, DENV-1, DENV-2, and DENV-4. Binding was measured by biolayer interferometry using E glycoproteins. FlowNT neutralization was used to measure neutralization against ZIKV, and DENV1-4 viruses. EDE2-A11 and MZ4 monoclonal antibodies are included for comparison. Gray sphere is a 50-50 mixture of A11 and MZ4 monoclonal antibodies. (B) Binding and Neutralization of BTB-MZ20-MZ4 against ZIKV, DENV-1, DENV-2, and DENV-4. Binding was measured by biolayer interferometry using E glycoproteins. FlowNT neutralization was used to measure neutralization against ZIKV, and DENV1-4 viruses. EDE2-A11 and MZ4 monoclonal antibodies are included for comparison. Gray sphere is a 50-50 mixture of A11 and MZ4 monoclonal antibodies.
Figure 36B:
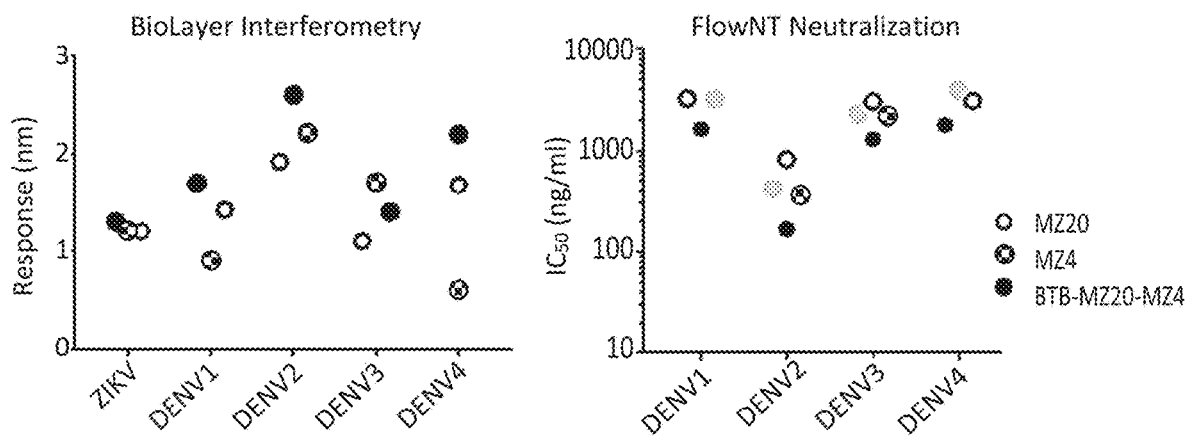
Figure 38A:
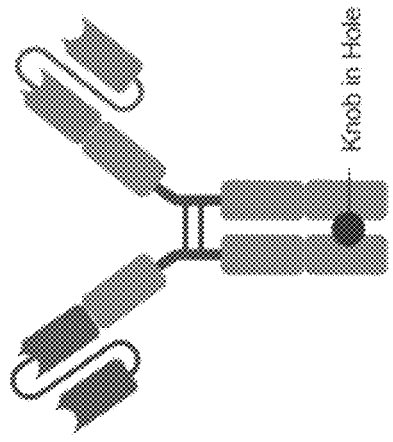
FIG. 38. Characterization of multi-specific Flavivirus neutralizing antibody BB-MZ4-A11. (A) Schematic of Bi-specific bivalent antibody BB-MZ4-A11, and cartoon. (B) BB-MZ4-A11 analysis by SDS-PAGE, and gel filtration profile. (C) Binding and Neutralization of BB-MZ4-A11 against ZIKV, DENV-1, DENV-2, and DENV-4. Binding was measured by biolayer interferometry using E glycoproteins. FlowNT neutralization was used to measure neutralization against ZIKV, and DENV1-4 viruses.
Figure 38B:
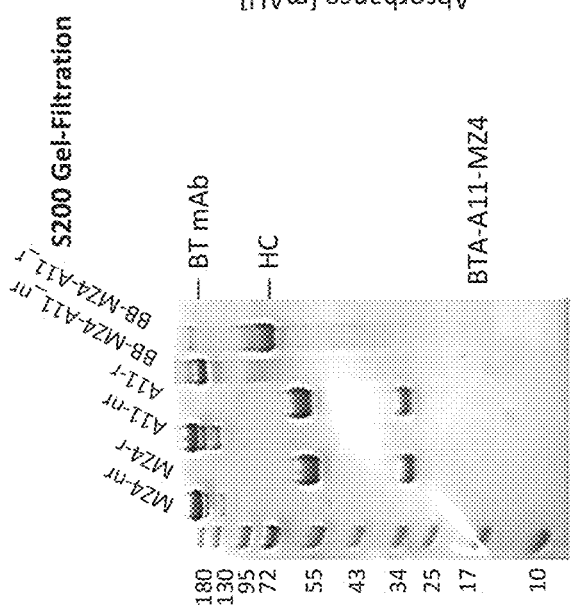
Figure 38C:
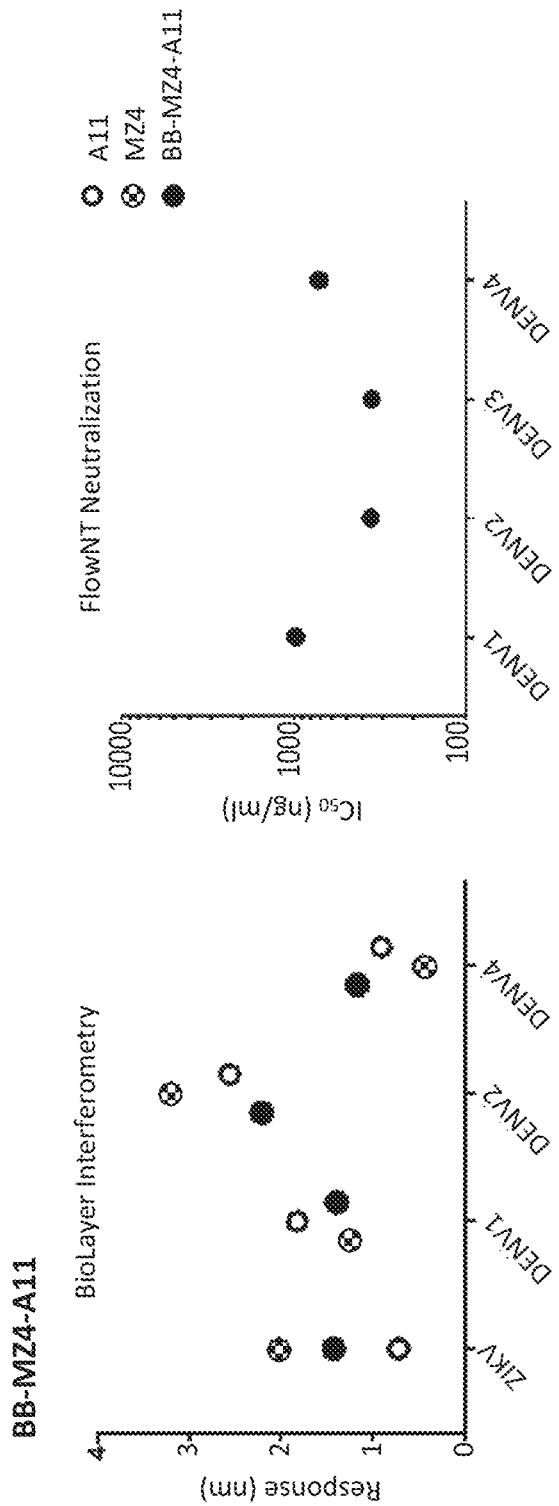

The question of how exposure to flavivirus prior to vaccination shaped the ZPIV-elicited responses was investigated next. An analysis of longitudinal plasma samples from Participant #00015 for neutralization activity, strikingly showed that high magnitude ZIKV and DENV-2 binding and neutralizing antibody responses were observed two weeks after injection of the first ZIPV dose (FIG. 26a). All these responses were maintained to a similar level following the second ZPIV dose. Binding responses and off-rates to ZIKV and DENV-2 E proteins followed the same kinetics (FIG. 27a). In contrast, flavivirus naïve donors (n=5) that received the same vaccine regimen demonstrated modest titers 2 weeks following the first vaccination, with peak binding and neutralizing responses detected at week 8 after two immunizations (FIG. 26b, FIG. 27b), and those responses were specific to ZIKV with no cross-reactivity detected to DENV (FIG. 26b).

Since high binding and neutralizing titers were detected in serum from Participant #00015 after only one ZPIV vaccination, it was next determined if these were a result of the induction of MZ4-like antibodies. Therefore, the same sorting strategy was utilized to isolate antigen-positive B cells from cryopreserved PBMCs collected from Participant #00015 at 2 weeks following the first vaccination. One isolated antibody, called 'MZ2', for 2 weeks post the first vaccination, had high sequence similarity to MZ4 and similar heavy and light chain characteristics (FIG. 26d). MZ2 yielded nearly identical binding, neutralization and epitope mapping as MZ4, suggesting that a single dose of ZPIV was sufficient to elicit potent cross-reactive neutralizing antibodies to ZIKV and DENV (FIG. 26e-g, FIG. 27c-f).

While aspects of the present disclosure been particularly shown and described with references to preferred embodiments thereof, it will be understood by those skilled in the art that various changes in form and details may be made therein without departing from the scope of the invention encompassed by the appended claims. The claims are intended to cover the components and steps in any sequence which is effective to meet the objectives there intended, unless the context specifically indicates the contrary.

The invention claimed is:

1. An antibody or fragment thereof that selectively binds Zika virus, wherein said antibody comprises:
   (a) a heavy chain variable region comprising complementarity determining regions (CDRs) having amino acid sequences SEQ ID NO: 5 for CDR1, SEQ ID NO: 6 for CDR2, and SEQ ID NO: 7 for CDR3; and a light chain variable region comprising CDRs having amino acid sequences of SEQ ID NO: 8 for CDR1, SEQ ID NO: 9 for CDR2 and SEQ ID NO: 10 for CDR3; or
   (b) a heavy chain variable region comprising CDRs having amino acid sequences SEQ ID NO: 15 for CDR1, SEQ ID NO: 16 for CDR2, and SEQ ID NO: 17 for CDR3; and a light chain variable region comprising CDRs having amino acid sequences of SEQ ID NO: 18 for CDR1, SEQ ID NO: 19 for CDR2 and SEQ ID NO: 20 for CDR3; or
   (c) a heavy chain variable region comprising CDRs having amino acid sequences SEQ ID NO: 25 for CDR1, SEQ ID NO: 26 for CDR2, and SEQ ID NO: 27 for CDR3; and a light chain variable region comprising CDRs having amino acid sequences of SEQ ID NO: 28 for CDR1, SEQ ID NO: 29 for CDR2 and SEQ ID NO: 30 for CDR3; or
   (d) a heavy chain variable region comprising CDRs having amino acid sequences SEQ ID NO: 35 for CDR1, SEQ ID NO: 36 for CDR2, and SEQ ID NO: 37 for CDR3; and a light chain variable region comprising CDRs having amino acid sequences of SEQ ID NO: 38 for CDR1, SEQ ID NO: 39 for CDR2 and SEQ ID NO: 40 for CDR3; or
   (e) a heavy chain variable region comprising CDRs having amino acid sequences SEQ ID NO: 45 for CDR1, SEQ ID NO: 46 for CDR2, and SEQ ID NO: 47 for CDR3; and a light chain variable region comprising CDRs having amino acid sequences of SEQ ID NO: 48 for CDR1, SEQ ID NO: 49 for CDR2 and SEQ ID NO: 50 for CDR3; or
   (f) a heavy chain variable region comprising CDRs having amino acid sequences SEQ ID NO: 55 for CDR1, SEQ ID NO: 56 for CDR2, and SEQ ID NO: 57 for CDR3; and a light chain variable region comprising CDRs having amino acid sequences of SEQ ID NO: 58 for CDR1, SEQ ID NO: 59 for CDR2 and SEQ ID NO: 60 for CDR3; or (g) a heavy chain variable region comprising CDRs having amino acid sequences SEQ ID NO: 65 for CDR1, SEQ ID NO: 66 for CDR2, and SEQ ID NO: 67 for CDR3; and a light chain variable region comprising CDRs having amino acid sequences of SEQ ID NO: 68 for CDR1, SEQ ID NO: 69 for CDR2 and SEQ ID NO: 70 for CDR3; or (h) a heavy chain variable region comprising CDRs having amino acid sequences SEQ ID NO: 75 for CDR1, SEQ ID NO: 76 for CDR2, and SEQ ID NO: 77 for CDR3; and a light chain variable region comprising CDRs having amino acid sequences of SEQ ID NO: 78 for CDR1, SEQ ID NO: 79 for CDR2 and SEQ ID NO: 80 for CDR3; or (i) a heavy chain variable region comprising CDRs having amino acid sequences SEQ ID NO: 85 for CDR1, SEQ ID NO: 86 for CDR2, and SEQ ID NO: 87 for CDR3; and a light chain variable region comprising CDRs having amino acid sequences of SEQ ID NO: 88 for CDR1, SEQ ID NO: 89 for CDR2 and SEQ ID NO: 90 for CDR3; or (j) a heavy chain variable region comprising CDRs having amino acid sequences SEQ ID NO: 95 for CDR1, SEQ ID NO: 96 for CDR2, and SEQ ID NO: 97 for CDR3; and a light chain variable region comprising CDRs having amino acid sequences of SEQ ID NO: 98 for CDR1, SEQ ID NO: 99 for CDR2 and SEQ ID NO: 100 for CDR3; or (k) a heavy chain variable region comprising CDRs having amino acid sequences SEQ ID NO: 105 for CDR1, SEQ ID NO: 106 for CDR2, and SEQ ID NO: 107 for CDR3; and a light chain variable region comprising CDRs having amino acid sequences of SEQ ID NO: 108 for CDR1, SEQ ID NO: 109 for CDR2 and SEQ ID NO: 110 for CDR3; or (l) a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3; or (m) a heavy chain variable region comprising CDRs having amino acid sequences SEQ ID NO: 125 for CDR1, SEQ ID NO: 126 for CDR2, and SEQ ID NO: 127 for CDR3; and a light chain variable region comprising CDRs having amino acid sequences of SEQ ID NO: 128 for CDR1, SEQ ID NO: 129 for CDR2 and SEQ ID NO: 130 for CDR3; or (n) a heavy chain variable region comprising CDRs having amino acid sequences SEQ ID NO: 135 for CDR1, SEQ ID NO: 136 for CDR2, and SEQ ID NO: 137 for CDR3; and a light chain variable region comprising CDRs having amino acid sequences of SEQ ID NO: 138 for CDR1, SEQ ID NO: 139 for CDR2 and SEQ ID NO: 140 for CDR3; or (o) a heavy chain variable region comprising CDRs having amino acid sequences SEQ ID NO: 145 for CDR1, SEQ ID NO: 146 for CDR2, and SEQ ID NO: 147 for CDR3; and a light chain variable region comprising CDRs having amino acid sequences of SEQ ID NO: 148 for CDR1, SEQ ID NO: 149 for CDR2 and SEQ ID NO: 150 for CDR3; or (p) a heavy chain variable region comprising CDRs having amino acid sequences SEQ ID NO: 155 for CDR1, SEQ ID NO: 156 for CDR2, and SEQ ID NO: 157 for CDR3; and a light chain variable region comprising CDRs having amino acid sequences of SEQ ID NO: 158 for CDR1, SEQ ID NO: 159 for CDR2 and SEQ ID NO: 160 for CDR3; or (q) a heavy chain variable region comprising CDRs having amino acid sequences SEQ ID NO: 165 for CDR1, SEQ ID NO: 166 for CDR2, and SEQ ID NO: 167 for CDR3; and a light chain variable region comprising CDRs having amino acid sequences of SEQ ID NO: 168 for CDR1, SEQ ID NO: 169 for CDR2 and SEQ ID NO: 170 for CDR3; or (r) a heavy chain variable region comprising CDRs having amino acid sequences SEQ ID NO: 175 for CDR1, SEQ ID NO: 176 for CDR2, and SEQ ID NO: 177 for CDR3; and a light chain variable region comprising CDRs having amino acid sequences of SEQ ID NO: 178 for CDR1, SEQ ID NO: 179 for CDR2 and SEQ ID NO: 180 for CDR3; or (s) a heavy chain variable region comprising CDRs having amino acid sequences SEQ ID NO: 185 for CDR1, SEQ ID NO: 186 for CDR2, and SEQ ID NO: 187 for CDR3; and a light chain variable region comprising CDRs having amino acid sequences of SEQ ID NO: 188 for CDR1, SEQ ID NO: 189 for CDR2 and SEQ ID NO: 190 for CDR3; or (t) a heavy chain variable region comprising CDRs having amino acid sequences SEQ ID NO: 195 for CDR1, SEQ ID NO: 196 for CDR2, and SEQ ID NO: 197 for CDR3; and a light chain variable region comprising CDRs having amino acid sequences of SEQ ID NO: 198 for CDR1, SEQ ID NO: 199 for CDR2 and SEQ ID NO: 200 for CDR3; or (u) a heavy chain variable region comprising CDRs having amino acid sequences SEQ ID NO: 205 for CDR1, SEQ ID NO: 206 for CDR2, and SEQ ID NO: 207 for CDR3; and a light chain variable region comprising CDRs having amino acid sequences of SEQ ID NO: 208 for CDR1, SEQ ID NO: 209 for CDR2 and SEQ ID NO: 210 for CDR3; or (v) a heavy chain variable region comprising CDRs having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

2. The antibody or fragment thereof of claim 1 wherein said antibody or antibody fragment comprises a heavy chain variable region comprising CDRs having amino acid sequences SEQ ID NO: 115 for CDR1, SEQ ID NO: 116 for CDR2, and SEQ ID NO: 117 for CDR3; and a light chain variable region comprising CDRs having amino acid sequences of SEQ ID NO: 118 for CDR1, SEQ ID NO: 119 for CDR2 and SEQ ID NO: 120 for CDR3.

3. The antibody or fragment thereof of claim 1 wherein said antibody or antibody fragment comprises a heavy chain variable region comprising CDRs having amino acid sequences SEQ ID NO: 215 for CDR1, SEQ ID NO: 216 for CDR2, and SEQ ID NO: 217 for CDR3; and a light chain variable region comprising CDRs having amino acid sequences of SEQ ID NO: 218 for CDR1, SEQ ID NO: 219 for CDR2 and SEQ ID NO: 220 for CDR3.

4. The antibody or fragment thereof of claim 1,
(a) wherein said antibody or antibody fragment inhibits or prevents Zika virus infection, Dengue virus infection, infection by Dengue virus serotype 2, infection by Dengue virus serotype 3, Zika virus transmission from a pregnant female to a fetus, sexual transmission of Zika virus, or infection of human testes by Zika virus;
(b) wherein said antibody or antibody fragment has an ED50 for neutralizing Zika infection of less than 10 mg/kg;
(c) wherein 100 μg/ml of said antibody or antibody fragment does not neutralize infection by a flavivirus selected from the group of Dengue virus, Japanese Encephalitis virus, West Nile virus, or Yellow Fever virus;
(d) wherein said antibody or antibody fragment has an IC50 for neutralizing Zika infection of less than 10 μM; and/or
(e) wherein said antibody or antibody fragment has an equilibrium dissociation constant (KD) in the range from $10^{-7}$ to $10^{-9}$ molar, or less than $10^{-7}$ molar.

5. The antibody or antibody fragment of claim 1 wherein:
(a) said antibody fragment is a Fab fragment;
(b) said antibody fragment is a single chain variable fragment (ScFv); or
(c) said antibody or antibody fragment is a humanized antibody, or humanized antibody fragment.

6. A polynucleotide comprising a nucleotide sequence encoding the antibody or antibody fragment of claim 1.

7. A host cell comprising the polynucleotide of claim 6.

8. A pharmaceutical composition comprising a pharmaceutically acceptable carrier and the antibody or antibody fragment of claim 1.

9. A method for the prevention or treatment of a flavivirus infection comprising administering to a patient a therapeutically effective amount of the pharmaceutical preparation of claim 8.

10. A method for inhibiting or preventing transmission of a flavivirus infection from a pregnant female to her fetus comprising administering to the pregnant female a therapeutically effective amount of the pharmaceutical preparation of claim 8.

11. A method of detecting the presence of a flavivirus in a biological sample, the method comprising contacting the antibody or antibody fragment of claim 1 with the biological sample and detecting the binding of the antibody or antibody fragment to a flavivirus.

12. A kit for detecting the presence of a flavivirus in a biological sample, the kit comprising the antibody or antibody fragment of claim 1 further comprising one or more buffers and/or a reporter.

13. A method of diagnosing or detecting infection by a flavivirus, the method comprising:
obtaining a biological sample from a subject at risk of a flavivirus infection;
contacting the biological sample with the antibody or antibody fragment of claim 1; and
determining if the antibody or antibody fragment has bound to a flavivirus antigen; wherein binding of the antibody or antibody fragment to a flavivirus antigen indicates that the subject is infected with a flavivirus.

14. A method of measuring the efficacy of a vaccine batch comprising contacting an aliquot of the vaccine batch with the antibody or antibody fragment of claim 1, and detecting the binding of the antibody or antibody fragment.

15. A method of purifying a flavivirus E glycoprotein comprising contacting the flavivirus E glycoprotein with the antibody or antibody fragment of claim 1.

16. The antibody or fragment thereof of claim 1, wherein the antibody or fragment thereof binds to the DI-DIII linker domain of a Zika virus.

17. The antibody or fragment thereof of claim 16 wherein binding to Zika virus is reduced by at least 70% when Zika virus E glycoprotein residue Tyrosine 305 is substituted with alanine.

* * * * *